(12) United States Patent
Yoo et al.

(10) Patent No.: US 11,660,352 B2
(45) Date of Patent: *May 30, 2023

(54) DUAL FUNCTION ANTIBODIES SPECIFIC TO GLYCOSYLATED PD-L1 AND METHODS OF USE THEREOF

(71) Applicants: STCUBE, INC., Seoul (KR); BOARD OF REGENTS, THE UNIVERSITY OF TEXAS SYSTEM, Austin, TX (US)

(72) Inventors: Stephen S. Yoo, Centreville, VA (US); Ezra M. Chung, North Potomac, MD (US); Yong-Soo Kim, Rockville, MD (US); Kyu Lee Han, Gaithersburg, MD (US); Andrew H. Park, Gaithersburg, MD (US); Mien-Chie Hung, Houston, TX (US); Chia-Wei Li, Houston, TX (US); Seung-Oe Lim, Houston, TX (US)

(73) Assignees: STCUBE, INC., Seoul (KR); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 62 days.

This patent is subject to a terminal disclaimer.

(21) Appl. No.: 16/086,582

(22) PCT Filed: Mar. 24, 2017

(86) PCT No.: PCT/US2017/024027
§ 371 (c)(1),
(2) Date: Sep. 19, 2018

(87) PCT Pub. No.: WO2017/172518
PCT Pub. Date: Oct. 5, 2017

(65) Prior Publication Data
US 2019/0083644 A1    Mar. 21, 2019

Related U.S. Application Data

(60) Provisional application No. 62/314,652, filed on Mar. 29, 2016, provisional application No. 62/361,312, filed on Jul. 12, 2016.

(51) Int. Cl.
| | | |
|---|---|---|
| A61K 39/395 | (2006.01) | |
| A61K 39/00 | (2006.01) | |
| A61K 39/44 | (2006.01) | |
| C07K 16/00 | (2006.01) | |
| C07K 16/46 | (2006.01) | |
| A61K 47/68 | (2017.01) | |
| C07K 16/28 | (2006.01) | |
| C07K 16/30 | (2006.01) | |
| A61P 35/00 | (2006.01) | |

(52) U.S. Cl.
CPC ...... *A61K 47/6811* (2017.08); *A61K 47/6849* (2017.08); *A61K 47/6851* (2017.08); *A61K 47/6879* (2017.08); *A61P 35/00* (2018.01); *C07K 16/2827* (2013.01); *C07K 16/3015* (2013.01); *C07K 16/3023* (2013.01); *C07K 2317/30* (2013.01); *C07K 2317/34* (2013.01); *C07K 2317/73* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | |
|---|---|---|
| 2003/0148406 A1 | 8/2003 | King et al. |
| 2008/0118978 A1 | 5/2008 | Sato et al. |
| 2008/0187954 A1 | 8/2008 | Kallmeier et al. |
| 2009/0041783 A1 | 2/2009 | Takayama et al. |
| 2009/0176317 A1 | 7/2009 | Kwon et al. |
| 2010/0285039 A1 | 11/2010 | Chen |
| 2011/0271358 A1 | 11/2011 | Freeman et al. |

(Continued)

FOREIGN PATENT DOCUMENTS

| | | |
|---|---|---|
| WO | WO 2006/004988 | 1/2006 |
| WO | WO 2006/121168 | 11/2006 |

(Continued)

OTHER PUBLICATIONS

Brown et al. Tolerance of single, but not multiple, amino acid replacements in antibody VH CDR2: a means of minimizing B cell wastage from somatic hypermutation? J. Immuno. May 1996, 3285-91. (Year: 1996).*

(Continued)

*Primary Examiner* — Maher M Haddad
(74) *Attorney, Agent, or Firm* — Ballard Spahr LLP

(57) ABSTRACT

Antibodies that bind specifically to glycosylated PD-L1 relative to unglycosylated PD-L1, block binding of PD-L1 to PD-1 and promote internalization and degradation of PD-L1 are provided. Antibodies that recognize specific epitopes on glycosylated PD-L1 protein and that exhibit the dual functions of both blocking the binding of PD-L1 to PD-1 and also facilitating the internalization of PD-L1 on cells are provided. In some aspects, PD-L1 polypeptides comprising glycosylated amino acid residues at amino and carboxy terminal positions of the PD-L1 extracellular domain are also provided. Methods for using such antibodies for the treatment of cancer, particularly PD-L1 positive cancer, are also provided.

28 Claims, 34 Drawing Sheets
Specification includes a Sequence Listing.

(56) References Cited

U.S. PATENT DOCUMENTS

| | | |
|---|---|---|
| 2012/0034229 A1 | 2/2012 | Rousselle et al. |
| 2013/0017251 A1 | 1/2013 | Huang et al. |
| 2014/0170134 A1 | 6/2014 | Schneewind et al. |
| 2017/0247454 A1 | 8/2017 | Benz et al. |
| 2018/0118830 A1 | 5/2018 | Yoo |
| 2019/0105403 A1* | 4/2019 | Yoo .................. G01N 33/563 |

FOREIGN PATENT DOCUMENTS

| | | |
|---|---|---|
| WO | WO 2008/156712 | 12/2008 |
| WO | WO 2011/066389 | 6/2011 |
| WO | 2013181634 A2 | 5/2013 |
| WO | WO 2013/079174 | 6/2013 |
| WO | WO 2014/055897 A2 | 4/2014 |
| WO | WO 2014/055897 A3 | 4/2014 |
| WO | WO 2015/035606 | 3/2015 |
| WO | WO 2015/061668 | 4/2015 |
| WO | WO 2015/095418 | 6/2015 |
| WO | WO 2015/112800 | 7/2015 |
| WO | WO 2016/160792 | 10/2016 |
| WO | WO 2017/055443 | 4/2017 |

OTHER PUBLICATIONS

Vajdos et al. Comprehensive functional maps of the antigen-binding site of an anti-ErbB2 antibody obtained with shotgun scanning mutagenesis. J. Mol. Biol., Jul. 5, 2002, 320(2):415-28. (Year: 2002).*
U.S. Appl. No. 15/778,663, filed May 24, 2018, Stephen S. Yoo.
U.S. Appl. No. 15/559,513, filed Sep. 19, 2017, Stephen S. Yoo.
U.S. Appl. No. 16/086,574, filed Sep. 19, 2018, Stephen S. Yoo.
U.S. Appl. No. 16/318,840, filed Jan. 18, 2019, Stephen S. Yoo.
Jacob Plieth et al.: 11 PD-I / PD-LI Combination Therapies 11, Sep. 8, 2015 (Sep. 18, 2015), XP055404205, Retrieved from the Internet: URL:nfo.evaluategroup.com/rs/607-YGS-364/i, mages/epv-pdct17. pdf [retrieved on Sep. 6, 2017].
M36239, GenBank Accession No. M36239, "Mouse Ig Kappa-chain mRNA V region, partial cds, from hybridoma H147-25H1VK," Apr. 27, 1993, retrieved on Jun. 9, 2016, http://www.ncbi.nlm.nih.gov/nuccore/M36239.
DQ372788, GenBank Accession No. DQ372788, "Mus Muculus clone AiDWTimmB-27 immunoglobulin kappa light chain mRNA, partial cds," Feb. 2, 2006, retrieved on Jun. 9, 2016, http://www.ncbi.nlm.nih.gov/nuccore/DQ372788.
Wang, C et al., In Vitro Characterization of the Anti-PD-1 Antibody Nivolumab, BMS-936558, and In Vivo Toxicology in Non-Human Primates. Cancer Immunology Research. May 28, 2014; vol. 2, No. 9; pp. 846-856; p. 848, col. 2, paragraph 4; DOI:10.1158/2326-6066.CIR-14-0040.
Jeffries, R, Glycosylation as a Strategy to Improve Antibody-Based Therapeutics. Nature Reviews Drug DIscovt1ry. M<trdr, 2009, Vul. 8, Nu. 3; pp. 220-234; p. 229, col. 1, paragraph 4—p. 229, col. 2, paragraph 1; DOI: 10.1038/nrd2804.
Warrington, Arthur E et al: 1-39 11 Neuron-binding human mono-clonal antibodies support central nervous system neurite extension 11, Journal of Neuropathology and Experimental Neurol, Lippincott Williams and Wilkins, New York, NY, vol. 63, No. 5, May 1, 2004 (May 1, 2004), pp. 461-473.

A J Hamilton et al: "A 34-to 38-Kilodalton Cryptococcus neoformans Glycoprotein Produced as an Exoantigen Bearing a Glycosylated Species-Specific Epitope 11",Infection and Immunity, vol. 60. No. 1 • Jan. 1, 1992 (Jan. 1, 1992). pp. 143-149.
Antje Danielczyk et al: 11 Pank0Mab: a potent new generation anti-tumour MUCI antibody 11 • Cancer Immunology, Immunotherapy, Springer, Berlin, DE, vol. 55, No. 11, Feb. 17, 2006 (Feb. 17, 2006). pp. 1337-1347.
Hertzog et al: 11 Oncofetal expression of the human intestinal mucin glycoprotein antigens in gastrointestinal epithelium defined by monoclonal antibodies. 11, International Journal of Cancer May 30, 1991. vol. 48, No. 3, May 30, 1991 (May 30, 1991), pp. 355-363.
US National Library of Medicine (NLM), Bethesda, MD, US; Nov. 2011 (Nov. 2011).Zhou Ying et al: 11 [Preparation and character-ization of three novel monoclonal antibodies against human PD-LI]. 11, XP002770553, Database accession No. NLM22078450, abstract & Zhou Ying et al: 11 [Preparation and characterization of three novel monoclonal antibodies against human PD-LI]. 11, Xi Bao Yu Fen Zi Mian Yi Xue Za Zhi=Chinese Journal of Cellular and Molecular Immunology Nov. 2011, vol. 27, No. 11, Nov. 2011 pp. 1208-1211.
Maria-Luisa Del Rio, et al: "Antibody-mediated signaling through PD-1 costimulates T cells and enhances CD28-dependent prolifera-tion", European Journal of Immunology, vol. 35, No. 12, Dec. 1, 2005, pp. 3545-3560.
K. M. Mahoney et al: "PD-LI Antibodies to Its Cytoplasmic Domain Most Clearly Delineate Cell Membranes in Immunohistochemical Staining of Tumor Cells", Cancer Immunology Research, vol. 3 , No. 12, Dec. 1, 2015 (Dec. 1, 2015), pp. 1308-1315.
J W Kim et al: "Prospects for Targeting PD-1 and PD-LI in Various Tumor Types", Oncology (Norwalk), vol. 28, No. Suppl. 3, Nov. 10, 2014 (Nov. 10, 2014), pp. 15-28.
Chia-Wei Li et al: "Glycosylation and stabilization of prograrnned death ligand-1 suppresses T-cell activity", Nature Communications, vol. 7, Aug. 30, 2016 (Aug. 30, 2016), p. 12632.
Gang Hao et al., "Epitope characterization of an anti-PD-L 1 antibody using orthogonal approaches", J. Mal. Recagnit. 2015; 28: pp. 269-276.
Supplementary European Search Report issued for EP Patent Appli-cation No. EP 16871487 dated Apr. 18, 2019, 12 pages.
Yan G. Ni et al., "Development and Fit-for-Purpose Validation of a Soluble Human Programmed Death-1 Protein Assay", The AAPS Journal, vol. 17, No. 4, May 1, 2015 (May 1, 2015), pp. 976-987.
Eszter Lazar-Molnar "Crystal structure of the complex between programmed death-1 (PD-1) and its ligand PD-L2", Proceedings of the National Academy of Sciences of the United States of America, vol. 105, No. 30, Jul. 18, 2008 (Jul. 18, 2008), pp. 10483-10488.
Brown et al. Tolerance of single, but not multiple, amino acid replacements in antibody VH CDR 2: a means of minimizing B cell wastage from somatic hypermutation? J Immunol. May 1, 1996; 156(9):3285-91. (Year: 1996).
Morales-Betanzos et al. Quantitative Mass Spectrometry Analysis of PD-L 1 Protein Expression, N-glycosylation and Expression Stoichiometry with PD-1 and PD-L2 in Human Melanoma. Molecu-lar & Cellular Proteomics 16: 10.107 4/mcp. RA 117.000037, 1705-1717, 2017. (Year: 2017).

* cited by examiner

FIGS. 2A-2G
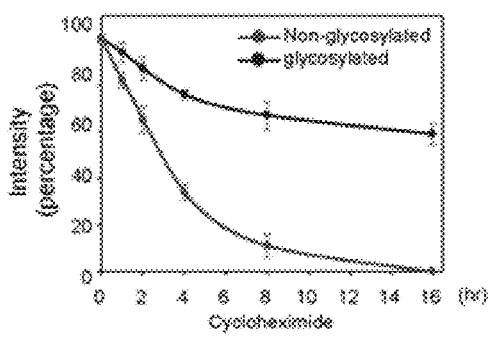
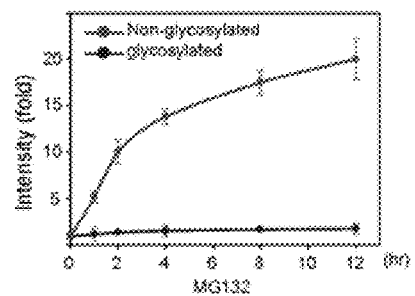
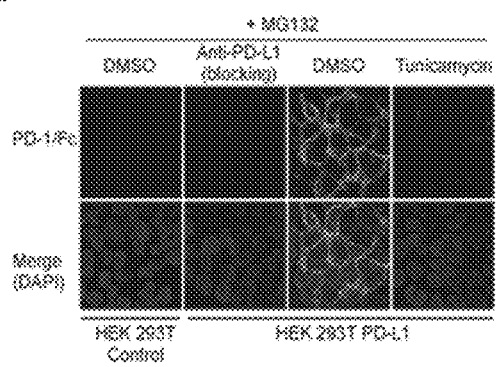
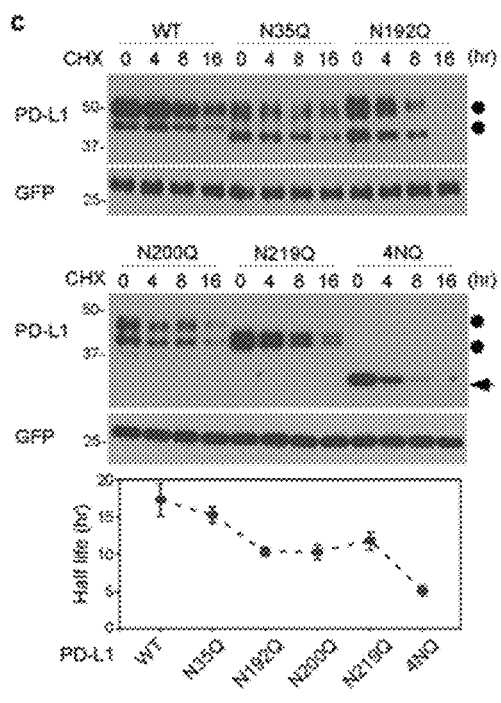
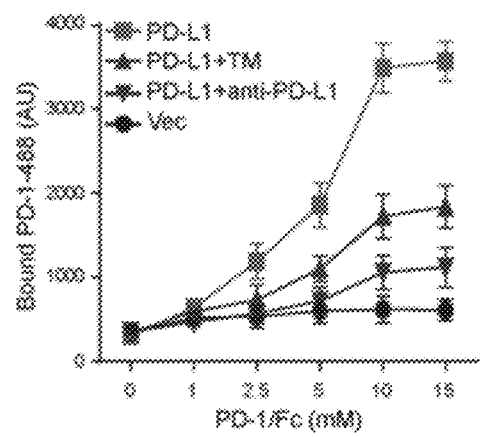

a b c d

FIGS. 5A-5E
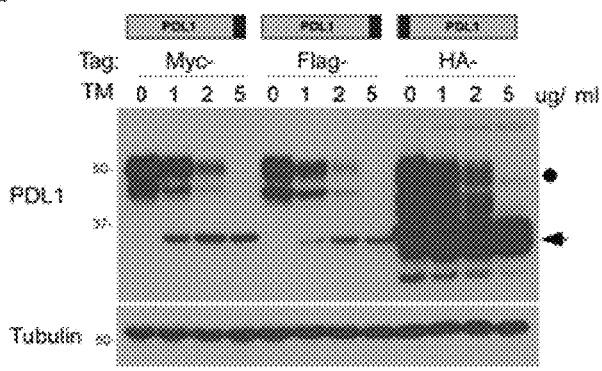
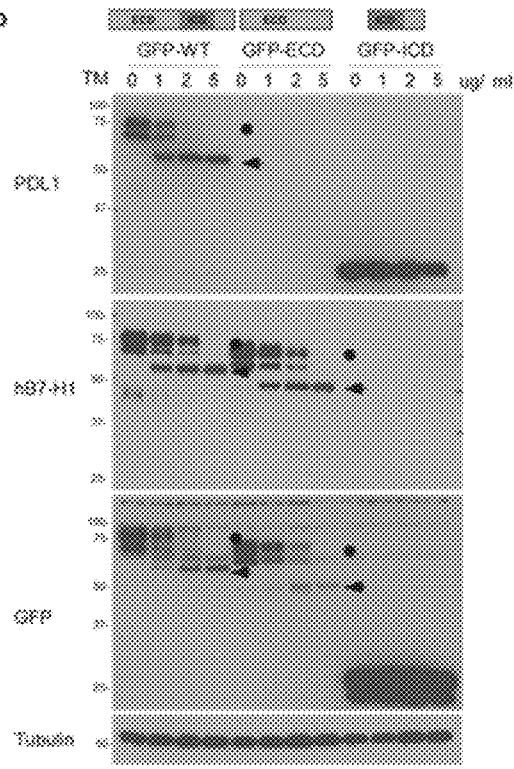
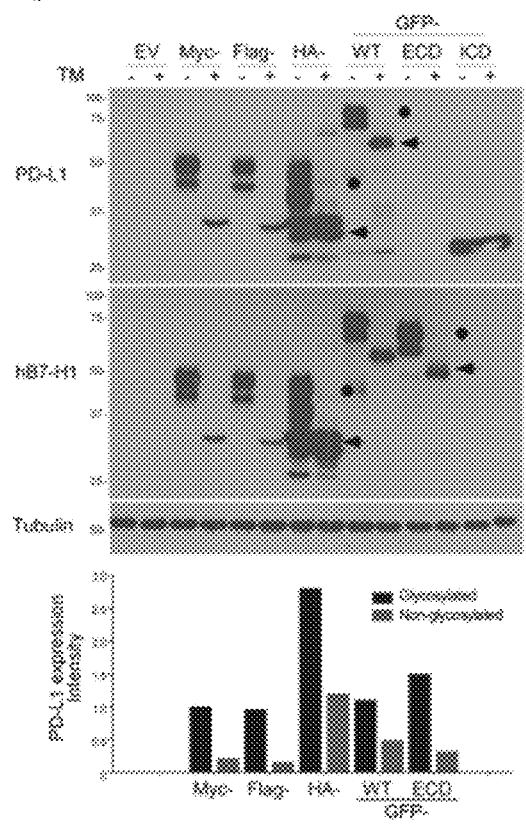

FIGS. 6A and 6B
A
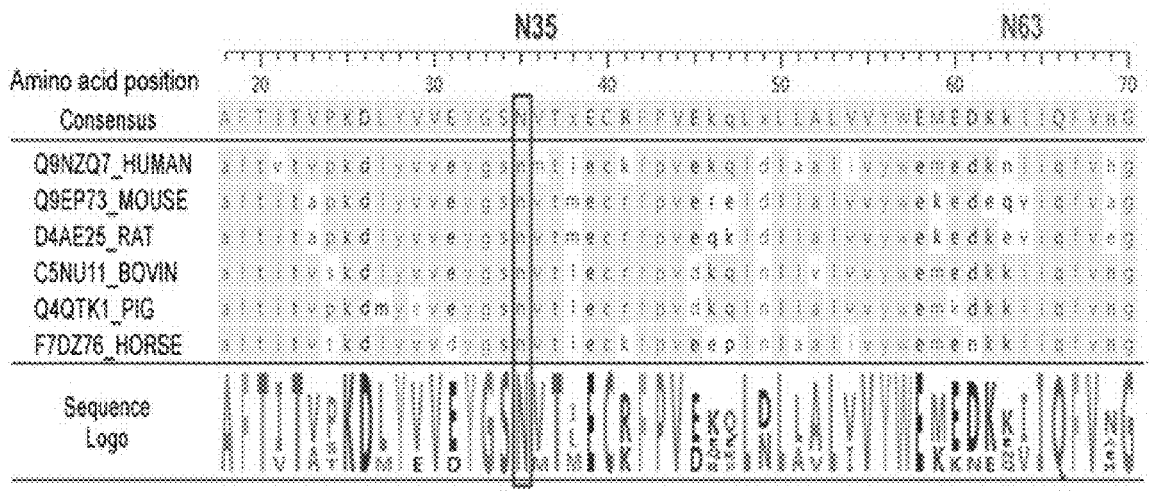
B
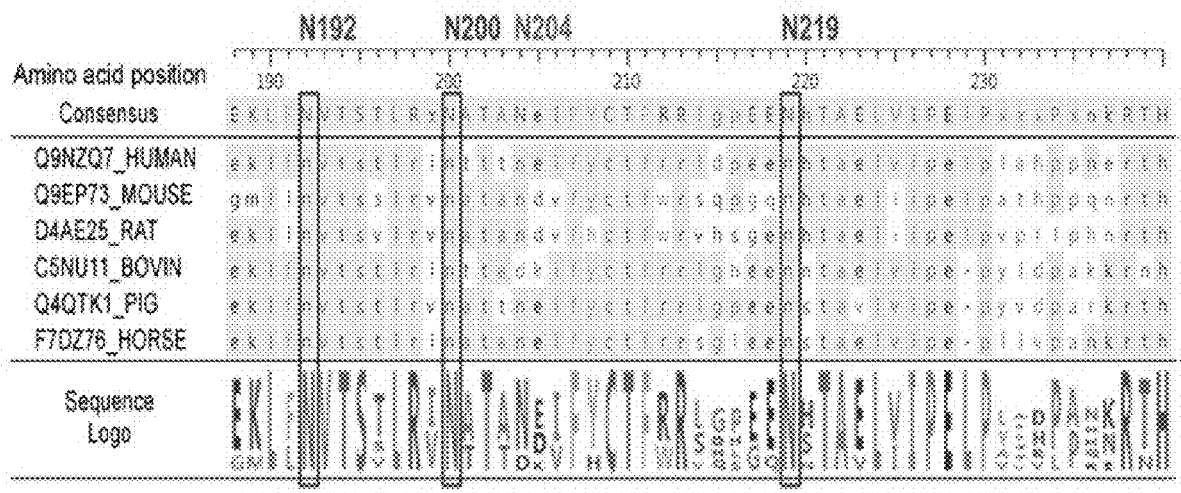
FIG. 6A:
Consensus (SEQ ID NO: 74)
Q9NZQ7_HUMAN (SEQ ID NO: 75)
Q9EP73_MOUSE (SEQ ID NO: 76)
D4AE25_RAT (SEQ ID NO: 77)
C5NU11_BOVIN (SEQ ID NO: 78)
Q4QTK1_PIG (SEQ ID NO: 79)
F7DZ76_HORSE (SEQ ID NO: 80)
FIG. 6B:
Consensus (SEQ ID NO: 94)
Q9NZQ7_HUMAN (SEQ ID NO: 95)
Q9EP73_MOUSE (SEQ ID NO: 96)
D4AE25_RAT (SEQ ID NO: 97)
C5NU11_BOVIN (SEQ ID NO: 98)
Q4QTK1_PIG (SEQ ID NO: 99)
F7DZ76_HORSE (SEQ ID NO: 100)

FIGS. 7A-7H (Con't)
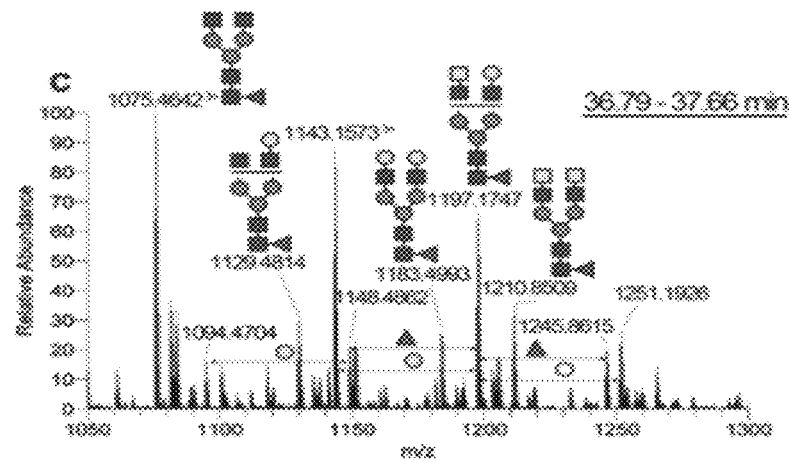
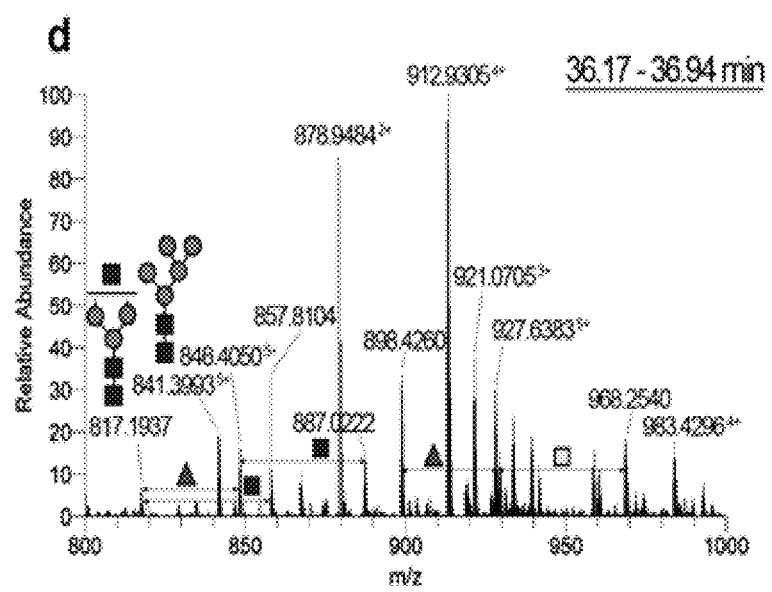

FIGS. 7A-7H (Cont'd)
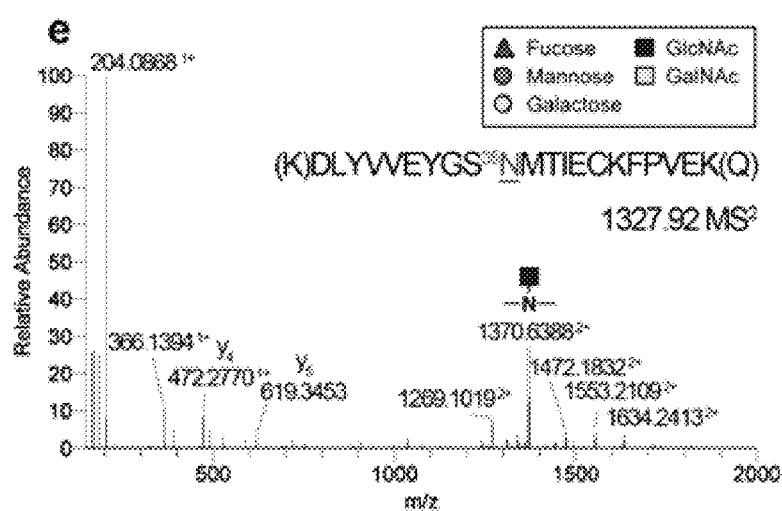
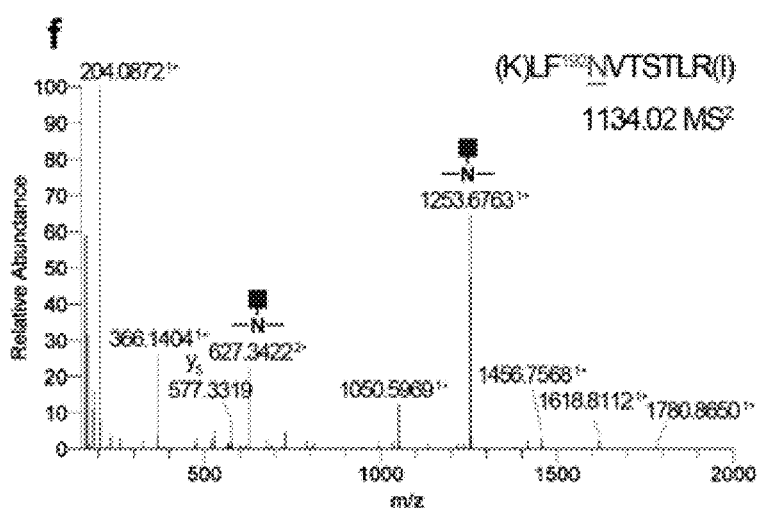

FIGS. 9A-9F (Cont'd)
d
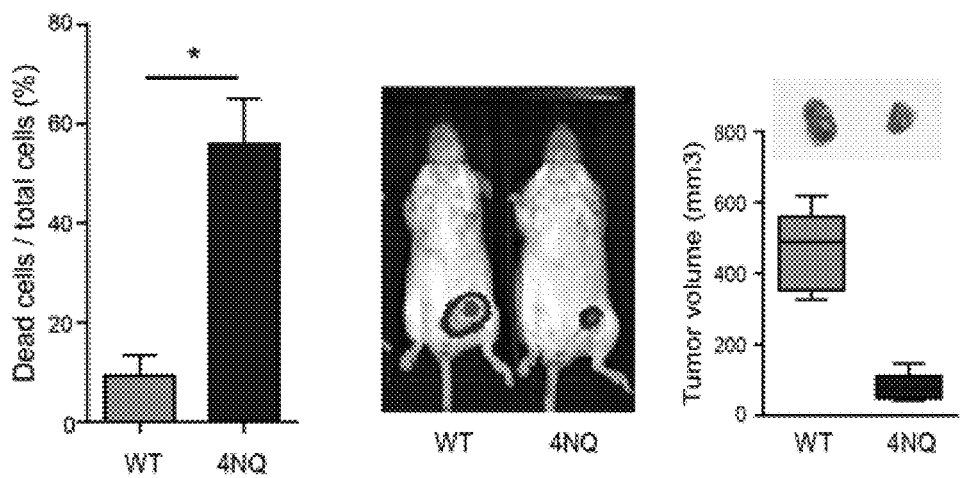
e
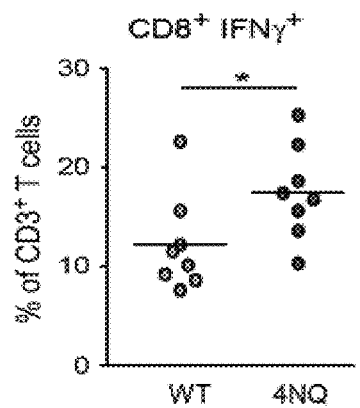
f
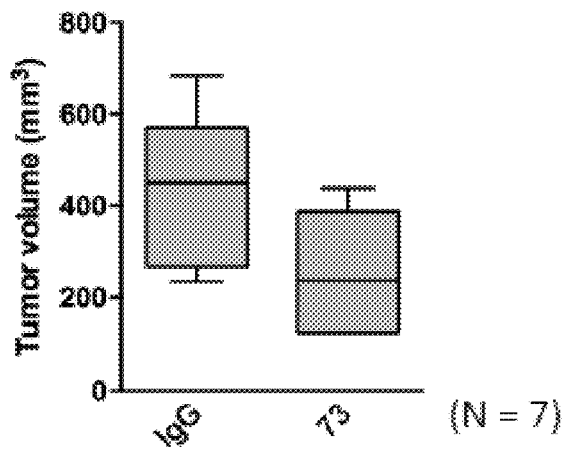

A

B

C

FIGS. 12A-12C
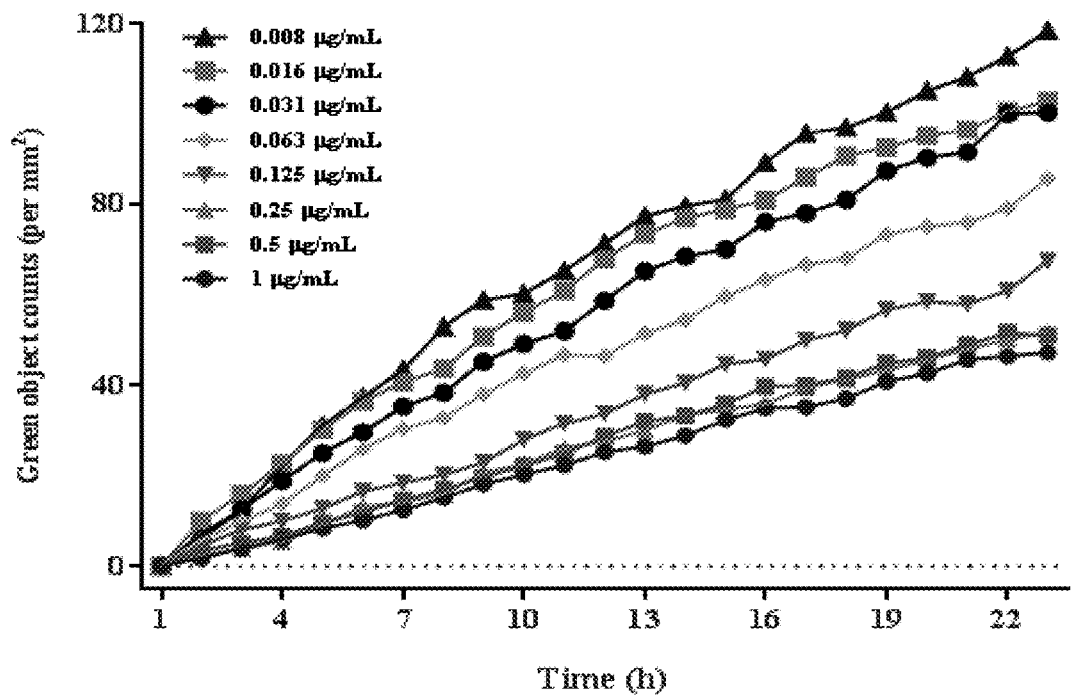
A
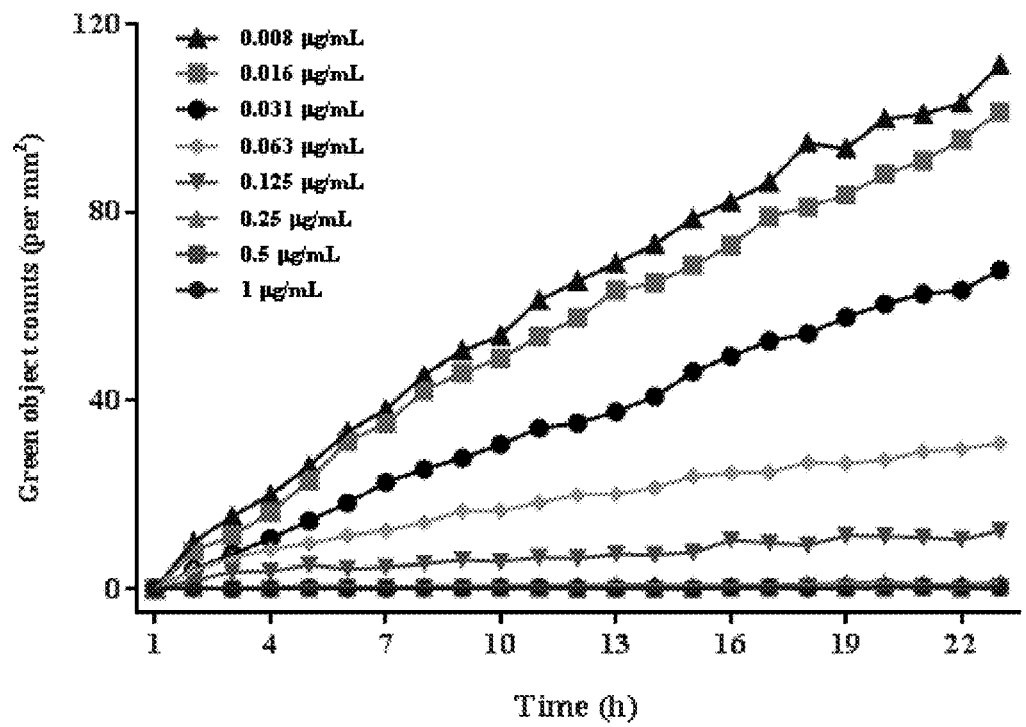
B

FIGS. 14A-14E
A
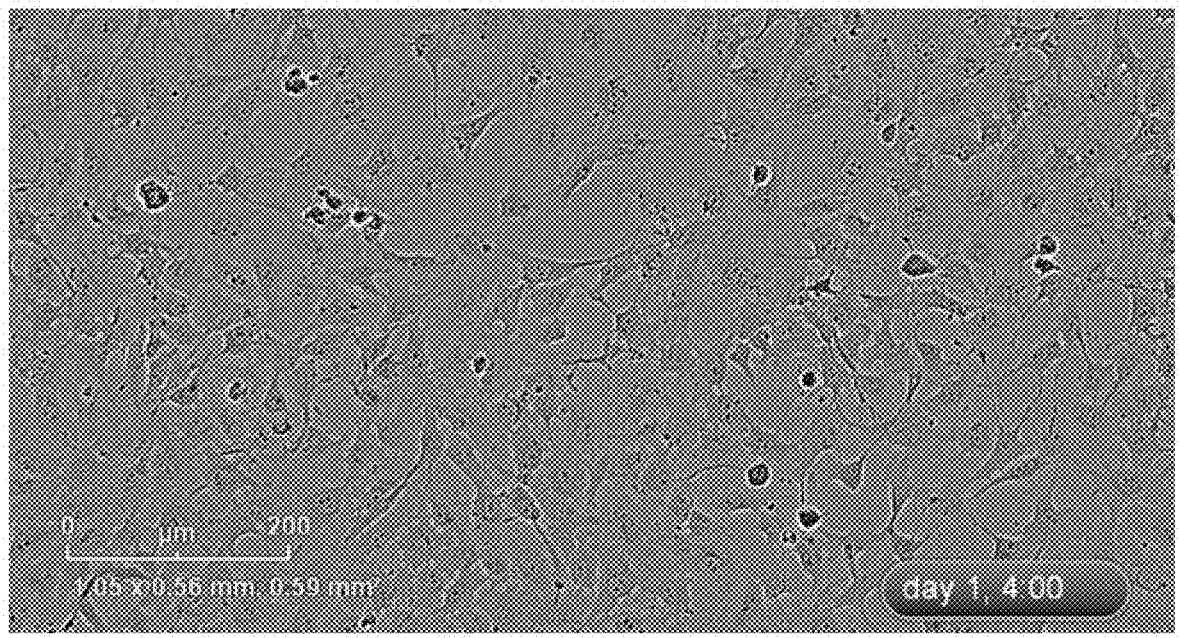
BT549
B
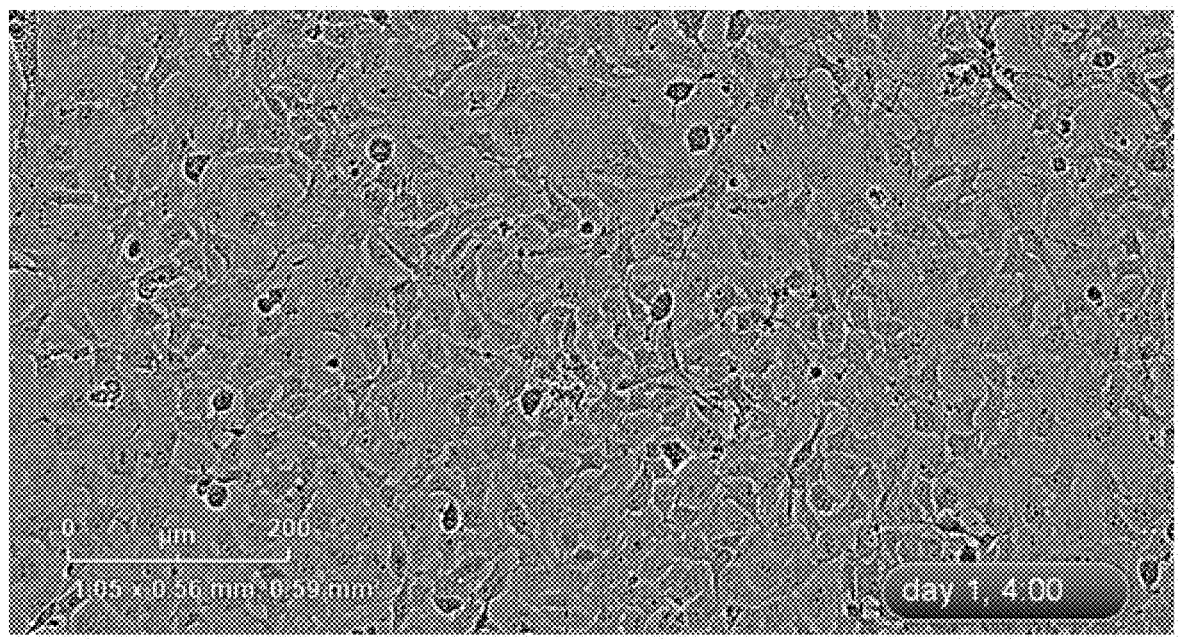
BT549 PD-L1

FIGS. 14A-14E (Cont'd)
C
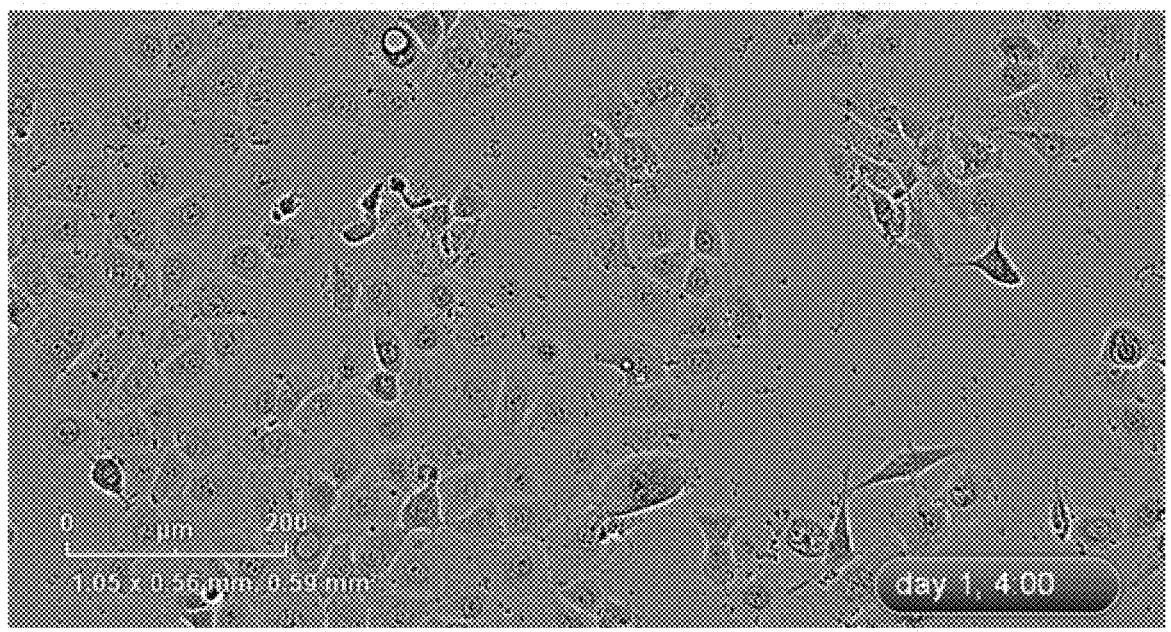
NCI-H226
D
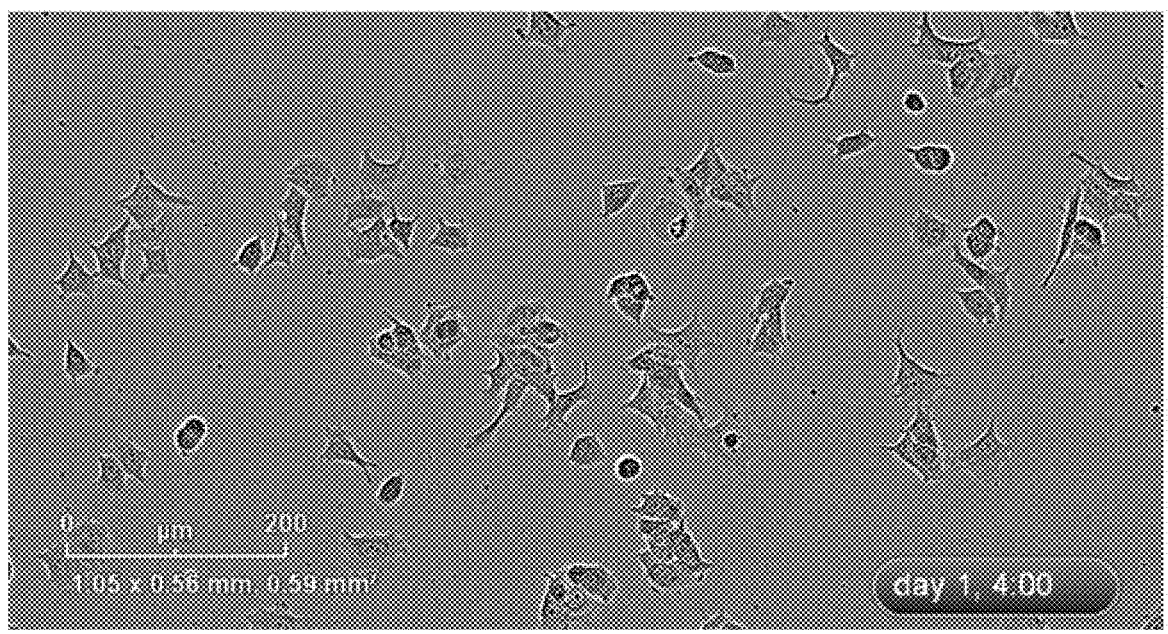
MCF-7

E

Time 0

2 minutes 4 minutes

FIGS. 16A-16L
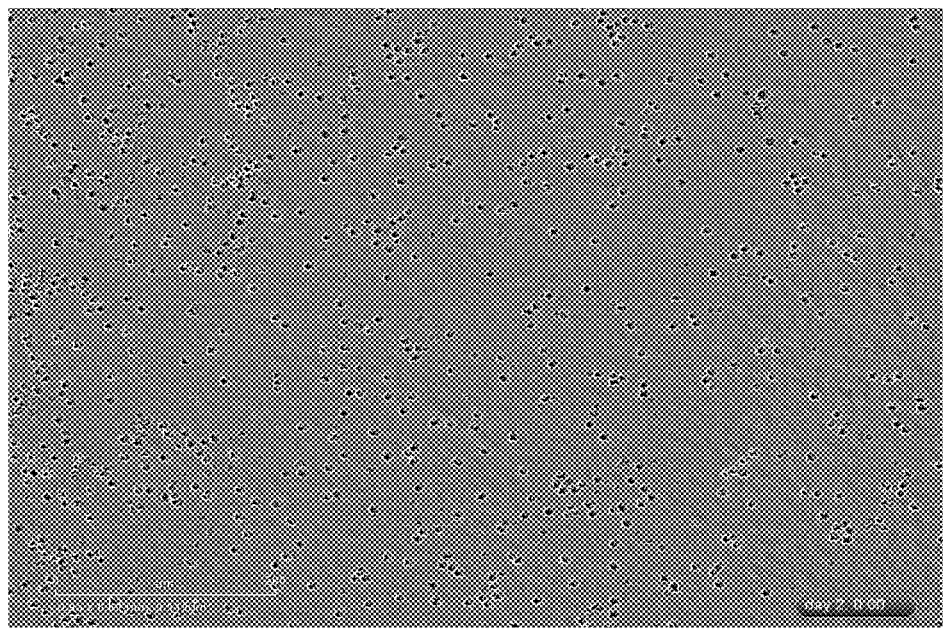
mIgG Control
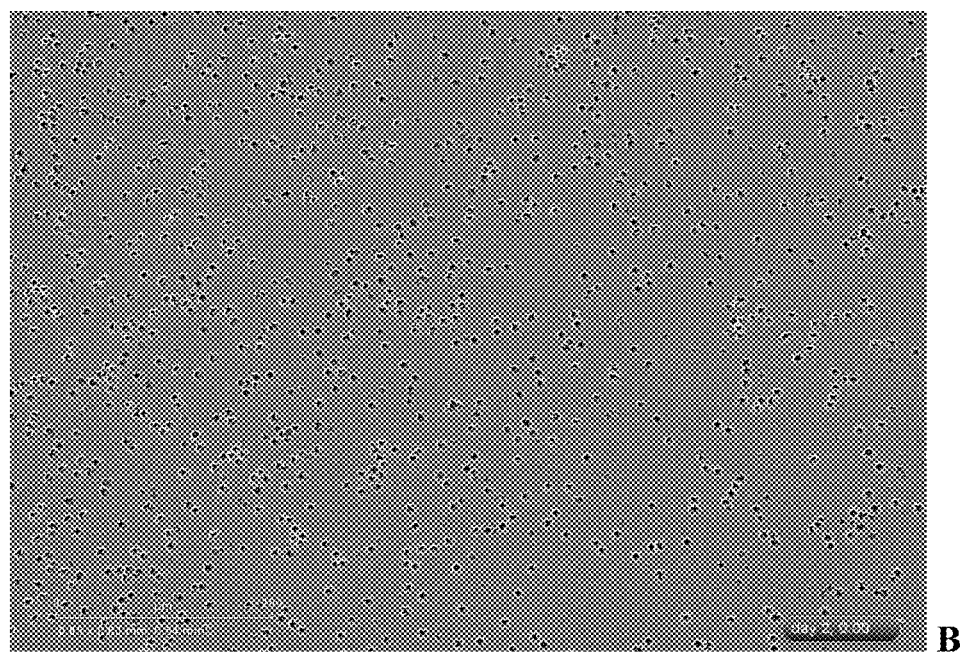
STM004 Antibody

FIGS. 16A-16L (Cont'd)
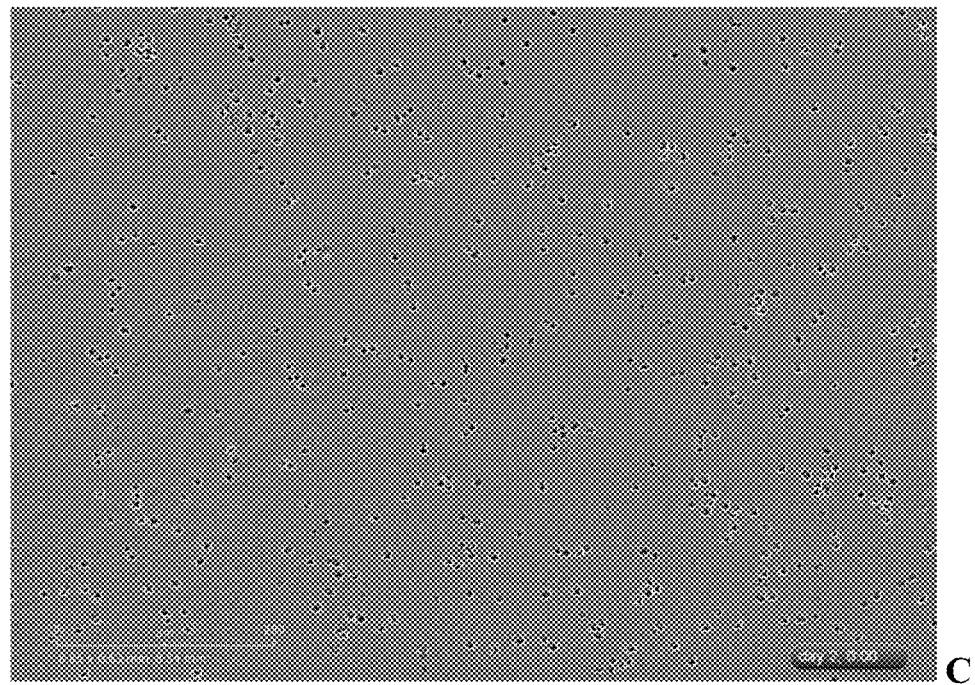
STM073 Antibody
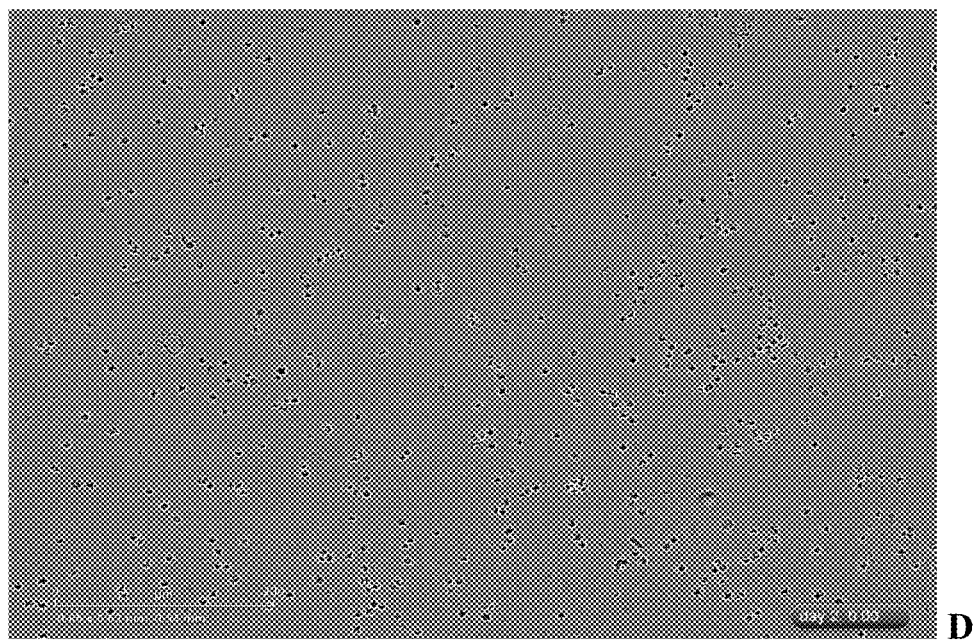
STM108 Antibody

FIGS. 16A-16L (Cont'd)
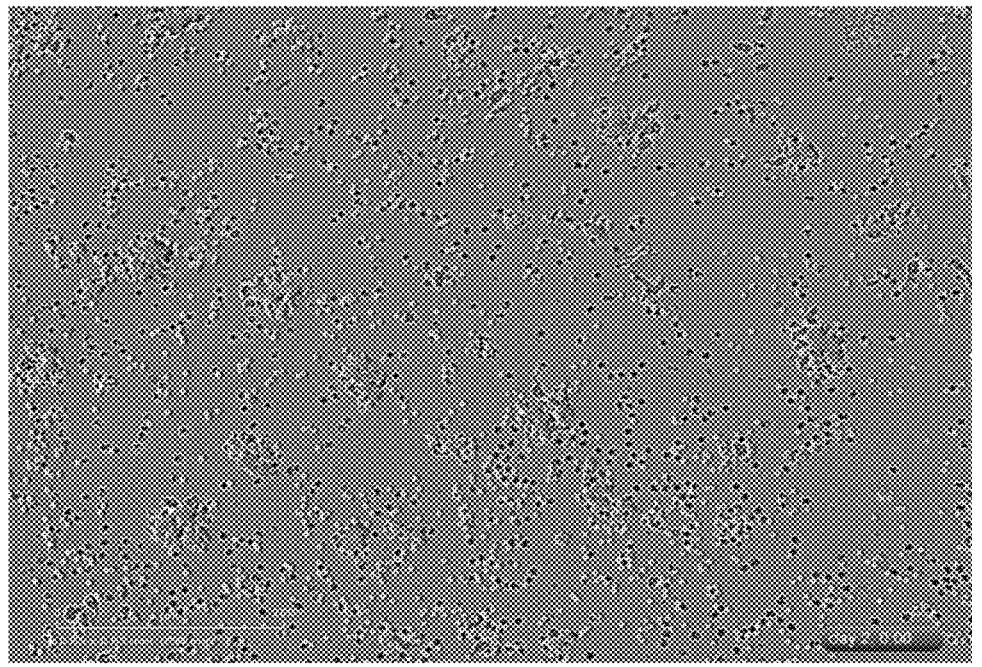
mIgG Control
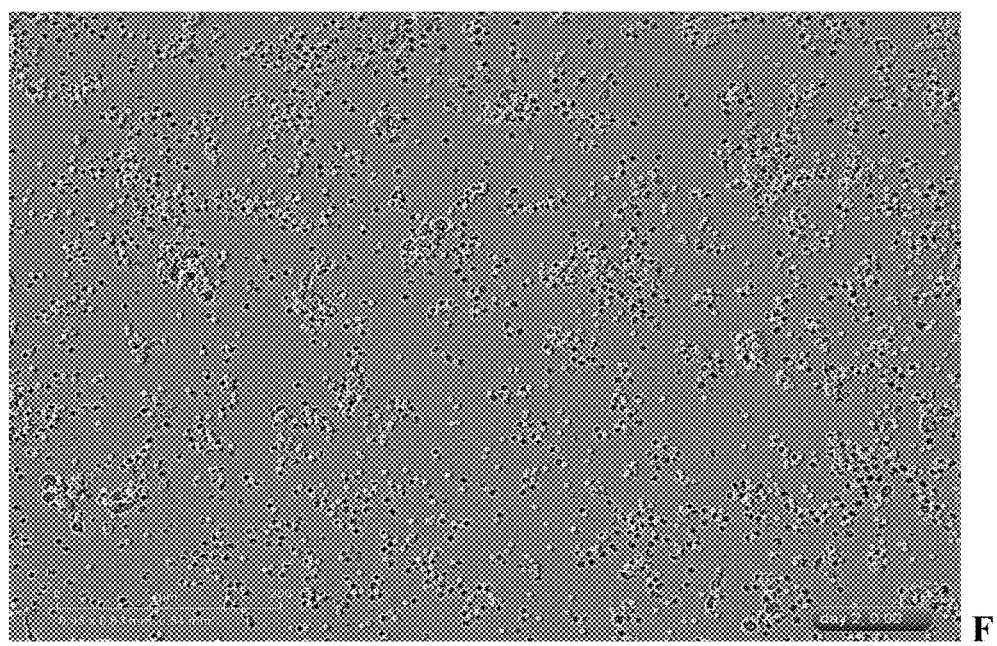
STM004 Antibody

FIGS. 16A-16L (Cont'd)
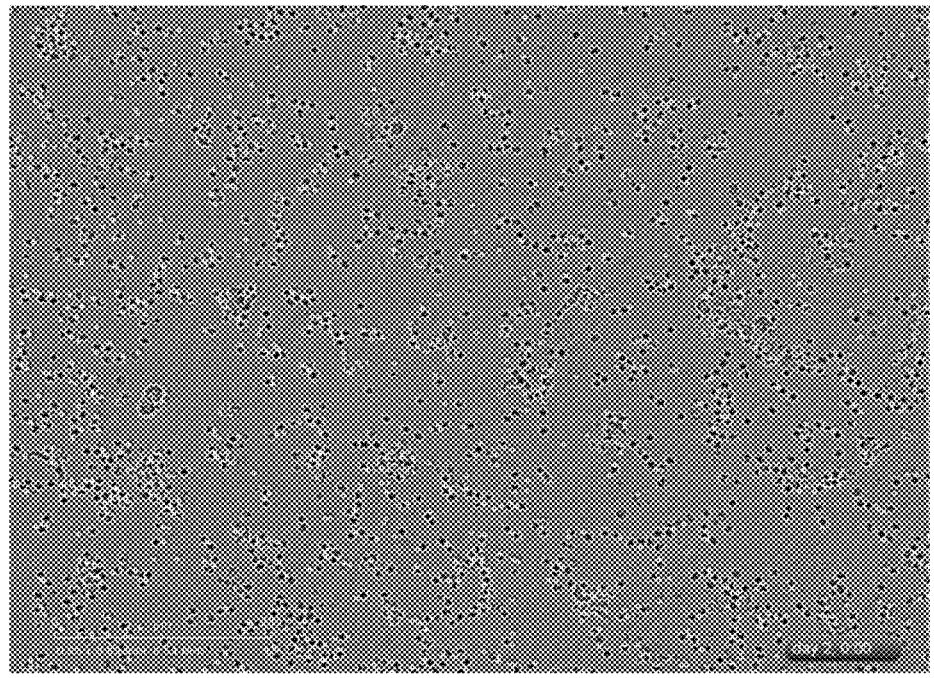
STM073 Antibody
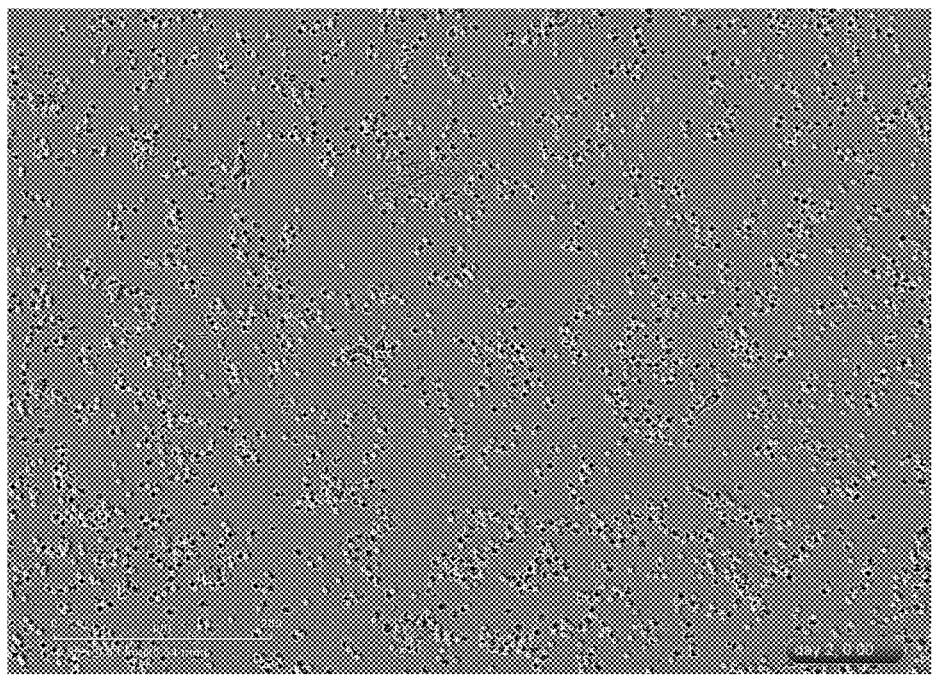
STM108 Antibody

FIGS. 16A-16L (Cont'd)
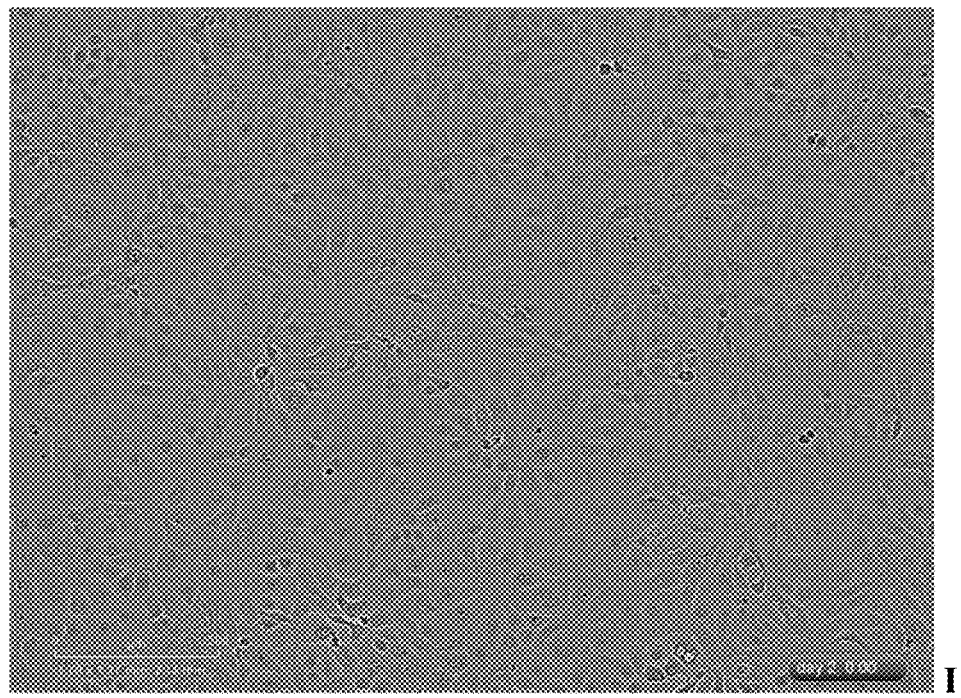
mIgG Control
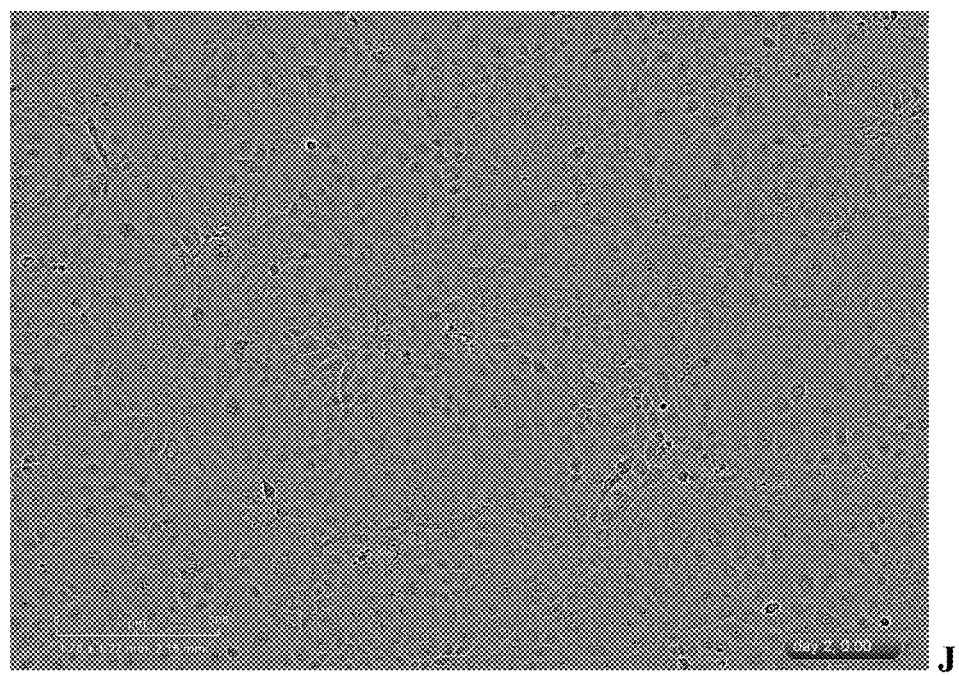
STM004 Antibody

FIGS. 16A-16L (Cont'd)
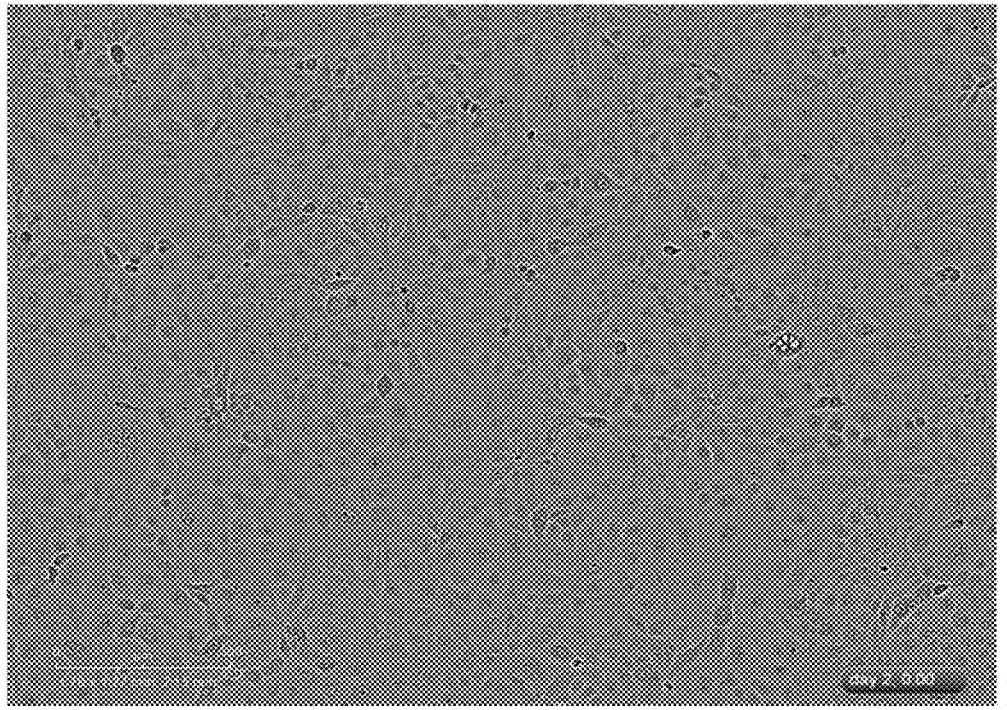
STM073 Antibody
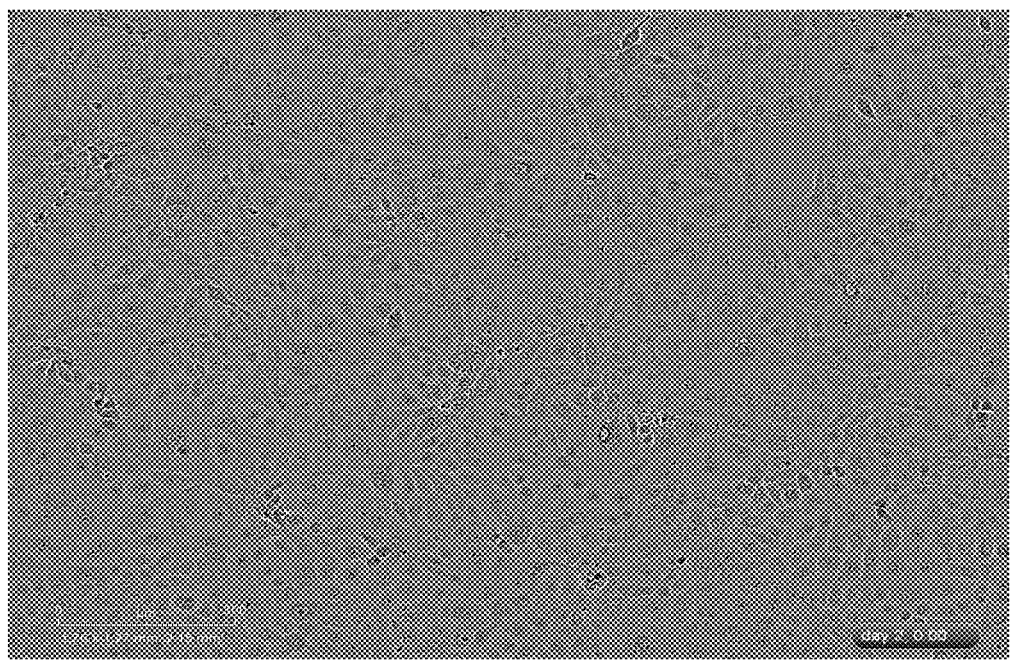
STM108 Antibody

SEQUENCE LISTING

```
<160> NUMBER OF SEQ ID NOS: 100

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 350
<212> TYPE: DNA
```

-continued

<213> ORGANISM: Artificial Sequence
<220> FEATURE:
<223> OTHER INFORMATION: Description of Artificial Sequence: Synthetic
      polynucleotide

<400> SEQUENCE: 2
aagtgcagct ggtggagtct gggggagcct tagtgaagcc tggagggtcc ctgaaactct     60
cctgtgcagc ctctggattc actttcagta actctgccat gtcttgggtt cgccagactc    120
cagagaagag gctggagtgg gtcgcaacca ttagtagtgc tggtagttat acctactatc    180
cagacagtgt gaagggtcga ttcaccatct ccagagacaa tgccaagaac accctgtacc    240
tgcaaatgag cagtctgagg tctgaggaca cggccttgta ttactgtaca agacattatg    300
attactactt tgactactgg ggccaaggcg ccactctcac agtctcctca              350

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Ser
            20                  25                  30

Ala Met Ser Trp Val Arg Gln Thr Pro Glu Lys Arg Leu Glu Trp Val
        35                  40                  45

Ala Thr Ile Ser Ser Ala Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Thr Arg His Tyr Asp Tyr Tyr Phe Asp Tyr Trp Gly Gln Gly Ala Thr
            100                 105                 110

Leu Thr Val Ser Ser
        115

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Asn Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

-continued

Asn Ser Ala Met Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Ala Gly Ser Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ile Ser Ser Ala Gly Ser Tyr Thr Tyr Tyr Pro Asp Ser Val Lys
1               5                   10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Arg His Tyr Asp Tyr Tyr Phe Asp Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Arg His Tyr Asp Tyr Tyr Phe Asp Tyr
1               5                   10

<210> SEQ ID NO 10
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caaattgttc tcacccagtc tccagcaatc atgtctgcat ctccagggga gaaggtcacc      60
ttgacctgca gtgccagctc aagtgtaagt tacatgcatt ggtaccagca gaagccagga    120
tcctccccca gactcgtgat ttatgacaca tccaacctgg cttctggagt ccctgttcgc    180
ttcagtggca gtgggtctgg gacctcttac tctctcacag tcagccgaat ggaggctgaa    240

```
gatgctgcca cttattactg ccagcagtgg agtgatcacc cgctcacgtt cggtgctggg      300
accaagctgg agctgaaac                                                   319
```

<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 11

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Tyr Met
            20                  25                  30

His Trp Tyr Gln Gln Lys Pro Gly Ser Ser Pro Arg Leu Val Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Trp Ser Asp His Pro Leu Thr
                85                  90                  95

Phe Gly Ala Gly Thr Lys Leu Glu Leu Lys
            100                 105

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 12

Ser Ala Ser Ser Ser Val Ser Tyr Met His
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 13

Ser Ala Ser Ser Ser Val Ser Tyr Met His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 14

Asp Thr Ser Asn Leu Ala Ser
1               5

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Thr Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Trp Ser Asp His Pro Leu Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Trp Ser Asp His Pro Leu Thr
1               5

<210> SEQ ID NO 18
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaagtgatgc tggtggagtc tgggggagcc ttagtgaagc ctggagggtc cctgaaactc      60
tcctgtgcag cttctggatt cagtttgagt aactatgtca tgtcttgggt tcgccagact     120
ccagagaaga ggctggagtg ggtcgcaacc attagtagtg gtggtaggta tatctactat     180
acagacagtg tgaagggtcg attcaccatc tccagggaca atgccaggaa caccctgtac     240
ctgcaaatga gcagtctgag gtctgaggac acggccatgt attattgtgc aagagacggt     300
agtaccttgt actactttga ctattggggc caaggcacca ctctcacagt ctcctca       357

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Met Leu Val Glu Ser Gly Gly Ala Leu Val Lys Pro Gly Gly
1               5                   10                  15
```

```
Ser Leu Lys Leu Ser Cys Ala Ala Ser Gly Phe Ser Leu Ser Asn Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Arg Tyr Ile Tyr Tyr Thr Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Asp Gly Ser Thr Leu Tyr Tyr Phe Asp Tyr Trp Gly Gln Gly
            100                 105                 110

Thr Thr Leu Thr Val Ser Ser
        115

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Phe Ser Leu Ser Asn Tyr
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Tyr Val Met Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ser Gly Gly Arg Tyr
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Ile Ser Ser Gly Gly Arg Tyr Ile Tyr Tyr Thr Asp Ser Val Lys
1               5                   10                  15

Gly
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Asp Gly Ser Thr Leu Tyr Tyr Phe Asp Tyr
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Asp Gly Ser Thr Leu Tyr Tyr Phe Asp Tyr
1               5                   10
```

<210> SEQ ID NO 26
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
caagtgcaga ttttcagctt cctgctaatc agtgcctcag tcatactgtc cagaggacaa      60
actgttctca cccagtctcc agcaatcatg tctgcatctc caggggagaa ggtcaccatg     120
acctgcagtg ccagctcaag tgtagattac atgtactggt accagcagaa gccaggatcc     180
tcccccagac tcctgattta tgacacatcc aacctggctt ctggagtccc tgttcgcttc     240
agtggcagtg ggtctgggac ctcttactct ctcacaatca gccgaatgga ggctgaagat     300
gctgccactt attactgcca gcagtggagt agttccccac ccatcacgtt cggtactggg     360
accaaggtgg agctgaaa                                                   378
```

<210> SEQ ID NO 27
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Gln Ile Phe Ser Phe Leu Leu Ile Ser Ala Ser Val Ile Leu
1               5                   10                  15

Ser Arg Gly Gln Thr Val Leu Thr Gln Ser Pro Ala Ile Met Ser Ala
            20                  25                  30

Ser Pro Gly Glu Lys Val Thr Met Thr Cys Ser Ala Ser Ser Ser Val
        35                  40                  45

Asp Tyr Met Tyr Trp Tyr Gln Gln Lys Pro Gly Ser Ser Pro Arg Leu
    50                  55                  60

Leu Ile Tyr Asp Thr Ser Asn Leu Ala Ser Gly Val Pro Val Arg Phe
65                  70                  75                  80
```

Ser Gly Ser Gly Ser Gly Thr Ser Tyr Ser Leu Thr Ile Ser Arg Met
                85                  90                  95

Glu Ala Glu Asp Ala Ala Thr Tyr Tyr Cys Gln Gln Trp Ser Ser Ser
            100                 105                 110

Pro Pro Ile Thr Phe Gly Thr Gly Thr Lys Val Glu Leu Lys
        115                 120                 125

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ala Ser Ser Ser Val Asp Tyr Met Tyr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Ser Ser Ser Val Asp Tyr Met Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Thr Ser Asn Leu Ala Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Thr Ser Asn Leu Ala Ser
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Trp Ser Ser Ser Pro Pro Ile Thr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Trp Ser Ser Ser Pro Pro Ile Thr
1               5                   10

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcaattgtca tattgctac                                                  19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttgactccat ctttcttca                                                  19

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtggtagagt atggtagcca aatgacaatt gaatgcaaa                            39

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttgcattca attgtcattt ggctaccata ctctaccac                            39

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagaggagaa gcttttccag gtgaccagca cactgag                              37

<210> SEQ ID NO 39
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctcagtgtgc tggtcacctg gaaaagcttc tcctctc                              37

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaccagcaca ctgagaatcc agacaacaac taatgagat                            39

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atctcattag ttgttgtctg gattctcagt gtgctggtc                            39

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagagaggag aagcttttcc aagtgaccag cacactgaga                           40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctcagtgtg ctggtcactt ggaaaagctt ctcctctctc                           40

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcataacgaa cctaaccctc ag                                              22

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gcccaatgtc cactgtgata                                               20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gtaacctcag tcacctgcc                                                19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
attccgctcc acaatctctg                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tcttcaacct cacgctcaag                                               20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gtgtgcaaag acgtcatcat c                                             21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
caccatcacc ctcctttcta ttc                                           23

<210> SEQ ID NO 51

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaacaacagg tctgggattt ct                                              22

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52 gcctttttgcc atcgacatg                                                 19

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agtcagattc ttgcatccct g                                               21

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caaggagagc attaggacca ag                                              22

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccccattaaa cctcaggact g                                               21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcgtcatggt gtggtattcc                                                 20

<210> SEQ ID NO 57
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caggaagatg ggctgatcc                                                      19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaccgcactc atcttacacc                                                     20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggaggttggc tgaaggaata c                                                   21

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcccctgctt taaccatcg                                                      19

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttgtcaccta tactggcgtt g                                                   21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctgagtgatg gaacgagtga g                                                   21

<210> SEQ ID NO 63
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 63
tagagatgac cagatgcaac g                                          21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gagtccaact tcacggctta t                                          21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agtggtccag gaagacatag a                                          21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tgtgagggaa agatcaagtg g                                          21

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gctctccaag gtaaatgagg ac                                         22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccactgagtt cgtcaagagg                                            20

<210> SEQ ID NO 69
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 69
acttccttgc catctgtcac                                                 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggctcgctg ataagttctg                                                 20

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtgagtctgg tttgggagaa g                                               21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcaaagacct gtacgccaac a                                               21

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgcatcctgt cggcaatg                                                   18

<210> SEQ ID NO 74
<211> LENGTH: 53
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (21)..(21)
<223> OTHER INFORMATION: Ile, Met or Leu
<220> FEATURE:
<221> NAME/KEY: MOD_RES
<222> LOCATION: (32)..(32)
<223> OTHER INFORMATION: Asp or Asn

<400> SEQUENCE: 74
```

Ala Phe Thr Ile Thr Val Pro Lys Asp Leu Tyr Val Val Glu Tyr Gly
1               5                   10                  15

Ser Asn Val Thr Xaa Glu Cys Arg Phe Pro Val Glu Lys Gln Leu Xaa
            20                  25                  30

Leu Leu Ala Leu Val Val Tyr Trp Glu Met Glu Asp Lys Lys Ile Ile
        35                  40                  45

Gln Phe Val Asn Gly
    50

<210> SEQ ID NO 75
<211> LENGTH: 53
<212> TYPE: PRT
<213> ORGANISM: Homo sapiens

<400> SEQUENCE: 75

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly
    50

<210> SEQ ID NO 76
<211> LENGTH: 53
<212> TYPE: PRT
<213> ORGANISM: Mus musculus

<400> SEQUENCE: 76

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Arg Glu Leu Asp
            20                  25                  30

Leu Leu Ala Leu Val Val Tyr Trp Glu Lys Glu Asp Glu Gln Val Ile
        35                  40                  45

Gln Phe Val Ala Gly
    50

<210> SEQ ID NO 77
<211> LENGTH: 53
<212> TYPE: PRT
<213> ORGANISM: Rattus norvegicus

<400> SEQUENCE: 77

Ala Phe Thr Ile Thr Ala Pro Lys Asp Leu Tyr Val Val Glu Tyr Gly
1               5                   10                  15

Ser Asn Val Thr Met Glu Cys Arg Phe Pro Val Glu Gln Lys Leu Asp
            20                  25                  30

Leu Leu Ala Leu Val Val Tyr Trp Glu Lys Glu Asp Lys Glu Val Ile
        35                  40                  45

Gln Phe Val Glu Gly
    50

<210> SEQ ID NO 78
<211> LENGTH: 53
<212> TYPE: PRT
<213> ORGANISM: Bos taurus

<400> SEQUENCE: 78

```
Ala Phe Thr Ile Thr Val Ser Lys Asp Leu Tyr Val Glu Tyr Gly
1               5                   10                  15

Ser Asn Val Thr Leu Glu Cys Arg Phe Pro Val Asp Lys Gln Leu Asn
            20                  25                  30

Leu Leu Val Leu Val Tyr Trp Glu Met Glu Asp Lys Lys Ile Ile
        35                  40                  45

Gln Phe Val Asn Gly
    50
```

<210> SEQ ID NO 79
<211> LENGTH: 53
<212> TYPE: PRT
<213> ORGANISM: Sus scrofa

<400> SEQUENCE: 79

```
Ala Phe Thr Ile Thr Val Pro Lys Asp Met Tyr Glu Val Glu Tyr Gly
1               5                   10                  15

Ser Asn Val Thr Leu Glu Cys Arg Phe Pro Val Asp Lys Gln Leu Asn
            20                  25                  30

Leu Leu Ala Leu Val Tyr Trp Glu Met Lys Asp Lys Lys Ile Ile
        35                  40                  45

Gln Phe Val Asn Gly
    50
```

<210> SEQ ID NO 80
<211> LENGTH: 53
<212> TYPE: PRT
<213> ORGANISM: Equus caballus

<400> SEQUENCE: 80

```
Ala Phe Thr Ile Thr Val Thr Lys Asp Leu Tyr Val Val Asp Tyr Gly
1               5                   10                  15

Ser Asn Val Thr Ile Glu Cys Lys Phe Pro Val Glu Glu Pro Leu Asn
            20                  25                  30

Leu Ala Ala Leu Ile Val Tyr Trp Glu Met Glu Asn Lys Lys Ile Ile
        35                  40                  45

Gln Phe Val Asn Gly
    50
```

<210> SEQ ID NO 81
<211> LENGTH: 23
<212> TYPE: PRT
<213> ORGANISM: Homo sapiens

<400> SEQUENCE: 81

```
Lys Asp Leu Tyr Val Val Glu Tyr Gly Ser Asn Met Thr Ile Glu Cys
1               5                   10                  15

Lys Phe Pro Val Glu Lys Gln
            20
```

<210> SEQ ID NO 82
<211> LENGTH: 11
<212> TYPE: PRT
<213> ORGANISM: Homo sapiens

<400> SEQUENCE: 82

```
Lys Leu Phe Asn Val Thr Ser Thr Leu Arg Ile
1               5                   10
```

-continued

<210> SEQ ID NO 83
<211> LENGTH: 16
<212> TYPE: PRT
<213> ORGANISM: Homo sapiens

<400> SEQUENCE: 83

Arg Ile Asn Thr Thr Thr Asn Glu Ile Phe Tyr Cys Thr Phe Arg Arg
1               5                   10                  15

<210> SEQ ID NO 84
<211> LENGTH: 28
<212> TYPE: PRT
<213> ORGANISM: Homo sapiens

<400> SEQUENCE: 84

Arg Arg Leu Asp Pro Glu Glu Asn His Thr Ala Glu Leu Val Ile Pro
1               5                   10                  15

Glu Leu Pro Leu Ala His Pro Pro Asn Glu Arg Thr
            20                  25

<210> SEQ ID NO 85
<211> LENGTH: 61
<212> TYPE: PRT
<213> ORGANISM: Homo sapiens

<400> SEQUENCE: 85

Val His Gly Glu Glu Asp Leu Lys Val Gln His Ser Ser Tyr Arg Gln
1               5                   10                  15

Arg Ala Arg Leu Leu Lys Asp Gln Leu Ser Leu Gly Asn Ala Ala Leu
            20                  25                  30

Gln Ile Thr Asp Val Lys Leu Gln Asp Ala Gly Val Tyr Arg Cys Met
        35                  40                  45

Ile Ser Tyr Gly Gly Ala Asp Tyr Lys Arg Ile Thr Val
    50                  55                  60

<210> SEQ ID NO 86
<211> LENGTH: 21
<212> TYPE: PRT
<213> ORGANISM: Homo sapiens

<400> SEQUENCE: 86

Asp Ala Gly Val Tyr Arg Cys Met Ile Ser Tyr Gly Gly Ala Asp Tyr
1               5                   10                  15

Lys Arg Ile Thr Val
            20

<210> SEQ ID NO 87
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atgaacttgt ggctcagctt ggttttcctt gtccttgttt taaaaggtgt ccagtgtgaa      60
gtgcagctgg tggagtctgg gggagcctta gtgaagcctg agggtccct gaaactctcc     120 tgtgcagcct ctggattcac tttcagtaac tctgccatgt cttgggttcg ccagactcca     180
gagaagaggc tggagtgggt cgcaaccatt agtagtgctg gtagttatac ctactatcca     240
gacagtgtga agggtcgatt caccatctcc agagacaatg ccaagaacac cctgtacctg     300
caaatgagca gtctgaggtc tgaggacacg gccttgtatt actgtacaag acattatgat       360
tactactttg actactgggg ccaaggcgcc actctcacag tctcctca                    408

<210> SEQ ID NO 88
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asn Leu Trp Leu Ser Leu Val Phe Leu Val Leu Val Leu Lys Gly
1               5                   10                  15

Val Gln Cys Glu Val Gln Leu Val Glu Ser Gly Gly Ala Leu Val Lys
            20                  25                  30

Pro Gly Gly Ser Leu Lys Leu Ser Cys Ala Ala Ser Gly Phe Thr Phe
        35                  40                  45

Ser Asn Ser Ala Met Ser Trp Val Arg Gln Thr Pro Glu Lys Arg Leu
    50                  55                  60

Glu Trp Val Ala Thr Ile Ser Ser Ala Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Arg Ser Glu Asp Thr Ala Leu
            100                 105                 110

Tyr Tyr Cys Thr Arg His Tyr Asp Tyr Tyr Phe Asp Tyr Trp Gly Gln
        115                 120                 125

Gly Ala Thr Leu Thr Val Ser Ser
    130                 135

<210> SEQ ID NO 89
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atggattttc aagtgcagat tttcagcttc ctgctaatca gtgcctcagt catactgtcc       60
agaggacaaa ttgttctcac ccagtctcca gcaatcatgt ctgcatctcc aggggagaag      120
gtcaccttga cctgcagtgc cagctcaagt gtaagttaca tgcattggta ccagcagaag      180
ccaggatcct cccccagact cgtgatttat gacacatcca acctggcttc tggagtccct      240
gttcgcttca gtggcagtgg gtctgggacc tcttactctc tcacagtcag ccgaatggag      300
gctgaagatg ctgccactta ttactgccag cagtggagtg atcacccgct cacgttcggt      360
gctgggacca agctggagct gaaac                                            385

<210> SEQ ID NO 90
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Asp Phe Gln Val Gln Ile Phe Ser Phe Leu Leu Ile Ser Ala Ser

```
  1               5                  10                  15
Val Ile Leu Ser Arg Gly Gln Ile Val Leu Thr Gln Ser Pro Ala Ile
           20                  25                  30
Met Ser Ala Ser Pro Gly Glu Lys Val Thr Leu Thr Cys Ser Ala Ser
           35                  40                  45
Ser Ser Val Ser Tyr Met His Trp Tyr Gln Gln Lys Pro Gly Ser Ser
       50                  55                  60
Pro Arg Leu Val Ile Tyr Asp Thr Ser Asn Leu Ala Ser Gly Val Pro
65                  70                  75                  80
Val Arg Phe Ser Gly Ser Gly Ser Gly Thr Ser Tyr Ser Leu Thr Val
                   85                  90                  95
Ser Arg Met Glu Ala Glu Asp Ala Ala Thr Tyr Tyr Cys Gln Gln Trp
               100                 105                 110
Ser Asp His Pro Leu Thr Phe Gly Ala Gly Thr Lys Leu Glu Leu Lys
           115                 120                 125
```

<210> SEQ ID NO 91
<211> LENGTH: 414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atgaacttcg ggctcagctt gattttcctt gtccttattt taaaaggtgt ccagtgtgaa      60
gtgatgctgg tggagtctgg gggagcctta gtgaagcctg agggtccct gaaactctcc     120
tgtgcagctt ctggattcag tttgagtaac tatgtcatgt cttgggttcg ccagactcca     180
gagaagaggc tggagtgggt cgcaaccatt agtagtggtg gtaggtatat ctactataca     240
gacagtgtga aggtcgatt caccatctcc aggacaatg ccaggaacac cctgtacctg      300
caaatgagca gtctgaggtc tgaggacacg gccatgtatt attgtgcaag agacggtagt     360
accttgtact actttgacta ttggggccaa ggcaccactc tcacagtctc ctca           414
```

<210> SEQ ID NO 92
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Met Asn Phe Gly Leu Ser Leu Ile Phe Leu Val Leu Ile Leu Lys Gly
1               5                   10                  15
Val Gln Cys Glu Val Met Leu Val Glu Ser Gly Gly Ala Leu Val Lys
           20                  25                  30
Pro Gly Gly Ser Leu Lys Leu Ser Cys Ala Ala Ser Gly Phe Ser Leu
           35                  40                  45
Ser Asn Tyr Val Met Ser Trp Val Arg Gln Thr Pro Glu Lys Arg Leu
       50                  55                  60
Glu Trp Val Ala Thr Ile Ser Ser Gly Gly Arg Tyr Ile Tyr Tyr Thr
65                  70                  75                  80
Asp Ser Val Lys Gly Arg Phe Thr Ile Ser Arg Asp Asn Ala Arg Asn
                   85                  90                  95
Thr Leu Tyr Leu Gln Met Ser Ser Leu Arg Ser Glu Asp Thr Ala Met
               100                 105                 110
```

Tyr Tyr Cys Ala Arg Asp Gly Ser Thr Leu Tyr Tyr Phe Asp Tyr Trp
            115                 120                 125

Gly Gln Gly Thr Thr Leu Thr Val Ser Ser
    130                 135

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 93

His His His His His His
1               5

<210> SEQ ID NO 94
<211> LENGTH: 53
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (12)..(12)
<223> OTHER INFORMATION: Ile or Val
<220> FEATURE:
<221> NAME/KEY: MOD_RES
<222> LOCATION: (44)..(44)
<223> OTHER INFORMATION: Leu, Ala, Val or Tyr
<220> FEATURE:
<221> NAME/KEY: MOD_RES
<222> LOCATION: (45)..(45)
<223> OTHER INFORMATION: Ala, Thr, Pro, Leu, Val or Ile
<220> FEATURE:
<221> NAME/KEY: MOD_RES
<222> LOCATION: (46)..(46)
<223> OTHER INFORMATION: His, Arg, Asp or Val
<220> FEATURE:
<221> NAME/KEY: MOD_RES
<222> LOCATION: (48)..(48)
<223> OTHER INFORMATION: Pro or Ala

<400> SEQUENCE: 94

Glu Lys Leu Phe Asn Val Thr Ser Thr Leu Arg Xaa Asn Ala Thr Ala
1               5                   10                  15

Asn Glu Ile Phe Tyr Cys Thr Phe Arg Arg Leu Gly Pro Glu Glu Asn
                20                  25                  30

His Thr Ala Glu Leu Val Ile Pro Glu Leu Pro Xaa Xaa Xaa Pro Xaa
            35                  40                  45

Asn Lys Arg Thr His
    50

<210> SEQ ID NO 95
<211> LENGTH: 53
<212> TYPE: PRT
<213> ORGANISM: Homo sapiens

<400> SEQUENCE: 95

Glu Lys Leu Phe Asn Val Thr Ser Thr Leu Arg Ile Asn Thr Thr Thr
1               5                   10                  15

Asn Glu Ile Phe Tyr Cys Thr Phe Arg Arg Leu Asp Pro Glu Glu Asn
                20                  25                  30

His Thr Ala Glu Leu Val Ile Pro Glu Leu Pro Leu Ala His Pro Pro

```
                35                  40                  45
Asn Glu Arg Thr His
    50

<210> SEQ ID NO 96
<211> LENGTH: 53
<212> TYPE: PRT
<213> ORGANISM: Mus musculus

<400> SEQUENCE: 96

Gly Met Leu Leu Asn Val Thr Ser Ser Leu Arg Val Asn Ala Thr Ala
1               5                   10                  15

Asn Asp Val Phe Tyr Cys Thr Phe Trp Arg Ser Gln Pro Gly Gln Asn
            20                  25                  30

His Thr Ala Glu Leu Ile Ile Pro Glu Leu Pro Ala Thr His Pro Pro
        35                  40                  45

Gln Asn Arg Thr His
    50

<210> SEQ ID NO 97
<211> LENGTH: 53
<212> TYPE: PRT
<213> ORGANISM: Rattus norvegicus

<400> SEQUENCE: 97

Glu Lys Leu Leu Asn Val Thr Ser Val Leu Arg Val Asn Ala Thr Ala
1               5                   10                  15

Asn Asp Val Phe His Cys Thr Phe Trp Arg Val His Ser Gly Glu Asn
            20                  25                  30

His Thr Ala Glu Leu Ile Ile Pro Glu Leu Pro Val Pro Arg Leu Pro
        35                  40                  45

His Asn Arg Thr His
    50

<210> SEQ ID NO 98
<211> LENGTH: 52
<212> TYPE: PRT
<213> ORGANISM: Bos taurus

<400> SEQUENCE: 98

Glu Lys Leu Phe Asn Val Thr Ser Thr Leu Arg Ile Asn Thr Thr Ala
1               5                   10                  15

Asp Lys Ile Phe Tyr Cys Thr Phe Arg Arg Leu Gly His Glu Glu Asn
            20                  25                  30

Asn Thr Ala Glu Leu Val Ile Pro Glu Pro Tyr Leu Asp Pro Ala Lys
        35                  40                  45

Lys Arg Asn His
    50

<210> SEQ ID NO 99
<211> LENGTH: 52
<212> TYPE: PRT
<213> ORGANISM: Sus scrofa

<400> SEQUENCE: 99

Glu Lys Leu Phe Asn Val Thr Ser Thr Leu Arg Val Asn Ala Thr Thr
1               5                   10                  15

Asn Glu Ile Phe Tyr Cys Thr Phe Arg Arg Leu Gly Pro Glu Glu Asn
            20                  25                  30
```

-continued

```
Ser Thr Ala Val Leu Val Ile Pro Glu Pro Tyr Val Asp Pro Ala Arg
        35                  40                  45

Lys Arg Thr His
    50

<210> SEQ ID NO 100
<211> LENGTH: 52
<212> TYPE: PRT
<213> ORGANISM: Equus caballus

<400> SEQUENCE: 100

Glu Lys Leu Phe Asn Val Thr Ser Thr Leu Arg Ile Asn Ala Thr Ala
1               5                   10                  15

Asn Glu Ile Phe Tyr Cys Thr Phe Arg Arg Ser Gly Leu Glu Glu Asn
            20                  25                  30

Ser Thr Ala Glu Leu Val Ile Pro Glu Pro Leu Ile Val Pro Ala Asn
        35                  40                  45

Lys Arg Thr His
    50
```

DUAL FUNCTION ANTIBODIES SPECIFIC TO GLYCOSYLATED PD-L1 AND METHODS OF USE THEREOF

SEQUENCE LISTING

The instant application contains a Sequence Listing which has been submitted electronically in ASCII format and is hereby incorporated by reference in its entirety. Said ASCII copy, created on Mar. 23, 2017, is named 24258_105007_SL.txt and is 40,452 bytes in size.

RELATED FIELDS

The present disclosure relates generally to the fields of molecular biology, medicine and oncology. More particularly, new antibodies that specifically bind glycosylated PD-L1 and their use for treating cancers are provided.

BACKGROUND

Perpetuation of T-cell activation has drastically reshaped the treatment of a broad spectrum of malignant cancers. For instance, the development of ipilimumab, the first FDA approved checkpoint blockade targeting T-cell response made treating metastatic melanoma probable (Hodi, F. S. et al., 2010, NEJM, 363:711-723; Robert, C. et al., 2013, Clin. Cancer Res., 19:2232-2239; and Robert, C. et al., 2011, NEJM, 364:2517-2526). While the anti-cytotoxic T lymphocyte antigen-4 (CTLA-4) monoclonal antibody showed promising results in treating melanoma patients, second-generation checkpoint inhibitors targeting both PD-1 and PD-L1 have demonstrated better clinical activity and safety in phase III clinical trials (Topalian, S. L. et al., 2012, NEJM, 366:2443-54; and Brahmer, J. R. et al., 2012, NEJM, 366: 2455-2465). Because PD-L1 also possesses oncogenic potential that induces cancer cells progression (Topalian, S. L. et al., Id.; Page, D. B. et al., 2014, Ann. Rev. Med., 65:185-202). In addition to its immunosuppression activity, targeting the PD-1/PD-L1 interaction provides dual efficacy by blocking immunosuppression via PD-1 while reducing cell progression via PD-L1 and is expected to have more sensitive outcome (Topalian, S. L. et al., Id.; Brahmer, J. R. et al., Id.; and Hamid, O., 2013, NEJM, 369:134-144). In 2014, there were over 10 clinical trials ongoing in the U.S. testing the efficacy of anti-PD-L1 and/or anti-PD-1 antibodies either as a single agent or in combination (Page, D. B. et al., Id.). The US FDA has approved two anti-PD-1 therapeutic antibodies for treatment of certain cancers KEYTRUDA® (pembrolizumab) and OPDIVO® (nivolumab). However, the pathophysiological function and regulatory mechanism of PD-L1 remains incompletely defined.

Reawakening silenced immune response, particularly effector T-cells, has been recently added to a repertoire of treatment options that include surgical removal, chemotherapy, radiotherapy, and targeted therapies. While the use of anti-CTLA-4 monoclonal antibody (Dunn, G. P., et al., 2002, Nat. Immunol., 3:991-998; and Leach, D. R., et al., 1996, Science, 271:1734-1736) initially demonstrated success in treating metastatic melanoma, it has been shown to also induce an autoimmune response. Unlike anti-CTLA-4 antibodies, which affect only immune cells, anti-PD-L1 antibodies and anti-PD-1 antibodies act at a cellular level and at tumor sites to block the interaction between PD-1-expressing effector T-cells and PD-L1-expressing tumor cells. This creates a dual impact from both the tumor cell and the T-cell, thereby limiting the adverse effects and providing better therapeutic efficacy (Okazaki, T., et al., 2013, Nature immunology, 14:1212-1218). A better understanding of the pathophysiological mechanism underlying the PD-L1 mediated immune suppression and pro-oncogenic effect on tumor cells is needed to develop more robust therapeutics targeting this pathway. There remains a need for new and more effective therapeutics and methodologies that successfully target the PD-1/PD-L1 pathway and activate effector cells of the immune system to attack the tumor cells and treat cancers.

SUMMARY

The inventors have discovered that glycosylation of PD-L1 (also known as CD274, PDCD1L1, or B7-H1) expressed on tumor cells promotes or enhances binding to PD-1 expressed on immune effector cells, such as T cells, thereby increasing the suppression of T cell activity against the tumor cells. The inventors further discovered that glycosylation of PD-L1 can stabilize PD-L1 expression on the cell surface, thus reducing the rate of internalization and intracellular degradation of the PD-L1. The inventors have identified antibodies that preferentially bind to glycosylated human PD-L1 polypeptide relative to unglycosylated human PD-L1 polypeptide. As used herein, such antibodies that preferentially bind glycosylated human PD-L1 are referred to as "anti-glycPD-L1 antibodies." The anti-glycPD-L1 antibodies as described herein also have a dual functionality in that they block the PD-L1/PD-1 interaction and also promote internalization and intracellular degradation of PD-L1 on PD-L1-expressing cells; thus, these antibodies are termed "dual function" antibodies. Accordingly, such anti-glycPD-L1 antibodies that exhibit the dual functionality of inhibiting PD-1/PD-L1 binding and promoting PD-L1 internalization and degradation are provided.

Further provided are methods of treating cancer, particularly cancers whose cells express or overexpress PD-L1, in a subject in need thereof by administering one or more anti-glycPD-L1 antibodies. The anti-glycPD-L1 antibodies as described herein inhibit or block the interaction between PD-1 and PD-L1 and also reduce the levels of PD-L1 on the tumor cells, and thereby inhibit immunosuppression which results from the PD-1/PD-L1 interaction and promote the perpetuation of the cytotoxic activity of PD-1-expressing effector T-cells against tumor cells that express PD-L1. By inhibiting the PD-1/PD-L1 interaction and reducing levels of glycosylated PD-L1 on the tumor cell surface, the anti-glycPD-L1 antibodies as described can enhance effector T-cell responses and mediate anti-tumor activity. As used herein, the terms tumor and cancer are used interchangeably. Unless otherwise indicated, "PD-L1" as used herein refers to PD-L1 protein, polypeptide, or peptide, particularly human PD-L1 (the amino acid sequence of which is SEQ ID NO: 1); and "PD-1" refers to PD-1 protein, polypeptide, or peptide, particularly human PD-1.

The inventors have further found that human PD-L1 is glycosylated at four sites in the extracellular domain at amino acid positions N35, N192, N200 and/or N219 of the human PD-L1 protein, e.g., as set forth in SEQ ID NO: 1. The anti-glycPD-L1 antibodies as described may bind to one or more of these sites and, for example, may not bind to PD-L1 that has a mutation (for example, substitution of glutamine for asparagine within the glycosylation consensus sequence) at one of more of these glycosylation sites and, thus, is not glycosylated at those one or more sites. Accordingly, in some embodiments, the anti-glycPD-L1 antibody specifically binds to one or more glycosylation motifs in the PD-L1 glycopolypeptide or peptides thereof. In some embodiments, the anti-glycPD-L1 antibody binds to a PD-L1 glycopeptide which comprises a glycosylation motif and the adjacent peptide. In some embodiments, the anti-glycPD-L1 antibody binds to a peptide sequence that is located near one or more of the glycosylation motifs in three dimensions. Accordingly, in embodiments, the anti-glycPD-L1 antibody recognizes and selectively binds to a conformational epitope of glycosylated PD-L1. By way of example, in certain embodiments, the anti-glycPD-L1 antibody binds to glycosylated PD-L1 with a $K_d$ of less than 85%, less than 80%, less than 75%, less than 70%, less than 65%, less than 60%, less than 55%, less than 50%, less than 45% of the $K_d$ exhibited relative to unglycosylated PD-L1, but in embodiments, no more than 5%, 10%, 15%, 20% or 25% of the $K_d$ exhibited relative to unglycosylated PD-L1, but still exhibits the dual anti-glycosylated PD-L1 function. It is to be understood that values in between as well as equal to the foregoing $K_d$ values are encompassed. In an embodiment the anti-glycPD-L1 antibody binds to glycosylated PD-L1 with a $K_d$ of less than half of the $K_d$ exhibited relative to unglycosylated PD-L1, but still exhibits the dual anti-glycosylated PD-L1 function. In an embodiment, the anti-glycPD-L1 antibody binds to glycosylated PD-L1 protein with a $K_d$ at least 5 times less than the $K_d$ exhibited relative to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1 protein. In certain embodiments, the anti-glycPD-L1 antibody preferentially binds to cells expressing the WT glycosylated PD-L1 with at least 1.5 times, 2, times, 3 times, 4 times, 5 times, 6 times, 7 times, 8 times, 9 times, or 10 times greater frequency than to cells expressing unglycosylated PD-L1 as assayed in, for example, a cell flow cytometry assay in which the cells expressing WT PD-L1 and unglycosylated PD-L1 are mixed and differentially labeled, and then contacted with the antibody to be assayed labeled with a detectable marker, for example, as described in Example 6, and as measured, for example, by the measured fluorescence intensity (MFI) for the two populations of cells when the antibody is labeled with a fluorescent marker. In an embodiment, the anti-glycPD-L1 antibody selectively binds to glycosylated PD-L1 protein with an affinity of from 5-20 nM, 5-10 nM, or 10-20 nM. In an embodiment, the antibody is a monoclonal antibody and, more preferably a chimeric or humanized or human antibody. The terms "specifically bind" and "selectively bind" are used interchangeably herein.

The anti-glycPD-L1 antibodies described herein specifically bind glycosylated PD-L1 versus non-glycosylated PD-L1; reduce, block, or inhibit binding of PD-L1 to PD-1; and promote internalization and intracellular degradation of PD-L1. In certain embodiments, the dual function anti-glycPD-L1 antibodies bind PD-L1 epitopes that are nonlinear, conformational epitopes. In addition, and without being bound by theory, the anti-glycPD-L1 antibodies bind PD-L1 epitopes that contain or are proximal in the three dimensional structure of PD-L1 to glycosylated amino acids; such glycosylated regions of PD-L1 are believed to be particularly involved in the PD-L1/PD-1 interaction. By binding epitope amino acids in regions of PD-L1 that are glycosylated, the anti-glycPD-L1 antibodies as described may effectively function to mask or neutralize binding sites or regions of the glycosylated PD-L1 protein that are involved in the PD-L1/PD-1 interaction and/or in the stabilization of PD-L1 expression on the tumor cell surface.

The anti-glycPD-L1 antibodies as described exert dual functionalities by virtue of their binding to glycosylated PD-L1 and are thus termed 'dual function' antibodies herein. It is believed, although not being bound by theory, that the N-terminal glycosylation site of the ECD (N35) is involved primarily with PD-L1/PD-1 binding, while the more C-terminal glycosylation sites (N192, N200 and N219) of the ECD are involved primarily with the stabilization of PD-L1 on cell membranes, although each of these regions may contribute to both PD-L1/PD-1 binding and the stabilization of PD-L1 on the membranes. Accordingly, anti-glycPD-L1 antibodies that bind to, block and/or mask the glycosylation at N35 may inhibit PD-L1/PD-1 binding and antibodies that bind to, block and/or mask the glycosylation at N192, N200 and/or N219 promote PD-L1 internalization and degradation. The antibodies as provided herein have both functionalities.

Provided in particular aspects are dual function anti-glycPD-L1 monoclonal antibodies STM073 (which has a $V_H$ domain amino acid sequence of SEQ ID NO: 3 and a $V_L$ domain amino acid sequence of SEQ ID NO: 11, as also provided in Table 3, infra) and STM108 (which has a $V_H$ domain amino acid sequence of SEQ ID NO: 19 and a $V_L$ domain amino acid sequence of SEQ ID NO: 27, as also provided in Table 3, infra), and binding fragments thereof specific for glycosylated PD-L1, as well as chimeric and humanized forms thereof. In one embodiment, STM073 specifically binds an epitope on PD-L1 corresponding to amino acid residues encompassing positions H69, Y112, R113 and K124 of the human PD-L1 amino acid sequence of SEQ ID NO: 1 herein. This STM073 epitope is non-contiguous within the amino acid sequence and is a conformational epitope. In one embodiment, the portion of the human PD-L1 polypeptide encompassing the STM073 MAb epitope has the sequence VHGEEDLKVQH------DAGV YRCMISYGGADYKRITV (SEQ ID NO: 85), in which the amino acid residues H69, Y112, R113 and K124, which comprise the epitope recognized by MAb STM073, are underlined and the dashes between amino acid residue histidine (H) at position 78 and amino acid residue aspartic acid (D) at position 108 represent amino acids at positions 79-107 of the human PD-L1 amino acid sequence of SEQ ID NO: 1. Provided are antibodies that bind the STM073 epitope and antibodies that compete for binding to PD-L1 with STM073.

In another embodiment, the STM108 MAb specifically binds an epitope on PD-L1 corresponding to amino acid residues encompassing positions S80, Y81, K162 and S169 of the human PD-L1 amino acid sequence of SEQ ID NO: 1 herein. This STM108 epitope is non-contiguous within the amino acid sequence and is a conformational epitope. In one embodiment, the portion of the human PD-L1 polypeptide encompassing the STM073 MAb epitope has the sequence LKVQHSSYRQR------EGYPKAEVIWTSSDHQ (residues 74-173 of SEQ ID NO: 1) in which the amino acid residues S80, Y81, K162 and S169, which comprise the epitope recognized by MAb STM108, are underlined and the dashes between amino acid residue arginine (R) at position 84 and amino acid residue glutamic acid (E) at position 158 represent amino acids at positions 85-157 of the human PD-L1 amino acid sequence of SEQ ID NO: 1, i.e., the mature PD-L1 protein from amino acids 19-290 of SEQ ID NO: 1. Provided are antibodies that bind the STM108 epitope and antibodies that compete for binding to PD-L1 with STM108.

The nucleic acid (DNA) and corresponding amino acid sequences of the heavy and light chain variable (V) domains of the STM073 MAb are shown in Table 3 infra. Table 3 provides both the nucleotide and amino acid sequences of the mature (i.e., not containing the signal peptide) $V_H$ and $V_L$ domains of STM073 (SEQ ID NOS 2, 3, 10, and 11, respectively) and the $V_H$ and $V_L$ domain sequences containing the signal peptides (SEQ ID NOS: 87, 88, 89, and 90, respectively). In the heavy chain DNA and protein V domain sequences of the signal sequence containing heavy and light chain domains shown in Table 3, the amino terminal signal sequence (nucleotides 1-58 and amino acids 1-19 of the $V_H$ domain and nucleotides 1-66 and amino acids 1-22 of the $V_L$ domain, respectively) is represented in italicized font. Also shown in Table 3 are the STM073 MAb heavy and light chain V domain CDRs, using both the Kabat and Chothia numbering definitions.

In an embodiment, the dual function anti-glycPD-L1 antibody that specifically binds glycosylated PD-L1 comprises a $V_H$ domain of SEQ ID NO: 3 and a $V_L$ domain of SEQ ID NO: 11. In an embodiment, the dual function anti-glycPD-L1 antibody competes for specific binding to glycosylated PD-L1 with an antibody comprising a $V_H$ domain of SEQ ID NO: 3 and a $V_L$ domain of SEQ ID NO: 11. In an embodiment, the dual function anti-glycPD-L1 antibody that specifically binds glycosylated PD-L1 comprises a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof. In an embodiment, the dual function anti-glycPD-L1 antibody competes for specific binding to glycosylated PD-L1 with an antibody comprising a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof. In an embodiment, the dual function anti-glycPD-L1 antibody that specifically binds PD-L1 comprises a $V_L$ domain comprising CDRs 1-3 having amino acid sequences of SEQ ID NO: 12, SEQ ID NO: 14, and SEQ ID NO: 16, respectively. In an embodiment, the dual function anti-glycPD-L1 antibody competes for specific binding to glycosylated PD-L1 with an antibody comprising a $V_L$ domain comprising CDRs 1-3 having amino acid sequences of SEQ ID NO: 12, SEQ ID NO: 14, and SEQ ID NO: 16, respectively. In an embodiment, the dual function anti-glycPD-L1 antibody that specifically binds glycosylated PD-L1 comprises (a) a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof; and (b) a $V_L$ domain comprising CDRs 1-3 having amino acid sequences of SEQ ID NO: 12, SEQ ID NO: 14, and SEQ ID NO: 16, respectively. In embodiments, the anti-glycPD-L1 antibody competes for specific binding to glycosylated PD-L1 with an antibody comprising the above-described $V_H$ and $V_L$ domains and the CDRs therein.

In an embodiment, the dual function anti-glycPD-L1 antibody that specifically binds glycosylated PD-L1 comprises a $V_H$ domain that is 80%, 85%, 90%, 95% 98% or 99% identical to the amino acid sequence of SEQ ID NO: 3 and/or a $V_L$ domain that is 80%, 85%, 90%, 95% 98% or 99% identical to the amino acid sequence of SEQ ID NO: 11, and which inhibits or blocks binding of glycosylated PD-L1 to PD-1. In an embodiment, the dual function anti-glycPD-L1 antibody that specifically binds glycosylated PD-L1 comprises a $V_H$ domain comprising CDRs 1-3 with at least 1, 2, or all 3 CDRs having at least 1, 2, 3, 4 or 5 amino acid substitutions with respect to the amino acid sequences of SEQ ID NO: 4, SEQ ID NO: 6, and SEQ ID NO: 8, respectively, or amino acid sequences of SEQ ID NO: 5, SEQ ID NO: 7, and SEQ ID NO: 9, respectively, which dual function anti-glycPD-L1 antibody blocks binding of glycosylated PD-L1 to PD-1. In an embodiment, the dual function anti-glycPD-L1 antibody that specifically binds PD-L1 comprises a $V_L$ domain comprising CDRs 1-3 with at least 1, 2, or all 3 CDRs having at least 1, 2, 3, 4 or 5 amino acid substitutions with respect to amino acid sequences of SEQ ID NO: 12, SEQ ID NO: 14, and SEQ ID NO: 16, respectively. In an embodiment, the anti-glycPD-L1 antibody that specifically binds glycosylated PD-L1 comprises (a) a $V_H$ domain comprising CDRs 1-3 with at least 1, 2, or all 3 CDRs having at least 1, 2, 3, 4 or 5 amino acid substitutions with respect to the amino acid sequences of SEQ ID NO: 4, SEQ ID NO: 6, and SEQ ID NO: 8, respectively, or amino acid sequences of SEQ ID NO: 5, SEQ ID NO: 7, and SEQ ID NO: 9, respectively; and (b) a $V_L$ domain comprising CDRs 1-3 with at least 1, 2, or all 3 CDRs having at least 1, 2, 3, 4 or 5 amino acid substitutions with respect to amino acid sequences of SEQ ID NO: 12, SEQ ID NO: 14, and SEQ ID NO: 16, respectively, which antibody blocks binding of glycosylated PD-L1 to PD-1. Preferably these antibodies have human framework regions, i.e., are humanized forms of STM073, and optionally have human constant domains. Also provided are humanized forms of STM073 using the AbM, Contact or IMGT defined CDRs, with human framework regions and, optionally, human constant domains. It will be appreciated by those skilled in the art that one or more amino acid substitutions may be made in framework regions and/or the CDRs of a humanized antibody to improve binding affinity.

In embodiments, the dual function anti-glycPD-L1 antibody competes for specific binding to glycosylated PD-L1 with an antibody comprising the above-described $V_H$ and $V_L$ domains and the CDRs therein. In embodiments, the anti-glycPD-L1 antibody binds to glycosylated PD-L1 with a $K_d$ less than half of the $K_d$ exhibited relative to unglycosylated PD-L1. In an embodiment, the anti-glycPD-L1 antibody binds to glycosylated PD-L1 protein with a $K_d$ at least 5 times less than the $K_d$ exhibited relative to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1 protein. In an embodiment, in a cell flow cytometry binding assay as described in Example 6, the antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1. In an embodiment, the binding affinity of the STM073 antibody, or humanized or chimeric form thereof, or antibody that competes for binding with the foregoing for glycosylated PD-L1 is from 5-20 nM or from 5-10 nM inclusive of the lower and upper values. In an embodiment, the antibody inhibits the interaction of PD-1 with PD-L1, and particularly inhibits the interaction of PD-1 expressed by effector T-cells with PD-L1, particularly, glycosylated PD-L1, expressed by tumor cells and also reduces the levels of PD-L1, particularly glycosylated PD-L1, on the surface of the tumor cells, particularly, by increasing the internalization and intracellular degradation of the PD-L1. Internalization of the PD-L1 expressed on tumor cells following binding by the anti-glycosylated PD-L1 antibodies provided herein is a beneficial feature of the anti-glycPD-L1 antibodies, as less glycosylated PD-L1 is available on the tumor cell for interaction with PD-1 on T cells, thereby increasing T cell cytotoxic effector function against the tumor cells and reducing T cell anergy resulting from the PD-L1/PD-1 interaction.

In another particular embodiment, an antibody, or a binding fragment thereof, is provided that specifically binds glycosylated PD-L1 which is the anti-glycPD-L1 monoclonal antibody STM108. The nucleic acid (DNA) and corresponding amino acid sequences of the mature heavy and light chain variable (V) domains (SEQ ID NOs: 18, 19, 26 and 27) of the STM108 MAb are shown in Table 3 infra. The DNA and amino acid sequences of the unprocessed heavy chain V domain sequence (i.e., those containing a signal sequence at the N-terminal) are also shown in Table 3 (SEQ ID NOs: 91 and 92) and the amino terminal signal sequence is represented in italicized font (nucleotides 1-57 and amino acids 1-19 of the $V_H$ domain). Also shown in Table 3 are the STM108 MAb heavy and light chain V domain CDRs, according to both the Kabat and Chothia definitions.

In an embodiment, the dual function anti-glycPD-L1 antibody that specifically and preferentially binds glycosylated PD-L1 comprises a $V_H$ domain of the amino acid sequence of SEQ ID NO: 19 and a $V_L$ domain of the amino acid sequence of SEQ ID NO: 27. In an embodiment, the anti-glycPD-L1 antibody competes for specific binding to glycosylated PD-L1 with an antibody comprising a $V_H$ domain of the amino acid sequence of SEQ ID NO: 19 and a $V_L$ domain of the amino acid sequence of SEQ ID NO: 27. In an embodiment, the anti-glycPD-L1 antibody that specifically and preferentially binds glycosylated PD-L1 comprises a $V_H$ domain comprising Chothia CDRs1-3 having amino acid sequences of SEQ ID NO: 20, SEQ ID NO: 22, and SEQ ID NO: 24, respectively, or Kabat CDRs 1-3 having amino acid sequences of SEQ ID NO: 21, SEQ ID NO: 23, and SEQ ID NO: 25, respectively, or a combination thereof. In an embodiment, the anti-glycPD-L1 antibody competes for specific binding to glycosylated PD-L1 with an antibody comprising a $V_H$ domain comprising Chothia CDRs 1-3 with amino acid sequences of SEQ ID NO: 20, SEQ ID NO: 22, and SEQ ID NO: 24, respectively, or Kabat CDRs 1-3 with amino acid sequences of SEQ ID NO: 21, SEQ ID NO: 23, and SEQ ID NO: 25, respectively, or a combination thereof. In an embodiment, the anti-glycPD-L1 antibody that specifically and preferentially binds glycosylated PD-L1 comprises a $V_L$ domain comprising CDRs 1-3 having amino acid sequences of SEQ ID NO: 28, SEQ ID NO: 30, and SEQ ID NO: 32, respectively. In an embodiment, the anti-glycPD-L1 antibody competes for specific binding to glycosylated PD-L1 with an antibody comprising a $V_L$ domain comprising CDRs 1-3 having amino acid sequences of SEQ ID NO: 28, SEQ ID NO: 30, and SEQ ID NO: 32, respectively. In an embodiment, the anti-glycPD-L1 antibody that specifically and preferentially binds glycosylated PD-L1 comprises (a) a $V_H$ domain comprising Chothia CDRs1-3 having amino acid sequences of SEQ ID NO: 20, SEQ ID NO: 22, and SEQ ID NO: 24, respectively, or Kabat CDRs 1-3 having amino acid sequences of SEQ ID NO: 21, SEQ ID NO: 23, and SEQ ID NO: 25, respectively, or a combination thereof; and (b) a $V_L$ domain comprising CDRs 1-3 having amino acid sequences of SEQ ID NO: 28, SEQ ID NO: 30, and SEQ ID NO: 32, respectively. In embodiments, the anti-glycPD-L1 antibody competes for specific binding to glycosylated PD-L1 with an antibody comprising the above-described VH and VL domains and the CDRs therein.

In an embodiment, the anti-glycPD-L1 antibody that specifically and preferentially binds glycosylated PD-L1 comprises a $V_H$ domain that is 80%, 85%, 90%, 95% 98% or 99% identical to the amino acid sequence of SEQ ID NO: 19 and a $V_L$ domain that is 80%, 85%, 90%, 95% 98% or 99% identical to the amino acid sequence of SEQ ID NO: 27. In an embodiment, the anti-glycPD-L1 antibody that specifically and preferentially binds glycosylated PD-L1 comprises a $V_H$ domain comprising CDRs 1-3 with at least 1, 2, or all 3 CDRs having at least 1, 2, 3, 4 or 5 amino acid substitutions with respect to the amino acid sequences of SEQ ID NO: 20, SEQ ID NO: 22, and SEQ ID NO: 24, respectively, or CDRs 1-3 having amino acid sequences of SEQ ID NO: 21, SEQ ID NO: 23, and SEQ ID NO: 25, respectively, or a combination thereof. In an embodiment, the anti-glycPD-L1 antibody that specifically and preferentially binds glycosylated PD-L1 comprises a $V_L$ domain comprising CDRs 1-3 with at least 1, 2, or all 3 CDRs having at least 1, 2, 3, 4 or 5 amino acid substitutions with respect to the amino acid sequences of SEQ ID NO: 28, SEQ ID NO: 30, and SEQ ID NO: 32, respectively. In an embodiment, the anti-glycPD-L1 antibody that specifically and preferentially binds glycosylated PD-L1 comprises (a) a $V_H$ domain comprising CDRs 1-3 with at least 1, 2, or all 3 CDRs having at least 1, 2, 3, 4 or 5 amino acid substitutions with respect to the amino acid sequences of SEQ ID NO: 20, SEQ ID NO: 22, and SEQ ID NO: 24, respectively, or with respect to the amino acid sequences of SEQ ID NO: 21, SEQ ID NO: 23, and SEQ ID NO: 25, respectively, or a combination thereof; and/or (b) a $V_L$ domain comprising CDRs 1-3 with at least 1, 2, or all 3 CDRs having at least 1, 2, 3, 4 or 5 amino acid substitutions with respect to the amino acid sequences of SEQ ID NO: 28, SEQ ID NO: 30, and SEQ ID NO: 32, respectively.

Also provided are humanized forms of STM108 using the AbM, Contact or IMGT defined CDRs, with human framework regions and, optionally, human constant domains. Preferably these antibodies have human framework regions, i.e., are humanized forms of STM108, and optionally have human constant domains.

In embodiments, the anti-glycPD-L1 antibody competes for specific binding to glycosylated PD-L1 with an antibody comprising the above-described $V_H$ and $V_L$ domains and the CDRs therein. The humanized forms of STM108 may have one or more amino acid substitutions, deletions or insertions in the CDRs and/or framework regions that improve one or more properties of the antibody, such as antigen affinity. In embodiments, the anti-glycPD-L1 antibody binds to glycosylated PD-L1 with a $K_d$ less than half of the $K_d$ exhibited relative to unglycosylated PD-L1. In an embodiment, the anti-glycPD-L1 antibody binds to glycosylated PD-L1 protein with a $K_d$ at least 5 times less than the $K_d$ exhibited relative to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1 protein. In an embodiment, in a cell flow cytometry binding assay as described in Example 6, the antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1. In an embodiment, the binding affinity of STM108 MAb, or chimeric or humanized form thereof, for glycosylated PD-L1 is from 5-20 nM or from 5-10 nM inclusive of the lower and upper values. In an embodiment, the antibody inhibits the interaction of PD-1 with PD-L1, and particularly inhibits the interaction of PD-1 expressed by effector T-cells with PD-L1, particularly, glycosylated PD-L1, expressed by tumor cells. The antibody preferably has human framework regions and in certain embodiments a human constant domain.

Also encompassed by the present embodiments is an isolated dual function anti-glycPD-L1 monoclonal antibody, or chimeric or humanized form thereof, that binds an epitope within the human PD-L1 amino acid sequence DAGVYRCMISYGGADYKRITV (SEQ ID NO: 86), which is a peptide portion of the human PD-L1 sequence of SEQ ID NO: 1. In an embodiment, the epitope bound by the antibody includes non-contiguous amino acids, and the epitope is a conformational epitope. In an embodiment, the antibody specifically binds a human PD-L1 epitope corresponding to non-contiguous amino acid residues encompassing positions Y112, R113 and S117 of the human PD-L1 amino acid sequence SEQ ID NO: 1 shown as the underlined amino acid residues in the following sequence: DAGVYRCMISYGGADYKRITV (SEQ ID NO: 86).

Provided in another aspect is an isolated dual function anti-glycPD-L1 antibody, e.g., a monoclonal antibody, or a binding fragment thereof, particularly a humanized or human antibody, that specifically binds to an epitope within an amino acid sequence selected from VHGEEDLKVQH------DAGVYRCMISYGGADYKRITV (SEQ ID NO: 85), or DAGVYRCMISYGGADYKRITV (SEQ ID NO: 86), which sequence is located within the mature human PD-L1 polypeptide sequence of SEQ ID NO: 1. The antibody preferably has human framework regions and in certain embodiments a human constant domain. Provided in another aspect is an isolated dual function anti-glycPD-L1 antibody, e.g., a monoclonal antibody, or a binding fragment thereof, particularly a humanized or human antibody, that specifically binds to an epitope within the amino acid sequence LKVQHSSYRQR------EGYPKAEVIWTSSDHQ, which are amino acids 74 to 84 and 158 to 173 of SEQ ID NO:1. The antibody preferably has human framework regions and in certain embodiments a human constant domain In a certain embodiment, an isolated anti-glycPD-L1 antibody, particularly a monoclonal, humanized, or human antibody, that binds an epitope that comprises amino acid residues H69, Y112, R113 and K124 of SEQ ID NO: 1 is provided. In an aspect, an isolated anti-glycPD-L1 antibody is provided that specifically binds glycosylated human PD-L1, such that when bound to human PD-L1, the antibody binds at least one of the following amino acid residues: H69, Y112, R113 and K124 of SEQ ID NO: 1. In another embodiment, an isolated anti-glycPD-L1 antibody, particularly a monoclonal, humanized, or human antibody, that binds an epitope that comprises amino acid residues S80, Y81, K162 and S169 of SEQ ID NO: 1 is provided. In an aspect, an isolated anti-glycPD-L1 antibody is provided that specifically binds glycosylated human PD-L1, such that when bound to human PD-L1, the antibody binds at least one of the following amino acid residues: S80, Y81, K162 and S169 of SEQ ID NO: 1.

In another aspect, an isolated dual function anti-glycPD-L1 antibody, particularly a monoclonal, humanized, or human antibody, is provided that specifically binds glycosylated human PD-L1, such that when bound to human PD-L1, the antibody binds at least one of the following amino acid residues: Y112, R113 and S117 of SEQ ID NO: 1.

Provided in another aspect is an isolated dual function anti-glycPD-L1 antibody, particularly a monoclonal, humanized, or human antibody, that specifically binds glycosylated human PD-L1, such that when bound to human PD-L1, the antibody binds at least one amino acid within the amino acid region from V68 to V128 of SEQ ID NO: 1 or within the amino acid region from D108 to V128 of SEQ ID NO: 1. In an aspect, an isolated dual function anti-glycPD-L1 antibody is provided that specifically binds glycosylated human PD-L1, such that when bound to human PD-L1, the monoclonal antibody binds the following group of amino acid residues: H69, Y112, R113 and K124 within the amino acid region from V68 to V128 of SEQ ID NO: 1. In an aspect, an isolated dual function anti-glycPD-L1 antibody is provided that specifically binds glycosylated human PD-L1, such that when bound to human PD-L1, the monoclonal antibody binds the following group of amino acid residues: Y112, R113, S117 within the amino acid region from D108 to V128 of SEQ ID NO: 1.

In an aspect, the dual function anti-glycPD-L1 antibody binds within the region of L74 to R84 and/or E158 to Q173 of SEQ ID NO:1, and preferably, one or more of residues S80, Y81, K162 and S169 of SEQ ID NO: 1.

Provided in another aspect is an isolated dual function anti-glycPD-L1 antibody, or a binding fragment thereof, particularly a monoclonal, humanized, or human antibody, that specifically binds glycosylated human PD-L1 protein versus non-glycosylated, such that when bound to human PD-L1, the antibody binds at least amino acid region V68-V128 or at least amino acid region D108-V128 of the PD-L1 protein (SEQ ID NO: 1), or a combination thereof. The antibody preferably has human framework regions and in certain embodiments a human constant domain.

Provided in another aspect is an isolated dual function anti-glycPD-L1 antibody or a binding fragment thereof, comprising (a) a $V_H$ domain comprising a CDR1 comprising an amino acid sequence of SEQ ID NO: 5, SEQ ID NO: 21, SEQ ID NO: 4 or SEQ ID NO: 20; a CDR2 comprising an amino acid sequence of SEQ ID NO: 7, SEQ ID NO: 23, SEQ ID NO: 6 or SEQ ID NO: 22; and a CDR3 comprising an amino acid sequence of SEQ ID NO: 9, SEQ ID NO: 25, SEQ ID NO: 8 or SEQ ID NO: 24; and (b) a $V_L$ domain comprising a CDR1 comprising an amino acid sequence of SEQ ID NO: 12 or SEQ ID NO: 28; a CDR2 comprising an amino acid sequence of SEQ ID NO: 14 or SEQ ID NO: 30; and a CDR3 comprising an amino acid sequence of SEQ ID NO: 16 or SEQ ID NO: 32. In an embodiment, the antibody is a humanized antibody that has human framework regions, and, optionally, a human antibody constant domain.

Provided in another aspect is an isolated nucleic acid molecule comprising a nucleotide sequence selected from SEQ ID NOs: 2 or 18, which encodes a $V_H$ domain and/or a nucleotide sequence selected from SEQ ID NO: 10 or 26, which encodes a $V_H$ domain. An embodiment provides an isolated nucleotide sequence encoding a $V_H$ domain of a dual function anti-glycPD-L1 antibody, wherein the nucleotide sequence is at least 90-98% identical to the nucleotide sequence of SEQ ID NOs: 2 or 18. Another embodiment provides an isolated nucleotide sequence encoding a $V_L$ domain of a dual function anti-glycPD-L1 antibody, wherein the nucleotide sequence is at least 90-98% identical to the nucleotide sequence of SEQ ID NOs: 19 or 26. In embodiments, the nucleotide sequences encoding the $V_H$ and/or the $V_L$ domains are 90%, 91%, 92%, 93%, 94%, 95%, 96%, 97%, 98%, 99%, or more identical to SEQ ID NOs: 2 or 18, or SEQ ID NOs: 10 or 26, respectively.

In certain aspects, the dual function anti-glycPD-L1 antibody is an IgG, IgM, IgA, an isotype thereof, such as IgG1, IgG2a, IgG2b, IgG4, or an antigen binding fragment thereof. In other aspects, anti-glycPD-L1 antibody is an Fab', a F(ab')2, a F(ab')3, a monovalent scFv, a bivalent scFv, a bispecific antibody, a bispecific scFv, or a single domain antibody. In some aspects, the anti-glycPD-L1 antibody is a chimeric antibody, human antibody or a humanized antibody. In an aspect, the dual function anti-glycPD-L1 antibody is recombinantly produced. In further aspects, the dual function anti-glycPD-L1 antibody is conjugated to an imaging agent, a chemotherapeutic agent, a toxin, or a radionuclide.

In an aspect, a composition comprising a dual function anti-glycPD-L1 antibody (e.g., an antibody that selectively and preferentially binds to glycosylated PD-L1 relative to unglycosylated PD-L1 and effectuates internalization and/or degradation of PD-L1 as described herein) in a pharmaceutically acceptable carrier or medium is provided.

Provided in a further aspect is an isolated polypeptide comprising a peptide of at least 7 (e.g., at least 8, 9, 10, 11, 12, 13, 14, 15, 16, 17, 18, 19, 20 or more) contiguous amino acids of human PD-L1 comprising at least one amino acid corresponding to position N35, N192, N200 or N219 within the extracellular domain (ECD) of human PD-L1. In an embodiment, the isolated polypeptide comprises a peptide of at least 7 (e.g., at least 8, 9, 10, 11, 12, 13, 14, 15, 16, 17, 18, 19, 20 or more) contiguous amino acids of human PD-L1, comprising at least one amino acid corresponding to position N35, N192, N200 or N219 of human PD-L1, in which at least one of the amino acids corresponding to position N35, N192, N200 or N219 of PD-L1 is glycosylated. In an embodiment, the isolated polypeptide is fused or conjugated to an immunogenic polypeptide (e.g., keyhole limpet hemocyanin, KLH). In certain aspects, the polypeptide further comprises a cysteine (Cys) residue at its amino (N)- or carboxy (C)-terminus. For example, the polypeptide may be conjugated to an immunogenic polypeptide by a disulfide linkage at the Cys residue. In a particular embodiment, the PD-L1 peptide comprising at least one amino acid residue glycosylated at a position corresponding to position N35, N192, N200 or N219 of human PD-L1 is used as an immunogen to generate anti-glycPD-L1 antibodies.

In a further aspect, a composition is provided comprising a polypeptide comprising a peptide of at least 7 (e.g., at least 8, 9, 10, 11, 12, 13, 14, 15, 16, 17, 18, 19, 20 or more) contiguous amino acids of human PD-L1 comprising at least one amino acid corresponding to position N35, N192, N200 or N219 within the ECD of human PD-L1, wherein at least one of said amino acids corresponding to position N35, N192, N200 or N219 of PD-L1 is glycosylated, wherein the polypeptide is formulated in a pharmaceutically acceptable carrier, diluent, excipient, or vehicle.

In yet a further aspect, an immunogenic composition is provided comprising a polypeptide comprising a peptide fragment of at least 7 contiguous amino acids of human PD-L1, which comprises at least one amino acid corresponding to position N35, N192, N200 or N219 of the human PD-L1 polypeptide, wherein at least one of the amino acids corresponding to position N35, N192, N200 or N219 within the ECD of the PD-L1 polypeptide is glycosylated, and wherein the polypeptide is formulated in a pharmaceutically acceptable carrier, diluent, excipient, or vehicle. In some aspects, the immunogenic composition further comprises an adjuvant, such as alum or Freund's adjuvant.

Provided in a further aspect is a method for treating a subject in need, such as a subject with a cancer, which comprises administering to the subject an effective amount of a dual function anti-glycPD-L1 antibody as described herein. In specific embodiments, the anti-glycPD-L1 antibody is a humanized or chimeric form of one of MAbs STM073 or STM108. In other embodiments, the dual function anti-glycPD-L1 antibody is an antibody that competes for binding to glycosylated PD-L1 with MAb STM073 or MAb STM108. In an embodiment, a method of treating a cancer in a subject in need thereof, is provided in which the method comprises administering an effective amount of an antibody as described herein to the subject. In certain preferred embodiments, the cancer cells are positive for PD-L1, particularly glycosylated PD-L1. The cancer cells may also be positive for one or more other cancer cell markers, such as, but not limited to, EGFR. In nonlimiting embodiments, the cancer, disease or pathology to be treated in the subject is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In certain embodiments, the cancer to be treated is an adrenal cancer, an anal cancer, a bile duct cancer, a bone cancer, a brain/CNS tumor in an adult, a brain/CNS tumor in a child, a breast cancer in a man, cancer in an adolescent, cancer in a child, cancer in a young adult, cancer of unknown primary, Castleman disease, cervical cancer, endometrial cancer, Ewing family tumor, eye cancer, gallbladder cancer, gastrointestinal carcinoid tumor, gastrointestinal stromal tumor (GIST), gestational trophoblastic disease, Hodgkin's disease, Kaposi sarcoma, kidney cancer, laryngeal or hypopharyngeal cancer, leukemia (e.g., adult acute lymphocytic (ALL), acute myeloid (AML), chronic lymphocytic (CLL), chronic myeloid (CML), chronic myelomonocytic (CMML), childhood leukemia), lung cancer (e.g., non-small cell, small cell), lung carcinoid tumor, lymphoma, lymphoma of the skin, malignant mesothelioma, multiple myeloma, myelodysplastic syndrome, naval cavity cancer, paranasal sinus cancer, nasopharyngeal cancer, neuroblastoma, non-Hodgkin lymphoma, non-Hodgkin lymphoma in a child, oral cavity cancer, oropharyngeal cancer, osteosarcoma, penile cancer, pituitary tumors, prostate cancer, retinoblastoma, rhabdomyosarcoma, salivary gland cancer, sarcoma (e.g., adult soft tissue cancer), skin cancer (e.g., basal and squamous cell, melanoma, merkel cell), small intestine cancer, stomach cancer, testicular cancer, thymus cancer, thyroid cancer, uterine sarcoma, vaginal cancer, vulvar cancer, Waldenstrom macroglobulinemia, or Wilms tumor.

In certain aspects, the anti-glycPD-L1 antibody is formulated in a pharmaceutically acceptable composition. In further aspects, the antibody is administered systemically or parenterally. In particular aspects, the antibody is administered intravenously, intradermally, intratumorally, intramuscularly, intraperitoneally, subcutaneously, intrathecally, or locally. In other aspects, one or more than one type of dual function anti-glycPD-L1 antibody may be co-administered to a subject in need. Co-administration of antibodies may involve the administration of one antibody before, after, or concurrently with another antibody.

In an aspect, a method of treating a subject who has a cancer or tumor, particularly a cancer or tumor that expresses PD-L1 on the cancer or tumor cell surface is provided. Such a method comprises administering to the subject in need thereof an effective amount of a dual function anti-glycPD-L1 antibody to inhibit or block the interaction of PD-L1 with PD-1 and prevent immunosuppression and promote killing of the cancer or tumor cells by the subject's effector T lymphocytes. In embodiments, the anti-glycPD-L1 antibody is a chimeric or humanized form of STM073 or STM108, or an antibody that competes with one or both of these antibodies for selectively binding to glycosylated PD-L1.

In some aspects, the methods comprise administering at least a second anticancer therapy or drug to the subject who is receiving treatment with an anti-glycPD-L1 antibody. The second anticancer therapy may constitute, without limitation, a surgical therapy, chemotherapy, radiation therapy, cryotherapy, hormonal therapy, immunotherapy or cytokine therapy. The second anticancer drug is also not intended to be limited and will be able to be practically or empirically determined by the clinician, medical professional (e.g., oncologist) skilled in the art. As will be appreciated by one having skill in the art, the administration of at least a second anticancer therapy or drug may occur before, after, or simultaneously with the administration of a dual function anti-glycPD-L1 antibody.

Provided in another aspect is a method of determining if a patient with cancer is likely to benefit from treatment with (i.e., is a candidate for treatment with) an agent that blocks binding of PD-L1 with PD-1, the method comprising testing for the presence of glycosylated PD-L1 on cells derived from a sample of the patient's cancer cells using an antibody as described herein, wherein detecting the binding of the antibody to the patient's cancer cells indicates that the patient is a candidate for therapy. The method may further comprise administering to the patient an effective amount of an agent that prevents binding of PD-L1 to PD-1 if subject's cancer cells are found to be positive for the expression of glycosylated PD-L1 protein. In an embodiment, the agent that prevents binding of PD-L1 to PD-1 is an anti-glycPD-L1 antibody, preferably a dual function anti-glycPD-L1 antibody, an anti-PD-1 antibody, or a combination thereof. In an embodiment, the anti-glycPD-L1 antibody and/or anti-PD-1 antibody is administered in combination with another anti-cancer drug or therapeutic. In an embodiment, an anti-glycPD-L1 antibody is administered in combination with another anti-glycPD-L1 antibody, such as described herein. In an embodiment, the method further involves obtaining the cancer cell sample from the patient.

Provided in yet another aspect is a method for assessing glycosylation, N-linked glycosylation, or N-glycosylation of PD-L1 protein in a biological sample, in which the method comprises contacting the PD-L1-containing sample with an antibody as described herein. In some aspects, the method is an in vitro method or assay. In certain aspects, the biological sample is cell sample, a tissue sample, a body fluid (e.g., plasma, serum, blood, urine, sputum, lymph, ascites fluid, intraperitoneal fluid, cerebral or spinal fluid, and the like). In particular embodiments, the sample is a cell sample or a cell sample from a tumor or cancer obtained from a subject having a cancer or tumor. Such a cancer or tumor cell sample may be assayed for glycosylated PD-L1 on the cancer or tumor cell surface using the dual function anti-glycPD-L1 antibodies as described herein, particularly to determine that, if glycosylated PD-L1 is present on the subject's cancer or tumor cells, then the cells would likely be appropriate targets for treatment with the anti-glycPD-L1 antibodies as described.

Provided in another aspect is a method of making an antibody in which the method comprises administering to a subject (e.g., an animal) a polypeptide according to the embodiments (e.g., a polypeptide comprising a fragment of at least 7 contiguous amino acids of human PD-L1 comprising at least one amino acid corresponding to position N35, N192, N200 or N219 of human PD-L1, wherein at least one of said amino acids corresponding to position N35, N192, N200 or N219 of PD-L1 is glycosylated) and isolating the antibody from the subject. By way of example, the animal can be a non-human primate, mouse, rat, rabbit, goat, or a human. In certain aspects a method further comprises identifying the CDRs of the antibody and humanizing the sequences (i.e., framework sequences) surrounding the CDRs to produce a humanized antibody using methods and procedures known in the art. In still further aspects, the method comprises recombinantly expressing the humanized antibody. Thus, in a further embodiment, there is provided an isolated antibody produced by the foregoing method. Thus, in some embodiments, there is provided an isolated antibody that selectively binds to an epitope, such as a conformational epitope, of a glycosylated PD-L1 polypeptide (e.g., a polypeptide comprising a fragment of at least 7 contiguous amino acids of human PD-L1 comprising at least one amino acid corresponding to position N35, N192, N200 or N219 of human PD-L1, wherein at least one of said amino acids corresponding to position N35, N192, N200 or N219 of PD-L1 is glycosylated) relative to unglycosylated PD-L1. Another aspect provides a method for immunizing a subject to produce an immune response, e.g., an antibody response directed against an antigen, comprising administering an effective amount of a polypeptide of the embodiments (e.g., a glycosylated PD-L1 polypeptide) as immunogenic antigen to the subject.

In specific embodiments, the invention provides methods of making biparatopic antibodies that have two different antigen binding domains that each bind an epitope that does not overlap with the epitope of the other antigen binding domain of glycosylated PD-L1, and at least one binding domain (and in certain embodiments, both binding domains) binds preferentially to a glycosylated form of PD-L1, for example by binding an epitope containing one or more of the glycosylation sites listed herein. These antibodies can cross-link cell surface proteins promoting internalization, lysosomal trafficking and degradation. Such biparatopic antibodies may be generated by screening for antibodies that preferentially bind to a glycosylated PD-L1 protein relative to a non-glycosylated form of PD-L1 using screening methods known in the art and also as described in co-pending provisional application No. 62/361,298, identifying two antibodies that bind non-overlapping epitopes of glycosylated PD-L1, where preferably one or both preferentially bind the glycosylated form of PD-L1 as compared to the non-glycosylated form. Antibodies against any of the glycosylation containing epitopes or epitopes described herein to which antibodies preferentially bind to glycosylated PD-L1 can be used. The two antigen binding domains can be arranged in an antibody molecule, for example, as described in Dimasi et al., *J. Mol. Biol.*, 393:672-692 (2009). In specific embodiments, one of the antigen binding domains is engineered to be in the format of a single chain Fv which is then linked to the N terminus of the heavy and/or light chains of an antibody having the other antigen binding domain or to the C-terminus of the CH3 domain, e.g., via a peptide linker.

In another aspect, antibody-drug conjugates (ADCs) are provided, in which the anti-glycPD-L1 antibodies as described herein, in particular, those that show effective internalization activity following binding to glycosylated PD-L1, are chemically linked to antineoplastic drugs and agents to produce an anti-glycPD-L1 antibody-drug conjugate, as described and exemplified herein. In embodiments, the anti-glycPD-L1 MAb ADCs are highly effective in killing tumor or cancer cells and in antineoplastic therapies for treating subjects with cancer. In embodiments, the antiglycPD-L1 antibody component of the ADC is a bispecific, multispecific, biparatopic, or multiparatopic antibody, or an antigen binding portion thereof. In other embodiments, the anti-glycPD-L1 antibody is chemically linked to an antimitotic agent, such as a maytansine derivative, e.g., a maytansinoid such as DM1 or DM4, or to a tubulin-polymerizing auristatin, e.g., monomethyl auristatin E (MMAE) or monomethyl auristatin F (MMAF), as described further herein. In an embodiment, the linker to the anti-glycPD-L1 antibody is stable in extracellular fluid, but is cleaved by cathepsin once the ADC has entered a tumor or cancer cell, thus activating the antimitotic mechanism of MMAE or other toxin drug. In an embodiment, the antibody component of the ADC is STM073 MAb or STM108 MAb as described herein. In an embodiment, the STM108 MAb-containing ADC (STM108-ADC) is chemically linked to MMAE via a cleavable linker. In a particular embodiment, the STM108-ADC comprises a structure in which the STM108 MAb is chemically linked via cysteine residues in its C-region to a maleimide and caproic acid (MC) attachment group, which is chemically linked to a cathepsin-cleavable linker, such as "vc" consisting of valine (Val) and citruline (Cit), which is chemically attached to the spacer "PAB", i.e., paraminobenzoic acid, which is chemically linked to MMAE cytotoxin, thus producing the ADC, designated by its component structure STM108-MC-vc-PAB-MMAE.

BRIEF DESCRIPTION OF THE DRAWINGS

The following drawings form part of the present specification and are included to further demonstrate certain aspects of the embodiments described herein without being limiting. The patent or application file contains at least one drawing executed in color. Copies of this patent or patent application publication with color drawing(s) will be provided by the Office upon request and payment of the necessary fee.

FIGS. 6A and 6B. N-glycosylation Sites of PD-L1 Protein. A sequence alignment of the PD-L1 amino acid sequences from different species. Four NXT motifs, N35, N192, N200, and N219 are boxed and presented in red, and two non-NXT motifs, N63 and N204 are presented in green. Red box=conserved NXT motif. FIG. 6A: Consensus sequence (SEQ ID NO: 74); Q9NZQ7_HUMAN (SEQ ID NO: 75); Q9EP73_MOUSE (SEQ ID NO: 76); D4AE25_RAT (SEQ ID NO: 77); C5NU11_BOVINE (SEQ ID NO: 78); Q4QTK1_PIG (SEQ ID NO: 79); and F7DZ76_HORSE (SEQ ID NO: 80). FIG. 6B: Consensus sequence (SEQ ID NO: 94); Q9NZQ7_HUMAN (SEQ ID NO: 95); Q9EP73_MOUSE (SEQ ID NO: 96); D4AE25_RAT (SEQ ID NO: 97); C5NU11_BOVINE (SEQ ID NO: 98); Q4QTK1_PIG (SEQ ID NO: 99); and F7DZ76_HORSE (SEQ ID NO: 100).

FIG. 11 shows cell death of BT549 (RFP PD-L1 (WT) cells treated with MAb STM073 in real time. In FIG. 11, the bottom plotted line (solid orange diamonds) represents the control (no T cells from PBMCs); the solid inverted purple triangles represent a No Antibody control; the solid green triangles represent 10 µg/ml of the STM073 MAb used in the assay; the solid red squares represent 20 µg/ml of the STM073 MAb used in the assay; and the solid blue circles represent 40 µg/ml of the STM073 MAb used in the assay. As observed from FIG. 11, a dose proportional killing of PD-L1 bearing tumor cells over time is demonstrated.

FIGS. 12A-12C show the results of a binding assay as described in Example 10, in which the STM073 MAb (A) and the STM108 MAb (B) are seen to block binding of PD-1 to BT549 target cells expressing WT PD-L1 in a dose dependent manner versus assay controls, i.e., No PD-1/Fc; No Ab; mIgG Ab controls (C).

FIG. 13 shows the results of a Western blot of PD-L1 protein from A431 cells cultured overnight in serum free medium and treated with anti-glycPD-L1 antibody (10 µg) as described herein for 2 days. Shorter and longer exposures of the blot are presented. Tubulin is presented as a control. The lane designated "73," represents treatment of A431 cells with the STM073 MAb and shows decreased levels of PD-L1 in the STM073-treated cells relative to treatment with control (IgG lane). The results support the promotion or enhancement of internalization and degradation of PD-L1 by anti-glycPD-L1 antibodies, such as STM073, as described herein.

FIG. 14A: Wild type BT 549 cells (human ductal carcinoma, breast cancer cell line) incubated with STM073; FIG. 14B: BT 549 cells molecularly engineered to express PD-L1 WT (glycosylated) incubated with STM073; FIG. 14C: NCI-H226 cells (human lung cancer cell line, squamous cell mesothelioma) incubated with STM073; FIG. 14D: MCF-7 cells (human breast cancer cell line, adenocarcinoma) incubated with STM073; and FIG. 14E: BT 549 cells expressing PD-L1 WT (glycosylated) incubated with STM108.

FIGS. 15A-15C show the results of live cell imaging of PD-L1-expressing cells incubated with dual function anti-glycPD-L1 antibody. In FIGS. 15A-15C, the anti-PD-L1 antibody is STM108 MAb conjugated to a red fluorescent dye, pHrodo™ Red (succinimidyl ester (pHrodo™ Red, SE), (ThermoFisher Scientific, Waltham, Mass.). pHrodo™ Red dye conjugates are non-fluorescent outside the cell, but fluoresce brightly red in phagosomes, which makes them useful reagents for studies ranging from phagocytosis of bioparticles to receptor internalization. Green staining reflects cells stained with LysoTracker® Green DND-26, which is a cell permeable green dye that stains acidic compartments (lysosomes) in live cells imaged via live cell imaging. FIG. 15A shows that at a first time point (Time 0), STM108 is internalized into cells as depicted by the intense red intracellular staining of cells indicated by the arrow. FIG. 15B shows the weakened intracellular red staining in the same cells depicted in FIG. 15A, at a time 2 minutes after the time point in FIG. 15A. FIG. 15C shows the lack of red intracellular staining 4 minutes after the time point in FIG. 15A, which reflects the degradation of the STM108 antibody and/or the antibody-antigen complex inside the cells.

FIGS. 16A-16L. Internalization of PD-L1 Bound by Anti-PD-L1 Antibodies in Tumor Cells Versus Total T Cells. FIGS. 16A-16L present images of cells showing the ability of the dual function anti-glycPD-L1 antibodies to internalize into PD-L1 positive tumor cells, but not into either activated or non-activated T cells. FIGS. 16A-16D show images of non-activated total T cells from peripheral blood following incubation with the following antibodies: mouse IgG antibody control (FIG. 16A); non-internalizing anti-glycPD-L1 MAb STM004 (FIG. 16B); dual function anti-glycPD-L1 MAb STM073 (FIG. 16C); and dual function anti-glycPD-L1 antibody STM108 (FIG. 16D). FIGS. 16A-16D show that none of the antibodies tested were internalized into non-activated total T cells. FIGS. 16E-16H show images of activated total T cells from peripheral blood following incubation with the following antibodies: mouse IgG antibody control (FIG. 16E); non-internalizing STM004 (FIG. 16F); dual function STM073 (FIG. 16G); and dual function STM108 (FIG. 16H). For T cell activation, total T cells were mixed with beads, e.g., inert, superparamagnetic beads, covalently coupled with anti-CD3 and anti-CD28 antibodies (e.g., ThermoFisher Scientific, Rochester, N.Y.) at a 1:1 ratio. FIGS. 16E-16H show that virtually no internalization into activated total T cells was observed with any of the antibodies tested. FIGS. 16I-16L show images of NCI-H226 cells (human lung cancer cell line, squamous cell mesothelioma) following incubation with the following antibodies: mouse IgG antibody control (FIG. 16I); non-internalizing anti-glycPD-L1 antibody STM004 (FIG. 16J); dual function anti-glycPD-L1 MAb STM073 (FIG. 16K); and dual function anti-glycPD-L 1 MAb STM108 (FIG. 16L). FIGS. 16I-16L show that the dual function, internalizing STM073 and STM108 MAbs were internalized into NCI-H226 cells following incubation with these cells, as evidenced by red intracellular staining, compared with the control antibody, mIgG (FIG. 16I) and with a non-internalizing STM004 MAb.

FIGS. 17A-17D present the results of experiments evaluating the efficacy of ADCs comprising dual function anti-glycPD-L1 MAb STM108, coupled to MMAE to produce an antibody-drug conjugate (STM108-ADC as described herein, in killing PD-L1-expressing and non-PD-L1-expressing tumor cells and in reducing the volume of tumors in tumor-grafted mice following injection of tumored animals with the STM108-ADC compared with tumored animals injected with controls (IgG and STM108 MAb alone). FIG. 17A shows the % viability of PD-L1-expressing MDA-MB231 (human breast carcinoma cell line) tumor cells ("MB231") following exposure to different concentrations (nM) of STM108-ADC (filled black circles) compared with the % viability of MB231 cells molecularly engineered to knock out their expression of PD-L1 ("MB231 PDL1 KO") following exposure to different concentrations of STM108-ADC, i.e., "ADC108" (filled black squares). In FIG. 17B, an MDA-MB231 mouse model of breast cancer was used in which animals grafted with tumors derived from MB231 cells were treated with either an IgG-MMAE control (100 μg); or with STM108-ADC ("ADC") at 50 at 100 or at 150 μg; or with 100 μg of STM108 MAb, as indicated on the graph in FIG. 17B. Complete response ("CR") was observed in 3 of 5 mice administered 100 μg STM108-ADC and in 4 of 5 mice administered 150 μg STM108-ADC. FIG. 17C shows the % viability of 4T1 mammary carcinoma cells molecularly engineered to express human PD-L1 on the cell surface ("4T1 hPDL1") following exposure to different concentrations (nM) of STM108-ADC (open red circles) compared with the % viability of 4T1 cells that naturally do not express PD-L1 ("4T1") following exposure to different concentrations of STM108-ADC, i.e., "ADC108" (open red squares). In FIG. 17D, 4T1 syngeneic mouse models of breast cancer were used in which the animals (Balb/c mice) were grafted with tumors derived from 4T1 mammary carcinoma cells that had been molecularly engineered to express PD-L1 or the cell surface ("4T1 hPD-L1"), or in which the Balb/c mice were grafted with tumors derived from untransfected 4T1 mammary carcinoma cells that do not naturally express PD-L1 on the cell surface ("4T1"). Animals harboring tumors derived from the two types of 4T1 cells were treated with either an IgG-MMAE control (100 μg); or with STM108 MAb (100 μg), or with STM108-ADC (100 m), as indicated on the graph of FIG. 17D. See, Example 14.

Other aspects, features and advantages of the described embodiments will become apparent from the following detailed description and illustrative examples.

DETAILED DESCRIPTION OF THE EMBODIMENTS

The extracellular interaction between programmed death ligand-1 protein (PD-L1) expressed on tumor cells and programmed death-1 protein (PD-1) expressed on immune effector cells, e.g., T-cells, has a marked impact on tumor-associated immune escape. Despite the clinical success of immune checkpoint blockade using anti-PD-1 or anti-PD-L1 antibodies, the regulatory mechanisms and structural features underlying the PD-L1 and PD-1 interaction remain largely unknown. In accordance with the findings described herein, it has been demonstrated that N-linked glycosylation of PD-L1 stabilizes the PD-L1 protein ligand as present on tumor cells and also facilitates and enhances its binding to PD-1, which promotes the suppression of T cell-mediated immune response. Conversely, it has been found that aberrant or loss of N-linked glycosylation, such as from partial or complete deglycosylation of the PD-L1 polypeptide expressed on tumor cells, adversely affects, e.g., weakens or disrupts, the PD-L1/PD-1 interaction and promotes the internalization and degradation of PD-L1 on the tumor cells, which, in turn, inhibits immunosuppression and promotes effector T-cell cytotoxic activity and killing of tumor cells. In addition, because the survival of patients whose tumors express highly glycosylated PD-L1 is poor, glycosylated PD-L1 is recognized, based on the findings herein, as an effective therapeutic target for cancer treatment. Provided and described herein are cancer therapeutics, such as dual function anti-glycPD-L1 antibodies, that specifically and preferentially bind and interact with glycosylated PD-L1 to disrupt a glycosylated PD-L1/PD-1 interaction and to destabilize the PD-L1 expressed on the tumor cell surface, thereby inhibiting immunosuppression and promoting T-cell effector function against the tumor cells so as to treat cancer. Tumor treatment with the dual function anti-glycosylated PD-L1 antibodies as described herein offers enhanced immunosuppression inhibitory effects relative to anti-PD-L1 antibodies that are not specific for glycosylated forms of PD-L1. In embodiments, the anti-glycPD-L1 antibodies are monoclonal antibodies, designated "MAbs" herein.

Figures 1A, 1B, 1C, 1D, 1E, 1F, 1G, 1H:
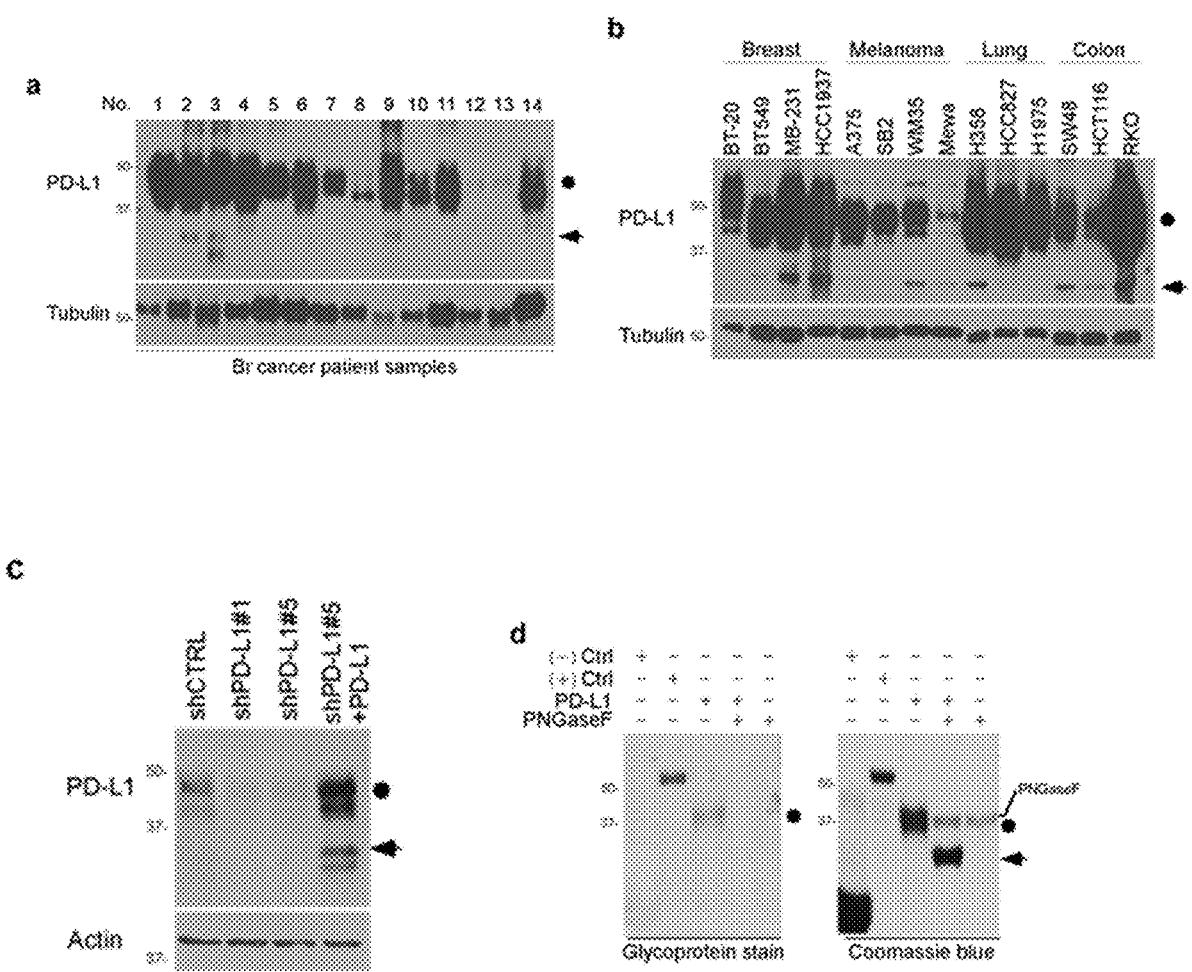
FIGS. 1A-1H. PD-L1 is Glycosylated in Cancer Cells. 1A. Expression of PD-L1 protein in primary breast cancer patient samples. Western blot analysis of PD-L1 in representative breast cancer patient samples. 1B. Western blot analysis of PD-L1 in four representative breast cancer cell lines, four melanoma cell lines, three lung cancer cell lines and three colon cancer cell lines. 1C. Western blot analysis of PD-L1 expression in shCTRL and two independent shPD-L1 stable clones of A431 cells. PD-L1 was transiently transfected into the shPD-L1 #5 clone. D. Glycoprotein staining of purified PD-L1 protein with or without PNGase F treatment. The Coomassie blue stained panel represents the total amount of PD-L1 protein. The upper bands which appear in lanes 4 and 5 are from the loading of PNGase F. (−) Ctrl, a control for non-glycoprotein; (+) Ctrl, a control for glycoprotein. E. Glycosylation pattern of PD-L1-GFP, HA-PD-L1, and PD-L1-Flag proteins. Cell lysates were treated with PNGase F and Endo H and analyzed by Western blot. F. GFP-tagged PD-L1 full length (WT), extracellular domain (ECD), or intracellular domain (ICD) was transiently expressed in 293T cells. Cells were then treated with or without 5 μg/ml tunicamycin (TM) overnight. Protein expression of PD-L1 was examined using Western blot. G. Schematic diagram of a representative PD-L1 protein expression construct as used in the experimental studies described herein, showing the full-length PD-L1 protein and its component extracellular domain (ECD), intracellular domain (ICD), signal peptide (SP), transmembrane domain (TM). In the diagram, four N-glycosylation sites (NXT motifs) in the ECD domain of PD-L1 are shown in red. The numbers indicate the positions of the amino acid residues in the PD-L1 polypeptide. H. Western blot analysis of the protein expression pattern of PD-L1 WT and glycosylation mutants (NQ mutants) of PD-L1. Lane 14 indicates non-glycosylated, wild-type (WT) PD-L1 treated overnight with tunicamycin (TM). In the figures, the black circles indicate glycosylated PD-L1, and the black arrowheads indicate non-glycosylated PD-L1.
Figures 1A, 1B, 1C, 1D, 1E, 1F, 1G, 1H:
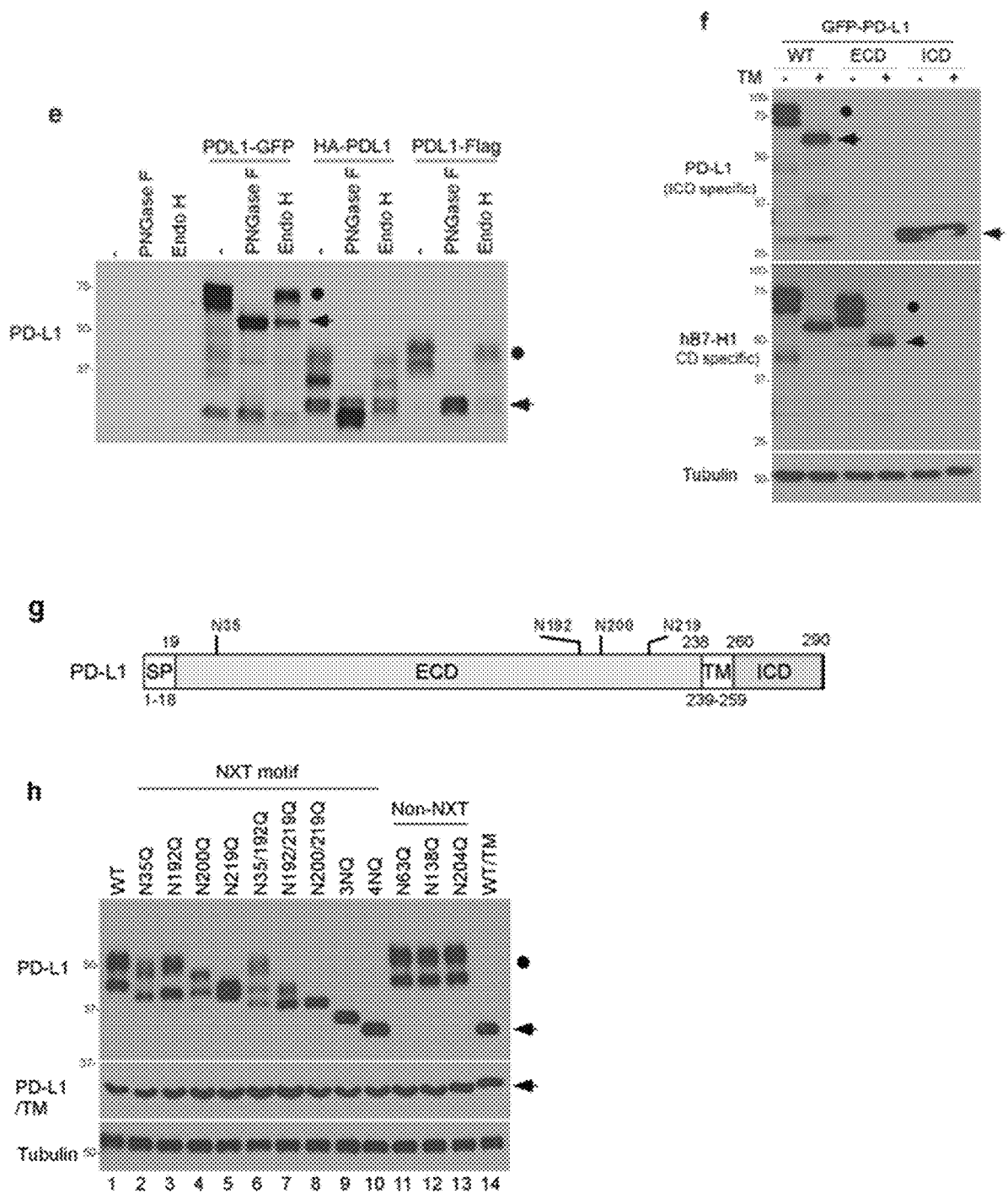

Provided herein are dual function anti-glycPD-L1 antibodies that bind epitopes in the extracellular domain (ECD) of PD-L1 corresponding to glycosylation sites, particularly in the N-terminal and C-terminal portions of the PD-L1 ECD or alternatively binding so as to block or mask those glycosylation sites. The amino acids that are glycosylated in the PD-L1 protein are in its extracellular domain, as shown in FIG. 1G, at positions 35, 192, 200 and 219 of PD-L1 as numbered in SEQ ID NO: 1 herein. In accordance with the present findings, the anti-glycPD-L1 antibodies described herein are dual functional in that they reduce, block, or inhibit binding of PD-L1 to PD-1 and also promote PD-L1 internalization and degradation to reduce the levels of PD-L1 expressed on the tumor cell. In embodiments, the dual functional anti-glycPD-L1 antibodies as described bind nonlinear, conformational epitopes. In addition, and without wishing to be bound by theory, the anti-glycPD-L1 antibodies bind epitopes that contain glycosylated amino acids or are proximal in the three dimensional space to glycosylated amino acids; such glycosylated amino acids are believed to be particularly involved in the PD-L1/PD-1 interaction and also involved in maintenance of the PD-L1 on the surface of the tumor cell. Not to be bound by theory, glycan structures associated with N35 within the ECD N-terminus of glycosylated PD-L1 may comprise or contribute to a functional structure or configuration of the glycosylated PD-L1 protein that is recognized and bound by PD-1 protein and that plays a significant role in the PD-1/PD-L1 interaction. By binding an epitope comprising the amino acid at position 35, in the N-terminal region of the PD-L1 ECD, or an epitope proximal to position 35, the dual function anti-glycPD-L1 antibodies as described mask the binding sites or regions of the glycosylated PD-L1 protein that may be particularly involved in the PD-L1/PD-1 interaction. By binding or, through binding, masking, amino acids in the C-terminal region of the PD-L1 ECD that comprises glycosylated amino acid residues (N192, N200 and N219), the dual function anti-glycPD-L1 antibodies as described effectively mask the binding sites or regions of the glycosylated PD-L1 protein that may be particularly involved in the stabilization of PD-L1 on the surface of the tumor cell, thereby promoting PD-L1 internalization and degradation and reducing the levels of PD-L1 on the tumor cells.

The dual function anti-glycPD-L1 antibodies described herein may bind to epitopes comprising or masking amino acids in both the N- and C-terminal regions of PD-L1 ECD, particularly amino acids within nonlinear, conformation epitopes, resulting in the masking or concealment by the anti-glycPD-L1 antibodies of those glycan-containing residues or regions of the PD-L1 protein that are involved in the PD-L1/PD-1 interaction and in the stabilization of PD-L1 on the tumor cell surface. Such anti-glycPD-L1 antibodies inhibit or block the binding of PD-L1 to PD-1 and also reduce the levels of PD-L1 on the tumor cell surface such that fewer PD-L1 molecules are available to bind to PD-1. The anti-glycPD-L1 antibodies, when provided in mixtures with effector T-cells and PD-1-bearing tumor or cancer calls, promote the killing of such tumor or cancer cells by the T-cells, which are not immunosuppressed by the PD-1/PD-L1 interaction. (See, e.g., FIG. 11 and Example 9).

The Examples described herein provide experimental results showing a significant difference, e.g., 2-3 fold, in binding of glycosylated PD-L1 versus non-glycosylated PD-L1 by the anti-glycPD-L1 antibodies as described herein. In embodiments, the anti-glycPD-L 1 antibodies exhibit a binding affinity for glycosylated PD-L1 in the nanomolar range, e.g., from about 5-20 nM or about 10-20 nM, relative to non-glycosylated PD-L1. The Examples further show that the anti-glycPD-L1 antibodies are internalized by PD-L1 expressing tumor cells but not by T cells (either activated or non-activated) (FIGS. 16A-16L); the anti-glycPD-L1 antibodies also reduce viability and tumor volume of PD-L1 expressing tumor cells in a mouse model harboring tumors derived from tumor cell lines (FIGS. 17A-17D).

Definitions

As used herein, the term "a" or "an" may mean one or more.

As used herein, the term "or" means "and/or" unless explicitly indicated to refer to alternatives only or the alternatives are mutually exclusive, although the disclosure supports a definition that refers to only alternatives and "and/or."

As used herein, the term "another" means at least a second or more.

As used herein, the term "about" is used to indicate that a value includes the inherent variation of error for the device, the method being employed to determine the value, or the variation that exists among the study subjects.

As used herein, the term "programmed death ligand-1" or "PD-L1" refers to a polypeptide (the terms "polypeptide" and "protein" are used interchangeably herein) or any native PD-L1 from any vertebrate source, including mammals such as primates (e.g., humans, cynomolgus monkey (cyno)), dogs, and rodents (e.g., mice and rats), unless otherwise indicated, and, in certain embodiments, included various PD-L1 isoforms, related PD-L1 polypeptides, including SNP variants thereof.

An exemplary amino acid sequence of human PD-L1 (UniProtKB/Swiss-Prot: Q9NZQ7.1; GI:83287884), is provided below:

MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET (SEQ ID NO: 1). In SEQ ID NO: 1, the amino terminal amino acids 1-18 constitute the signal sequence of the human PD-L 1 protein. Accordingly, the mature human PD-L1 protein consists of amino acids 19-290 of SEQ ID NO: 1.

Abbreviations for the amino acid residues that comprise polypeptides and peptides described herein, and conservative substitutions for these amino acid residues are shown in Table 1 below. A polypeptide that contains one or more conservative amino acid substitutions or a conservatively modified variant of a polypeptide described herein refers to a polypeptide in which the original or naturally occurring amino acids are substituted with other amino acids having similar characteristics, for example, similar charge, hydrophobicity/hydrophilicity, side-chain size, backbone conformation, structure and rigidity, etc. Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity.

TABLE 1

Amino Acid Residues and Examples of Conservative Amino Acid Substitutions

| Original residue Three letter code and Single letter code | Conservative substitution(s) |
|---|---|
| Alanine (Ala) (A) | Gly; Ser |
| Arginine (Arg) (R) | Lys; His |
| Asparagine (Asn) (N) | Gln; His |
| Aspartic Acid (Asp) (D) | Glu; Asn |
| Cysteine (Cys) (C) | Ser; Ala |
| Glutamine (Gln) (Q) | Asn |
| Glutamic Acid (Glu) (E) | Asp; Gln |
| Glycine (Gly) (G) | Ala |
| Histidine (His) (H) | Asn; Gln |
| Isoleucine (Ile) (I) | Leu; Val |
| Leucine (Leu) (L) | Ile; Val |
| Lysine (Lys) (K) | Arg; His |
| Methionine (Met) (M) | Leu; Ile; Tyr |
| Phenylalanine (Phe) (F) | Tyr; Met; Leu |
| Proline (Pro) (P) | Ala |
| Serine (Ser) (S) | Thr |
| Threonine (Thr) (T) | Ser |
| Tryptophan (Trp) (W) | Tyr; Phe |
| Tyrosine (Tyr) (Y) | Trp; Phe |
| Valine (Val) (V) | Ile; Leu |

The terms "antibody," "immunoglobulin," and "Ig" are used interchangeably herein in a broad sense and specifically cover, for example, individual anti-PD-L1 antibodies, such as the monoclonal antibodies described herein, (including agonist, antagonist, neutralizing antibodies, full length or intact monoclonal antibodies, peptide fragments of antibodies that maintain antigen binding activity), anti-unglycosylated PD-L1 antibodies and anti-glycosylated PD-L1 antibodies; anti-PD-L1 antibody compositions with polyepitopic or monoepitopic specificity, polyclonal or monovalent antibodies, multivalent antibodies, multi specific antibodies (e.g., bispecific antibodies or biparatopic antibodies, so long as they exhibit the desired biological activity), formed from at least two intact antibodies, single chain anti-PD-L1 antibodies, and fragments of anti-PD-L1 antibodies, as described below. An antibody can be human, humanized, chimeric and/or affinity matured. An antibody may be from other species, for example, mouse, rat, rabbit, etc. The term "antibody" is intended to include a polypeptide product of B cells within the immunoglobulin class of polypeptides that is able to bind to a specific molecular antigen. An antibody is typically composed of two identical pairs of polypeptide chains, wherein each pair has one heavy chain (about 50-70 kDa) and one light chain (about 25 kDa); and wherein the amino-terminal portion of the heavy and light chains includes a variable region of about 100 to about 130 or more amino acids and the carboxy-terminal portion of each chain includes a constant region (See, *Antibody Engineering*, Borrebaeck (ed.), 1995, Second Ed., Oxford University Press.; Kuby, 1997, *Immunology*, Third Ed., W.H. Freeman and Company, New York). In specific embodiments, the specific molecular antigen bound by an antibody provided herein includes a PD-L1 polypeptide, a PD-L1 peptide fragment, or a PD-L1 epitope. The PD-L1 polypeptide, PD-L1 peptide fragment, or PD-L1 epitope can be unglycosylated or glycosylated. In a particular embodiment, the PD-L1 polypeptide, PD-L1 peptide fragment, or PD-L1 epitope is glycosylated, An antibody or a peptide fragment thereof that binds to a PD-L1 antigen can be identified, for example, by immunoassays, Biacore, or other techniques known to those of skill in the art. An antibody or a fragment thereof binds specifically to a PD-L1 antigen when it binds to a PD-L1 antigen with higher affinity than to any cross-reactive antigen as determined using experimental techniques, such as radioimmunoassays (MA) and enzyme linked immunosorbent assays (ELISAs). Typically, a specific or selective binding reaction will be at least twice background signal or noise, and more typically more than 5-10 times background signal or noise. See, e.g., *Fundamental Immunology Second Edition*, Paul, ed., 1989, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigen-binding fragments such as PD-L1 binding fragments) of any of the above. A binding fragment refers to a portion of an antibody heavy or light chain polypeptide, such as a peptide portion, that retains some or all of the binding activity of the antibody from which the fragment is derived. Non-limiting examples of functional fragments (e.g., antigen-binding fragments such as PD-L1 binding fragments) include single-chain Fvs (scFv) (e.g., including monospecific, bispecific, biparatopic, monovalent (e.g., with a single $V_H$ or $V_L$ domain) or bivalent, etc.), Fab fragments, F(ab') fragments, F(ab)$_2$ fragments, F(ab')$_2$ fragments, disulfide-linked Fvs (sdFv), Fd fragments, Fv fragments, diabodies, triabodies, tetrabodies and minibodies. In particular, antibodies provided herein include immunoglobulin molecules and immunologically active portions of immunoglobulin molecules, for example, antigen binding domains or molecules that contain an antigen-binding site that binds to a PD-L1 antigen, in particular, a glycosylated PD-L1 antigen, (e.g., one or more complementarity determining regions (CDRs) of an anti-PD-L1 antibody). Description of such antibody fragments can be found in, for example, Harlow and Lane, 1989, *Antibodies: A Laboratory Manual*, Cold Spring Harbor Laboratory, New York; *Molec. Biology and Biotechnology: A Comprehensive Desk Reference*, Myers (ed.), New York: VCH Publisher, Inc.; Huston et al., 1993, *Cell Biophysics*, 22:189-224; Plückthun and Skerra, 1989, *Meth. Enzymol.*, 178:497-515 and in Day, E. D., 1990, *Advanced Immunochemistry*, Second Ed., Wiley-Liss, Inc., New York, N.Y. The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In certain embodiments, the anti-PD-L1 antibodies are fully human, such as fully human monoclonal anti-PD-L1 antibodies. In certain embodiments, the anti-PD-L1 antibodies are humanized, such as humanized monoclonal anti-PD-L1 antibodies. In certain embodiments, the antibodies provided herein are IgG antibodies, or a class (e.g., human IgG1 or IgG4) or subclass thereof, in particular, IgG1 subclass antibodies.

A four-chain antibody unit is a heterotetrameric glycoprotein composed of two identical light (L) chains and two identical heavy (H) chains. In the case of IgGs, the molecular weight of the four-chain (unreduced) antibody unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. At the N-terminus, each H chain has a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its carboxy terminus. The $V_L$ domain is aligned with the $V_H$ domain, and the $C_L$ domain is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site (although certain $V_H$ and $V_L$ domains can bind antigen independently of the counterpart $V_H$ or $V_L$, respectively). The basic structure of immunoglobulin molecules is understood by those having skill in the art. For example, the structure and properties of the different classes of antibodies may be found in Stites, Daniel P. et al., 1994, *Basic and Clinical Immunology*, 8th edition, Appleton & Lange, Norwalk, Conn., page 71 and Chapter 6.

As used herein, the term "antigen" or "target antigen" is a predetermined molecule to which an antibody can selectively bind. A target antigen can be a polypeptide, peptide, carbohydrate, nucleic acid, lipid, hapten, or other naturally occurring or synthetic compound. In embodiments, a target antigen is a small molecule. In certain embodiments, the target antigen is a polypeptide or peptide, preferably a glycosylated PD-L1 polypeptide.

As used herein, the term "antigen binding fragment," "antigen binding domain," "antigen binding region," and similar terms refer to that portion of an antibody which includes the amino acid residues that interact with an antigen and confer on the antibody as binding agent its specificity and affinity for the antigen (e.g., the CDRs of an antibody are antigen binding regions). The antigen binding region can be derived from any animal species, such as rodents (e.g., rabbit, rat, or hamster) and humans. In specific embodiments, the antigen binding region can be of human origin.

An "isolated" antibody is substantially free of cellular material or other contaminating proteins from the cell or tissue source and/or other contaminant components from which the antibody is derived, or is substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of an antibody that have less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and can include enzymes, hormones, and other proteinaceous or nonproteinaceous solutes. In certain embodiments, the antibody is purified (1) to greater than or equal to 95% by weight of the antibody, as determined by the Lowry method (Lowry et al., 1951, *J. Bio. Chem.*, 193: 265-275), such as 95%, 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody also includes the antibody in situ within recombinant cells since at least one component of the antibody's natural environment will not be present. An isolated antibody is typically prepared by at least one purification step. In some embodiments, the antibodies provided herein are isolated.

As used herein, the term "binds" or "binding" refers to an interaction between molecules including, for example, to form a complex. Illustratively, such interactions embrace non-covalent interactions, including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site of an antibody and its epitope on a target (antigen) molecule, such as PD-L1, is the affinity of the antibody or functional fragment for that epitope. The ratio of association ($k_{on}$) to dissociation ($k_{off}$) of an antibody to a monovalent antigen ($k_{on}/k_{off}$) is the association constant $K_a$, which is a measure of affinity. The value of $K_a$ varies for different complexes of antibody and antigen and depends on both $k_{on}$ and $k_{off}$. The association constant $K_a$ for an antibody provided herein may be determined using any method provided herein or any other method known to those skilled in the art. The affinity at one binding site does not always reflect the true strength of the interaction between an antibody and an antigen. When complex antigens containing multiple antigenic determinants, such as a glycosylated PD-L1, come into contact with antibodies containing multiple binding sites, the interaction of antibody with antigen at one site will increase the probability of an interaction at a second binding site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen or receptor and ligand). The affinity of a binding molecule X for its binding partner Y can generally be represented by the dissociation constant ($K_d$). Affinity can be measured by common methods known in the art, including those described herein. Low-affinity antibodies generally bind antigen slowly and tend to dissociate readily, while high-affinity antibodies generally bind antigen faster and tend to remain bound longer to antigen. A variety of methods for measuring binding affinity are known in the art, any of which may be used for purposes of the present disclosure. Specific illustrative embodiments include the following: In one embodiment, the "$K_d$" or "$K_d$ value" is measured by assays known in the art, for example, by a binding assay. The $K_d$ can be measured in a radiolabeled antigen binding assay (RIA), for example, performed with the Fab portion of an antibody of interest and its antigen (Chen et al., 1999, *J. Mol. Biol.*, 293:865-881). The $K_d$ or $K_d$ value may also be measured by using surface plasmon resonance (SPR) assays (by Biacore) using, for example, a BIAcore™-2000 or a BIAcore™-3000 (BIAcore, Inc., Piscataway, N.J.), or by biolayer interferometry (BLI) using, for example, the OctetQK384 system (ForteBio, Menlo Park, Calif.), or by quartz crystal microbalance (QCM) technology. An "on-rate" or "rate of association" or "association rate" or "$k_{on}$" can also be determined with the same surface plasmon resonance or biolayer interferometry techniques described above, using, for example, a BIAcore™-2000 or a BIAcore™-3000 (BIAcore, Inc., Piscataway, N.J.), or the OctetQK384 system (ForteBio, Menlo Park, Calif.).

The terms "anti-PD-L1 antibody," "an antibody that specifically binds to PD-L1," or "antibody that is specific for PD-L1," "antibodies that specifically bind to a PD-L1 epitope," "an antibody that selectively binds to PD-L1," "antibodies that selectively bind to a PD-L1 epitope," "an antibody that preferentially binds to PD-L1, and analogous terms are used interchangeably herein and refer to antibodies capable of binding PD-L1, i.e., glycosylated or WT PD-L1, with sufficient affinity and specificity, particularly compared with non-glycosylated PD-L1 or glycosylation mutants of PD-L1. "Preferential binding" of the anti-glycPD-L1 antibodies as provided herein may be determined or defined based on the quantification of fluorescence intensity of the antibodies' binding to PD-L1, i.e., glycosylated PD-L1 polypeptide, or PD-L1 WT, or glycosylated PD-L1 expressed on cells versus an appropriate control, such as binding to non-glycosylated or variant PD-L1 (e.g., 4NQ PD-L1), or to cells expressing a non-glycosylated or variant form of PD-L1 (e.g., 4NQ PD-L1), for example, molecularly engineered cells, cell lines or tumor cell isolates, such as described herein, e.g., in Example 6. Preferential binding of an anti-glycPD-L1 antibody as described to a glycosylated PD-L1 polypeptide or to a glycosylated PD-L1 (PD-L1 WT)-expressing cell is indicated by a measured fluorescent binding intensity (MFI) value, as assessed by cell flow cytometry, of at least 1.5-fold, at least 2-fold, at least 3-fold, at least 4-fold, at least 5-fold, at least 6-fold, at least 7-fold, at least 8-fold, at least 10-fold, at least 15-fold, at least 20-fold or greater, as compared with binding of the antibody to a non-glycosylated or mutant glycosylated PD-L1 polypeptide or a non-glycosylated or mutant glycosylated PD-L1-expressing cell, and wherein the antibody to be assayed is directly or indirectly detectable by a fluorescent label or marker. In an embodiment, the antibody is directly labeled with a fluorescent marker, such as FITC. In embodiments, an anti-glycPD-L1 antibody that preferentially or selectively binds glycosylated PD-L1 exhibits an MFI value of from 1.5-fold to 25-fold, or from 2-fold to 20-fold, or from 3-fold to 15-fold, or from 4-fold to 8-fold, or from 2-fold to 10-fold, or from 2-fold to 5-fold or more greater than the MFI value of the same antibody for binding a non-glycosylated PD-L1 or a PD-L1 glycosylation variant as described herein e.g., 4NQ PD-L1, which is not glycosylated. Fold-fluorescence intensity values between and equal to all of the foregoing are intended to be included. In an embodiment, the anti-glycPD-L1 antibodies specifically and preferentially bind to a glycosylated PD-L1 polypeptide, such as a glycosylated PD-L1 antigen, peptide fragment, or epitope (e.g., human glycosylated PD-L1 such as a human glycosylated PD-L1 polypeptide, antigen or epitope). An antibody that specifically binds to PD-L1, (e.g., glycosylated or wild type human PD-L1) can bind to the extracellular domain (ECD) or a peptide derived from the ECD of PD-L1. An antibody that specifically binds to a PD-L1 antigen (e.g., human PD-L1) can be cross-reactive with related antigens (e.g., cynomolgus (cyno) PD-L1). In a preferred embodiment, an antibody that specifically binds to a PD-L1 antigen does not cross-react with other antigens. An antibody that specifically binds to a PD-L1 antigen can be identified, for example, by immunofluorescence binding assays, immunoassay methods, immunohistochemistry assay methods, Biacore, or other techniques known to those of skill in the art.

In certain other embodiments, an antibody that binds to PD-L1, as described herein, has a dissociation constant ($K_d$) of less than or equal to 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In certain embodiments, an anti-PD-L1 antibody binds to an epitope of PD-L1 that is conserved among PD-L1 proteins from different species (e.g., between human and cynomolgus PD-L1). An antibody binds specifically to a PD-L1 antigen when it binds to a PD-L1 antigen with higher affinity than to any cross reactive antigen as determined using experimental techniques, such as radioimmunoassays (MA) and enzyme linked immunosorbent assays (ELISAs). Typically a specific or selective reaction will be at least twice background signal or noise and can be more than 10 times background. See, e.g., *Fundamental Immunology Second Edition*, Paul, ed., 1989, Raven Press, New York at pages 332 336 for a discussion regarding antibody specificity. In such embodiments, the extent of binding of the antibody to a "non-target" protein will be less than about 10% of the binding of the antibody to its particular target protein, for example, as determined by fluorescence activated cell sorting (FACS) analysis or radioimmunoprecipitation (RIA).

Anti-PD-L1 antibodies as described herein include anti-glycosylated PD-L1 antibodies or anti-wild type PD-L1 antibodies, wherein wild type PD-L1 protein is glycosylated, which are specific for glycosylated PD-L1. In some embodiments, the anti-glycosylated PD-L1 antibodies bind to a linear glycosylation motif of PD-L1. In some embodiments, the anti-glycosylated PD-L1 antibodies bind to a peptide sequence that is located near one or more of the glycosylation motifs in three dimensions. In some embodiments, the anti-glycosylated PD-L1 antibodies selectively bind to one or more glycosylation motifs of PD-L1 or a PD-L1 peptide having a glycosylation motif of PD-L1 relative to unglycosylated PD-L1. In other embodiments, the anti-glycPD-L1 antibodies bind to a linear epitope comprising amino acids of the PD-L1 protein. In some embodiments, the anti-glycosylated PD-L1 antibodies selectively bind to one or more glycosylation motifs of PD-L1, in which the glycosylation motifs comprise N35, N192 N200, and/or N219 of the PD-L1 polypeptide of SEQ ID NO: 1. In yet other embodiments, the anti-glycPD-L1 antibodies bind to a conformational (nonlinear) epitope comprising amino acids of the PD-L1 protein. In some embodiments, an anti-glycPD-L1 antibody, or a binding portion thereof, binds to glycosylated PD-L1 with a $K_d$ less than at least 30%, 35%, 40%, 45%, 50%, 55%, 60%, 65%, 70%, 75%, 80%, 85%, or 90% of the $K_d$ exhibited relative to unglycosylated PD-L1. In certain embodiments, an anti-glycPD-L1 antibody, or a binding portion thereof, binds to glycosylated PD-L1 with a $K_d$ less than 50% of the $K_d$ exhibited relative to unglycosylated PD-L1. In some embodiments, an anti-glycPD-L1 antibody, or a binding portion thereof, binds to glycosylated PD-L1 with a $K_d$ that is less than 1%, 2%, 3%, 4%, 5%, 6%, 7%, 8%, 9%, 10%, 15%, 20%, 30%, 40%, 50%, 55%, 60%, 65%, 70%, 75%, 80%, 85%, or 90% of the $K_d$ exhibited relative to unglycosylated PD-L1. In further aspects, an anti-glycPD-L1 antibody, or a binding portion thereof, binds to glycosylated PD-L1 with a $K_d$ at least 5-10 times less than the $K_d$ exhibited relative to unglycosylated PD-L1. In an embodiment, an anti-glycPD-L1 antibody, or a binding portion thereof, binds to glycosylated PD-L1 with a $K_d$ at least 10 times less than the $K_d$ exhibited relative to unglycosylated PD-L1. In certain embodiments, the antibody binds to glycosylated PD-L1 with a $K_d$ that is no more than 1%, 2%, 3%, 4%, 5%, 6%, 7%, 8%, 9%, 10%, 15%, or 20% of the $K_d$ exhibited by binding to unglycosylated PD-L1. In an embodiment, an anti-glycPD-L1 antibody, or a binding portion thereof, binds to glycosylated PD-L1 with a nanomolar affinity, such as an affinity of from 5-20 nM or from 10-20 nM, inclusive of the lower and upper values.

In an embodiment, in a cell flow cytometry binding assay as described in Example 6, the antibody exhibits binding as expressed as MFI to cells expressing WT PD-L1 that is at least or is 1.5 times, 2 times, 3, times, 4 times, 5 times, 6 times, 7 times, 8 times, 9 times or 10 times greater than the MFI for binding to cells expressing unglycosylated PD-L1, and in certain embodiments, is no more than 10 times, 20 times 50 times or 100 times greater than the MFI for binding to cells expressing unglycosylated PD-L1.

As used herein in reference to an antibody, the term "heavy (H) chain" refers to a polypeptide chain of about 50-70 kDa, wherein the amino-terminal portion includes a variable (V) region (also called V domain) of about 115 to 130 or more amino acids and a carboxy-terminal portion that includes a constant (C) region. The constant region (or constant domain) can be one of five distinct types, (e.g., isotypes) referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes (e.g., isotypes) of antibodies, namely, IgA, IgD, IgE, IgG and IgM, respectively, including four subclasses of IgG, namely IgG1, IgG2, IgG3 and IgG4. An antibody heavy chain can be a human antibody heavy chain.

As used herein in reference to an antibody, the term "light (L) chain" refers to a polypeptide chain of about 25 kDa, wherein the amino-terminal portion includes a variable domain of about 100 to about 110 or more amino acids and a carboxy-terminal portion that includes a constant region. The approximate length of a light chain (both the V and C domains) is 211 to 217 amino acids. There are two distinct types of light chains, referred to as kappa (κ) and lambda (λ), based on the amino acid sequence of the constant domains. Light chain amino acid sequences are well known in the art. An antibody light chain can be a human antibody light chain.

As used herein, the term "variable (V) region" or "variable (V) domain" refers to a portion of the light (L) or heavy (H) chains of an antibody polypeptide that is generally located at the amino-terminus of the L or H chain. The H chain V domain has a length of about 115 to 130 amino acids, while the L chain V domain is about 100 to 110 amino acids in length. The H and L chain V domains are used in the binding and specificity of each particular antibody for its particular antigen. The V domain of the H chain can be referred to as "$V_H$." The V region of the L chain can be referred to as "$V_L$." The term "variable" refers to the fact that certain segments of the V domains differ extensively in sequence among different antibodies. While the V domain mediates antigen binding and defines specificity of a particular antibody for its particular antigen, the variability is not evenly distributed across the 110-amino acid span of antibody V domains. Instead, the V domains consist of less variable (e.g., relatively invariant) stretches called framework regions (FRs) of about 15-30 amino acids separated by shorter regions of greater variability (e.g., extreme variability) called "hypervariable regions" or "complementarity determining regions" (CDRs) that are each about 9-12 amino acids long. The V domains of antibody H and L chains each comprise four FRs, largely adopting a β sheet configuration, connected by three hypervariable regions, called, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., 1991, *Sequences of Proteins of Immunological Interest*, 5th Ed. Public Health Service, National Institutes of Health, Bethesda, Md.)). The C domains are not involved directly in binding an antibody to an antigen, but exhibit various effector functions, such as antibody dependent cellular cytotoxicity (ADCC) and complement dependent cytotoxicity (CDC). The V domains differ extensively in sequence among different antibody classes or types. The variability in sequence is concentrated in the CDRs, which are primarily responsible for the interaction of the antibody with antigen. In specific embodiments, the variable domain of an antibody is a human or humanized variable domain.

As used herein, the terms "complementarity determining region," "CDR," "hypervariable region," "HVR," and "HV" are used interchangeably. A "CDR" refers to one of three hypervariable regions (H1, H2 or H3) within the non-framework region of the antibody $V_H$ β-sheet framework, or to one of three hypervariable regions (L1, L2 or L3) within the non-framework region of the antibody $V_L$ β-sheet framework. The term, when used herein, refers to the regions of an antibody V domain that are hypervariable in sequence and/or form structurally defined loops. Generally, antibodies comprise six hypervariable regions: three (H1, H2, H3) in the $V_H$ domain and three (L1, L2, L3) in the $V_L$ domain. Accordingly, CDRs are typically highly variable sequences interspersed within the framework region sequences of the V domain. "Framework" or "FR" residues are those variable region residues flanking the CDRs. FR residues are present, for example, in chimeric, humanized, human, domain antibodies, diabodies, linear antibodies, bispecific, or biparatopic antibodies.

A number of hypervariable region delineations are in use and are encompassed herein. CDR regions are well known to those skilled in the art and have been defined by, for example, Kabat as the regions of most hypervariability within the antibody V domains (Kabat et al., 1977, *J. Biol. Chem.*, 252:6609-6616; Kabat, 1978, *Adv. Prot. Chem.*, 32:1-75). The Kabat CDRs are based on sequence variability and are the most commonly used (see, e.g., Kabat et al., 1991, *Sequences of Proteins of Immunological Interest*, 5th Ed. Public Health Service, National Institutes of Health, Bethesda, Md.). CDR region sequences also have been defined structurally by Chothia as those residues that are not part of the conserved β-sheet framework, and thus are able to adopt different conformations (Chothia et al., 1987, *J. Mol. Biol.*, 196:901-917). Chothia refers instead to the location of the structural loops. The end of the Chothia CDR-H1 loop when numbered using the Kabat CDR numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). Both numbering systems and terminologies are well recognized in the art.

Recently, a universal numbering system has been developed and widely adopted, ImMunoGeneTics (IMGT) Information System® (Lefranc et al., 2003, *Dev. Comp. Immunol.*, 27(1):55-77). IMGT is an integrated information system specializing in immunoglobulins (Ig), T cell receptors (TR) and the major histocompatibility complex (MHC) of human and other vertebrates. Herein, the CDRs are referred to in terms of both the amino acid sequence and the location within the light or heavy chain. As the "location" of the CDRs within the structure of the immunoglobulin V domain is conserved between species and present in structures called loops, by using numbering systems that align variable domain sequences according to structural features, CDR and framework residues and are readily identified. This information can be used in grafting and in the replacement of CDR residues from immunoglobulins of one species into an acceptor framework from, typically, a human antibody. An additional numbering system (AHon) has been developed by Honegger et al., 2001, *J. Mol. Biol.* 309:657-670. Correspondence between the numbering system, including, for example, the Kabat numbering and the IMGT unique numbering system, is well known to one skilled in the art (see, e.g., Kabat, Id.; Chothia et al., 1987, *J. Mol. Biol.*, 196:901-917, supra; Martin, 2010, *Antibody Engineering*, Vol. 2, Chapter 3, Springer Verlag; and Lefranc et al., 1999, *Nuc. Acids Res.*, 27:209-212).

CDR region sequences have also been defined by AbM, Contact and IMGT. The AbM hypervariable regions represent a compromise between the Kabat CDRs and Chothia structural loops, and are used by Oxford Molecular's AbM antibody modeling software (see, e.g., Martin, Id.). The "contact" hypervariable regions are based on an analysis of the available complex crystal structures. The residues from each of these hypervariable regions or CDRs are noted below.

Exemplary delineations of CDR region sequences are illustrated in Table 2 below. The positions of CDRs within a canonical antibody variable region have been determined by comparison of numerous structures (Al-Lazikani et al., 1997, *J. Mol. Biol.*, 273:927-948; Morea et al., 2000, *Methods*, 20:267-279). Because the number of residues within a hypervariable region varies in different antibodies, additional residues relative to the canonical positions are conventionally numbered with a, b, c and so forth next to the residue number in the canonical variable region numbering scheme (Al-Lazikani et al., Id.). Such nomenclature is similarly well known to those skilled in the art.

TABLE 2

Exemplary Delineations of CDR Region Sequences

|  | IMGT | Kabat | AbM | Chothia | Contact |
| --- | --- | --- | --- | --- | --- |
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

An "affinity matured" antibody is one with one or more alterations (e.g., amino acid sequence variations, including changes, additions and/or deletions) in one or more HVRs thereof that result in an improvement in the affinity of the antibody for antigen, compared to a parent antibody which does not possess those alteration(s). In certain embodiments, affinity matured antibodies will have nanomolar or even picomolar affinities for the target antigen, such as the glycosylated PD-L1. Affinity matured antibodies are produced by procedures known in the art. For reviews, see Hudson and Souriau, 2003, *Nature Medicine* 9:129-134; Hoogenboom, 2005, *Nature Biotechnol.*, 23:1105-1116; Quiroz and Sinclair, 2010, *Revista Ingeneria Biomedia* 4:39-51.

A "chimeric" antibody is one in which a portion of the H and/or L chain, e.g., the V domain, is identical with or homologous to a corresponding amino acid sequence in an antibody derived from a particular species or belonging to a particular antibody class or subclass, while the remainder of the chain(s), e.g., the C domain, is identical with or homologous to corresponding sequences in antibodies derived from another species or belonging to another antibody class or subclass, as well as a fragment of such an antibody, so long as it exhibits the desired biological activity (see, e.g., U.S. Pat. No. 4,816,567; and Morrison et al., 1984, *Proc. Natl. Acad. Sci. USA*, 81:6851-6855).

A "humanized" nonhuman (e.g., murine) antibody is a chimeric form of an antibody that refers to a human immunoglobulin sequence (e.g., recipient antibody) in which the native CDR residues are replaced by residues from the corresponding CDRs of a nonhuman species (e.g., donor antibody) such as mouse, rat, rabbit or nonhuman primate having the desired specificity, affinity, and capacity for antigen binding and interaction. In some instances, one or more FR region residues of the human immunoglobulin may also be replaced by corresponding nonhuman residues. In addition, humanized antibodies can comprise residues that are not found in the recipient antibody or in the donor antibody. These modifications are made to further refine the humanized antibody's performance. One or more modifications in the CDR regions can also be made to improve and refine the humanized antibody's performance, for example, in an affinity matured antibody. A humanized antibody H or L chain may comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. While known to those skilled in the art, further details may be found, if desired, in, e.g., Jones et al., 1986, *Nature*, 321:522-525; Riechmann et al., 1988, *Nature*, 332:323-329; and Presta, 1992, *Curr. Op. Struct. Biol.*, 2:593-596; Carter et al., 1992, *Proc. Natl. Acd. Sci. USA*, 89:4285-4289; and U.S. Pat. No. 6,800,738 (issued Oct. 5, 2004), U.S. Pat. No. 6,719,971 (issued Sep. 27, 2005), U.S. Pat. No. 6,639,055 (issued Oct. 28, 2003), U.S. Pat. No. 6,407,213 (issued Jun. 18, 2002), and U.S. Pat. No. 6,054,297 (issued Apr. 25, 2000).

The terms "human antibody" and "fully human antibody" are used interchangeably herein and refer to an antibody that possesses an amino acid sequence which corresponds to that of an antibody produced by a human and/or has been made using any of the techniques for making human antibodies as practiced by those skilled in the art. This definition of a human antibody specifically excludes a humanized antibody comprising non-human antigen-binding residues. Human antibodies can be produced using various techniques known in the art, including phage-display libraries (Hoogenboom and Winter, 1991, *J. Mol. Biol.*, 227:381; Marks et al., 1991, *J. Mol. Biol.*, 222:581) and yeast display libraries (Chao et al., 2006, *Nature Protocols*, 1: 755-768). Also available for the preparation of human monoclonal antibodies are methods described in Cole et al., 1985, *Monoclonal Antibodies and Cancer Therapy*, Alan R. Liss, p. 77; Boerner et al., 1991, *J. Immunol.*, 147(1):86-95. See also van Dijk and van de Winkel, 2001, *Curr. Opin. Pharmacol.*, 5:368-74. Human antibodies can be prepared by administering an antigen to a transgenic animal whose endogenous Ig loci have been disabled, e.g, a mouse, and that has been genetically modified to harbor human immunoglobulin genes which encode human antibodies, such that human antibodies are generated in response to antigenic challenge (see, e.g., Jakobovits, A., 1995, *Curr. Opin. Biotechnol.*, 6(5):561-6; Brüggemann and Taussing, 1997, *Curr. Opin. Biotechnol.*, 8(4):455-8; and U.S. Pat. Nos. 6,075,181 and 6,150,584 regarding XENO-MOUSE™ technology). See also, for example, Li et al., 2006, *Proc. Natl. Acad. Sci. USA*, 103:3557-3562 regarding human antibodies generated via a human B-cell hybridoma technology. In specific embodiments, human antibodies comprise a variable region and constant region of human origin. "Fully human" anti-PD-L1 antibodies, in certain embodiments, can also encompass antibodies which bind PD-L1 polypeptides and are encoded by nucleotide sequences that are naturally occurring somatic variants of human germline immunoglobulin nucleic acid sequence. In a specific embodiment, the anti-PD-L1 antibodies provided herein are fully human antibodies. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). The phrase "recombinant human antibody" includes human antibodies that are prepared, expressed, created, or isolated by recombinant means, such as antibodies expressed using a recombinant expression vector transfected into a host cell; antibodies isolated from a recombinant, combinatorial human antibody library; antibodies isolated from an animal (e.g., a mouse or cow) that is transgenic and/or transchromosomal for human immunoglobulin genes (see e.g., Taylor, L. D. et al., 1992, *Nucl. Acids Res.* 20:6287-6295); or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al., Id). In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, the term "epitope" is the site(s) or region(s) on the surface of an antigen molecule to which a single antibody molecule binds, such as a localized region on the surface of an antigen, e.g., a PD-L1 polypeptide or a glycosylated PD-L1 polypeptide that is capable of being bound by one or more antigen binding regions of an anti-PD-L1 or anti-glycPD-L1 antibody. An epitope can be immunogenic and capable of eliciting an immune response in an animal. Epitopes need not necessarily be immunogenic. Epitopes often consist of chemically active surface groupings of molecules such as amino acids or sugar side chains and have specific three dimensional structural characteristics as well as specific charge characteristics. An epitope can be a linear epitope or a conformational epitope. A region of a polypeptide contributing to an epitope can be contiguous amino acids of the polypeptide, forming a linear epitope, or the epitope can be formed from two or more non-contiguous amino acids or regions of the polypeptide, typically called a conformational epitope. The epitope may or may not be a three-dimensional surface feature of the antigen. In certain embodiments, a PD-L1 epitope is a three-dimensional surface feature of a PD-L1 polypeptide. In other embodiments, a PD-L1 epitope is linear feature of a PD-L1 polypeptide. In some embodiments, the PD-L1 epitope is glycosylated at one or more sites. Generally an antigen has several or many different epitopes and can react with many different antibodies. In a particular embodiment, an anti-glycPD-L1 antibody as described herein binds an epitope of PD-L1, especially glycosylated PD-L1, that is a conformational epitope.

An antibody binds "an epitope" or "essentially the same epitope" or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies to antigen is measured using a detectable signal, e.g., radioactive, fluorescent or enzyme labels. In addition, the epitope of the antibody can be determined and then compared using methods known in the art and, for example, described in Example 8 herein.

The term "compete" when used in the context of anti-PD-L1 antibodies that compete for the same epitope or binding site on a PD-L1 target protein or peptide thereof means competition as determined by an assay in which the antibody under study prevents, blocks, or inhibits the specific binding of a reference molecule (e.g., a reference ligand, or reference antigen binding protein, such as a reference antibody) to a common antigen (e.g., PD-L1 or a fragment thereof). Numerous types of competitive binding assays can be used to determine if a test antibody competes with a reference antibody for binding to PD-L1 (e.g., human PD-L1 or human glycosylated PD-L1). Examples of assays that can be employed include solid phase direct or indirect radioimmunoassay (RIA); solid phase direct or indirect enzyme immunoassay (EIA); sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619); solid phase direct labeled assay; solid phase direct labeled sandwich assay (see, e.g., Harlow and Lane, 1988, *Antibodies, A Laboratory Manual*, Cold Spring Harbor Press); solid phase direct label RIA using labeled iodine ($1^{125}$ label) (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of a purified antigen (e.g., PD-L1 such as human PD-L1 or glycosylated PD-L1) bound to a solid surface, or cells bearing either of an unlabeled test antigen binding protein (e.g., test anti-PD-L1 antibody) or a labeled reference antigen binding protein (e.g., reference anti-PD-L1 antibody). Competitive inhibition can be measured by determining the amount of label bound to the solid surface or cells in the presence of a known amount of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference antibody causing steric hindrance to occur. Additional details regarding methods for determining competitive binding are described herein. Usually, when a competing antibody protein is present in excess, it will inhibit specific binding of a reference antibody to a common antigen by at least 15%, or at least 23%, for example, without limitation, 40%, 45%, 50%, 55%, 60%, 65%, 70% or 75% or greater, as well as percent amounts between the amounts stated. In some instance, binding is inhibited by at least 80%, 85%, 90%, 95%, 96% or 97%, 98%, 99% or more.

As used herein, the term "blocking" antibody or an "antagonist" antibody refers to an antibody that prevents, inhibits, blocks, or reduces biological or functional activity of the antigen to which it binds. Blocking antibodies or antagonist antibodies can substantially or completely prevent, inhibit, block, or reduce the biological activity or function of the antigen. For example, a blocking anti-PD-L1 antibody can prevent, inhibit, block, or reduce the binding interaction between PD-L1 and PD-1, thus preventing, blocking, inhibiting, or reducing the immunosuppressive functions associated with the PD-1/PD-L1 interaction. The terms block, inhibit, and neutralize are used interchangeably herein and refer to the ability of anti-PD-L1 antibodies as described herein to prevent or otherwise disrupt or reduce the PD-L1/PD-1 interaction.

As used herein, the term "polypeptide" or "peptide" refers to a polymer of amino acids of three or more amino acids in a serial array, linked through peptide bonds. "Polypeptides" can be proteins, protein fragments, protein analogs, oligopeptides and the like. The amino acids that comprise the polypeptide may be naturally derived or synthetic. The polypeptide may be purified from a biological sample. For example, a PD-L1 polypeptide or peptide may be composed of at least 3, 4, 5, 6, 7, 8, 9, 10, 11, 12, 13, 14, 15, 16, 17, 18, 19, 20, 21, 22, 23, 24, or 25 contiguous amino acids of human PD-L1 or glycosylated PD-L1. In some embodiments, the polypeptide has at least 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 270, 280, or 285 contiguous amino acids of human PD-L1 or glycosylated PD-L1. In certain embodiments, the PD-L1 polypeptide comprises at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, at least 250 contiguous amino acid residues of the amino acid sequence of a PD-L1 polypeptide or a glycosylated PD-L1 polypeptide.

As used herein, the term "analog" refers to a polypeptide that possesses a similar or identical function as a reference polypeptide but does not necessarily comprise a similar or identical amino acid sequence of the reference polypeptide, or possess a similar or identical structure of the reference polypeptide. The reference polypeptide may be a PD-L1 polypeptide, a fragment of a PD-L1 polypeptide, an anti-PD-L1 antibody, or an anti-glycPD-L1 antibody. A polypeptide that has a similar amino acid sequence with a reference polypeptide refers to a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the reference polypeptide, which can be a PD-L1 polypeptide or an anti-PD-L1 antibody as described herein. A polypeptide with similar structure to a reference polypeptide refers to a polypeptide that has a secondary, tertiary or quaternary structure similar to that of the reference polypeptide, which can be a PD-L1 polypeptide or a PD-L1 antibody described herein. The structure of a polypeptide can determined by methods known to those skilled in the art, including but not limited to, X-ray crystallography, nuclear magnetic resonance, and crystallographic electron microscopy. Preferably, the analog functions as a dual function anti-glycPD-L1 antibody.

As used herein, the term "variant" when used in relation to a PD-L1 polypeptide or to an anti-PD-L1 antibody refers to a polypeptide or an anti-PD-L1 antibody having one or more (such as, for example, about 1 to about 25, about 1 to about 20, about 1 to about 15, about 1 to about 10, or about 1 to about 5) amino acid sequence substitutions, deletions, and/or additions as compared to a native or unmodified PD-L1 sequence or anti-PD-L1 antibody sequence. For example, a PD-L1 variant can result from one or more (such as, for example, about 1 to about 25, about 1 to about 20, about 1 to about 15, about 1 to about 10, or about 1 to about 5 changes to an amino acid sequence of a native PD-L1. Also by way of example, a variant of an anti-PD-L1 antibody can result from one or more (such as, for example, about 1 to about 25, about 1 to about 20, about 1 to about 15, about 1 to about 10, or about 1 to about 5 changes to an amino acid sequence of a native or previously unmodified anti-PD-L1 antibody. Polypeptide variants can be prepared from the corresponding nucleic acid molecules encoding the variants. In certain embodiments, the variant is an anti-glycPD-L1 antibody that has one or more amino acid substitutions, deletions or insertions in one or more CDR or framework regions and, preferably, the analog functions as a dual function anti-glycPD-L1 antibody.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (e.g., an "algorithm"). Methods that may be used to calculate the identity of the aligned nucleic acids or polypeptides include those described in *Computational Molecular Biology*, Lesk, A. M., Ed., 1988, New York: Oxford University Press; *Biocomputing Informatics and Genome Projects*, Smith, D. W., Ed., 1993, New York: Academic Press; *Computer Analysis of Sequence Data, Part I*, Griffin, A. M., and Griffin, H. G., Eds., 1994, New Jersey: Humana Press; *Sequence Analysis in Molecular Biology*, von Heinje, G., 1987, New York: Academic Press; *Sequence Analysis Primer*, Gribskov, M. and Devereux, J., Eds., 1991, New York: M. Stockton Press; and Carillo et al., 1988, *SIAM J. Applied Math.*, 48:1073.

In calculating percent identity, the sequences being compared can be aligned in a way that gives the largest match between the sequences. An example of a computer program that can be used to determine percent identity is the GCG program package, which includes GAP (Devereux et al., 1984, *Nucl. Acid Res.*, 12:387; Genetics Computer Group, University of Wisconsin, Madison, Wis.), which is a computer algorithm used to align the two polypeptides or polynucleotides to determine their percent sequence identity. The sequences can be aligned for optimal matching of their respective amino acid or nucleotide sequences (the "matched span" as determined by the algorithm). A gap opening penalty (which is calculated as 3 times the average diagonal, wherein the "average diagonal" is the average of the diagonal of the comparison matrix being used, and the "diagonal" is the score or number assigned to each perfect amino acid match by the particular comparison matrix; and a gap extension penalty (which is usually $\frac{1}{10}$ times the gap opening penalty), as well as a comparison matrix such as PAM 250 or BLOSUM 62, are used in conjunction with the algorithm. In certain embodiments, a standard comparison matrix (see, Dayhoff et al., 1978, *Atlas of Protein Sequence and Structure*, 5:345-352 for the PAM 250 comparison matrix; Henikoff et al., 1992, *Proc. Natl. Acad. Sci. USA*, 89:10915-10919 for the BLOSUM 62 comparison matrix) is also used by the algorithm. Exemplary parameters for determining percent identity for polypeptides or nucleotide sequences using the GAP program include the following: (i)

Algorithm: Needleman et al., 1970, *J. Mol. Biol.*, 48:443-453; (ii) Comparison matrix: BLOSUM 62 from Henikoff et al., Id.; (iii) Gap Penalty: 12 (but with no penalty for end gaps); (iv) Gap Length Penalty: 4; and (v) Threshold of Similarity: 0.

Certain alignment schemes for aligning two amino acid sequences can result in matching only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans a representative number of amino acids, for example, at least 50 contiguous amino acids, of the target polypeptide.

Percent (%) amino acid sequence identity with respect to a reference polypeptide sequence is defined as the percentage of amino acid residues in a candidate sequence that is identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill of the practitioner in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the term "derivative" refers to a polypeptide that comprises an amino acid sequence of a reference polypeptide that has been altered by the introduction of amino acid residue substitutions, deletions or additions. The reference polypeptide can be a PD-L1 polypeptide or an anti-PD-L1 antibody. The term "derivative" as used herein also refers to a PD-L1 polypeptide or an anti-PD-L1 antibody that has been chemically modified, e.g., by the covalent attachment of any type of molecule to the polypeptide. For example, a PD-L1 polypeptide or an anti-PD-L1 antibody can be chemically modified, e.g., by glycosylation, acetylation, pegylation, phosphorylation, amidation, derivatization by known protecting/blocking groups, proteolytic cleavage, linkage to a cellular ligand, linkage to a peptide or protein tag molecule, or other protein, etc. The derivatives are modified in a manner that is different from the naturally occurring or starting peptide or polypeptides, either in the type or location of the molecules attached. Derivatives may further include deletion of one or more chemical groups which are naturally present on the peptide or polypeptide. A derivative of a PD-L1 polypeptide or an anti-PD-L1 antibody may be chemically modified by chemical modifications using techniques known to those of skill in the art, including, but not limited to, specific chemical cleavage, acetylation, formulation, metabolic synthesis by tunicamycin, etc. Further, a derivative of a PD-L1 polypeptide or an anti-PD-L1 antibody can contain one or more non-classical amino acids. A polypeptide derivative possesses a similar or identical function as the reference polypeptide, which can be a PD-L1 polypeptide or an anti-PD-L1 antibody described herein, especially a dual function anti-glycPD-L1 monoclonal antibody.

The term "fusion protein" as used herein refers to a polypeptide that includes amino acid sequences of at least two heterologous polypeptides. The term "fusion" when used in relation to a PD-L1 polypeptide or to an anti-PD-L1 antibody refers to the joining, fusing, or coupling of a PD-L1 polypeptide or an anti-PD-L1 antibody, variant and/or derivative thereof, with a heterologous peptide or polypeptide. In certain embodiments, the fusion protein retains the biological activity of the PD-L1 polypeptide or the anti-PD-L1 antibody. In certain embodiments, the fusion protein includes a PD-L1 antibody $V_H$ region, $V_L$ region, $V_H$ CDR (one, two or three $V_H$ CDRs), and/or $V_L$ CDR (one, two or three $V_L$ CDRs) coupled, fused, or joined to a heterologous peptide or polypeptide, wherein the fusion protein binds to an epitope on a PD-L1 protein or peptide. In other embodiments, glycosylated PD-L1 peptides fused to an Fc domain (preferably a human Fc domain) are provided. Fusion proteins may be prepared via chemical coupling reactions as practiced in the art, or via molecular recombinant technology.

As used herein, the term "composition" refers to a product containing specified component ingredients (e.g., a polypeptide or an antibody provided herein) in, optionally, specified or effective amounts, as well as any desired product which results, directly or indirectly, from the combination or interaction of the specific component ingredients in, optionally, the specified or effective amounts.

As used herein, the term "carrier" includes pharmaceutically acceptable carriers, excipients, diluents, vehicles, or stabilizers that are nontoxic to the cell or mammal being exposed thereto at the dosages and concentrations employed. Often, the physiologically acceptable carrier is an aqueous pH buffered solution. Examples of physiologically acceptable carriers include buffers such as phosphate, citrate, succinate, and other organic acids; antioxidants including ascorbic acid; low molecular weight (e.g., less than about 10 amino acid residues) polypeptides; proteins, such as serum albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, sucrose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The term "carrier" can also refer to a diluent, adjuvant (e.g., Freund's adjuvant, complete or incomplete), excipient, or vehicle with which the therapeutic is administered. Such carriers, including pharmaceutical carriers, can be sterile liquids, such as water and oils, including those of petroleum, animal, vegetable or synthetic origin, such as peanut oil, soybean oil, mineral oil, sesame oil and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include, without limitation, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc.

Examples of suitable pharmaceutical carriers are described in *Remington Pharmaceutical Sciences,* 1990, Mack Publishing Co., Easton, Pa. Compositions, including pharmaceutical compounds, can contain a therapeutically effective amount of an anti-PD-L1 antibody, such as an anti-glycPD-L1 antibody, for example, in isolated or purified form, together with a suitable amount of carrier so as to provide the form for proper administration to the subject (e.g., patient). The composition or formulation should suit the mode of administration.

As used herein, the term "excipient" refers to an inert substance which is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, for reference, *Remington's Pharmaceutical Sciences,* Id., which is hereby incorporated by reference in its entirety.

As used herein, the term "pharmaceutically acceptable" or "pharmacologically acceptable" refers to molecular entities, formulations and compositions that do not produce an adverse, allergic, or other untoward or unwanted reaction when administered, as appropriate, to an animal, such as a human. The preparation of a pharmaceutical composition comprising an antibody or additional active ingredient are known to those of skill in the art in light of the present disclosure, as exemplified by *Remington's Pharmaceutical Sciences, Id.* Moreover, for animal (e.g., human) administration, it will be understood that preparations should meet sterility, pyrogenicity, general safety, and purity standards as required by a regulatory agency of the Federal or a state government, such as the FDA Office of Biological Standards or as listed in the U.S. Pharmacopeia, European Pharmacopeia, or other generally recognized Pharmacopeia for use in animals, and more particularly, in humans.

The term "pharmaceutical formulation" refers to a preparation which is in such form as to permit the biological activity of the active ingredient (e.g., an anti-PD-L1 antibody and an anti-glycPD-L1 antibody) to be effective, and which contains no additional components that would be unacceptably toxic to a subject to whom the formulation would be administered. Such a formulation can be sterile, i.e., aseptic or free from all living microorganisms and their spores, etc.

The term "package insert" is used to refer to instructions customarily included in commercial packages of therapeutic products, that contain information about the indications, usage, dosage, administration, contraindications and/or warnings concerning the use of such therapeutic products.

As used herein, the term "treat," "treatment," or "treating" refers to administration or application of a therapeutic agent to a subject in need thereof, or performance of a procedure or modality on a subject, for the purpose of obtaining at least one positive therapeutic effect or benefit, such as treating a disease or health-related condition. For example, a treatment can include administration of a pharmaceutically effective amount of an antibody, or a composition or formulation thereof, that specifically binds to glycosylated PD-L1 for the purpose of treating various types of cancer. The terms "treatment regimen," "dosing regimen," or "dosing protocol," are used interchangeably and refer to the timing and dose of a therapeutic agent, such as an anti-glycPD-L1 antibody as described. As used herein, the term "subject" refers to either a human or a non-human animal, such as primates, mammals, and vertebrates having a cancer or diagnosed with a cancer. In preferred embodiments, the subject is a human. In some embodiments, the subject is a cancer patient. In an embodiment, the subject in need will or is predicted to benefit from a dual function anti-glycPD-L1 antibody treatment.

As used herein, the term "therapeutic benefit" or "therapeutically effective" refers the promotion or enhancement of the well-being of a subject in need (e.g., a subject with a cancer or diagnosed with a cancer) with respect to the medical treatment, therapy, dosage administration, of a condition, particularly as a result of the use of the dual function anti-glycPD-L1 antibodies and the performance of the described methods. This includes, but is not limited to, a reduction in the frequency or severity of the signs or symptoms of a disease. For example, treatment of a cancer may involve, for example, a reduction in the size of a tumor, a reduction in the invasiveness or severity of a tumor, a reduction infiltration of cancer cells into a peripheral tissue or organ; a reduction in the growth rate of the tumor or cancer, or the prevention or reduction of metastasis. Treatment of cancer may also refer to achieving a sustained response in a subject or prolonging the survival of a subject with cancer.

As used herein, the term "administer" or "administration" refers to the act of physically delivering, e.g., via injection or an oral route, a substance as it exists outside the body into a patient, such as by oral, subcutaneous, mucosal, intradermal, intravenous, intramuscular delivery and/or any other method of physical delivery described herein or known in the art. When a disease, disorder or condition, or a symptom thereof, is being treated therapeutically, administration of the substance typically occurs after the onset of the disease, disorder or condition or symptoms thereof. Prophylactic treatment involves the administration of the substance at a time prior to the onset of the disease, disorder or condition or symptoms thereof.

As used herein, the term "effective amount" refers to the quantity or amount of a therapeutic (e.g., an antibody or pharmaceutical composition provided herein) which is sufficient to reduce, diminish, alleviate, and/or ameliorate the severity and/or duration of a cancer or a symptom related thereto. This term also encompasses an amount necessary for the reduction or amelioration of the advancement or progression of a cancer; the reduction or amelioration of the recurrence, development, or onset of a cancer; and/or the improvement or enhancement of the prophylactic or therapeutic effect(s) of another cancer therapy (e.g., a therapy other than administration of an anti-PD-L1 antibody or anti-glycPD-L1 antibody provided herein). In some embodiments, the effective amount of an antibody provided herein is from about or equal to 0.1 mg/kg (mg of antibody per kg weight of the subject) to about or equal to 100 mg/kg. In certain embodiments, an effective amount of an antibody provided therein is about or equal to 0.1 mg/kg, about or equal to 0.5 mg/kg, about or equal to 1 mg/kg, about or equal to 3 mg/kg, about or equal to 5 mg/kg, about or equal to 10 mg/kg, about or equal to 15 mg/kg, about or equal to 20 mg/kg, about or equal to 25 mg/kg, about or equal to 30 mg/kg, about or equal to 35 mg/kg, about or equal to 40 mg/kg, about or equal to 45 mg/kg, about or equal to 50 mg/kg, about or equal to 60 mg/kg, about or equal to 70 mg/kg, 80 mg/kg, 90 mg/kg, or 100 mg/kg. These amounts are meant to include amounts and ranges therein. In some embodiments, "effective amount" also refers to the amount of an antibody provided herein to achieve a specified result (e.g., preventing, blocking, or inhibiting cell surface PD-1 binding to cell surface PD-L1; or preventing, blocking, or inhibiting PD-1/PD-L1 mediated immunosuppression).

The term "in combination" in the context of the administration of other therapies (e.g., other agents, cancer drugs, cancer therapies) includes the use of more than one therapy (e.g., drug therapy and/or cancer therapy). Administration "in combination with" one or more further therapeutic agents includes simultaneous (e.g., concurrent) and consecutive administration in any order. The use of the term "in combination" does not restrict the order in which therapies are administered to a subject. By way of nonlimiting example, a first therapy (e.g., agent, such as an anti-glycPD-L1 antibody) may be administered before (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks or longer) the administration of a second therapy (e.g., agent) to a subject having or diagnosed with a cancer.

The combination of therapies (e.g., use of agents, including therapeutic agents) may be more effective than the additive effects of any two or more single therapy (e.g., have a synergistic effect) or may have other benefits that are not predicted a priori such as improved side effect profile, increased efficacy or duration of therapeutic effect, broader patient population in which the combination is effective, etc. Such an effect is typically unexpected and cannot be predicted. For example, a synergistic effect of a combination of therapeutic agents frequently permits the use of lower dosages of one or more of the agents and/or less frequent administration of the agents to a cancer patient. The ability to utilize lower dosages of therapeutics and cancer therapies and/or to administer the therapies less frequently reduces the potential for toxicity associated with the administration of the therapies to a subject without reducing the effectiveness of the therapies. In addition, a synergistic effect may result in improved efficacy of therapies in the treatment or alleviation of a cancer. Also, a synergistic effect demonstrated by a combination of therapies (e.g., therapeutic agents) may avoid or reduce adverse or unwanted side effects associated with the use of any single therapy.

Dual Function Anti-Glycosylated PD-L1 Antibodies

Provided herein are antibodies or binding fragments thereof that bind to glycosylated PD-L1 protein (e.g., a PD-L1 protein having a specific N-glycan structure; specific glycopeptides of PD-L1) or glycosylated PD-L1 peptides and are dual function in that they reduce or block the binding of PD-L1/PD-1 interaction and also promote internalization and degradation of the PD-L1 on the tumor cell, as well as the use of such antibodies in the treatment of disease, particularly cancer. The antibodies preferentially bind to glycosylated PD-L1 as compared to unglycosylated PD-L1. The dual function anti-glycPD-L1 antibodies as described herein may of the IgG, IgM, IgA, IgD, and IgE Ig classes, as well as polypeptides comprising antibody CDR domains that retain antigen binding activity. Illustratively, the dual function anti-glycPD-L1 antibodies may be chimeric, affinity matured, humanized, or human antibodies. In a preferred embodiment, the dual function anti-glycPD-L1 antibodies are monoclonal antibodies. In certain embodiments, the monoclonal anti-glycPD-L1 antibodies are STM073 or STM108. In another preferred embodiment, the dual function anti-glycPD-L1 antibody is a humanized antibody or a chimeric antibody, particularly a humanized or chimeric form of STM073 or STM108. By known means and as described herein, polyclonal or monoclonal antibodies, antibody fragments, binding domains and CDRs (including engineered forms of any of the foregoing) may be created that are specific for glycosylated PD-L1 antigen, one or more of its respective epitopes, or conjugates of any of the foregoing, whether such antigens or epitopes are isolated from natural sources or are synthetic derivatives or variants of the natural compounds. The antibodies may be bispecific or biparatopic.

In an embodiment, the antibody is a chimeric antibody, for example, an antibody comprising antigen binding sequences (e.g., V domains and/or CDRs) from a non-human donor grafted to a heterologous non-human, human or humanized sequence (e.g., framework and/or constant domain sequences). In one embodiment, the non-human donor sequences are from mouse or rat. In specific embodiments the $V_H$ and $V_L$ domains are non-human, e.g., murine and the constant domains are human. In one embodiment, an antigen binding sequence is synthetic, e.g., obtained by mutagenesis (e.g., phage display screening of a human phage library, etc.). In one embodiment, a chimeric antibody has murine V regions and human C regions. In one embodiment, the murine light chain V region is fused to a human kappa light chain C region. In one embodiment, the murine heavy chain V region is fused to a human IgG1 C region.

In an embodiment, the antibody is an immunoglobulin single variable domain derived from a camelid antibody, preferably from a heavy chain camelid antibody, devoid of light chains, which are known as $V_H H$ domain sequences or Nanobodies™. A Nanobody™ (Nb) is the smallest functional fragment or single variable domain ($V_H H$) of a naturally occurring single-chain antibody and is known to the person skilled in the art. They are derived from heavy chain only antibodies seen in camelids (Hamers-Casterman et al., 1993, *Nature*, 363:446-448; Desmyter et al., 1996, *Nat. Struct. Biol.*, p. 803-811). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a $V_H H$ antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanized. Nbs are stable, survive the gastro-intestinal system and can easily be manufactured.

In another embodiment, the antibody is a bispecific antibody. Unifying two antigen binding sites of different specificity into a single construct, bispecific antibodies have the ability to bring together two discreet antigens with exquisite specificity and therefore have great potential as therapeutic agents. Bispecific antibodies were originally made by fusing two hybridomas, each capable of producing a different immunoglobulin. Bispecific antibodies are also produced by joining two scFv antibody fragments while omitting the Fc portion present in full immunoglobulins. Each scFv unit in such constructs can contain one variable domain from each of the heavy ($V_H$) and light ($V_L$) antibody chains, joined with one another via a synthetic polypeptide linker, the latter often being genetically engineered so as to be minimally immunogenic while remaining maximally resistant to proteolysis. Respective scFv units may be joined by a number of known techniques, including incorporation of a short (usually less than 10 amino acids) polypeptide spacer bridging the two scFv units, thereby creating a bispecific single chain antibody. The resulting bispecific single chain antibody is therefore a species containing two $V_H/V_L$ pairs of different specificity on a single polypeptide chain, in which the $V_H$ and $V_L$ domains in a respective scFv unit are separated by a polypeptide linker long enough to allow intramolecular association between these two domains, such that the so-formed scFv units are contiguously tethered to one another through a polypeptide spacer kept short enough to prevent unwanted association between, for example, the $V_H$ domain of one scFv unit and the $V_L$ of the other scFv unit.

In another embodiment, the antibody is a biparatopic antibody. As used herein the term "biparatopic antibody" refers to a bispecific binding molecule that comprises two antigen binding domains which recognize and bind to two different non-overlapping epitopes, antigenic determinants, or domains on the same protein target, e.g., a tumor-associated PD-L1 target antigen, or a glycosylated PD-L1 target antigen as described herein. In an embodiment, a biparatopic antibody directed against a glycPD-L1 or one or more peptide portions thereof, as described herein, comprises a first immunoglobulin variable domain and a second immunoglobulin variable domain, wherein the two binding domains bind to two different non-overlapping epitopes of the same target glycPD-L1 protein. One or both of the epitopes recognized by the first and second immunoglobulin binding domains may be glycosylated or contain glycosylated residues. Preferably, at least one of the immunoglobulins preferentially binds the glycosylated form of the glycPD-L1 protein relative to the unglycosylated form.

In another embodiment, a biparatopic antibody comprises an immunoglobulin (preferably a tetravalent IgG) that binds to an epitope on a glycPD-L1 target molecule and a scFv that binds to a different and non-overlapping epitope on the same glycPD-L1 target molecule, in which the immunoglobulin and the scFv are linked by a linker so as to permit the binding of the immunoglobulin and the scFv to the different and non-overlapping epitopes on the glycPD-L1 target molecule. Accordingly, biparatopic antibodies are created from two anti-glycPD-L1 antibodies that bind to different epitopes (or domains) on the same glycPD-L1 target (i.e., biparatopic binding) to enhance binding affinity/avidity; to increase antibody load on tumor cells for enhanced effector functions, such as antibody dependent cellular cytotoxicity (ADCC) and/or complement dependent cytotoxicity (CDC); and/or to improve or increase tumor retention time. In addition, bivalent biparatopic antibodies that target two non-overlapping epitopes on a tumor-associated glycPD-L1 antigen have the potential to induce clustering of glycPD-L1 target molecules in the cell membrane, which, in turn, may promote increased internalization, lysosomal trafficking and degradation. Biparatopic antibodies directed against two different, non-overlapping epitopes on a target protein/antigen may be generated using techniques known in the art. See, e.g., B. Roberts et al., 1999, *Int. J. Cancer*, Vol. 81:285-291 (carcinoembryonic antigen, CEA); D. Lu et al., 1999, *J. Immunol. Methods, Vol.* 230:159-71 (vascular endothelial growth factor receptor 2, VEGF2); WO 2009/068627, Ablynx NV, published Jun. 4, 2009; WO 2010/142534, and Ablynx NV, published Dec. 16, 2010.

In an embodiment, a bivalent biparatopic antibody may be produced by using variable domain sequences from two different anti-glycPD-L1 antibodies, identified as described herein, that recognize and bind to different non-overlapping epitopes on a given glycPD-L1 target protein, wherein the antibody contains the single-chain variable fragment (scFv) of one of the anti-glycPD-L1 antibodies attached to the N-terminus of the H chain and/or the L chain, or, alternatively, the C-terminus of the $C_H3$ domain, of the second anti-PD-L1 antibody that recognizes a different and non-overlapping epitope on glycPD-L1. The scFv may be linked to the second anti-PD-L1 antibody via a peptide linker, for example, such as those used to link binding domains in an scFv. See, e.g., Dimasi et al., *J. Mol. Biol.*, 393:672-692 (2009). The resulting binding molecule product, or biparatopic antibody, contains four anti-glycPD-L1 binding units, or two binding units on each arm of the molecule, that are able to interact with and bind to two different epitopes on glycPD-L1. According to this embodiment, a bivalent biparatopic antibody that targets two non-overlapping epitopes on glycPD-L1 expressed on the surface of a tumor cell could effectively crosslink the glycPD-L1 s through epitope binding to induce clustering of glycPD-L1 on the cell surface, leading to the formation of large complexes that elicit and promote enhanced internalization and lysosomal degradation. In an embodiment, the biparatopic antibody is linked to a toxin or anti-cancer drug to produce an antibody-drug conjugate (ADC) as described further herein. The enhanced internalization and endocytosis of such anti-PD-L1 biparatopic antibodies and lysosomal trafficking ultimately results in the delivery of greater amounts of toxin into the target cells and greater tumor cell killing or regression. Such effects were observed both in vitro and in vivo as described for a biparatopic anti-HER2 ADC (J. Y. Li et al., 2016, *Cancer Cell*, Vol. 29:117-129). Illustratively, biparatopic anti-glycPD-L1 antibodies or anti-glycPD-L1 ADCs may be produced that specifically bind to two non-overlapping epitopes of glycosylated membrane-bound PD-L1 to prevent or block its interaction with its PD-1 cognate binding partner and to promote their internalization and degradation, as well as killing of the tumor cells if an anti-glycPD-L1 ADC is used. In particular embodiments, the anti-glycPD-L1 antibody is STM073, STM108, or ADC forms thereof.

In other embodiments, anti-glycPD-L1 binding molecules or antibodies encompassed by the invention may be multiparatopic, i.e., contain antigen binding domains which recognize and bind three, four, or more different, preferably non-overlapping, epitopes or antigenic determinants on the same glycPD-L1 target molecule. In yet other embodiments, the anti-glycPD-L1 antibodies are both bi- or multiparatopic and multivalent, i.e., also comprise antigen binding sites or "paratopes" that recognize and bind to one or more different epitopes or antigenic determinants on different target glycPD-L1 molecules.

Examples of antibody fragments suitable for use include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), in which a $V_H$ domain and a $V_L$ domain are linked by a peptide linker that allows the two domains to associate to form a binding domain; (viii) bi-specific single chain Fv dimers (see U.S. Pat. No. 5,091,513); and (ix)

diabodies, multivalent, or multispecific fragments constructed by gene fusion (U.S. Patent Appln. Pub. No. 20050214860). Fv, scFv, or diabody molecules may be stabilized by the incorporation of disulfide bridges linking the $V_H$ and $V_L$ domains. Minibodies comprising a scFv joined to a $C_{H3}$ domain (Hu et al., 1996, *Cancer Res.*, 56:3055-3061) may also be useful. In addition, antibody-like binding peptidomimetics are also contemplated in embodiments. "Antibody like binding peptidomimetics" (ABiPs), which are peptides that act as pared-down antibodies and have certain advantages of longer serum half-life as well as less cumbersome synthesis methods, have been reported by Liu et al., 2003, *Cell Mol. Biol.*, 49:209-216.

Animals may be inoculated with an antigen, such as a glycosylated PD-L1 polypeptide or peptide to generate an immune response and produce antibodies specific for the glycosylated PD-L1 polypeptide. Frequently, an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single, clonal species of antibody wherein every antibody molecule recognizes the same epitope because all antibody producing cells are derived from a single, antibody-producing B-lymphocyte. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions. Hybridoma technology as used in monoclonal antibody production involves the fusion of a single, antibody-producing B lymphocyte isolated from a mouse previously immunized with a glycosylated PD-L1 protein or peptide with an immortalized myeloma cell, e.g., a mouse myeloma cell line. This technology provides a method to propagate a single antibody-producing cell for an indefinite number of generations, such that unlimited quantities of structurally identical antibodies having the same antigen or epitope specificity, i.e., monoclonal antibodies, may be produced.

Engineered antibodies may be created using monoclonal and other antibodies and recombinant DNA technology to produce other antibodies or chimeric molecules that retain the antigen or epitope binding specificity of the original antibody, i.e., the molecule has a specific binding domain. Such techniques may involve introducing DNA encoding the immunoglobulin variable region or the CDRs of an antibody into the genetic material for the framework regions, constant regions, or constant regions plus framework regions, of a different antibody. See, for instance, U.S. Pat. Nos. 5,091,513 and 6,881,557, which are incorporated herein by reference.

By known means as described herein, polyclonal or monoclonal antibodies, antibody fragments having binding activity, binding domains and CDRs (including engineered forms of any of the foregoing), may be created that specifically bind to glycosylated PD-L1 protein, one or more of its respective epitopes, and have a dual function of blocking PD-L1 to PD-1 binding and promoting internalization of PD-L1 in tumor cells, or conjugates of any of the foregoing, whether such antigens or epitopes are isolated from natural sources or are synthetic derivatives or variants of the natural compounds.

Antibodies may be produced from any animal source, including birds and mammals. Preferably, the antibodies are ovine, murine (e.g., mouse and rat), rabbit, goat, guinea pig, camel, horse, or chicken. In addition, human antibodies can be obtained by screening human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in Marks, 1992, *Bio/Technol.*, 10:779-783; Stemmer, 1994, *Nature*, 370:389-391; Gram et al., 1992, *Proc. Natl. Acad. Sci. USA*, 89:3576-3580; Barbas et al., 1994, *Proc. Natl. Acad. Sci. USA*, 91:3809-3813; and Schier et al., 1996, *Gene*, 169(2):147-155.

Methods for producing polyclonal antibodies in various animal species, as well as for producing monoclonal antibodies of various types, including humanized, chimeric, and fully human, are well known in the art and are highly reproducible. For example, the following U.S. patents provide descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098.

It is expected that antibodies directed to glycosylated PD-L1 as provided herein will have the ability to neutralize, block, inhibit, or counteract the effects of glycosylated PD-L1 regardless of the animal species, monoclonal cell line or other source of the antibody. Certain animal species may be less preferable for generating therapeutic antibodies because they may be more likely to cause an immune or allergic response due to activation of the complement system through the "Fc" portion of the antibody. However, whole antibodies may be enzymatically digested into the "Fc" (complement binding) fragment, and into peptide fragments having the binding domains or CDRs. Removal of the Fc portion reduces the likelihood that this antibody fragment will elicit an undesirable immunological response and, thus, antibodies without an Fc portion may be preferential for prophylactic or therapeutic treatments. As described above, antibodies may also be constructed so as to be chimeric, humanized, or partially or fully human, so as to reduce or eliminate potential adverse immunological effects resulting from administering to an animal an antibody that has been produced in, or has amino acid sequences from, another species.

Antibody proteins may be recombinant, or synthesized in vitro. It is contemplated that in anti-glycPD-L1 antibody-containing compositions as described herein there is between about 0.001 mg and about 10 mg of total antibody polypeptide per ml. Thus, the concentration of antibody protein in a composition can be about, at least about or at most about or equal to 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, at most about, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds glycosylated PD-L1.

An antibody or an immunological portion of an antibody that retains binding activity, can be chemically conjugated to, or recombinantly expressed as, a fusion protein with other proteins. For the purposes as described herein, all such fused proteins are included in the definition of antibodies or an immunological portion of an antibody. In some embodiments, the dual functional antibodies and antibody-like molecules generated against glycosylated PD-L1, or polypeptides that are linked to at least one agent to form an antibody conjugate or payload are encompassed. In order to increase the efficacy of antibody molecules as diagnostic or therapeutic agents, the antibody may be linked or covalently bound or complexed with at least one desired molecule or moiety to the antibody. Such a linked molecule or moiety may be, but is not limited to, at least one effector or reporter molecule. Effector molecules comprise molecules having a desired activity, e.g., cytotoxic activity. Non-limiting examples of effector molecules that may be attached to antibodies include toxins, therapeutic enzymes, antibiotics, radio-labeled nucleotides and the like. By contrast, a reporter molecule is defined as any moiety that may be detected using an assay. Non-limiting examples of reporter molecules that may be conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin, and the like. Several methods are known in the art for attaching or conjugating an antibody to a conjugate molecule or moiety. Some attachment methods involve the use of a metal chelate complex, employing by way of nonlimiting example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Antibodies, particularly the antibodies as described herein, may also be reacted with an enzyme in the presence of a coupling agent such as glutaraldehyde or periodate. Conjugates with fluorescein markers are conventionally prepared in the presence of these coupling agents or by reaction with an isothiocyanate. In another embodiment, a dual functional anti-glycPD-L1 antibody as described herein may be coupled or linked to a compound or substance, such as polyethylene glycol (PEG), to increase its in vivo half-life in plasma, serum, or blood following administration.

Provided in a particular embodiment are antibodies, such as monoclonal antibodies, and humanized and chimeric forms thereof, and antigen binding fragments thereof, that specifically and preferentially bind glycosylated PD-L1 protein relative to non-glycosylated PD-L1 protein and have a dual activity in blocking PD-L1/PD-1 binding and promoting PD-L1 internalization and degradation. In an embodiment, the dual function anti-glycPD-L1 antibody specifically or preferentially binds to PD-L1 protein that is glycosylated at positions 35, 192, 200 and/or 219 of the amino acid sequence of the PD-L1 protein, e.g., as set forth in SEQ ID NO: 1. For example, specific or selective binding of the anti-glycPD-L1 antibody involves binding of the antibody to glycosylated PD-L1 antigen with a $K_d$ less than half of the $K_d$ exhibited related to unglycosylated PD-L1. In an embodiment, the anti-glycPD-L1 antibody binds to glycosylated PD-L1 protein with a $K_d$ at least 5 times less than the $K_d$ exhibited relative to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1. In an embodiment, in a cell flow cytometry binding assay as described in Example 6, the antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1.

Provided in an embodiment is a dual function antibody or a binding fragment thereof specific for and which preferentially binds to glycosylated PD-L1 that specifically binds the PD-L1 epitope bound by STM073. In certain embodiments, the dual function anti-glycPD-L 1 antibody binds an epitope on PD-L1 encompassing positions H69, Y112, R113 and K124 of the human PD-L1 amino acid sequence of SEQ ID NO: 1. In an embodiment, the amino acids of the epitope are non-contiguous and the epitope is a conformational epitope. The regions of the human PD-L1 polypeptide encompassing the STM073 MAb epitope have the sequence V<u>H</u>GEEDLKVQH------DAGV<u>YR</u>CMISYGGADY<u>K</u>RITV (i.e., SEQ ID NO: 85 or V68-V128 of SEQ ID NO: 1), in which the amino acid residues H69, Y112, R113 and K124, which comprise the epitope recognized by MAb STM073, are underlined. In the STM073 epitope sequence, the dashes between amino acid residue histidine (H) at position 78 and amino acid residue aspartic acid (D) at position 108 represent amino acids at positions 79-107 of the human PD-L1 amino acid sequence of SEQ ID NO: 1.

Provided in another embodiment is a dual function antibody or a binding fragment thereof specific for and that preferentially binds glycosylated PD-L1 which is the anti-glycPD-L1 monoclonal antibody STM108, or humanized or chimeric forms thereof. In specific embodiments, the dual function anti-glycPD-L1 specifically binds an epitope on PD-L1 encompassing positions S80, Y81, K162 and S169 of the human PD-L1 amino acid sequence of SEQ ID NO: 1 herein. The regions of the human PD-L1 polypeptide encompassing the STM108 MAb epitope have the amino acid sequence LKVQHS<u>SY</u>RQR------EGYP<u>K</u>AEVIWT<u>S</u>SDHQ (i.e., L74-Q173 of SEQ ID NO: 1), in which the amino acid residues S80, Y81, K162 and S169, comprising the epitope recognized by MAb STM108, are underlined. In the STM108 epitope regions, the dashes between amino acid residue arginine (R) at position 84 and amino acid residue glutamic acid (E) at position 158 represent amino acids at positions 85-157 of the human PD-L1 amino acid sequence of SEQ ID NO: 1. Thus, the amino acids of the STM108 MAb epitope are non-contiguous, and the epitope is a conformational epitope.

The nucleic acid (DNA) and corresponding amino acid sequences of the heavy and light chain variable (V) domains of the STM073 MAb are shown in in Table 3 infra. Table 3 provides both the nucleotide and amino acid sequences of the mature (i.e., not containing the signal peptide) $V_H$ and $V_L$ domains of STM073 (SEQ ID NOS 2, 3, 10, and 11, respectively) and the $V_H$ and $V_L$ domain sequences containing the signal peptides (SEQ ID NOS: 87, 88, 89, and 90, respectively). In the heavy chain DNA and protein V domain sequences shown in Table 3 the amino terminal signal sequence is represented in italicized font. Also shown in Table 3 are the STM073 MAb heavy and light chain V domain CDRs, as determined by both the Kabat and Chothia definitions.

In an embodiment, the dual function anti-glycPD-L1 antibody that specifically and preferentially binds glycosylated PD-L1 comprises a $V_H$ domain of SEQ ID NO: 3 and a $V_L$ domain of SEQ ID NO: 11. In an embodiment, the dual function anti-glycPD-L1 antibody competes for specific binding to glycosylated PD-L1 with an antibody comprising a $V_H$ domain of SEQ ID NO: 3 and a $V_L$ domain of SEQ ID NO: 11. In an embodiment, the dual function anti-glycPD-L1 antibody that specifically and preferentially binds glycosylated PD-L1 comprises a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof. In an embodiment, the dual function anti-glycPD-L1 antibody competes for specific binding to glycosylated PD-L1 with an antibody comprising a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof. In an embodiment, the dual function anti-glycPD-L1 antibody that specifically and preferentially binds glycosylated PD-L1 comprises a $V_L$ domain comprising CDRs 1-3 having amino acid sequences of SEQ ID NO: 12, SEQ ID NO: 14, and SEQ ID NO: 16, respectively. In an embodiment, the dual function anti-glycPD-L1 antibody competes for specific binding to glycosylated PD-L1 with an antibody comprising a $V_L$ domain comprising CDRs 1-3 having amino acid sequences of SEQ ID NO: 12, SEQ ID NO: 14, and SEQ ID NO: 16, respectively. In an embodiment, the dual function anti-glycPD-L1 antibody that specifically and preferentially binds glycosylated PD-L1 comprises (a) a $V_H$ domain comprising Chothia CDRs 1-3 having amino acid sequences of SEQ ID NO: 4, SEQ ID NO: 6, and SEQ ID NO: 8, respectively, or Kabat CDRs 1-3 having amino acid sequences of SEQ ID NO: 5, SEQ ID NO: 7, and SEQ ID NO: 9, respectively, or a combination thereof; and (b) a $V_L$ domain comprising CDRs 1-3 having amino acid sequences of SEQ ID NO: 12, SEQ ID NO: 14, and SEQ ID NO: 16, respectively. In embodiments, the dual function anti-glycPD-L1 antibody competes for specific binding to glycosylated PD-L1 with an antibody comprising the above-described $V_H$ and $V_L$ domains and the CDRs therein.

In an embodiment, the dual function anti-glycPD-L1 antibody that specifically binds glycosylated PD-L1 comprises a $V_H$ domain that is 80%, 85%, 90%, 95% 98% or 99% identical to the amino acid sequence of SEQ ID NO: 3 and/or a $V_L$ domain that is 80%, 85%, 90%, 95% 98% or 99% identical to the amino acid sequence of SEQ ID NO: 11, and which inhibits or blocks binding of glycosylated PD-L1 to PD-1 and promotes destabilization of PD-L1 expression on the cell membrane. In an embodiment, the dual function anti-glycPD-L1 antibody that specifically and preferentially binds glycosylated PD-L1 comprises a $V_H$ domain comprising CDRs 1-3 with at least 1, 2, or all 3 CDRs having at least 1, 2, 3, 4 or 5 amino acid substitutions with respect to the amino acid sequences of SEQ ID NO: 4, SEQ ID NO: 6, and SEQ ID NO: 8, respectively, or amino acid sequences of SEQ ID NO: 5, SEQ ID NO: 7, and SEQ ID NO: 9, respectively, which anti-glycPD-L1 antibody blocks binding of glycosylated PD-L1 to PD-1 and promotes destabilization of expression of PD-L1 on the cell membrane. In an embodiment, the dual function anti-glycPD-L1 antibody that specifically and preferentially binds glycosylated PD-L1 comprises a $V_L$ domain comprising CDRs 1-3 with at least 1, 2, or all 3 CDRs having at least 1, 2, 3, 4 or 5 amino acid substitutions with respect to amino acid sequences of SEQ ID NO: 12, SEQ ID NO: 14, and SEQ ID NO: 16, respectively. In an embodiment, the dual function anti-glycPD-L1 antibody that specifically and preferentially binds glycosylated PD-L1 comprises (a) a $V_H$ domain comprising CDRs 1-3 with at least 1, 2, or all 3 CDRs having at least 1, 2, 3, 4 or 5 amino acid substitutions with respect to the amino acid sequences of SEQ ID NO: 4, SEQ ID NO: 6, and SEQ ID NO: 8, respectively, or amino acid sequences of SEQ ID NO: 5, SEQ ID NO: 7, and SEQ ID NO: 9, respectively; and (b) a $V_L$ domain comprising CDRs 1-3 with at least 1, 2, or all 3 CDRs having at least 1, 2, 3, 4 or 5 amino acid substitutions with respect to amino acid sequences of SEQ ID NO: 12, SEQ ID NO: 14, and SEQ ID NO: 16, respectively, which antibody blocks binding of glycosylated PD-L1 to PD-1 and promotes destabilization of PD-L1 expression on the cell membrane. Also provided are humanized forms of STM073 using the AbM, Contact or IMGT defined CDRs, with human framework regions and, optionally, human constant domains.

The foregoing dual function anti-glycPD-L1 antibodies bind to glycosylated PD-L1 with a $K_d$ less than half of the $K_d$ exhibited relative to unglycosylated PD-L1. In an embodiment, the dual function anti-glycPD-L1 antibodies bind to glycosylated PD-L1 protein with a $K_d$ at least 5 times less than the $K_d$ exhibited relative to unglycosylated PD-L1. In an embodiment, the dual function anti-glycPD-L1 antibodies bind to glycosylated PD-L1 protein with a $K_d$ at least 10 times less than the $K_d$ exhibited relative to unglycosylated PD-L1 protein. In an embodiment, the binding affinity of the dual function anti-glycPD-L1 antibody for glycosylated PD-L1 is from 5-20 nM or from 5-10 nM inclusive of the lower and upper values. In an embodiment, in a cell flow cytometry binding assay as described in Example 6, the antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1.

In an embodiment, the antibody inhibits the interaction of PD-1 with PD-L1, and particularly inhibits the interaction of PD-1 expressed by effector T-cells with PD-L1, particularly, glycosylated PD-L1, expressed by tumor cells. The antibody further promotes internalization of PD-L1 and degradation of PD-L1, thereby reducing the level of PD-L1 on the cell surface.

In another particular embodiment, an antibody, or a binding fragment thereof, is provided that specifically and preferentially binds glycosylated PD-L1 which is the antiglycPD-L1 monoclonal antibody STM108. The nucleic acid (DNA) and corresponding amino acid sequences of the mature heavy and light chain variable (V) domains (SEQ ID NOs: 18, 19, 26 and 27) of the STM108 MAb are shown in Table 3 infra. The DNA and amino acid sequences of the unprocessed heavy chain V domain (i.e., containing a signal sequence at the N-terminal) are also shown in Table 3 (SEQ ID NOs: 91 and 92, respectively). Also shown in Table 3 are the STM108 MAb heavy and light chain V domain CDRs, according to both the Kabat and Chothia definitions.

In an embodiment, the dual function anti-glycPD-L1 antibody that specifically and preferentially binds glycosylated PD-L1 comprises a $V_H$ domain of the amino acid sequence of SEQ ID NO: 19 and a $V_L$ domain of the amino acid sequence of SEQ ID NO: 27. In an embodiment, the dual function anti-glycPD-L1 antibody competes for specific binding to glycosylated PD-L1 with an antibody comprising a $V_H$ domain of the amino acid sequence of SEQ ID NO: 19 and a $V_L$ domain of the amino acid sequence of SEQ ID NO: 27. In an embodiment, the dual function anti-glycPD-L1 antibody that specifically and preferentially binds glycosylated PD-L1 comprises a $V_H$ domain comprising Chothia CDRs1-3 having amino acid sequences of SEQ ID NO: 20, SEQ ID NO: 22, and SEQ ID NO: 24, respectively, or Kabat CDRs 1-3 having amino acid sequences of SEQ ID NO: 21, SEQ ID NO: 23, and SEQ ID NO: 25, respectively, or a combination thereof. In an embodiment, the dual function anti-glycPD-L1 antibody competes for specific binding to glycosylated PD-L1 with an antibody comprising a $V_H$ domain comprising Chothia CDRs 1-3 with amino acid sequences of SEQ ID NO: 20, SEQ ID NO: 22, and SEQ ID NO: 24, respectively, or Kabat CDRs 1-3 with amino acid sequences of SEQ ID NO: 21, SEQ ID NO: 23, and SEQ ID NO: 25, respectively, or a combination thereof. In an embodiment, the dual function anti-glycPD-L1 antibody that specifically and preferentially binds glycosylated PD-L1 comprises a $V_L$ domain comprising CDRs 1-3 having amino acid sequences of SEQ ID NO: 28, SEQ ID NO: 30, and SEQ ID NO: 32, respectively. In an embodiment, the dual function anti-glycPD-L1 antibody competes for specific binding to glycosylated PD-L1 with an antibody comprising a $V_L$ domain comprising CDRs 1-3 having amino acid sequences of SEQ ID NO: 28, SEQ ID NO: 30, and SEQ ID NO: 32, respectively. In an embodiment, the dual function anti-glycPD-L1 antibody that specifically and preferentially binds glycosylated PD-L1 comprises (a) a $V_H$ domain comprising Chothia CDRs1-3 having amino acid sequences of SEQ ID NO: 20, SEQ ID NO: 22, and SEQ ID NO: 24, respectively, or Kabat CDRs 1-3 having amino acid sequences of SEQ ID NO: 21, SEQ ID NO: 23, and SEQ ID NO: 25, respectively, or a combination thereof; and (b) a $V_L$ domain comprising CDRs 1-3 having amino acid sequences of SEQ ID NO: 28, SEQ ID NO: 30, and SEQ ID NO: 32, respectively. In embodiments, the anti-glycPD-L1 antibody competes for specific binding to glycosylated PD-L1 with an antibody comprising the above-described $V_H$ and $V_L$ domains and the CDRs therein.

In an embodiment, the dual function anti-glycPD-L1 antibody that specifically and preferentially binds glycosylated PD-L1 comprises a $V_H$ domain that is 80%, 85%, 90%, 95% 98% or 99% identical to the amino acid sequence of SEQ ID NO: 19 and a $V_L$ domain that is 80%, 85%, 90%, 95% 98% or 99% identical to the amino acid sequence of SEQ ID NO: 27. In an embodiment, the dual function anti-glycPD-L1 antibody that specifically and preferentially binds glycosylated PD-L1 comprises a $V_H$ domain comprising CDRs 1-3 with at least 1, 2, or all 3 CDRs having at least 1, 2, 3, 4 or 5 amino acid substitutions with respect to the amino acid sequences of SEQ ID NO: 20, SEQ ID NO: 22, and SEQ ID NO: 24, respectively, or CDRs 1-3 having amino acid sequences of SEQ ID NO: 21, SEQ ID NO: 23, and SEQ ID NO: 25, respectively, or a combination thereof. In an embodiment, the dual function anti-glycPD-L1 antibody that specifically and preferentially binds glycosylated PD-L1 comprises a $V_L$ domain comprising CDRs 1-3 with at least 1, 2, or all 3 CDRs having at least 1, 2, 3, 4 or 5 amino acid substitutions with respect to the amino acid sequences of SEQ ID NO: 28, SEQ ID NO: 30, and SEQ ID NO: 32, respectively. In an embodiment, the dual function anti-glycPD-L1 antibody that specifically and preferentially binds glycosylated PD-L1 comprises (a) a $V_H$ domain comprising CDRs 1-3 with at least 1, 2, or all 3 CDRs having at least 1, 2, 3, 4 or 5 amino acid substitutions with respect to the amino acid sequences of SEQ ID NO: 20, SEQ ID NO: 22, and SEQ ID NO: 24, respectively, or with respect to the amino acid sequences of SEQ ID NO: 21, SEQ ID NO: 23, and SEQ ID NO: 25, respectively, or a combination thereof; and/or (b) a $V_L$ domain comprising CDRs 1-3 with at least 1, 2, or all 3 CDRs having at least 1, 2, 3, 4 or 5 amino acid substitutions with respect to the amino acid sequences of SEQ ID NO: 28, SEQ ID NO: 30, and SEQ ID NO: 32, respectively. Also provided are humanized forms of STM108 using the AbM, Contact or IMGT defined CDRs, with human framework regions and, optionally, human constant domains.

In embodiments, the foregoing anti-glycPD-L1 antibodies bind to glycosylated PD-L1 with a $K_d$ less than half of the $K_d$ exhibited relative to unglycosylated PD-L1. In an embodiment, the anti-glycPD-L1 antibodies bind to glycosylated PD-L1 protein with a $K_d$ at least 5 times less than the $K_d$ exhibited relative to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1 protein. In an embodiment, the binding affinity of STM108 MAb for glycosylated PD-L1 is from 5-20 nM or from 5-10 nM inclusive of the lower and upper values. In an embodiment, in a cell flow cytometry binding assay as described in Example 6, the antibody exhibits binding as expressed as MFI to cells expressing WT PD-L1 that is 1.5 times, 2 times, 3 times, 4 times, 5 times, 6 times, 7 times, 8 times, 9 times or 10 times greater than the MFI for binding to cells expressing unglycosylated PD-L1. These anti-glycPD-L1 antibodies inhibit the interaction of PD-1 with PD-L1, and particularly inhibit the interaction of PD-1 expressed by effector T-cells with PD-L1, particularly, glycosylated PD-L1, expressed by tumor cells.

Also encompassed in an embodiment is an isolated dual function anti-glycPD-L1 antibody that binds an epitope within the human PD-L1 amino acid sequence DAGVYRCMISYGGADYKRITV (i.e., D108-V128 of SEQ ID NO: 1). In an embodiment, an isolated dual function anti-glycPD-L1 antibody specifically binds a human PD-L1 epitope that is non-contiguous and encompasses positions Y112, R113 and S117 of the human PD-L1 amino acid sequence SEQ ID NO: 1 shown as the underlined amino acid residues in the following sequence: DAGV<u>YR</u>CMI<u>S</u>YGGADYKRITV (SEQ ID NO: 86).

Provided in an embodiment is an isolated dual function anti-glycPD-L1 antibody comprising (a) a $V_H$ domain comprising a Chothia CDR H1 having an amino acid sequence of SEQ ID NO: 4 or a Kabat CDR H1 having an amino acid sequence of SEQ ID NO: 5; a Chothia CDR H2 having an amino acid sequence of SEQ ID NO: 6 or a Kabat CDR H2 having an amino acid sequence of SEQ ID NO: 7; and a Chothia CDR H3 having an amino acid sequence of SEQ ID NO: 8 or a Kabat CDR H3 having an amino acid sequence of SEQ ID NO: 9; and a $V_L$ domain comprising a CDR L1 having an amino acid sequence of SEQ ID NO: 12; a CDR L2 having an amino acid sequence of SEQ ID NO: 14; and a CDR L3 having an amino acid sequence of SEQ ID NO: 16. Also provided is an isolated dual function anti-glycPD-L1 antibody that is a humanized form of STM073 having CDRs according to the IMGT, AbM or Contact definitions as detailed in Table 2, supra.

Provided in another embodiment is an isolated dual function anti-glycPD-L1 antibody comprising (a) a $V_H$ domain comprising a Chothia CDR H1 having an amino acid sequence of SEQ ID NO: 20 or a Kabat CDR H1 having an amino acid sequence of SEQ ID NO: 21; a Chothia CDR H2 having an amino acid sequence of SEQ ID NO: 22 or a Kabat CDR H2 having an amino acid sequence of SEQ ID NO: 23; and a Chothia CDR H3 having an amino acid sequence of SEQ ID NO: 24 or a Kabat CDR H3 having an amino acid sequence of SEQ ID NO: 25; and a $V_L$ domain comprising a CDR L1 having an amino acid sequence of SEQ ID NO: 28; a CDR L2 having an amino acid sequence of SEQ ID NO: 30; and a CDR L3 having an amino acid sequence of SEQ ID NO: 32. Also provided is an isolated dual function anti-glycPD-L1 antibody that is a humanized form of STM108 having CDRs according to the IMGT, AbM or Contact definitions as detailed in Table 2, supra.

Provided in another embodiment is an isolated dual function anti-glycPD-L1 antibody, e.g., a monoclonal antibody, chimeric or humanized form thereof, or binding fragment thereof, that specifically binds to an epitope within an amino acid sequence selected from VHGEEDLKVQH------DAGVYRCMISYGGADYKRITV (SEQ ID NO: 85), DAGVYRCMISYGGADYKRITV (SEQ ID NO: 86), or LKVQHSSYRQR------EGYP-KAEVIWTSSDHQ (which are amino acids 74 to 84 and 158 to 173, respectively, of SEQ ID NO: 1), which sequences are located within the human PD-L1 polypeptide sequence of SEQ ID NO: 1, i.e., the mature PD-L1 protein comprising amino acids 19-290 of SEQ ID NO: 1. In an embodiment, the antibody inhibits the interaction of PD-1 with PD-L1, and particularly inhibits the interaction of PD-1 expressed by effector T-cells with PD-L1, particularly, glycosylated PD-L1, expressed by tumor cells, as well as facilitates internalization of PD-L1 from the cell membrane into the cell and intracellular degradation of the PD-L1.

Provided in another embodiment is an isolated dual function anti-glycPD-L1 antibody, e.g., a monoclonal antibody, chimeric or humanized form thereof, or binding fragment thereof, that binds the same epitope as MAb STM073, or an isolated anti-glycPD-L1 MAb as described herein, wherein the epitope comprises amino acid residues H69, Y112, R113 and K124 of SEQ ID NO: 1. In another embodiment, an isolated dual function anti-glycPD-L1 antibody, e.g., a monoclonal antibody, chimeric or humanized form thereof, or binding fragment thereof, that, when bound to glycosylated PD-L1, contacts at least one of the following amino acid residues: H69, Y112, R113 and K124 of SEQ ID NO: 1 is provided. In embodiments, the anti-glycPD-L1 antibody contacts at least two, at least three, or four of the amino acid residues comprising the epitope region(s) of PD-L1, i.e., glycosylated human PD-L1.

Provided in another embodiment is an isolated dual function anti-glycPD-L1 antibody, e.g., a monoclonal antibody, chimeric or humanized form thereof, or binding fragment thereof, that binds the same epitope as MAb STM108, or an isolated anti-glycPD-L1 MAb which binds an epitope comprising amino acid residues S80, Y81, K162 and S169 of SEQ ID NO: 1. In another embodiment, an isolated dual function anti-glycPD-L1 antibody that, when bound to glycosylated PD-L1, contacts at least one of the following amino acid resides: S80, Y81, K162 and S169 of SEQ ID NO: 1 is provided.

Provided in another embodiment is an isolated dual function anti-glycPD-L1 antibody, e.g., a monoclonal antibody, chimeric or humanized form thereof, or binding fragment thereof, that, when bound to glycosylated PD-L1, contacts at least one of the following amino acid residues: Y112, R113 and S117 of SEQ ID NO: 1.

Provided in another embodiment is an isolated dual function anti-glycPD-L1 antibody, e.g., a monoclonal antibody, chimeric or humanized form thereof, or binding fragment thereof, that, when bound to glycosylated PD-L1, contacts at least one amino acid within the amino acid region from V68 to V128 of SEQ ID NO: 1, or within the amino acid region from D108 to V128 of SEQ ID NO: 1, or within the amino acid region from L74 to Q173 of SEQ ID NO: 1, or within the amino acid regions from L74 to R84 as well as from E158 to Q173 of SEQ ID NO: 1. In another embodiment, there is provided an isolated dual function anti-glycPD-L1 antibody, e.g., a monoclonal antibody, chimeric or humanized form thereof, or binding fragment thereof, that, when bound to glycosylated PD-L1, contacts at least one of the following group of amino acid residues: H69, Y112, R113 and K124 within the amino acid region from V68 to V128 of SEQ ID NO: 1. In another embodiment, there is provided an isolated dual function anti-glycPD-L1 antibody, e.g., a monoclonal antibody, chimeric or humanized form thereof, or binding fragment thereof, that, when bound to glycosylated PD-L1, contacts at least one, at least two, at least three, or four of the following group of amino acid residues: H69, S80, Y81, Y112, R113, K124, K162, S169 within the amino acid region from V68 to V173 of SEQ ID NO: 1. In an embodiment, an isolated dual function anti-glycPD-L1 antibody, e.g., a monoclonal antibody, chimeric or humanized form thereof, or binding fragment thereof, that, when bound to glycosylated PD-L1, contacts the following group of amino acid residues: Y112, R113, S117 within the amino acid region from D108 to V128 of SEQ ID NO: 1 is provided.

Provided in another embodiment is an isolated dual function anti-glycPD-L1 antibody, e.g., a monoclonal antibody, chimeric or humanized form thereof, or binding fragment thereof, that, when bound to glycosylated PD-L1, binds at least amino acid region V68-V128 or at least amino acid region D108-V128 of the PD-L1 protein (SEQ ID NO: 1), or a combination thereof.

Yet another embodiment provides an isolated nucleic acid comprising a nucleotide sequence of SEQ ID NO: 2 or 18 encoding a $V_H$ domain and a nucleotide sequence of SEQ ID NO: 10 or 26 encoding an antibody $V_L$ domain. In an embodiment, an isolated nucleotide sequence encoding an anti-glycPD-L1 antibody $V_H$ domain, wherein the nucleotide sequence is at least 90-98% identical to the nucleotide sequence of SEQ ID NOs: 2 or 18 is provided. In an embodiment, an isolated nucleotide sequence encoding an anti-glycPD-L1 antibody $V_L$ domain, wherein the nucleotide sequence is at least 90-98% identical to the nucleotide sequence of SEQ ID NOs: 19 or 26 is provided. In embodiments, the nucleotide sequences encoding the $V_H$ and/or the $V_L$ domains are 90%, 91%, 92%, 93%, 94%, 95%, 96%, 97%, 98%, 99%, or more identical to SEQ ID NOs: 2 or 18, or SEQ ID NOs: 10 or 26, respectively.

TABLE 3

Nucleotide and Amino Acid Sequences of anti-glycPD-L1 MAbs

| SEQ ID NO: | Sequence | Description |
|---|---|---|
| SEQ ID NO: 2 | aagtgcagctggtggagtctgggggagccttagtg aagcctggagggtccctgaaactctcctgtgcagc ctctggattcactttcagtaactctgccatgtctt gggttcgccagactccagagaagaggctggagtgg gtcgcaaccattagtagtgctggtagttataccta ctatccagacagtgtgaagggtcgattcaccatct ccagagacaatgccaagaacaccctgtacctgcaa atgagcagtctgaggtctgaggacacggccttgta ttactgtacaagacattatgattactactttgact actggggccaaggcgccactctcacagtctcctca | Nucleotide (DNA) sequence encoding mature STM073 heavy chain V domain (Not including amino terminal nucleotides 1-58 encoding the signal sequence) |
| SEQ ID NO: 3 | EVQLVESGGALVKPGGSLKLSCAASGFTFSNSAMS WVRQTPEKRLEWVATISSAGSYTYYPDSVKGRFTI SRDNAKNTLYLQMSSLRSEDTALYYCTRHYDYYFD YWGQGATLTVSS | Protein sequence of the mature MAb STM073 heavy chain V domain (Not including amino terminal residues M1-C19 which constitute the signal sequence) |
| SEQ ID NO: 4 | GFTFSNS | MAb STM073 heavy chain V domain Chothia CDR1 |
| SEQ ID NO: 5 | NSAMS | MAb STM073 heavy chain V domain Kabat CDR1 |
| SEQ ID NO: 6 | SSGGSY | MAb STM073 heavy chain V domain Chothia CDR2 |
| SEQ ID NO: 7 | TISSAGSYTYYPDSVKG | MAb STM073 heavy chain V domain Kabat CDR2 |
| SEQ ID NO: 8 | TRHYDYYFDY | MAb STM073 heavy chain V domain Chothia CDR3 |
| SEQ ID NO: 9 | TRHYDYYFDY | MAb STM073 heavy chain V domain Kabat CDR3 |
| SEQ ID NO: 10 | caaattgttctcacccagtctccagcaatcatgtc tgcatctccaggggagaaggtcaccttgacctgca gtgccagctcaagtgtaagttacatgcattggtac cagcagaagccaggatcctcccccagactcgtgat ttatgacacatccaacctggcttctggagtccctg ttcgcttcagtggcagtgggtctgggacctcttac tctctcacagtcagccgaatggaggctgaagatgc tgccacttattactgccagcagtggagtgatcacc cgctcacgttcggtgctgggaccaagctggagctg aaac | Nucleotide (DNA) sequence encoding the mature STM073 kappa light chain V domain (Not including amino terminal nucleotides 1-66 encoding the signal sequence) |
| SEQ ID NO: 11 | QIVLTQSPAIMSASPGEKVTLTCSASSSVSYMHWY QQKPGSSPRLVIYDTSNLASGVPVRFSGSGSGTSY SLTVSRMEAEDAATYYCQQWSDHPLTFGAGTKLEL K | Protein sequence of the mature MAb STM073 kappa light chain V domain (Not including amino terminal residues M1-G22 which constitute the signal sequence) |
| SEQ ID NO: 12 | SASSSVSYMH | MAb STM073 kappa light chain V domain Chothia CDR1 |
| SEQ ID NO: 13 | SASSSVSYMH | MAb STM073 kappa light chain V domain Kabat CDR1 |
| SEQ ID NO: 14 | DTSNLAS | MAb STM073 kappa light chain V domain Chothia CDR2 |
| SEQ ID NO: 15 | DTSNLAS | MAb STM073 kappa light chain V domain Kabat CDR2 (f |
| SEQ ID NO: 16 | QQWSDHPLT | MAb STM073 kappa light chain V domain Chothia CDR3 |

TABLE 3-continued

Nucleotide and Amino Acid Sequences of anti-glycPD-L1 MAbs

| SEQ ID NO: | Sequence | Description |
| --- | --- | --- |
| SEQ ID NO: 17 | QQWSDHPLT | MAb STM073 kappa light chain V domain Kabat CDR3 |
| SEQ ID NO: 18 | gaagtgatgctggtggagtctgggggagccttagtgaagcctggagggtccctgaaactctcctgtgcagcttctggattcagtttgagtaactatgtcatgtcttgggttcgccagactccagagaagaggctggagtgggtcgcaaccattagtagtggtggtaggtatatctactatacagacagtgtgaagggtcgattcaccatctccagggacaatgccaggaacaccctgtacctgcaaatgagcagtctgaggtcgaggacacggccatgtattattgtgcaagagacggtagtaccttgtactactttgactattggggccaaggcaccactctcacagtctcctca | Nucleotide (DNA) sequence encoding the mature MAb STM108 heavy chain V domain (Not including amino terminal nucleotides 1-57 encoding the signal sequence) |
| SEQ ID NO: 19 | EVMLVESGGALVKPGGSLKLSCAASGFSLSNYVMSWVRQTPEKRLEWVATISSGGRYIYYTDSVKGRFTISRDNARNTLYLQMSSLRSEDTAMYYCARDGSTLYYFDYWGQGTTLTVSS | Protein sequence of the mature MAb STM108 heavy chain V domain (Not including amino terminal residues M1-C19 which constitute the signal sequence) |
| SEQ ID NO: 20 | GFSLSNY | MAb STM108 heavy chain V domain Chothia CDR1 |
| SEQ ID NO: 21 | NYVMS | MAb STM108 heavy chain V domain Kabat CDR1 |
| SEQ ID NO: 22 | SSGGRY | MAb STM108 heavy chain V domain Chothia CDR2 |
| SEQ ID NO: 23 | TISSGGRYIYYTDSVKG | MAb STM108 heavy chain V domain Kabat CDR2 |
| SEQ ID NO: 24 | DGSTLYYFDY | MAb STM108 heavy chain V domain Chothia CDR3 |
| SEQ ID NO: 25 | DGSTLYYFDY | MAb STM108 heavy chain V domain Kabat CDR3 |
| SEQ ID NO: 26 | caagtgcagattttcagcttcctgctaatcagtgcctcagtcatactgtccagaggacaaactgttctcacccagtctccagcaatcatgtctgcatctccaggggagaaggtcaccatgacctgcagtgccagctcaagtgtagattacatgtactggtaccagcagaagccaggatcctcccccagactcctgatttatgacacatccaacctggcttctggagtccctgttcgcttcagtggcagtgggtctgggacctcttactctctcacaatcagccgaatggaggctgaagatgctgccacttattactgccagcagtggagtagttccccacccatcacgttcggtactgggaccaaggtggagctgaaa | Nucleotide sequence (DNA) encoding the mature MAb STM108 kappa light chain V domain |
| SEQ ID NO: 27 | QVQIFSFLLISASVILSRGQTVLTQSPAIMSASPGEKVTMTCSASSSVDYMYWYQQKPGSSPRLLIYDTSNLASGVPVRFSGSGSGTSYSLTISRMEAEDAATYYCQQWSSSPPITFGTGTKVELK | Protein sequence of the mature MAb STM108 kappa light chain V domain |
| SEQ ID NO: 28 | SASSSVDYMY | MAb STM108 kappa light chain V domain Chothia CDR1 |
| SEQ ID NO: 29 | SASSSVDYMY | MAb STM108 kappa light chain V domain Kabat CDR1 |
| SEQ ID NO: 30 | DTSNLAS | MAb STM108 kappa light chain V domain Chothia CDR2 |
| SEQ ID NO: 31 | DTSNLAS | MAb STM108 kappa light chain V domain Kabat CDR2 |
| SEQ ID NO: 32 | QQWSSSPPIT | MAb STM108 kappa light chain V domain Chothia CDR3 |

TABLE 3-continued

Nucleotide and Amino Acid Sequences of anti-glycPD-L1 MAbs

| SEQ ID NO: | Sequence | Description |
| --- | --- | --- |
| SEQ ID NO: 33 | QQWSSSPPIT | MAb STM108 kappa light chain V domain Kabat CDR3 |
| SEQ ID NO: 87 | *atgaacttgtggctcagcttggttttccttgtcct tgttttaaaaggtgtccagtgtg*aagtgcagctgg tggagtctgggggagccttagtgaagcctggaggg tccctgaaactctcctgtgcagcctctggattcac tttcagtaactctgccatgtcttgggttcgccaga ctccagagaagaggctggagtgggtcgcaaccatt agtagtgctggtagttatacctactatccagacag tgtgaagggtcgattcaccatctccagagacaatg ccaagaacaccctgtacctgcaaatgagcagtctg aggtctgaggacacggccttgtattactgtacaag acattatgattactactttgactactggggccaag gcgccactctcacagtctcctca | Nucleotide (DNA) sequence encoding the STM073 heavy chain V domain, including amino terminal nucleotides 1-58 (in italics) which encode the signal sequence |
| SEQ ID NO: 88 | *MNLWLSLVFLVLVLKGVQC*EVQLVESGGALVKPGG SLKLSCAASGFTFSNSAMSWVRQTPEKRLEWVATI SSAGSYTYYPDSVKGRFTISRDNAKNTLyLQMSSL RSEDTALYYCTRHYDYYFDYWGQGATLTVSS | Protein sequence of the MAb STM073 heavy chain V domain, including amino terminal residues M1-C19 (in italics) which constitute the signal sequence |
| SEQ ID NO: 89 | *atggatttcaagtgcagattttcagcttcctgct aatcagtgcctcagtcatactgtccagagga*caaa ttgttctcacccagtctccagcaatcatgtctgca tctccaggggagaaggtcaccttgacctgcagtgc cagctcaagtgtaagttacatgcattggtaccagc agaagccaggatcctcccccagactcgtgatttat gacacatccaacctggcttctggagtccctgttcg cttcagtggcagtgggtctgggacctcttactctc tcacagtcagccgaatggaggctgaagatgctgcc acttattactgccagcagtggagtgatcacccgct cacgttcggtgctgggaccaagctggagctgaaac | Nucleotide (DNA) sequence encoding the STM073 kappa light chain V domain, including amino terminal nucleotides 1-66 (in italics) which encode the signal sequence |
| SEQ ID NO: 90 | *MDFQVQIFSFLLISASVILSRG*QIVLTQSPAIMSA SPGEKVTLTCSASSSVSYMHWYQQKPGSSPRLVIY DTSNLASGVPVRFSGSGSGTSYSLTVSRMEAEDAA TYYCQQWSDHPLTFGAGTKLELK | Protein sequence of the MAb STM073 kappa light chain V domain, including amino terminal residues M1-G22 (in italics) which constitute the signal sequence |
| SEQ ID NO: 91 | *atgaacttcgggctcagctgatttccttgtccttat tttaaaaggtgtccagtgt*gaagtgatgctggtggagt ctggggagccttagtgaagcctggagggtccctgaaa ctctcctgtgcagcttctggattcagtttgagtaacta tgtcatgtcttgggttcgccagactccagagaaggagc tggagtgggtcgcaaccattagtagtggtggtaggtat atctactatacagacagtgtgaagggtcgattccaccat ctccagggacaatgccaggaacaccctgtacctgcaaa tgagcagtctgaggtctgaggacacggccatgtattat tgtgcaagagacggtagtaccttgtactactttgacta ttggggccaaggcaccactctcacagtctcctca | Nucleotide (DNA) sequence encoding the STM108 heavy chain V domain, including amino terminal nucleotides 1-57 (in italics) which encode the signal sequence of the STM108 protein |
| SEQ ID NO: 92 | *MNFGLSLIFLVLILKGVQC*EVMLVESGGALVKPGG SLKLSCAASGFSLSNYVMSWVRQTPEKRLEWVATI SSGGRYIYYTDSVKGRFTISRDNARNTLYLQMSSL RSEDTAMYYCARDGSTLYYFDYWGQGTTLIVSS | Protein sequence of the MAb STM108 heavy chain V domain, including amino terminal residues M1-C19 (in italics) which constitute the signal sequence |

Disease Treatment

In certain aspects, an antibody or antigen binding fragment thereof, as described in the embodiments herein (e.g., a dual function antibody that specifically binds to glycosylated PD-L1) may be administered to treat a cancer in a subject suffering therefrom or to prevent cancer in a subject with a predisposition (such as a genetic predisposition, prior environmental exposure to a carcinogen, prior incidence of cancer, etc.) to develop a cancer. Accordingly, provided herein are methods of treating a cancer by administering to a subject in need a therapeutically effective amount of at least one dual function anti-glycPD-L1 antibody to treat the cancer. As noted herein, treatment involves reducing, preventing, inhibiting, or blocking the growth, proliferation, migration, etc. of cancer cells, and includes causing cell killing or apoptosis of cancer cells. The treatment may also prevent or cause regression of metastasis of tumor cells. The methods described herein provide a benefit to the subject, e.g., a human patient, undergoing treatment, with particular regard to tumor cells that express glycosylated PD-L1 cell surface proteins that can bind/interact with PD-1 expressed on the cell surface of immune effector cells, such as T-cells, particularly, killer or cytotoxic T-cells.

Treatment of these subjects with an effective amount of at least one of the dual function anti-glycPD-L1 antibodies as described is expected to result in binding of the antibody (ies) to glycosylated PD-L1 on the tumor cells and preventing, blocking, or inhibiting the interaction of PD-L1 and PD-1 and promoting the internalization and degradation of PD-L1 to prevent, block or inhibit the interaction of the PD-L1-expressing tumor cells with PD-1-expressing T cells, thereby preventing or avoiding immunosuppression of T-cell activity and allowing T cells to be activated to kill the PD-L1-bearing tumor cells. In a preferred embodiment, the dual function anti-PD-L1 antibody binds to human PD-L1 and the subject is a human patient. Accordingly, the methods provided herein are advantageous for a subject who is in need of, capable of benefiting from, or who is desirous of receiving the benefit of, the anti-cancer results achieved by the practice of the present methods. A subject's seeking the therapeutic benefits of the methods involving administration of at least one dual function anti-glycPD-L1 antibody in a therapeutically effective amount, or receiving such therapeutic benefits offer advantages to the art. In addition, the present methods offer the further advantages of eliminating or avoiding side effects, adverse outcomes, contraindications, and the like, or reducing the risk or potential for such issues to occur compared with other treatments and treatment modalities.

In specific embodiments, the subject suffering from or predisposed to cancer is administered a therapeutically effective amount of a humanized or chimeric form of STM073 or STM108 that is a dual function anti-glycPD-L1 antibody. It may be advantageous to administer more than one type of anti-glycPD-L1 antibody for the treatment of cancer. For example, chimeric or humanized forms of both STM073 and STM108 may be co-administered to a patient in need thereof. Alternatively, a chimeric or humanized form of STM073 may be co-administered with another anti-glycPD-L1 antibody to a patient in need thereof or a chimeric or humanized form of STM108 may be co-administered with another anti-glycPD-L1 antibody to a patient in need thereof. Co-administration of the anti-glycPD-L1 antibodies may be more therapeutically or prophylactically effective than administration of either antibody alone and/or may permit administration of a lower dose or with lower frequency than either antibody alone.

Cancers for which the present treatment methods are useful include any malignant cell type, such as those found in a solid tumor or a hematological tumor, particularly tumors with cells that express glycosylated PD-L1 on their surface. In general, a tumor refers to a malignant or a potentially malignant neoplasm or tissue mass of any size, and includes primary tumors and secondary tumors. A solid tumor is an abnormal tissue mass or growth that usually does not contain cysts or liquid. Exemplary solid tumors can include, but are not limited to, a tumor of an organ selected from the group consisting of pancreas, gall bladder, colon, cecum, stomach, brain, head, neck, ovary, testes, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological types, though it need not be limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma;

teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The cancer to be treated preferably is positive for PD-L1, particularly glycosylated PD-L1. In certain embodiments, the tumor cells are also positive for a tumor cell marker such as EGFR or HER2/neu expression, e.g., as expressed on breast cancer cells. The presence or absence of these markers may indicate that combination therapy with a targeted therapeutic, such as a tyrosine kinase inhibitor, e.g., gefitinib for an EGFR-positive cancer, or Herceptin for a HER2/neu-positive cancer, in combination with the dual function anti-glycPD-L1 antibodies as described herein, would provide a treatment benefit for a subject in need. In certain embodiments, the cancer is a BLBC.

Other markers that may be used to characterize cancers to guide choice of therapy or monitor therapy include ALK gene rearrangements and overexpression in non-small cell lung cancer and anaplastic large cell lymphoma; alpha-fetoprotein (AFP) for liver cancer and germ cell tumors; beta-2-microglobulin (B2M) for multiple myeloma, chronic lymphocytic leukemia, and some lymphomas; beta-human chorionic gonadotropin (Beta-hCG) for choriocarcinoma and germ cell tumors; BRCA1 and BRCA2 gene mutations for ovarian cancer and breast cancer; BCR-ABL fusion gene (Philadelphia chromosome) for chronic myeloid leukemia, acute lymphoblastic leukemia, and acute myelogenous leukemia; BRAF V600 mutations for cutaneous melanoma and colorectal cancer; C-kit/CD117 for gastrointestinal stromal tumor and mucosal melanoma; CA15-3/CA27.29 for breast cancer; CA19-9 for pancreatic cancer, gallbladder cancer, bile duct cancer, and gastric cancer; CA-125 for ovarian cancer; calcitonin for medullary thyroid cancer; carcinoembryonic antigen (CEA) for colorectal cancer and some other cancers; CD20 for non-Hodgkin lymphoma; Chromogranin A (CgA) for neuroendocrine tumors; chromosomes 3, 7, 17, and 9p21 for bladder cancer; cytokeratin fragment 21-1 for lung cancer; EGFR gene mutation analysis for non-small cell lung cancer; estrogen receptor (ER)/progesterone receptor (PR) for breast cancer; fibrin/fibrinogen for bladder cancer; HE4 for ovarian cancer; HER2/neu gene amplification or protein overexpression for breast cancer, gastric cancer, and gastroesophageal junction adenocarcinoma; immunoglobulins for multiple myeloma and Waldenström macroglobulinemia; KRAS gene mutation analysis for colorectal cancer and non-small cell lung cancer; lactate dehydrogenase for germ cell tumors, lymphoma, leukemia, melanoma, and neuroblastoma; neuron-specific enolase (NSE) for small cell lung cancer and neuroblastoma; nuclear matrix protein 22 for bladder cancer; prostate-specific antigen (PSA) for prostate cancer; thyroglobulin for thyroid cancer; and urokinase plasminogen activator (uPA) and plasminogen activator inhibitor (PAI-1) for breast cancer.

The dual function anti-glycPD-L1 antibodies may be used as antitumor agents in a variety of modalities. A particular embodiment relates to methods of using an antibody as an antitumor agent, and therefore comprises contacting a population of tumor cells with a therapeutically effective amount of the antibody, or a composition containing the antibody, for a time period sufficient to block or inhibit tumor cell growth or to effect apoptosis of the tumor cells. In an embodiment, contacting a tumor cell in vivo is accomplished by administering to a patient in need, for example, by intravenous, subcutaneous, intraperitoneal, or intratumoral injection, a therapeutically effective amount of a physiologically tolerable composition comprising a dual function anti-glycPD-L1 antibody as described herein. The antibody may be administered parenterally by injection or by gradual infusion over time. Useful administration and delivery regimens include intravenous, intraperitoneal, oral, intramuscular, subcutaneous, intracavity, intrathecal, transdermal, dermal, peristaltic means, or direct injection into the tissue containing the tumor cells.

Therapeutic compositions comprising antibodies are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle. The dual function anti-glycPD-L1 antibody containing compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient to be administered depend on the judgment of the practitioner and are peculiar to each individual. However, suitable dosage ranges for systemic application are disclosed herein and depend on the route of administration. Suitable regimens for initial and booster administration are also contemplated and may typically involve an initial administration followed by repeated doses at one or more intervals (hours) by a subsequent injection or other administration. Exemplary multiple administrations are suitable for maintaining continuously high serum and tissue levels of antibody. Alternatively, continuous intravenous infusion sufficient to maintain concentrations in the blood in the ranges specified for in vivo therapies are contemplated.

It is contemplated that an anti-glycPD-L1 antibody may be administered systemically or locally to treat disease, such as to inhibit tumor cell growth or to kill cancer cells in cancer patients with locally advanced or metastatic cancers. The antibodies may be administered alone or in combination with anti-proliferative drugs or anticancer drugs. In an embodiment, the anti-glycPD-L1 antibodies are administered to reduce the cancer load in the patient prior to surgery or other procedures. Alternatively, they can be administered at periodic intervals after surgery to ensure that any remaining cancer (e.g., cancer that the surgery failed to eliminate) is reduced in size or growth capacity and/or does not survive. As noted hereinabove, a therapeutically effective amount of an antibody is a predetermined amount calculated to achieve the desired effect. Thus, the dosage ranges for the administration of an anti-glycPD-L1 antibody are those large enough to produce the desired effect in which the symptoms of tumor cell division and cell cycling are reduced. Optimally, the dosage should not be so large as to cause adverse side effects, such as hyperviscosity syndromes, pulmonary edema, congestive heart failure, neurological effects, and the like. Generally, the dosage will vary with age of, condition of, size and gender of, and extent of the disease in the patient and can be determined by one of skill in the art such as a medical practitioner or clinician. Of course, the dosage may be adjusted by the individual physician in the event of any complication.

Treatment Methods

In certain embodiments, the compositions and methods as described involve the administration of a dual function anti-glycPD-L1 antibody, alone, or in combination with a second or additional drug or therapy. Such drug or therapy may be applied in the treatment of any disease that is associated with PD-L1 or glycosylated PD-L1, preferably with the interaction of human PD-L1 or glycosylated human PD-L1 with human PD-1. For example, the disease may be a cancer. The compositions and methods comprising at least one anti-PD-L1 antibody that preferentially binds to glycosylated PD-L1 protein and both blocks or inhibits PD-L1 to PD-1 binding and promotes PD-L1 internalization and degradation, or a binding portion thereof, have a therapeutic or protective effect in the treatment of a cancer or other disease, particularly by preventing, reducing, blocking, or inhibiting the PD-1/PD-L1 interaction, thereby providing a therapeutic effect and treatment.

The compositions and methods, including combination therapies, have a therapeutic or protective effect and may enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a dual function anti-glycPD-L 1 antibody or a binding fragment thereof and a second therapy. The second therapy may or may not have a direct cytotoxic effect. For example, the second therapy may be an agent that upregulates the immune system without having a direct cytotoxic effect. A tissue, tumor, and/or cell can be exposed to one or more compositions or pharmacological formulation(s) comprising one or more of the agents (e.g., an antibody or an anti-cancer agent), or by exposing the tissue, tumor, and/or cell with two or more distinct compositions or formulations, wherein one composition provides, for example, 1) an antibody, 2) an anti-cancer agent, 3) both an antibody and an anti-cancer agent, or 4) two or more antibodies. In some embodiments, the second therapy is also an anti-PD-L1 antibody, preferably an anti-glycPD-L1 antibody that preferentially binds glycosylated PD-L1 versus unglycosylated PD-L1 or, in other embodiments, an anti-PD-1 antibody. Without limitation, exemplary anti-PD-1 antibodies include pembrolizumab and nivolumab; exemplary anti-PD-L1 antibodies include atezolizumab. Also, it is contemplated that such a combination therapy can be used in conjunction with chemotherapy, radiotherapy, surgical therapy, or immunotherapy.

By way of example, the terms "contacted" and "exposed," when applied to a cell, are used herein to describe a process by which a therapeutic polypeptide, preferably an anti-glycPD-L1 antibody as described herein, is delivered to a target cell or is placed in direct juxtaposition with the target cell, particularly to bind specifically to the target antigen, e.g., PD-L1, particularly, glycosylated PD-L1, expressed or highly expressed on the surface of tumor or cancer cells. Such binding by a therapeutic anti-glycPD-L1 antibody or binding fragment thereof prevents, blocks, inhibits, or reduces the interaction of the tumor or cancer cell-expressed PD-L1 with PD-1 on an effector T-cell, thereby preventing immunosuppression associated with the PD-LI/PD-1 interaction. In embodiments, a chemotherapeutic or radiotherapeutic agent are also administered or delivered to the subject in conjunction with the anti-glycPD-L1 antibody or binding fragment thereof. To achieve cell killing, for example, one or more agents are delivered to a cell in a combined amount effective to kill the cell or prevent it from dividing.

An anti-glycPD-L1 antibody may be administered before, during, after, or in various combinations relative to another anti-cancer treatment. The administrations may be in intervals ranging from concurrently to minutes to days to weeks before or after one another. In embodiments in which the antibody is provided to a patient separately from an anti-cancer agent, it would be generally ensured that a significant period of time did not expire between the time of each delivery, such that the administered compounds would still be able to exert an advantageously combined effect for the patient. Illustratively, in such instances, it is contemplated that one may provide a patient with the antibody and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment or treatment cycle will last 1-90 days or more (this range includes intervening days and the last day). It is contemplated that one agent may be given on any day of day 1 to day 90 (this such range includes intervening days and the last day) or any combination thereof, and another agent is given on any day of day 1 to day 90 (this such range includes intervening days and the last day) or any combination thereof. Within a single day (24-hour period), the patient may be given one or multiple administrations of the agent(s). Moreover, after a course of treatment, it is contemplated that there may be a period of time at which no anti-cancer treatment is administered. This time period may last, for example, for 1-7 days, and/or 1-5 weeks, and/or 1-12 months or more (this such range includes intervening days and the upper time point), depending on the condition of the patient, such as prognosis, strength, health, etc. Treatment cycles would be repeated as necessary. Various combinations of treatments may be employed. In the representative examples of combination treatment regimens shown below, an antibody, such as an anti-glycPD-L1 antibody or binding fragment thereof is represented by "A" and an anti-cancer therapy is represented by "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A.

Administration of any antibody or therapy of the present embodiments to a patient will follow general protocols for the administration of such compounds, taking into account the toxicity, if any, of the agents. Therefore, in some embodiments there is a step of monitoring adverse events and toxicity, particularly those that may be attributable to combination therapy.

In an embodiment, a method is provided which involves the administration of a dual function anti-glycPD-L1 antibody alone or in combination with another anticancer agent to a patient in need thereof, i.e., a patient with a cancer or tumor. Prior to administration of the anti-glycPD-L1 antibody, a sample of the patient's tumor or cancer may be evaluated for the presence of PD-L1. If the results of such an evaluation reveals that the patient's tumor or cancer is positive for glycosylated PD-L1, the patient would be selected for treatment based on the likelihood that patient's glycPD-L1+ tumor or cancer would be more amenable to treatment with the anti-glycPD-L1 antibody and treatment may proceed with a more likely beneficial outcome. A medical professional or physician may advise the patient to proceed with the anti-glycPD-L1 antibody treatment method, and the patient may decide to proceed with treatment based on the advice of the medical professional or physician. In addition, during the course of treatment, the patient's tumor or cancer cells may be assayed for the presence of glycosylated PD-L1 as a way to monitor the progress or effectiveness of treatment. If the assay shows a change, loss, or decrease, for example, in glycosylated PD-L1 on the patient's tumor or cancer cells, a decision may be taken by the medical professional in conjunction with the patient as to whether the treatment should continue or be altered in some fashion, e.g., a higher dosage, the addition of another anti-cancer agent or therapy, and the like.

Chemotherapy

A wide variety of chemotherapeutic agents may be used in accordance with the treatment or therapeutic methods of the present embodiments. The term "chemotherapy" refers to the use of drugs to treat cancer. A "chemotherapeutic agent" connotes a compound or composition that is administered in the treatment of cancer. Such agents or drugs are categorized by their mode of activity within a cell, for example, whether and at what stage they affect the cell cycle and cell growth and proliferation. Alternatively, a chemotherapeutic agent may be characterized based on its ability to directly cross-link DNA, to intercalate into DNA, or to induce chromosomal and mitotic aberrations by affecting nucleic acid synthesis in a cell.

Nonlimiting examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma 1 and calicheamicin omega 1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabine, navelbine, farnesyl-protein tansferase inhibitors, transplatinum, and pharmaceutically acceptable salts, acids, or derivatives of any of the above.

Radiotherapy

Radiotherapy includes treatments with agents that cause DNA damage. Radiotherapy has been used extensively in cancer and disease treatments and embraces what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA itself, on the precursors of DNA, on the replication and repair of DNA, and on the assembly and maintenance of chromosomes. Exemplary dosage ranges for X-rays range from daily doses of 50 to 200 roentgens for prolonged periods of time (3 to 4 weeks) to single doses of 2000 to 6000 roentgens. Dosage ranges for radioisotopes vary widely and depend on the half-life of the isotope, the strength and type of radiation emitted, the uptake by the neoplastic cells, and tolerance of the subject undergoing treatment.

Immunotherapy

In some embodiments of the methods, immunotherapies may be used in combination or in conjunction with administration of dual function anti-glycPD-L1 antibodies as described herein. In the context of cancer treatment, immunotherapeutics generally rely on the use of immune effector cells and molecules to target and destroy cancer cells. Rituximab (RITUXAN®) is such an example. Other checkpoint inhibitors can also be administered in combination, including ipilimumab. The dual function anti-glycPD-L1 antibodies may also be administered in combination with other anti-PD-1 or anti-PD-L1 inhibitors, such as antibodies against PD-L1, which include atezolizumab, durvalumab, or avelumab, or antibodies against PD-1, including nivolumab, pembrolizumab, or pidilizumab. In addition, one or more of the dual function anti-glycPD-L1 antibodies of the embodiments may be administered in combination with each other. The immune effector may be, for example, an antibody specific for a marker (cell surface protein or receptor) on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target, e.g., the PD-1 on T-cells/PD-L1 on tumor cells interaction. Various effector cells include cytotoxic T cells and natural killer (NK) cells.

In one aspect of immunotherapy, the tumor cell must bear some marker (protein/receptor) that is amenable to targeting. Optimally, the tumor marker protein/receptor is not present on the majority of other cells, such as non-cancer cells or normal cells. Many tumor markers exist and any of these may be suitable for targeting by another drug or therapy administered with an anti-glycPD-L1 antibody in the context of the present embodiments. Common tumor markers include, for example, CD20, carcinoembryonic antigen (CEA), tyrosinase (p97), gp68, TAG-72, HMFG, Sialyl Lewis Antigen, MucA, MucB, PLAP, laminin receptor, erbB, and p155. An alternative aspect of immunotherapy is to combine anticancer effects with immune stimulatory effects. Immune stimulating molecules also exist and include cytokines, such as IL-2, IL-4, IL-12, GM-CSF, gamma-IFN; chemokines, such as MIP-1, MCP-1, IL-8; and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998, *Infection Immun.*, 66(11): 5329-5336; Christodoulides et al., 1998, Microbiology, 144 (Pt 11):3027-3037); cytokine therapy, e.g., α, β, and γ interferons; IL-1, GM-CSF, and TNF (Bukowski et al., 1998, *Clinical Cancer Res.*, 4(10):2337-2347; Davidson et al., 1998, *J. Immunother.*, 21(5):389-398; Hellstrand et al., 1998, *Acta Oncologica*, 37(4):347-353); gene therapy, e.g., TNF, IL-1, IL-2, and p53 (Qin et al., 1998, *Proc. Natl. Acad. Sci. USA*, 95(24):14411-14416; Austin-Ward et al., 1998, *Revista Medial de Chile*, 126(7):838-845; U.S. Pat. Nos. 5,830,880 and 5,846,945); and monoclonal antibodies, e.g., anti-CD20, anti-ganglioside GM2, and anti-p185 (Hollander, 2012, *Front. Immun.*, 3:3; Hanibuchi et al., 1998, *Int. J. Cancer*, 78(4):480-485; U.S. Pat. No. 5,824,311). It is contemplated that one or more anti-cancer therapies may be employed with the antibody therapies described herein.

Surgery

Approximately 60% of individuals with cancer undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as anti-glycPD-L1 antibody treatment as described herein, chemotherapy, radiotherapy, hormonal therapy, gene therapy, immunotherapy, and/or alternative therapies, as well as combinations thereof. Tumor resection refers to physical removal of at least part of a tumor. In addition to tumor resection, treatment by surgery includes laser surgery, cryosurgery, electrosurgery, and microscopically-controlled surgery (Mohs' surgery). Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Protein Purification

Protein, including antibody and, specifically, anti-glycPD-L1 antibody, purification techniques are well known to those of skill in the art. These techniques involve, at one level, the homogenization and crude fractionation of the cells, tissue, or organ into polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure protein or peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, the order of conducting the various purification steps may be changed, and/or certain steps may be omitted, and still result in a suitable method for the preparation of a substantially purified polypeptide.

A purified polypeptide, such as an anti-glycPD-L1 antibody as described herein, refers to a polypeptide which is isolatable or isolated from other components and purified to any degree relative to its naturally-obtainable state. An isolated or purified polypeptide, therefore, also refers to a polypeptide free from the environment in which it may naturally occur, e.g., cells, tissues, organs, biological samples, and the like. Generally, "purified" will refer to a polypeptide composition that has been subjected to fractionation to remove various other components, and which composition substantially retains its expressed biological activity. A "substantially purified" composition refers to one in which the polypeptide forms the major component of the composition, and as such, constitutes about 50%, about 60%, about 70%, about 80%, about 90%, about 95%, or more of the protein component of the composition.

Various methods for quantifying the degree of purification of polypeptides, such as antibody proteins, are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed polypeptide exhibits a detectable activity.

There is no general requirement that the polypeptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance (protein) to be isolated and a molecule to which it can specifically bind, e.g., a receptor-ligand type of interaction. The column material (resin) is synthesized by covalently coupling one of the binding partners to an insoluble matrix. The column material is then able to specifically adsorb the substance from the solution that is passed over the column resin. Elution occurs by changing the conditions to those in which binding will be disrupted/will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding; however, elution of the bound substance should occur without destroying the sample protein desired or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates, resulting in the separation of a solution of particles based on size. Provided that all of the particles are loaded simultaneously or near simultaneously, particles of the same size should elute together.

High-performance (aka high-pressure) liquid chromatography (HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

Pharmaceutical Preparations

Where clinical application of a pharmaceutical composition containing a dual function, anti-glycPD-L1 antibody or glycosylated PD-L1 polypeptide is undertaken, it is generally beneficial to prepare a pharmaceutical or therapeutic composition appropriate for the intended application. In general, pharmaceutical compositions may comprise an effective amount of one or more polypeptides or additional agents dissolved or dispersed in a pharmaceutically acceptable carrier. In certain embodiments, pharmaceutical compositions may comprise, for example, at least about 0.1% of a polypeptide or antibody. In other embodiments, a polypeptide or antibody may comprise between about 2% to about 75% of the weight of the unit, or between about 25% to about 60%, for example, and any range derivable therebetween, including the upper and lower values. The amount of active compound(s) in each therapeutically useful composition may be prepared in such a way that a suitable dosage will be obtained in any given unit dose. Factors, such as solubility, bioavailability, biological half-life, route of administration, product shelf life, as well as other pharmacological considerations, are contemplated by one skilled in the art of preparing such pharmaceutical formulations, and as such, a variety of dosages and treatment regimens may be desirable.

Further in accordance with certain aspects, the composition suitable for administration may be provided in a pharmaceutically acceptable carrier with or without an inert diluent. The carrier should be assimilable and include liquid, semi-solid, e.g., gels or pastes, or solid carriers. Examples of carriers or diluents include fats, oils, water, saline solutions, lipids, liposomes, resins, binders, fillers, and the like, or combinations thereof. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects, the composition is combined with the carrier in any convenient and practical manner, i.e., by solution, suspension, emulsification, admixture, encapsulation, absorption, grinding, and the like. Such procedures are routine for those skilled in the art.

In certain embodiments, the compositions may comprise different types of carriers depending on whether they are to be administered in solid, liquid, or aerosol form, and whether it needs to be sterile for the route of administration, such as injection. The compositions can be formulated for administration intravenously, intradermally, transdermally, intrathecally, intra-arterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art. See, for example, *Remington Pharmaceutical Sciences,* 18th Ed., 1990. Typically, such compositions can be prepared as either liquid solutions or suspensions; solid or reconstitutable forms suitable for use to prepare solutions or suspensions upon the addition of a liquid prior to injection can also be prepared; and, the preparations can also be emulsified.

The antibodies may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups may also be derived from inorganic bases, such as, for example, sodium, potassium, ammonium, calcium, or ferric hydroxides; or such organic bases as isopropylamine, trimethylamine, histidine, or procaine.

In further embodiments, a pharmaceutical lipid vehicle composition that includes polypeptides, one or more lipids, and an aqueous solvent may be used. As used herein, the term "lipid" refers to any of a broad range of substances that are characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods. One of ordinary skill in the art would be familiar with the range of techniques that can be employed for dispersing a composition in a lipid vehicle. For example, the antibody may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic antibody or composition containing the therapeutic antibody calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The foregoing doses include amounts between those indicated and are intended to also include the lower and upper values of the ranges. The practitioner responsible for administration will, in any event, determine the concentration of active ingredient(s) in a composition and appropriate dose(s) for the individual subject.

The particular nature of the therapeutic composition or preparation is not intended to be limiting. For example, suitable compositions may be provided in formulations together with physiologically tolerable liquid, gel, or solid carriers, diluents, and excipients. In some embodiments, the therapeutic preparations may be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects, as described supra.

Glycosylated PD-L1 as a Biomarker

Provided are methods involving the use of at least one dual function anti-glycPD-L1 antibody in assays for glycosylated PD-L1 as a biomarker. Such methods may be useful in biomarker evaluations of the tumor or cancer cells obtained from a subject who has a cancer or tumor. Provided is a method to determine whether a subject who has cancer also has a cancer or tumor that expresses glycosylated PD-L1, particularly, a detectable level of glycosylated PD-L1 on the cell surface of such cells. For example, if the subject's cancer or tumor cells are tested and determined to express glycosylated PD-L1 on the cell surface, then it is more likely that the subject treated with an anti-glycPD-L1 antibody as described, alone, or in combination with another anti-cancer agent, for example, would benefit from the treatment. Such methods comprise obtaining a sample from a subject having a cancer or tumor, testing the sample for the presence of glycosylated PD-L1 on cells derived from the subject's cancer or tumor using binding methods known and used in the art, or as described supra, and administering to the subject an effective amount of an anti-glycPD-L1 antibody alone, or in combination with another anti-cancer agent, if the subject's cancer or tumor is found to be positive for the cell surface expression of glycosylated PD-L1 protein. Diagnosing the subject as having a cancer or tumor expressing glycosylated PD-L1 prior to treatment allows for more effective treatment and benefit to the subject, as the administered anti-glycPD-L1 antibody is more likely to block or inhibit the interaction of the subject's glycosylated PD-L1-expressing cancer or tumor cells with the subject's PD-1-expressing T-cells, thereby preventing immunosuppression of the T-cell activity and promoting killing of the tumor or cancer cells by activated T-cell killing. In an embodiment, the method may involve first selecting a subject whose cancer or tumor may be amenable to testing for the presence of expressed glycosylated PD-L1 protein.

Similar methods may be used to monitor the presence of glycosylated PD-L1 on a patient's tumor cells during a course of cancer treatment or therapy, including combination treatments with an anti-glycPD-L1 antibody and another anticancer drug or treatment, over time, as well as after treatment has ceased. Such methods may also be used in companion diagnostic methods in which an anti-cancer treatment regimen, or combination treatment, involves testing or assaying a patient's tumor or cancer sample for glycosylated PD-L1-expressing tumor or cancer cells, prior to treatment and during the course of treatment, e.g., monitoring, to determine a successful outcome or the likelihood thereof.

In other embodiments, the anti-glycPD-L1 antibodies may be conjugated to a marker useful for in vivo imaging, for example, a radionuclide such as $1^{124}$ for PET or SPECT, a fluorochrome for optical imaging, or a paramagnetic chelate for MM. The labeled anti-glycPD-L1 antibodies can be administered to the patient, for example, intravenous or other parental mode of administration, and, after waiting the appropriate amount of time, detecting the presence and location of the labeled antibodies to localize and quantitate the tumor cells.

Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions may increase the anti-hyperproliferative effects on the neighboring hyperproliferative cell population. In other embodiments, cytostatic or differentiation agents may be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Kits and Diagnostics

In another embodiment, a kit containing therapeutic agents and/or other therapeutic and delivery agents is provided. In some embodiments, the kit is used for preparing and/or administering a therapy involving the anti-glycPD-L1 antibodies described herein. The kit may comprise one or more sealed vials containing any of the pharmaceutical compositions as described herein. The kit may include, for example, at least one anti-glycosylated PD-L1 antibody, as well as reagents to prepare, formulate, and/or administer one or more anti-glycPD-L 1 antibodies or to perform one or more steps of the described methods. In some embodiments, the kit may also comprise a suitable container means, which is a container that will not react with components of the kit, such as an Eppendorf tube, an assay plate, a syringe, a bottle, or a tube. The container may be made from sterilizable materials, such as plastic or glass.

The kit may further include an instruction sheet that outlines the procedural steps of the methods set forth herein, and will follow substantially the same procedures as described herein or are known to those of ordinary skill. The instruction information may be in a computer readable medium containing machine-readable instructions that, when executed using a computer, cause the display of a real or virtual procedure of delivering a pharmaceutically effective amount of the therapeutic agent.

Fusions and Conjugates

The anti-glycosylated PD-L1 antibodies or glycosylated PD-L1 polypeptides provided herein can also be expressed as fusion proteins with other proteins or chemically conjugated to another moiety. In some embodiments, the antibodies or polypeptides have an Fc portion that can be varied by isotype or subclass, can be a chimeric or hybrid, and/or can be modified, for example to improve effector functions, control half-life or tissue accessibility, augment biophysical characteristics, such as stability, and improve efficiency of production, which can be associated with cost reductions. Many modifications useful in the construction of fusion proteins and methods for making them are known in the art, for example, as reported by Mueller, J. P. et al., 1997, *Mol. Immun.* 34(6):441-452; Swann, P. G., 2008, *Curr. Opin. Immunol.,* 20:493-499; and Presta, L. G., 2008, *Curr. Opin. Immunol.,* 20:460-470. In some embodiments, the Fc region is the native IgG1, IgG2, or IgG4 Fc region of the antibody. In some embodiments, the Fc region is a hybrid, for example a chimera containing IgG2/IgG4 Fc constant regions. Modifications to the Fc region include, but are not limited to, IgG4 modified to prevent binding to Fc gamma receptors and complement; IgG1 modified to improve binding to one or more Fc gamma receptors; IgG1 modified to minimize effector function (amino acid changes); IgG1 with altered/no glycan (typically by changing expression host); and IgG1 with altered pH-dependent binding to FcRn. The Fc region can include the entire hinge region, or less than the entire hinge region of the antibody.

Another embodiment includes IgG2-4 hybrids and IgG4 mutants that have reduced binding to FcR which increase their half-life. Representative IG2-4 hybrids and IgG4 mutants are described, for example, in Angal et al., 1993, *Molec. Immunol.*, 30(1):105-108; Mueller et al., 1997, *Mol. Immun.*, 34(6):441-452; and U.S. Pat. No. 6,982,323; all of which are hereby incorporated by references in their entireties. In some embodiments, the IgG1 and/or IgG2 domain is deleted. For example, Angal et al., Id., describe proteins in which IgG1 and IgG2 domains have serine 241 replaced with a proline. In some embodiments, fusion proteins or polypeptides having at least 10, at least 20, at least 30, at least 40, at least 50, at least 60, at least 70, at least 80, at least 90 or at least 100 amino acids are contemplated.

In some embodiments, anti-glycosylated PD-L1 antibodies or glycosylated PD-L1 polypeptides are linked to or covalently bind or form a complex with at least one moiety. Such a moiety may be, but is not limited to, one that increases the efficacy of the antibody as a diagnostic or a therapeutic agent. In some embodiments, the moiety can be an imaging agent, a toxin, a therapeutic enzyme, an antibiotic, a radio-labeled nucleotide, a chemotherapeutic agent, and the like.

In some embodiments, the moiety that is conjugated or fused to an anti-glycPD-L1 antibody or glycosylated polypeptide or portion thereof may be an enzyme, a hormone, a cell surface receptor, a toxin, such as, without limitation, abrin, ricin A, *pseudomonas* exotoxin (i.e., PE-40), diphtheria toxin, ricin, gelonin, or pokeweed antiviral protein), a protein (such as tumor necrosis factor, interferon (e.g., α-interferon, (3-interferon), nerve growth factor (NGF), platelet derived growth factor (PDGF), tissue plasminogen activator (TPA), or an apoptotic agent (e.g., tumor necrosis factor-α, tumor necrosis factor-β)), a biological response modifier (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF"), or growth factors (e.g., growth hormone ("GH")), a cytotoxin (e.g., a cytostatic or cytocidal agent, such as paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, a tubulysin-based microtubule inhibitor, e.g., a Maytansinoid, such as Maytansinoid DM1 (N2'-deacetyl-N2'-(3-mercapto-1-oxopropyl)-maytansine; mertansine or emtansine, depending on the linker used; and Maytansinoid DM4 (N2'-deacetyl-n2'-(4-Mercapto-4-Methyl-1-oxopentyl)-6-MethylMaytansine; ravtansine), ImmunoGen, Inc., Waltham, Mass.) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclophosphamide, busulfan, dibromomannitol, streptozocin, mitomycin C, and cisdichlorodiamine platinum (II) (DDP) cisplatin), an anthracycline (e.g., daunorubicin (formerly daunomycin) and doxorubicin), an antibiotic (e.g., dactinomycin (formerly actinomycin), bleomycin, mithramycin, and anthramycin (AMC)), an anti-mitotic agent and/or tubulin inhibitor e.g., vincristine and vinblastine, monomethyl auristatin F (MMAF), monomethyl auristatin E (or desmethyl-auristatin E) (MMAE), e.g., vedotin; or combinations thereof.

Antibody-Drug Conjugates (ADCs)

Antibody drug conjugates (ADCs) are biologic therapeutic agents in which potent cytotoxic drugs are covalently linked via chemical linkers or coupling agents to antibodies, typically monoclonal antibodies, which are directed to specific target antigens, in particular, target antigens expressed or overexpressed on the surfaces of tumor or cancer cells. Such "loaded" antibodies are designed to deliver lethal cytotoxic cargoes to tumor or cancer cells. ADCs provide a means for targeting the payload drug to neoplastic cells while reducing side effects and minimizing systemic toxicity. ADCs bind to the cell surface-expressed target antigen by virtue of the specific interaction of the antibody component of the ADC and its target antigen. After binding to the target antigen, the ADC may be internalized into the cell, particularly, if the antibody has heightened internalization activity, as do the anti-glycPD-L1 antibodies of the embodiments described herein, e.g., STM108 and STM073. Accordingly, when such ADCs are internalized into the cell, they act directly to kill the cell or target a molecule inside the cell, which leads to apoptosis or cell death. Such ADCs comprising the anti-glycPD-L1 antibodies described herein, particularly, monoclonal, humanized, chimeric, or human antibodies, combine the specific targeting of antibodies to glycosylated PD-L1 on tumor and cancer cells with the cancer-killing ability of cytotoxic drugs or compounds, thereby providing further advantages for treatment and therapies with the anti-glycPD-L1 antibodies. Techniques for preparing and using ADCs are known in the art and are not intended to be limiting for the anti-glycPD-L1 antibodies described herein. (See, e.g., Valliere Douglass, J. F., et al., 2015, *Mol. Pharm.*, 12(6):1774-1783; Leal, M. et al., 2014, *Ann. N.Y. Acad. Sci.*, 1321:41-54; Panowski, S. et al., 2014, *mAbs*, 6(1):34-45; Beck, A. 2014, *mAbs*, 6(1):30-33; Behrens, C. R. et al., 2014, *mAbs*, 6(1):46-53; and Flygare, J. A. et al., 2013, *Chem. Biol. Drug Des.*, 81(1):113-121). In embodiments, some or all of the above-described moieties, particularly, toxins and cytotoxins, may be conjugated to an anti-glycPD-L1 antibody to produce effective ADCs for treating cancer. In embodiments, the anti-glycPD-L1 antibody component of the ADC may be a bispecific, multispecific, biparatopic, or multiparatopic antibody.

Techniques for conjugating therapeutic or cytotoxic moieties to antibodies are well known; See, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008);

Doronina et al., Nat. Biotechnol. 21(7):778-784(2003); Ducry et al., *Bioconjug Chem.* 21(1):5-13(2010); Senter, *Curr Opin. Chem. Biol.* 13(3):235-244 (2009); and Teicher, *Curr Cancer Drug Targets.* 9(8):982-1004 (2009). A review of ADCs and ADC oncology products is found in Lambert, *British J. Clin. Pharmacol.*, 76(2):248-262 (2013) and in Bouchard et al., *Bioorganic & Medicinal Chemistry Letters*, 24:5357-5363 (2014).

In specific embodiments, the anti-glycPD-L1 antibodies, which facilitate the internalization of PD-L1 into tumor cells, are conjugated to a highly potent biologically active drug or agent, such as a cytotoxic and/or chemotherapeutic agent, a toxin or cytotoxin as noted above, or a radionuclide, typically by chemical linkers with labile bonds, to produce an anti-glycPD-L1 antibody-drug conjugate (ADC), called an anti-glycPD-L1 antibody-ADC herein. The biologically active drug or cytotoxic agent, for example, serves as a "cytotoxic payload," which is delivered into a cell, particularly a tumor or cancer cell expressing a cell-surface target receptor or molecule that is bound by the anti-glycPD-L1 antibody-ADC. Such an anti-glycPD-L 1 antibody-ADC bound to its target molecule is internalized into the cell where the cytotoxic drug payload is released. Enhancement of the cancer cell-killing activity of the internalizing anti-glycPD-L1 antibodies described herein through conjugation to highly potent cytotoxic payloads affords anti-cancer ADC biologics having high anti-tumor activity and generally mild adverse effects that are well-tolerated.

An anti-glycPD-L1 antibody as described in the embodiments herein may be linked to various types of cytotoxic or DNA-acting payloads as known and used in the art, or as yet to be commercialized. For example, maytansine is a benzoansamacrolide that was first isolated from the bark of the Ethiopian shrub *Maytenus ovutus*. This cytotoxic agent and derivatives thereof (e.g., maytansinoids) bind to tubulin near the *Vinca* alkaloid binding site. They are considered to have a high affinity for tubulin located at the ends of microtubules and lower affinity to sites distributed throughout the microtubules. The suppression of microtubule dynamics causes cells to arrest in the G2/M phase of the cell cycle, ultimately resulting in cell death by apoptosis. (Oroudjev et al., *Mol. Cancer Ther.*, 10L2700-2713 (2010)). Two maytansine derivatives (thiol-containing maytansinoids) include DM1 and DM4 (ImmunoGen, Inc., Waltham, Mass.) have been widely used in combination with irreversible and reversible linkers. In particular, DM1 attached to an antibody with a thioether linker is called "emtansine;" DM1 attached to an antibody with an SPP linker is called "mertansine;". DM4 attached with an SPDB linker is called "ravtansine;" and DM4 attached with an sSPDB linker is called "soravtansine." (ImmunoGen, Inc., Waltham, Mass.). In an embodiment, the anti-glycPD-L1 antibody-ADC comprises the tubulin-acting maytansinoid payload DM1. In an embodiment, the anti-glycPD-L1 antibody-ADC comprises the tubulin-acting maytansinoid payload DM4. In an embodiment, the anti-glycPD-L1 antibody-ADC comprises a DNA-acting payload, e.g., DGN462 (ImmunoGen, Inc., Waltham, Mass.). In an embodiment, the anti-glycPD-L1 antibody component of the anti-glycPD-L1 antibody-ADC is STM073, or a binding portion thereof. In an embodiment, the anti-glycPD-L1 antibody component of the anti-glycPD-L1 antibody-ADC is STM108, or a binding portion thereof.

In a particular embodiment, the cytotoxic agent conjugated to the anti-glycPD-L1 antibody is MMAE (monomethyl auristatin E (or desmethyl-auristatin E)), a highly toxic, antineoplastic agent whose antimitotic activity involves inhibiting cell division by blocking the polymerization of tubulin. Vedotin, an International Nonproprietary Name, refers to MMAE plus its linking structure to an antibody in an MMAE-antibody conjugate. In more particular embodiments, the ADC is STM073-MMAE or STM108-MMAE.

A number of chemical linkers are known and used for conjugating a cytotoxic or DNA-acting drug payload to an antibody to produce ADCs. Certain linkers embraced for use alone or in combination for producing ADCs comprising the anti-glycPD-L1 antibodies, particularly, those that internalize after binding their target as described herein, include SMCC (4-(N-Maleimidomethyl) cyclohexanecarboxylic acid N-hydroxysuccinimide ester); SPDB (N-succinimidyl 3-(2-pyridyldithio)butyrate); SPP (N-succinimidyl 4-(2-pyridyldithio)pentanoate); sulfo-SPDB or sSPDB (N-succinimidyl-4-(2-pyridyldithio)-2-sulfobutanoate); the thioether linker succinimidyl-4-(N-maleimidomethyl) cyclohexane-1-carboxylate (MCC); and vc (valine-citrulline dipeptide linker). By way of example, engineered linkers (e.g., SMCC, SPDB, S-SPDB), (Immunogen, Inc.) have been designed to be stable prior to the binding of an ADC to a tumor and then to optimize payload efficacy once the ACD is internalized inside a cancer cell. Other linkers, such as the dipeptide vc linker, which is a cathepsin-cleavable linker, may be used to conjugate an antibody to a cytotoxic agent, such as an auristatin which is a mitotic inhibitor derived from dolastatin 10, e.g., monomethylauristatin E (MMAE), e.g., vedotin. The cytotoxins may be conjugated to the antibody such that more than one toxin molecule is attached to each antibody molecule, for example, there may be, on average, 2, 3, 4, 5, 6, 7 or 8 toxin molecules per antibody.

In a particular embodiment, MMAE is indirectly linked to antibody cysteines by a maleimidocaproyl (MC) attachment group, which is coupled to valine-citrulline-p-aminobenzyloxycarbonyl-MMAE (MC-vc-PAB-MMAE). In the "MC-vc-PAB-MMAE" linear structure, "MC" consists of maleimide and caproic acid and is the moiety that attaches to an antibody, typically via cysteine groups on the H chain. In turn, "MC" is attached to a "vc" linker which consists of valine (Val) and citruline (Cit) and which is a cathepsin-cleavable linker that is cleaved by cathepsin inside of tumor or cancer cells. "vc" is attached to the spacer "PAB", i.e., paraminobenzoic acid, to which the MMAE cytotoxin is linked. MC-vc-PAB-MMAE ADCs release free, membrane-permeable MMAE when cleaved by proteases such as cathepsin B. In an embodiment, the linker to the antibody is stable in extracellular fluid, but is cleaved by cathepsin once the ADC has entered a tumor or cancer cell, thus activating the antimitotic mechanism of MMAE or other toxin drug. In another embodiment, monomethylauristatin F, (MMAF) is linked to antibody cysteines by maleimidocaproyl (MC-MMAF). In contrast to MC-vc-PAB-MMAE ADCs, MC-MMAF ADCs are uncleavable, like MCC-DM1 ADCs, and must be internalized and degraded within a cell, releasing cysteine-MC-MMAF as the active drug inside the cell.

In an embodiment, the cytotoxic payload is released in the lysosome following internalization of the ADC into a cell. In the lysosome, lysosomal enzymes digest the antibody component of the ADC. Following lysosomal degradation, the drug (and drug-linker) payload is released into the cytoplasm, where the drug binds intracellular targets, ultimately causing cell death. Optimally, the released payload is fully active, with the linker still attached. In other embodiments in which the target bound to the ADC results in poor trafficking to the lysosome, linkers which are stable outside of the target cell, but which cleave the payload from the antibody component once inside the cell provide an alternative mode for payload release within the cell, but outside of the lysosome. In other embodiments, the linker is stable in extracellular fluid, but is cleaved by cathepsin once the ADC has entered a tumor or cancer cell, thus activating the antimitotic or other cytotoxic mechanism of the toxin drug. In other embodiments, a payload released by the action of cleavable linkers is able to enter a neighboring cancer cells and kill them via a bystander effect, thus augmenting the targeting and tumor killing activity of an ADC.

In an embodiment, an anti-glycPD-L1 antibody as described herein, such as dual function STM073 or STM108 MAbs, is coupled to DM1 via the linker SMCC (succinimidyl 4-(N-maleimidomethyl)cyclohexane-1-carboxylate). In another embodiment, an anti-glycPD-L1 antibody as described herein, such as STM073 or STM108, is coupled to DM4 via the linker SPDB (N-succinimidyl 3-(2-pyridyldithio)butyrate) or sSPDB (N-succinimidyl-4-(2-pyridyldithio)-2-sulfobutanoate). In another embodiment, the auristatin monomethylauristatin E is linked to cysteine residues of an anti-glycPD-L1 antibody as described herein, such as STM073 or STM108, by maleimidocaproyl-valine-citrulline-p-aminobenzyloxycarbonyl (MC-vc-PAB-MMAE). In a particular embodiment, the ADC is STM108-MC-vc-PAB-MMAE. In another particular embodiment, the ADC is STM073-MC-vc-PAB-MMAE. In an embodiment, the anti-glycPD-L1 antibody-ADC comprises multiple units of a drug, such as MMAE, per molecule, such as 1-10, 1-5, 2-5, 3-5, or 2, 3, 4, 5, 6, 7, 8, 9, 10 units of drug, such as MMAE, per molecule, as well as values therebetween. In other embodiments, the antibody-drug ratio may be 2, 3, 4, 5, 6, 7, 8, 9, 10, or greater, as well as ranges between 2-10 and values therebetween. In embodiments, the STM108 or STM073 antibody is a bispecific, multispecific, biparatopic, or multiparatopic antibody, or an antigen binding portion thereof. Such ADCs comprising a dual function anti-glycPD-L1 antibody as described herein, e.g., the above-mentioned STM108-MC-vc-PAB-MMAE, provide bolstered and multifaceted antineoplastic effects in the killing of tumor and cancer cells for cancer treatment. As but a few illustrative advantages, an anti-human glycPD-L1 antibody (e.g., MAb)-ADC, e.g., STM108-ADC, can block the PD-1/PD-L1 interaction, thereby enhancing T cell immunity and effector function against tumor cells; it can selectively target glycosylated PD-L1 expressed on tumor and cancer cells; it can internalize PD-L1 on tumor or cancer cells after binding, thereby reducing the surface-expressed PD-L1 on tumor or cancer cells and further reducing the oncogenic potential of PD-L1; it can cause apoptosis of tumor or cancer cells into which antibody is internalized and the toxic drug is released to damage and ultimately kill the cell; and it can facilitate a bystander effect by killing nearby or neighboring tumor or cancer cells through the release of toxic drug from the apoptosed tumor or cells.

In some embodiments, antibodies as described herein may be conjugated to a marker, such as a peptide, to facilitate purification. In some embodiments, the marker is a hexahistidine peptide (SEQ ID NO: 93), i.e., the hemagglutinin "HA" tag, which corresponds to an epitope derived from the influenza hemagglutinin protein (Wilson, I. A. et al., *Cell*, 37:767-778 (1984)), or the "flag" tag (Knappik, A. et al., *Biotechniques* 17(4):754-761 (1994)).

In other embodiments, the moiety conjugated to the antibodies and polypeptides as described herein may be an imaging agent that can be detected in an assay. Such imaging agents may be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, or colored particles or ligands, such as biotin. In embodiments, suitable enzymes include, but are not limited to, horseradish peroxidase, alkaline phosphatase, beta-galactosidase, or acetylcholinesterase; prosthetic group complexes include, but are not limited to, streptavidin/biotin and avidin/biotin; fluorescent materials include, but are not limited to, umbelliferone, fluorescein, fluorescein isothiocyanate, rhodamine, dichlorotriazinylamine fluorescein, dansylchloride or phycoerythrin; luminescent materials include, but are not limited to, luminol; bioluminescent materials include, but are not limited to, luciferase, luciferin, and aequorin; radioactive materials include, but are not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{150}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The imaging agent may be conjugated to the antibodies or polypeptides described herein either directly or indirectly through an intermediate (such as, for example, a linker known in the art) using techniques known in the art. See, for example, U.S. Pat. No. 4,741,900 which reports on metal ions that can be conjugated to antibodies and other molecules as described herein for use as diagnostics. Some conjugation methods involve the use of a metal chelate complex employing, for example, an organic chelating agent, such as diethylenetriaminepentaacetic acid anhydride (DTPA); ethylenetriaminetetraacetic acid; N-chloro-p-toluenesulfonamide; and/or tetrachloro-3-6α-diphenylglycouril-3, attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

In some embodiments, the anti-glycPD-L1 antibodies or glycPD-L1 polypeptides as described herein may be conjugated to a second antibody to form an antibody heteroconjugate, for example, as described in U.S. Pat. No. 4,676,980. Such heteroconjugate antibodies can additionally bind to haptens (e.g., fluorescein), or to cellular markers (e.g., without limitation, 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

In some embodiments, the anti-glycosylated PD-L1 antibodies or glycosylated PD-1 polypeptides described herein can also be attached to solid supports, which can be useful for carrying out immunoassays or purification of the target antigen or of other molecules that are capable of binding to the target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

EXAMPLES

The following examples are included to demonstrate embodiments that relate to the dual function anti-glycPD-L1 antibodies that preferentially bind glycosylated PD-L1 compared with unglycosylated PD-L1 and/or PD-L1 glycosylation mutants and methods of use described herein. Representative dual function anti-glycPD-L1 antibodies are exemplified. It should be appreciated by those of skill in the art that the disclosed dual function anti-glycPD-L1 antibodies are examples and are not intended to be limiting.

Example 1 Materials and Methods

Cell Culture, Stable Transfectants, and Transfection.

All cells were obtained from American Type Culture Collection (ATCC). These cells were grown in in DMEM/F12 or RPMI 1640 medium supplemented with 10% fetal bovine serum (FBS). PD-L1 stable transfectants in MDA-MB-468, BT549 and 293T cells were selected using puromycin (InvivoGen, San Diego, Calif., USA). For transient transfection, cells were transiently transfected with DNA, such as DNA encoding PD-L1, using SN liposomes (Hu, M. C. et al., 2004, *Cell*, 117:225-237) and Lipofectamine™ 2000 (Life Technologies, Carlsbad, Calif., USA).

Generation of Stable Cells Using Lentiviral Infection.

The lentiviral-based shRNA (pGIPZ plasmids) used to knockdown expression of PD-L1 (Shen, J. et al., 2013, *Nature*, 497:383-387) in cells was purchased from the shRNA/ORF Core Facility (UT MD Anderson Cancer Center). Based on knock-down efficiency of PD-L1 protein expression in MDA-MB-231 or A431 cells, the inventors selected two shPD-L1 clones for this study. The mature antisense sequences are as follows: TCAATTGTCATATTGCTAC (shPD-L1 #1, SEQ ID NO: 34), TTGACTC-CATCTTTCTTCA (shPD-L1 #5, SEQ ID NO: 35). Using a pGIPZ-shPD-L1/Flag-PD-L1 dual expression construct to knock down endogenous PD-L1 and reconstitute Flag-PD-L1 simultaneously, the inventors established endogenous PD-L1 knock-down and Flag-PD-L1 WT or 4NQ mutant expressing cell lines. To generate lentivirus-expressing shRNA for PD-L1 and Flag-PD-L1, the inventors transfected 293T cells with pGIPZ-non-silence (for vector control virus), pGIPZ-shPD-L1, or pGIPZ-shPD-L1/PD-L1 WT, or pGIPZ-shPD-L1/PD-L1 4NQ mutant with FuGENE 6 transfection reagent. Twenty-four hours after transfection the medium was changed, and then the medium was collected at 24-hour intervals. The collected medium containing lentivirus was centrifuged to eliminate cell debris, and filtered through 0.45-μm filters. Cells were seeded at 50% confluence 12 hours before infection, and the medium was replaced with medium containing lentivirus. After infection for 24 hours, the medium was replaced with fresh medium and the infected cells were selected with 1 μg/ml puromycin (InvivoGen).

Plasmids.

A human PD-L1 clone was obtained from the shRNA/ORF Core Facility (UT MD Anderson Cancer Center, Houston, Tex., USA) and cloned into pCDH lentiviral expression vectors to establish PD-L1-Flag or PD-L1-Myc expression cell lines using known molecular biological techniques. In addition, human PD-L1 nucleic acid was also cloned into pEGFP-N1 and pCMV-HA mammalian cell expression vectors for transient transfection. pCDH/PD-L1-Flag expression vector was used as a template to generate the PD-L1-Flag NQ mutants N35Q, N192Q, N200Q, N219Q, and 4NQ (N35Q/N192Q/N200Q/N219Q) by performing site directed mutagenesis using primers presented in Table 4 below. To create a pGIPZ-shPD-L1/Flag-PD-L1 dual expression construct to knock down endogenous PD-L1 and reconstitute Flag-PD-L1 simultaneously, a shPD-L1 construct (shPD-L1 #5) which targets the 3»-UTR region of PD-L1 mRNA was selected. The Flag-PD-L1 wild type (WT) or 4NQ mutant DNA was cloned into pGIPZ-shPD-L1 (Thermo Scientific, Pittsburgh, Pa., USA) which expresses shRNA specific for endogenous PD-L1. All constructs were confirmed using enzyme digestion and DNA sequencing.

TABLE 4

Primers for site directed mutagenesis

| Primers | | | Sequences (5' to 3') |
|---|---|---|---|
| N35Q | Forward | (SEQ ID NO: 36) | gtggtagagtatggtagccaaatgacaattgaatgcaaa |
|  | Reverse | (SEQ ID NO: 37) | tttgcattcaattgtcatttggctaccatactctaccac |
| N192Q | Forward | (SEQ ID NO: 38) | gagaggagaagcttttccaggtgaccagcacactgag |
|  | Reverse | (SEQ ID NO: 39) | ctcagtgtgctggtcacctggaaaagcttctcctctc |
| N200Q | Forward | (SEQ ID NO: 40) | gaccagcacactgagaatccagacaacaactaatgagat |
|  | Reverse | (SEQ ID NO: 41) | atctcattagttgttgtctggattctcagtgtgctggtc |
| N219Q | Forward | (SEQ ID NO: 42) | gagaggagaagcttttccaagtgaccagcacactgaga |
|  | Reverse | (SEQ ID NO: 43) | tctcagtgtgctggtcacttggaaaagcttctcctctctc | qRT-PCR assays were performed to measure the expression of mRNA (Shen et al., 2013, *Nature*, 497:383-7; and Chang et al., 2011, *Nature Cell Biology*, 13:317-23) (see Table 5 below). Cells were washed twice with PBS and immediately lysed in QIAzol. The lysed sample was subjected to total RNA extraction using RNeasy Mini Kit (Qiagen, Hilden, Germany). To measure the expression of mRNA, cDNA was synthesized from 1 μg purified total RNA by SuperScript III First-Strand cDNA synthesis system using random hexamers (Life Technologies) according to the manufacturer's instructions. qPCR was performed using a real-time PCR machine (iQ5, BioRad, Hercules, Calif., USA). All the data analysis was performed using the comparative Ct method. Results were first normalized to internal control β-actin mRNA.

TABLE 5

Primers for qRT-PCR.

| Gene | | Sequences (5' to 3') |
|---|---|---|
| B4GALT2 | Forward (SEQ ID NO: 44) | gcataacgaacctaaccctcag |
| | Reverse (SEQ ID NO: 45) | gcccaatgtccactgtgata |
| B4GALT3 | Forward (SEQ ID NO: 46) | gtaacctcagtcacctgcc |
| | Reverse (SEQ ID NO: 47) | attccgctccacaatctctg |
| B3GNT3 | Forward (SEQ ID NO: 48) | tcttcaacctcacgctcaag |
| | Reverse (SEQ ID NO: 49) | gtgtgcaaagacgtcatcatc |
| B3GAT1 | Forward (SEQ ID NO: 50) | caccatcaccctcctttctattc |
| | Reverse (SEQ ID NO: 51) | gaacaacaggtctgggatttct |
| B3GAT2 | Forward (SEQ ID NO: 52) | gccttttgccatcgacatg |
| | Reverse (SEQ ID NO: 53) | agtcagattcttgcatccctg |
| ST6GAL1 | Forward (SEQ ID NO: 54) | caaggagagcattaggaccaag |
| | Reverse (SEQ ID NO: 55) | ccccattaaacctcaggactg |
| ST3GAL4 | Forward (SEQ ID NO: 56) | tcgtcatggtgtggtattcc |
| | Reverse (SEQ ID NO: 57) | caggaagatgggctgatcc |
| MAN2A2 | Forward (SEQ ID NO: 58) | gaccgcactcatcttacacc |
| | Reverse (SEQ ID NO: 59) | ggaggttggctgaaggaatac |
| MAN2B1 | Forward (SEQ ID NO: 60) | tcccctgctttaaccatcg |
| | Reverse (SEQ ID NO: 61) | ttgtcacctatactggcgttg |
| UGGT1 | Forward (SEQ ID NO: 62) | ctgagtgatggaacgagtgag |
| | Reverse (SEQ ID NO: 63) | tagagatgaccagatgcaacg |
| MGAT3 | Forward (SEQ ID NO: 64) | gagtccaacttcacggcttat |
| | Reverse (SEQ ID NO: 65) | agtggtccaggaagacataga |
| MGAT5 | Forward (SEQ ID NO: 66) | tgtgagggaaagatcaagtgg |
| | Reverse (SEQ ID NO: 67) | gctctccaaggtaaatgaggac |
| MOGS | Forward (SEQ ID NO: 68) | ccactgagttcgtcaagagg |
| | Reverse (SEQ ID NO: 69) | acttccttgccatctgtcac |
| GNPTAB | Forward (SEQ ID NO: 70) | tggctcgctgataagttctg |
| | Reverse (SEQ ID NO: 71) | gtgagtctggtttgggagaag |
| ACTB | Forward (SEQ ID NO: 72) | gcaaagacctgtacgccaaca |
| | Reverse (SEQ ID NO: 73) | tgcatcctgtcggcaatg |

Antibodies and Chemicals.

The following antibodies were used in the experiments described in the Examples: Flag (F3165; Sigma-Aldrich, St. Louis, Mo., USA); Myc (11667203001; Roche Diagnostics, Indianapolis, Ind., USA); HA (11666606001; Roche Diagnostics); PD-L1 (13684; Cell Signaling Technology, Danvers, Mass., USA); PD-L1 (329702; BioLegend, San Diego, Calif., USA,); PD-L1 (GTX117446; GeneTex, Irvine, Calif., USA); PD-L1 (AF156; R&D Systems, Minneapolis, Minn., USA); PD-1 (ab52587; Abcam, Cambridge, Mass., USA); B3GNT3 (ab190458; Abcam); B3GNT3 (18098-1-AP; Proteintech, Chicago, Ill., USA); Granzyme B (ab4059; Abcam); EGFR (4267; Cell Signaling Technology); α-Tubulin (B-5-1-2; Sigma-Aldrich); and β-Actin (A2228; Sigma-Aldrich). For use in the experiments, epidermal growth factor (EGF), cycloheximide, and tunicamycin were purchased from Sigma-Aldrich. Gefitinib, erlotinib, lapatinib, cetuximab, and AG1478 were obtained from Calbiochem Corp (Billerica, Mass., USA).

Immunoblot Analysis, Immunocytochemistry and Immunoprecipitation.

Immunoblot analysis was performed as described previously (Lim et al., 2008, *Gastroenterology*, 135:2128-40; and Lee et al., 2007, *Cell*, 130:440-455). Image acquisition and quantification of band intensity were performed using an Odyssey® infrared imaging system (LI-COR Biosciences, Lincoln, Nebr., USA). For immunoprecipitation, the cells were lysed in buffer (50 mM Tris-HCl, pH 8.0, 150 mM NaCl, 5 mM ethylenediaminetetraacetic acid (EDTA) and 0.5% Nonidet P-40 (NP-40)) and centrifuged at 16,000×g for 30 minutes to remove debris. Cleared lysates were subjected to immunoprecipitation with antibodies. For immunocytochemistry, cells were fixed in 4% paraformaldehyde at room temperature for 15 minutes, permeabilized in 5% Triton X-100 for 5 minutes, and then were stained using primary antibodies. The secondary antibodies used were anti-mouse Alexa Fluor 488 or 594 dye conjugate and/or anti-rabbit Alexa Fluor 488 or 594 dye conjugate (Life Technologies). Nuclei were stained with 4',6-diamidino-2-phenylindole (DAPI blue) (Life Technologies). After mounting, the cells were visualized using a multiphoton confocal laser-scanning microscope (Carl Zeiss, Thornwood, N.Y., USA).

PD-L1 and PD-1 (PD-L1/PD-1) Interaction Assay.

To measure the interaction of PD-1 protein and PD-L1 protein, cells were fixed in 4% paraformaldehyde at room temperature for 15 minutes and then were incubated with recombinant human PD-1-Fc chimera protein (R&D Systems) for 1 hour. The secondary antibodies used were anti-human Alexa Fluor 488 dye conjugate (Life Technologies). Nuclei were stained with 4',6-diamidino-2-phenylindole (DAPI blue) (Life Technologies). The fluorescence intensity of Alexa Fluor 488 dye was then measured using a microplate reader Synergy Neo (BioTeK, Winooski, Vt., USA) and normalized to the intensity by total protein quantity. To take an image, after mounting, the cells were visualized using a confocal laser-scanning microscope (Carl Zeiss).

Co-Culture Experiments and IL-2 Expression Measurement.

Co-culture of Jurkat T cells and tumor cells and IL-2 expression measurement was performed as described previously (Sheppard, K. A. et al., 2004, *FEBS letters*, 574:37-41). To analyze the effect of tumor cells on T cell inactivation, tumor cells were co-cultured with activated Jurkat T cells expressing human PD-1 which were activated with Dynabeads® Human T-Activator CD3/CD28 (Life Technologies). Co-cultures at 5:1 (Jurkat:tumor cell) ratio were incubated for 12 or 24 hours. Secreted IL-2 level in medium was measured as described by the manufacturer (Human IL-2 ELISA Kits, Thermo Scientific).

Glycosylation Analysis of PD-L1.

To confirm glycosylation of PD-L1 protein, cell lysates were treated with the enzymes PNGase F, Endo H, O-glycosidase (New England BioLabs, Ipswich, Mass., USA) as described by the manufacturer. To stain glycosylated PD-L1 protein, purified PD-L1 protein was stained using the Glycoprotein Staining Kit (Peirce/Thermo Scientific) as described by the manufacturer.

Immunohistochemical Staining of Human Breast Tumor Tissue Samples.

Immunohistochemical (IHC) staining was performed as described previously (Lee et al., 2007, *Cell*, 130:440-455; Lo et al., 2007, *Cancer Research*, 67:9066-9076; Chang, C. J. et al., 2011, *Cancer cell*, 19:86-100). Briefly, tissue specimens were incubated with antibodies against PD-L1, EGFR, B3GNT3, or Granzyme B and a biotin-conjugated secondary antibody and then were incubated with an avidin-biotin-peroxidase complex. Visualization was performed using amino-ethylcarbazole chromogen. For statistical analysis, Fisher's exact test and Spearman rank correlation coefficient were used; a p-value less than 0.05 was considered statistically significant. According to histological scoring, the intensity of staining was ranked into four groups: high (score 3), medium (score 2), low (score 1) and negative (score 0).

Identification of N-Glycopeptide.

Purified His tagged PD-L1 protein was reduced with 10 mM dithiothreitol (DTT) at 37° C. for 1 hour, alkylated with 50 mM iodoacetamide in 25 mM ammonium bicarbonate buffer for 1 hour in the dark at room temperature, and then treated overnight with sequencing grade trypsin at an enzyme-to-substrate ratio of 1:50 at 37° C. The digested products were then diluted with formic acid to a final concentration with 0.1%, and further cleaned up by ZipTip C18 (Millipore) before LC-MS/MS analysis. LC-MS/MS data were acquired at the Academia *Sinica* Mass Spectrometry Facility at IBC. The peptide mixture was analyzed by nanospray LC-MS/MS on an Orbitrap Fusion Tribrid (Thermo Scientific) coupled to an UltiMate 3000 RSLCnano System (Dionex) with trap column Acclaim PepMap 100 (2 cm×100 μm i.d) (Dionex). Peptide mixtures were loaded onto an Acclaim PepMap RSLC 25 cm×75 μm i.d. column (Dionex) and separated at a flow rate of 500 nL/min using a gradient of 5% to 35% solvent B (100% acetonitrile with 0.1% formic acid) for 60 minutes. Solvent A was 0.1% formic acid in water. The parameters used for MS and MS/MS data acquisition under the HCD parallel with CID mode were: top speed mode with 3 s cycle time; FTMS: scan range (m/z)=400-2000; resolution=120 K; AGC target=2× $10^5$; maximum injection time (ms)=50; FTMSn (HCD): isolation mode=quadrupole; isolation window=1.6; collision energy (%)=30 with stepped collision energy 5%; resolution=30 K; AGC target=5×$10^4$; maximum injection time (ms)=60; ITMSn (CID): isolation mode=quadrupole; isolation window=1.6; collision energy (%)=30; AGC target=1×$10^4$. Raw data were converted to Mascot generic format (MGF) by *Proteome Discoverer* 1.4. For glycopeptide identification, the HCD $MS^2$ data were searched using Byonic (version 2.0-25) with the following search parameters: peptide tolerance=2 ppm; fragment tolerance=6 ppm; missed cleavages=1; modifications: carbamidomethyl cysteine (fixed), methionine oxidation (common 2), deamidation at N (rare 1). The glycopeptide hits suggested by Byonic were further checked manually by combining HCD and CID $MS^2$ results.

Statistical Analysis.

Data in bar graphs represents mean fold change relative to untreated or control groups with standard deviation of three independent experiments. Statistical analyses were performed using SPSS (Ver. 20, SPSS, Chicago, Ill.). The correlation between protein expression and BLBC subset was analyzed using Spearman's correlation and Mann-Whitney test. Student's t test was performed for experimental data. A P value <0.05 was considered statistically significant.

Example 2 PD-L1 Protein Expression Analysis

Figures 4A, 4B, 4C, 4D:
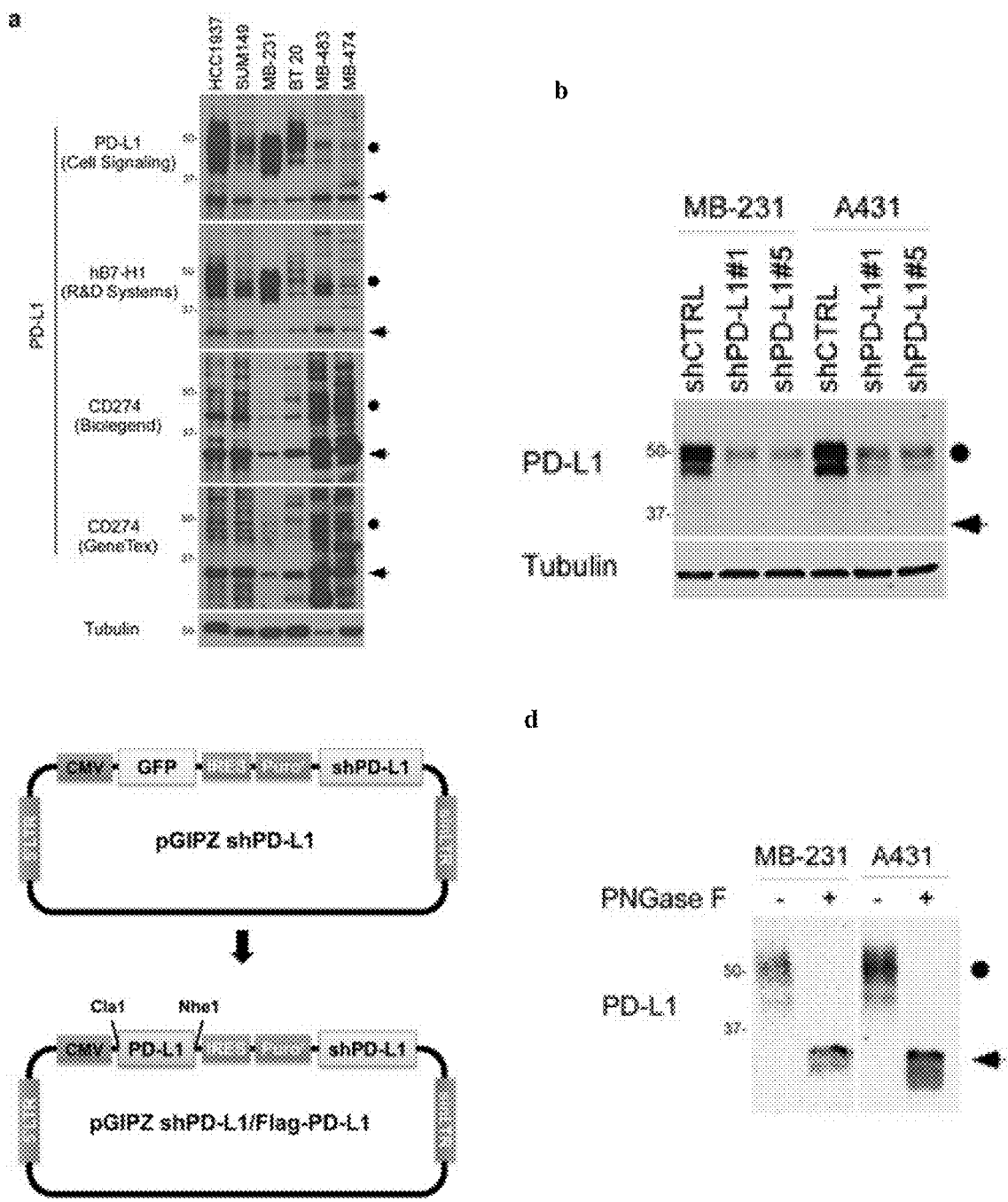
FIGS. 4A-4D. PD-L1 is Glycosylated in Cancer Cells. A. Western blot analysis of PD-L1 in cancer cells using different anti-PD-L1 antibodies. Four BLBC cell lines, HCC1937, SUM149, MB-231 and BT20, and two non-BLBC cell lines, MB-483 and MB-474 were selected to analyze the expression of PD-L1 using different antibodies. B. Western blot analysis of PD-L1 in shCTRL and two independent shPD-L1 stable clones of MDA-MB-231 and A431 cells. C. Schematic diagram of dual-expression construct for Flag-PD-L1 and shRNA of PD-L1. D. Glycosylation pattern of PD-L1 protein in MDA-MB-231 and A431 cells. Cell lysates were treated with PNGase F and analyzed by Western blot. Black circle=glycosylated PD-L1; arrowhead=non-glycosylated PD-L1.

To elucidate the underlying mechanism of PD-L1, the protein expression of PD-L1 was examined in human tumor tissues and cancer cell lines. FIGS. 1A and 1B and FIGS. 3A-3D illustrate protein expression in lung, breast, colon and ovarian cancer cell lines by Western blot analysis; FIG. 4A shows binding of PD-L1 protein in cells by different PD-L1 antibodies. It was observed that a majority of PD-L1 protein was detected at ~45 kDa (black circle), but a smaller fraction also appeared at 33 kDa (black arrowhead). Knocking down PD-L1 by lentiviral short-hairpin RNA (shRNA) targeting either the coding sequence (shPD-L1 #1) or the 3'UTR (shPD-L1 #5) downregulated expression of both the 33- and 45-kDa forms of PD-L1 (FIG. 4B). Reconstitution of PD-L1 restored expression of both forms in the shPD-L1 #5 clone (FIG. 1C; FIG. 4C shows the vector design). These results showed that both bands on the Western blot are PD-L1 protein and that the higher molecular weight form of PD-L1 is indicative of posttranslational modifications.

Glycosylated proteins frequently produce heterogeneous patterns in the Western blot, as observed for the higher molecular weight (~45 kDa) of PD-L1. To test whether the glycosylation pattern observed for PD-L1 corresponded to the glycosylated form, MDA-MB 231 and HeLa cells were treated with recombinant glycosidase (Peptide-N-Glycosidase F; PNGase F) to remove N-glycan structure and then were subjected to Western blot analysis. As shown in FIG. 4D, a significant portion of the 45-kDa PD-L1 was reduced to the 33-kDa form of PD-L1 upon PNGase F treatment. Consistently, positive staining of the glycan structure was observed in purified His-tagged PD-L1, but not in the presence of PNGase F (FIG. 1D). These results demonstrate that the higher molecular weight of PD-L1 is indeed the glycosylated form of the PD-L1 protein.

Figures 5A, 5B, 5C, 5D, 5E:
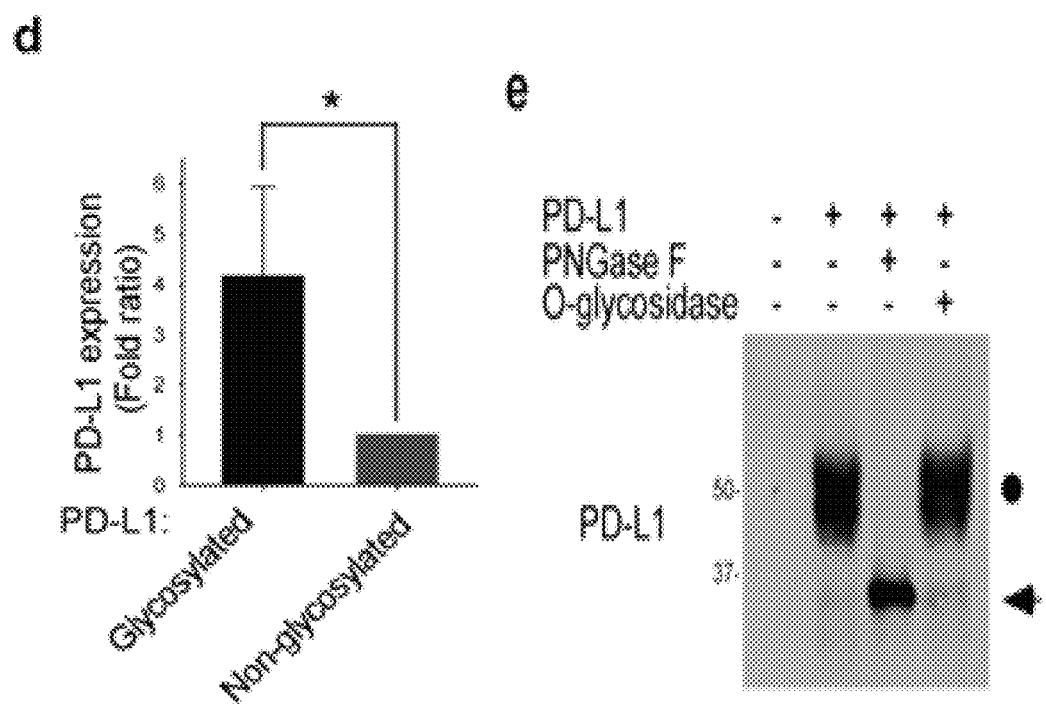
FIGS. 5A-5E. Expression of Glycosylated and Non-glycosylated PD-L1 Protein. A. Western blot analysis of PD-L1-Myc, PD-L1-Flag, and HA-PD-L1 proteins in tunicamycin (TM) treated cells. B. Western blot analysis of PD-L1-GFP-WT, PD-L1-GFP-ECD and PD-L1-GFP-ICD proteins in tunicamycin (TM) treated or untreated cells. C. Western blot analysis of PD-L1-Myc, PD-L1-Flag, HA-PD-L1, PD-L1-GFP-WT, PD-L1-GFP-ECD and PD-L1-GFP-ICD proteins in tunicamycin (TM) treated cells. The intensity of glycosylated PD-L1 protein (black bars) or non-glycosylated PD-L1 protein (red bars) was determined by a densitometry quantification (in bar graph below Western blot analysis). D. The mean of the intensity of glycosylated PD-L1 protein (black bar) or non-glycosylated PD-L1 protein (red bar) obtained from the bar graph shown in (C) above. Error bars represent standard deviation (SD). E. Glycosylation pattern of PD-L1 protein in PD-L1 expressing HEK 293T cells. Cell lysates were treated with or without PNGase F or O-glycosidase and analyzed by Western blot. Black circle=glycosylated PD-L1; arrowhead=non-glycosylated PD-L1. Tunicamycin is a nucleoside antibiotic that inhibits N-linked glycosylation of proteins.
Figures 7A, 7B, 7C, 7D, 7E, 7F, 7G, 7H:
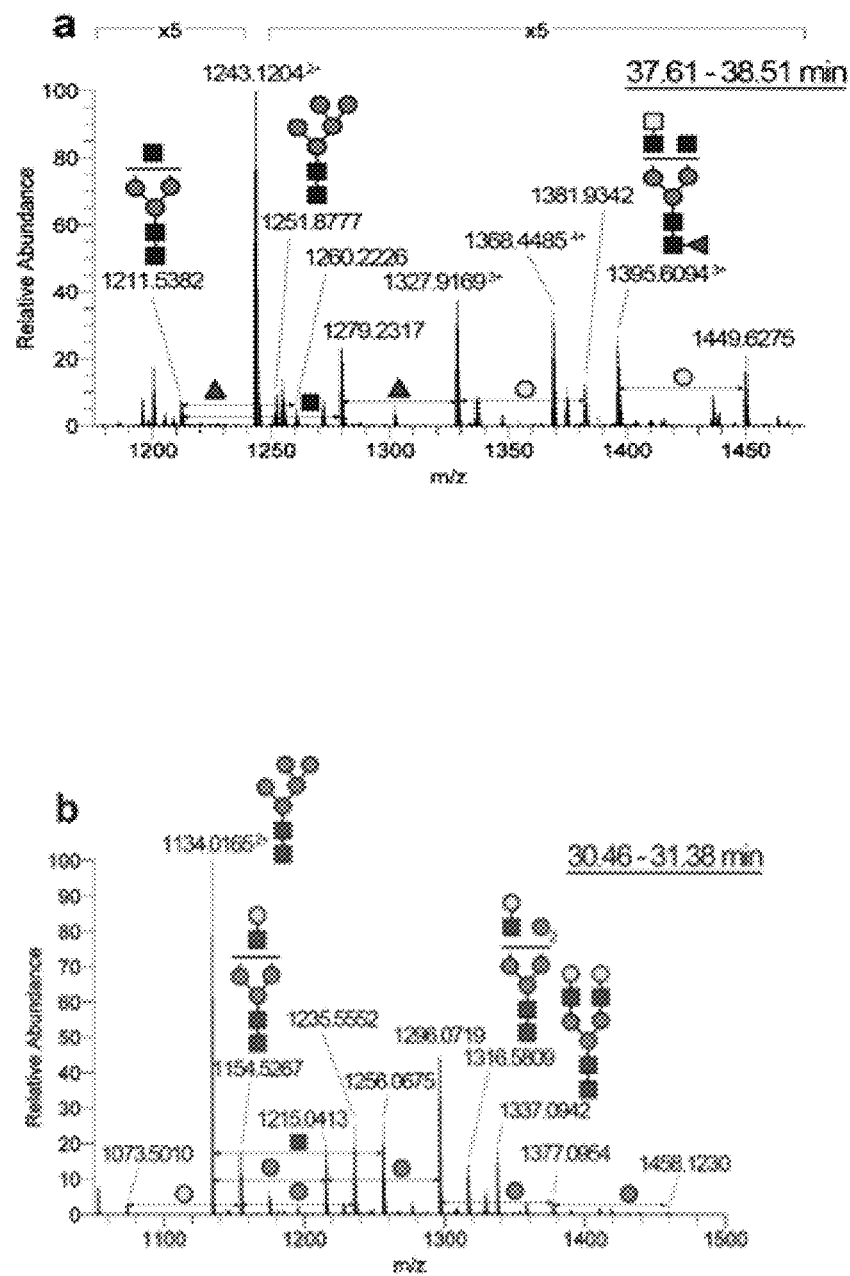
FIGS. 7A-7H. LC-MS/MS-based Identification of N-glycopeptides. LC-MS/MS-based identification of N-glycopeptides corresponding to each of the four N-glycosylation sites, N35 (A and E), N192 (B and F), N200 (C and G), and N219 (D and H) of PD-L1 from HEK 293 cells. The LC-MS profiles (A-D) are shown as spectra averaged over a period of elution time (as labeled in figures) when a representative subset of glycoforms were detected. For each N-glycosylation site, one representative HCD MS$^2$ spectrum (E-H) is shown to exemplify its identification based on detection of y1 ion (tryptic peptide backbone carrying the GlcNAc attached to the N-glycosylated Asn), along with the b and y ions defining its peptide sequence. The cartoon symbols used for the glycans (see inset) conform to the standard representation recommended by the Consortium for Functional Glycomics: Additional Hex and HexNAc were tentatively assigned as either lacNAc (Gal-GlcNAc) or lacdiNAc (GalNAc-GlcNAc) extension from the trimannosyl core (Man$_3$-GlcNAc$_2$), which can either be core fucosylated or not. The sequences depicted in FIGS. 7E-7H are set forth in SEQ ID NOs: 81-84, respectively.
Figures 7A, 7B, 7C, 7D, 7E, 7F, 7G, 7H:
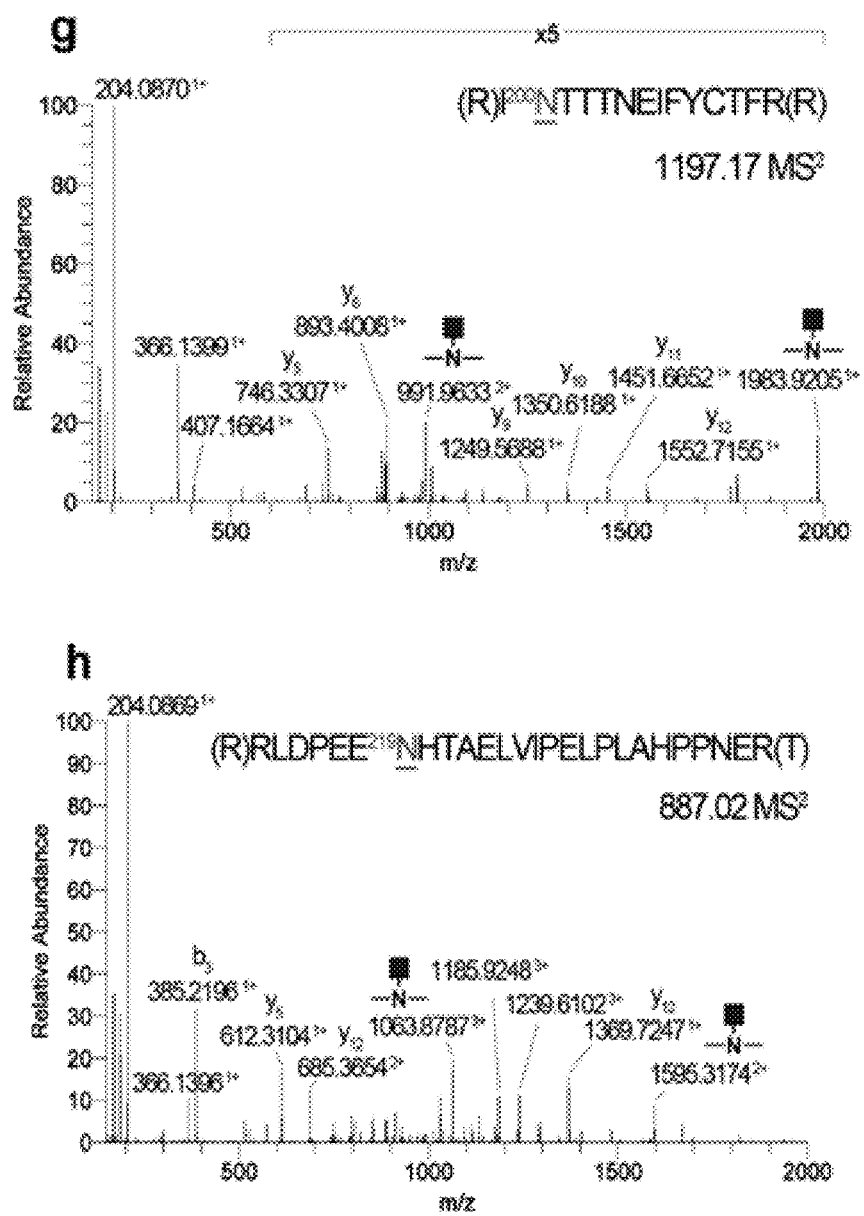

To recapitulate the expression of PD-L1 protein in cells, various overexpression constructs were generated to mimic endogenous expression of the protein. To avoid possible cleavage at the N-terminal signaling peptide, different tag sequences were fused at either the N- or the C-terminus (FIGS. 5A and 5B, above the blot). Similar to the results from endogenous PD-L1 expression analysis, transient transfection of all GFP-, HA-, Flag- or Myc-tagged PD-L1 had a ~15 kDa molecular-weight shift from its actual size on the Western blot (FIGS. 1E and 5A and 5B). In contrast to PNGase F treatment, which removes the all of the N-glycan structure on the PD-L1 protein, the addition of recombinant glycosidase, endoglycosidase H (Endo H), only partially reduced PD-L1 glycosylation, suggesting that complex types of N-linked glycan structures (containing both high mannose and hybrid types) exist predominantly on PD-L1. Furthermore, glycosylation of PD-L1 was completely inhibited when cells were treated with the N-linked glycosylation inhibitor, tunicamycin (TM), (FIGS. 1F and 5A-5D), but not 0-glycosidase (FIG. 5E). Together, these results indicate that PD-L1 is extensively N-linked glycosylated in the cells tested (Heifetz, A., et al., 1979, *Biochemistry*, 18:2186-2192).

Example 3 Glycosylation Analysis

Western blot analysis using two PD-L1-specific antibodies (anti-PD-L1 and anti-hB7-H1) indicated that PD-L1 glycosylation occurred on its extracellular domain (ECD, recognized by anti-hB7-H1) but not on its intracellular domain (ICD, recognized by anti-PD-L1) (FIGS. 1F and 5C). To pinpoint the glycosylation sites, a sequence alignment of the PD-L1 amino acid sequences from different species was performed to search for evolutionarily conserved NXT motifs, a consensus N-glycosylation recognition sequence (Schwarz, F., et al., 2011, *Current opinion in structural biology*, 21:576-582). Consistent with the earlier prediction (Cheng et al., 2013, *JBC*, 288:11771-85); and Vigdorovich et al., 2013, *Structure*, 21:707-17), four NXT motifs were identified (FIG. 1G and FIGS. 6A and 6B). To confirm if these sequences were indeed glycosylated, the tryptic peptides of a purified human PD-L1 were analyzed by nano LC-MS/MS. Glycopeptides carrying complex type N-glycans were identified for each of the 4 N-glycosylation sites (FIGS. 7A-7II), consistent with the apparent resistance to Endo H treatment (FIG. 1E). A series of asparagine (N) to glutamine (Q) substitutions were generated to determine the specific glycosylation site(s) on the PD-L1 protein. All four mutants, N35Q, N192Q, N200Q, and N219Q, exhibited a certain degree of reduction in glycosylation compared with the WT PD-L1 (FIG. 1H, lanes 2, 3, 4, and 5). No detectable differences in glycosylation were observed for the three non-NXT NQ PD-L1 mutants (FIG. 1H, lanes 11, 12, and 13). In addition, PD-L1 glycosylation was completely ablated in the PD-L1 4NQ variants in which all four asparagines were mutated to glutamine as indicated by the absence of signals corresponding to the glycosylated form at 45 kDa (FIG. 1H, lane 10 (4NQ) and lane 14 (WT)). Based on the crystal structure of the PD-1/PD-L1 complex (Lin, D. Y., et al., 2008, *Proceedings of the National Academy of Sciences of the United States of America*, 105:3011-3016, these four glycosylation sites of PD-L1 (N35, N192, N200 and N219) are exposed on the surface of the protein. Mutation of the PD-L1 glycosylation sites (PD-L1 4NQ) did not affect the overall structure based on the prediction. These results suggest that PD-L1 exists exclusively as an N-glycosylated glycoprotein in the cells and that all four NXT motifs are glycosylated.

Figures 2A, 2B, 2C, 2D, 2E, 2F, 2G:
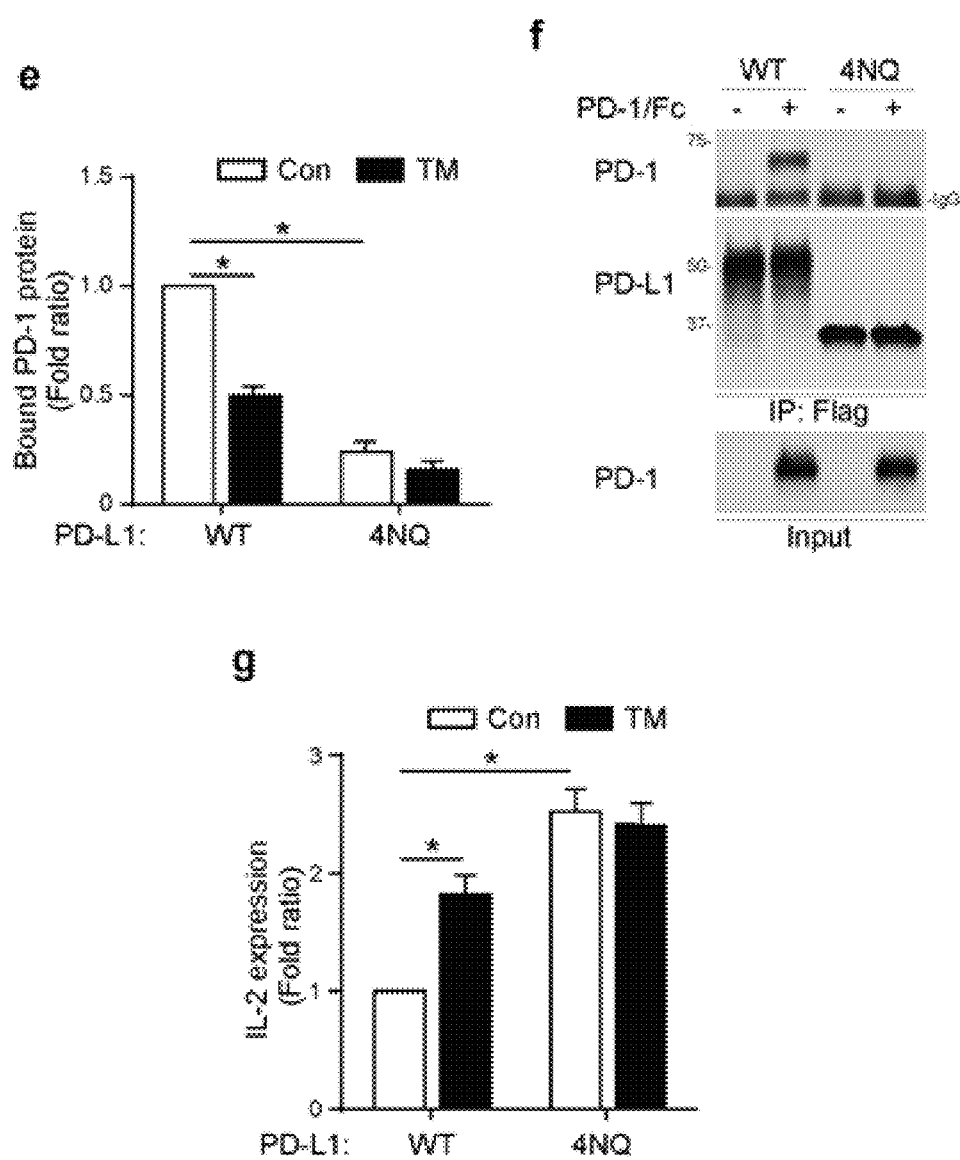
FIGS. 2A-2G. Glycosylation Stabilizes PD-L1 Expression and is Required for Cancer Cell-associated Immunosuppression. A and B: Results of Western blot analyses of PD-L1 protein in PD-L1-Flag expressing 293T cells. Cells were treated with 20 mM cycloheximide (CHX) (A) and 5 μM MG132, a proteosome inhibitor (B), at the indicated intervals and analyzed by Western blot. The intensity of the PD-L1 protein was quantified using a densitometer. C. Western blot analysis of protein stability of PD-L1WT, and PD-L1 glycosylation mutants N35Q, N192Q, N200Q, N219Q, and 4NQ determined as described in (A). Beneath the Western blot analysis result: Quantification of protein half-life of PD-L1 WT and the four NQ mutants via densitometry. D. Interaction of PD-1 and PD-L1 proteins with or without TM or anti-PD-L1 antibody treatment. Confocal image shows bound PD-1/Fc fusion protein on membrane of PD-L1 WT expressing 293T cells (staining panels on left). Quantification of bound PD-1 protein in PD-L1/PD-1 interaction assay (plot on right). E. Binding affinity of PD-1 with PD-L1 WT or 4NQ proteins. The lysates of PD-L1 WT or 4NQ expressing 293T cells were incubated with or without PD-1/Fc fusion protein. The PD-L1 proteins were then immunoprecipitated with anti-Flag antibody and analyzed by Western blot. F. Co-immunoprecipitation measuring the interaction of PD-1 and PD-L1 in PD-L1 WT or 4NQ expressing 293T cells. G. Levels of soluble IL-2 expression in co-cultures of Jurkat T-cells and PD-L1 WT or 4NQ expressing cells. Cells were pretreated with MG132 prior to the experiments shown in (D), (E) and (G). In the figure, black circles indicate glycosylated PD-L1; arrowheads indicate non-glycosylated PD-L1; TM: tunicamycin; * indicates statistically significant by Student's t test. All error bars are expressed as mean±SD of 3 independent experiments.
Figure 3A:
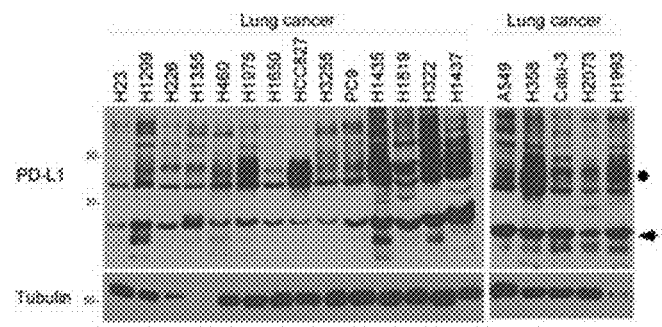
FIGS. 3A-3D. Expression of PD-L1 Protein in Cancer Cells. A. Western blot analysis of PD-L1 in lung cancer cells. B. Western blot analysis of PD-L1 in colon cancer cells. C. Western blot analysis of PD-L1 in breast cancer cells. D. Western blot analysis of PD-L1 in ovarian cancer cells. Black circles=glycosylated PD-L1; arrowheads=, non-glycosylated PD-L1.
Figure 3B:
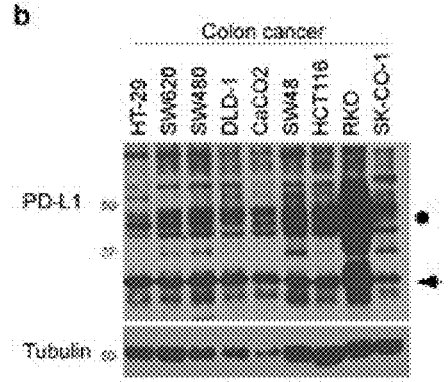
Figure 3C:
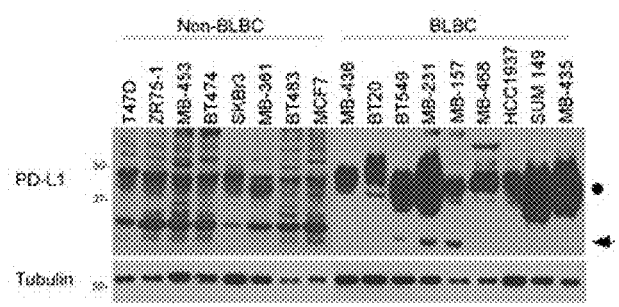
Figure 3D:
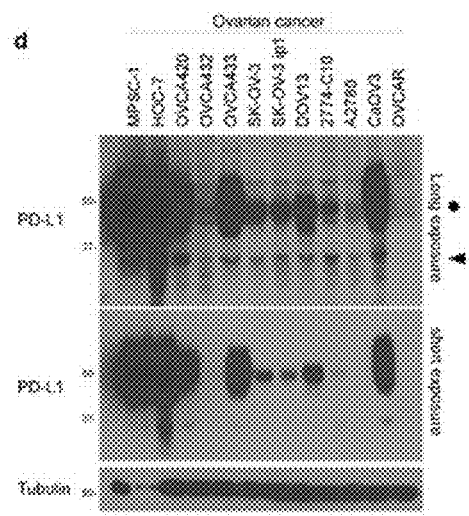
Figures 8A, 8B, 8C, 8D, 8E, 8F, 8G, 8H:
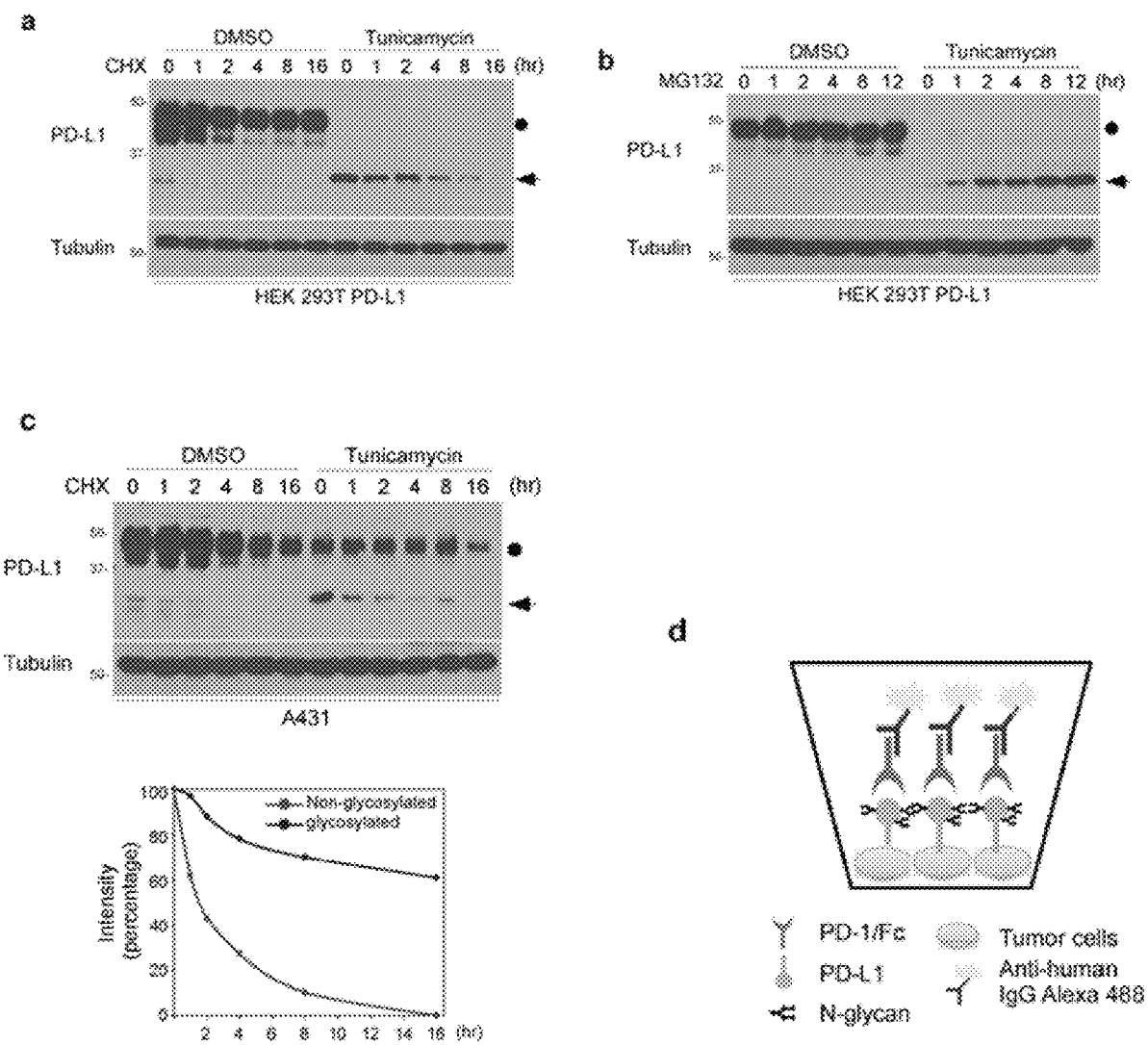
FIGS. 8A-8H. PD-L1 Glycosylation Changes Protein Stability and Immunosuppression Function of PD-L1. A-B. Western blot analysis of PD-L1 protein in PD-L1-Flag expressing HEK 293T cells. Cells treated with or without tunicamycin were treated with 20 mM cycloheximide (CHX) (A) and 5 µM MG132 (B), for the indicated intervals (hr) and analyzed by Western blot. C. Western blot analysis of PD-L1 in A431 cells either treated or not treated with tunicamycin and treated with 20 mM cycloheximide (CHX) for the designated times. The bottom panel shows a densitometry quantification of glycosylated versus non-glycosylated PD-L1 protein. D. Schematic diagram of a PD-L1/PD-1 interaction assay. E. Confocal images showing membrane localized PD-L1 WT or 4NQ proteins in A431 cells. F. Membrane localization of PD-L1 WT or PD-L1 4NQ proteins. After biotinylation of membrane localized PD-L1 WT or 4NQ proteins, the biotinylated proteins were pull-downed by streptavidin agarose. Membrane localized PD-L1 WT or 4NQ proteins were examined by Western blot. The ratio of membrane bound PD-L1 WT or 4NQ protein obtained from densitometry quantification of samples is shown beneath the blot. G. The interaction of PD-1 and PD-L1 proteins in PD-L1 WT-, N35Q-, N192Q-, N200Q-, N219Q-, or 4NQ-expressing cells. All error bars are expressed as mean±SD of 3 independent experiments. H. Schematic diagram of an ELISA designed to detect IL-2 production following T-cell/tumor cell interaction via PD-1/PD-L1, respectively. PD-L1-expressing tumor clones were co-cultured with Jurkat T-cells that overexpressed PD-1. IL-2 production from Jurkat cells was measured using ELISA, as set forth, e.g., in Examples 1, 4, and 5 infra. In A-C, black circle=glycosylated PD-L1; arrow head=non-glycosylated PD-L1.
Figures 8A, 8B, 8C, 8D, 8E, 8F, 8G, 8H:
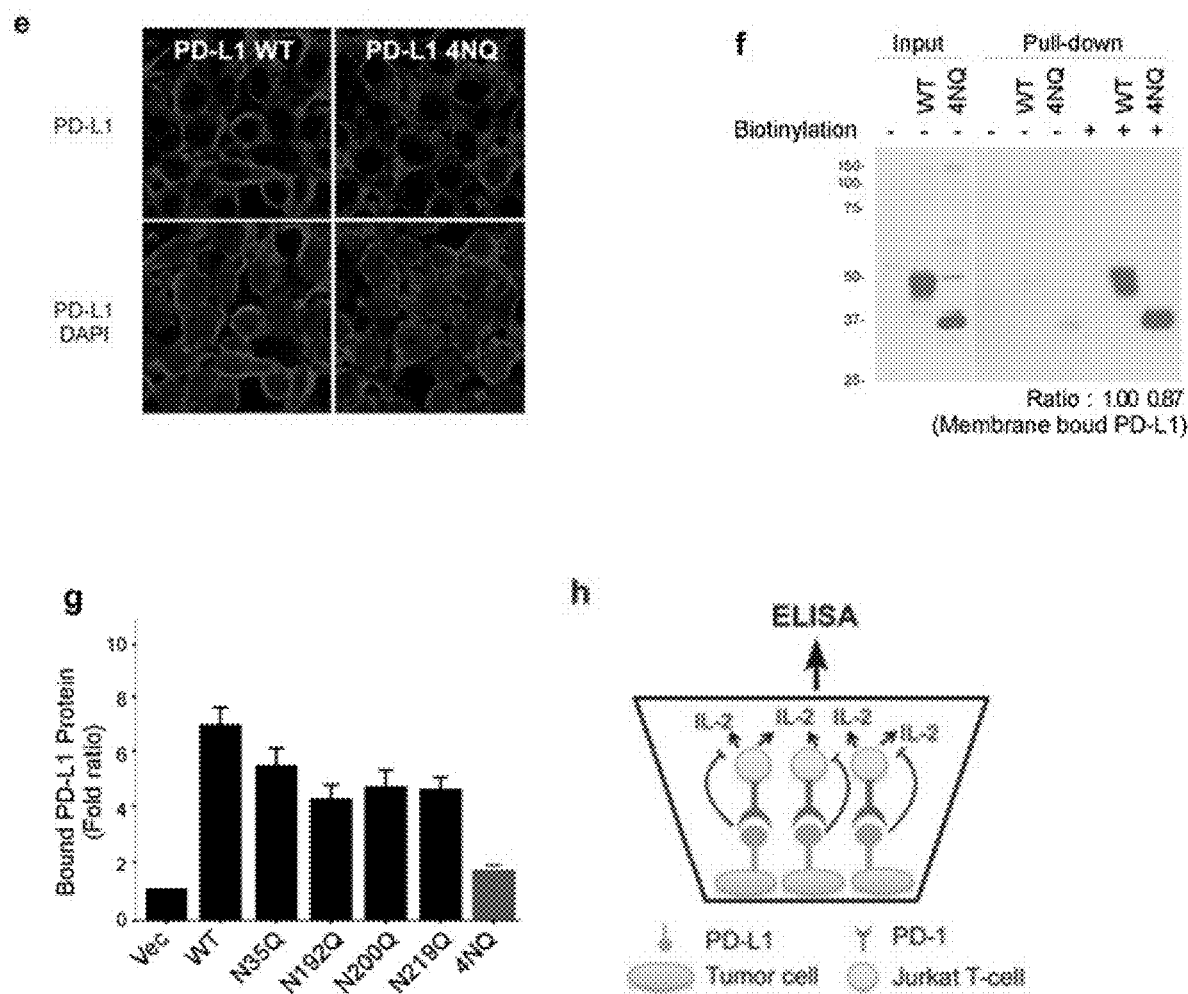

The levels of glycosylated PD-L1 observed were significantly higher than the non-glycosylated form of the PD-L1 protein (FIGS. 1A and 1B and 5C and 5D). Based on this finding, the inventors investigated whether glycosylation stabilizes the PD-L1 protein. To this end, the protein turnover rate was measured in the presence of protein synthesis inhibitor cycloheximide (CHX) to determine the effect of glycosylation on PD-L1 protein stability. The turnover rate of Flag-tagged PD-L1 was much faster in tunicamycin (TM)-treated than in DMSO-treated HEK 293T cells (FIGS. 2A; 8A and 8B). Similar results were observed for the endogenous PD-L1 in A431 cells (FIG. 8C). Under proteasome inhibition by MG132, the levels of non-glycosylated PD-L1 steadily increased over a 12-h period (FIG. 2B). Consistently, non-glycosylated PD-L1 4NQ was rapidly degraded with a half-life as short as 4 hours (FIG. 2C), similar to that of the non-glycosylated PD-L1 WT (FIG. 2A), suggesting that impaired glycosylation leads to degradation of PD-L1 via the 26S proteasome.

Example 4 Binding Affinity of PD-L1

PD-L1 is a key immune suppressor through its binding with PD-1 during cancer progression (Okazaki, T., et al., 2013, *Nature immunology*, 14:1212-1218. Thus, the binding affinities of WT PD-L1 and glycosylation-deficient mutant PD-L1 to PD-1 were compared. PD-L1 WT and the 4NQ mutant PD-L1 were stably expressed in MDA-MB-468 and HEK-293T cells, and stable clones with similar amounts of PD-L1 WT and 4NQ expression were selected and then incubated with recombinant PD-1/Fc fusion protein, followed by the addition of anti-human IgG (Fc specific) fluorescence conjugate for signal amplification (Cheng, X. et al., 2013, *The Journal of biological chemistry*, 288:11771-11785) (FIG. 8D). While there were no significant changes in membrane localization between glycosylated and non-glycosylated PD-L1 (FIGS. 8E (confocal image) and 8F (biotinylation pull-down)), a marked difference was observed in PD-1 binding on the cell membrane between stable transfectants treated with or without TM (FIG. 2D, quantification graph shown on the right). Furthermore, ablation of PD-L1 glycosylation by TM treatment, or expression of the 4NQ mutant, reduced the association of PD-L1 with PD-1 (FIGS. 2E and 8G). In vitro binding experiments also demonstrated the loss of PD-L1 4NQ/PD-1/Fc interaction, suggesting that glycosylation of PD-L1 enhances its association with PD-1 (FIG. 2F). Because immunosuppression activity is associated with cell-cell interaction involving cytotoxic T-cells, a co-culture experiment was performed to measure the IL-2 expression levels, an indicator of T-cell immune response that is suppressed by the PD-L1 and PD-1 interaction, in Jurkat T-cells after exposure to PD-L1 stable clones (Yang, W., et al., 2008, *Investigative ophthalmology & visual science*, 49:2518-2525) (FIG. 8H). Consistently, the loss of PD-L1 glycosylation impaired its interaction with PD-1 and enhanced the release of soluble IL-2 (FIG. 2G). These results reveal that the integrity of the PD-L1 glycophenotype is required for its immunosuppressive function.

Example 5 Functionality of the PD-L1 Glycophenotype

Figures 9A, 9B, 9C, 9D, 9E, 9F:
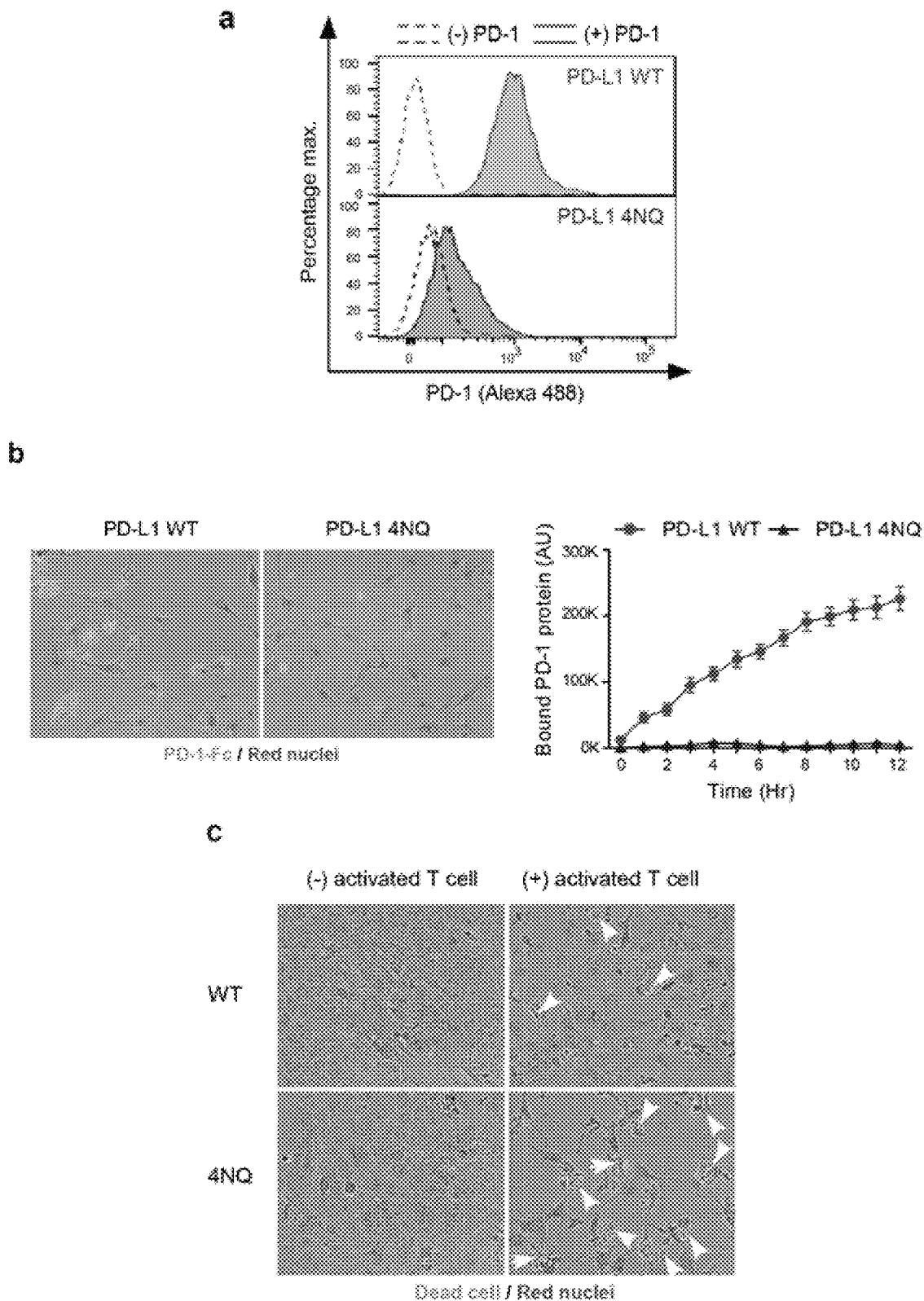
FIGS. 9A-9F. Glycosylation of PD-L1 is Required for Cancer Cell-associated Immunosuppression. A. Flow cytometry measuring the interaction of membrane bound PD-1 and PD-L1 WT or PD-L1 4NQ mutant protein expressed on BT549 cells. Cells were pretreated with MG132 prior to experiment. B. Time lapse microscopy image showing the dynamic interaction between PD-L1 and PD-1 at the last time point. Red fluorescent (nuclear restricted RFP) and green fluorescent (green fluorescent labeled PD-1/Fc protein) merged images (20×) of PD-L1 WT or 4NQ expressing cells. The kinetic graph at right in (B) shows the quantitative binding of the PD-1/Fc protein to PD-L1 WT or PD-L1 4NQ protein expressed on BT549 cells at every hour time point. C. T cell-meditated tumor cell killing (TTK) assay involving PD-L1 WT or 4NQ PD-L1 protein expressed on BT549 cells. Representative phase, red fluorescent (nuclear restricted RFP), and/or green fluorescent (NucView™ 488 Caspase 3/7 substrate) merged images (10×) of PD-L1 WT or 4NQ expressing cells, and PD-1-expressing T cell co-cultures in the presence of Caspase 3/7 substrate at 96 hours. T cells were activated with anti-CD3 antibody (100 ng/ml) and IL-2 (10 ng/ml). Green fluorescent cells were counted as dead cells. The quantitative ratio of dead cells versus total cells associated with PD-L1 WT or PD-L1 4NQ protein is presented in the bar graph at the right of the images. D. Tumor growth in BALB/c mice bearing tumors derived from injected 4T1 cells that expressed either PD-L1 WT or PD-L1 4NQ mutant protein. Tumor growth of 4T1-luc cells was shown in vivo by bioluminescence imaging using IVIS100 (at left in D). At right in D: Box plots showing the tumor volume and photos showing tumor size in mice bearing tumors derived from 4T1 cells expressing PD-L1 WT versus PD-L1 4NQ proteins. Tumors were measured and dissected at the endpoint. n=8 mice per group (right). E. Intracellular cytokine staining of IFNγ in CD8+CD3+ T cell populations. Significance was determined by two-way ANOVA, with *$p<0.05$ and **$p<0.001$; n=7 mice per group. * indicates statistically significant by Student's t test. All error bars are expressed as mean±SD of 3 independent experiments. F. Box plot showing the tumor volume in mice bearing tumors derived from 4T1 cells expressing PD-L1 WT (glycosylated) proteins treated with STM073 MAb ("73"), 100 µg, or with IgG control, 100 µg. Tumors were measured and dissected at the endpoint. n=7 mice per group. Treatment with STM073 resulted in reduced tumor volume.

PD-L1 WT and 4NQ mutants were stably expressed in endogenous PD-L1-depleted MDA-MB-468 and BT549 cells. Using these cell lines, PD-1 and PD-L1 binding affinity were analyzed. As shown, the association between glycosylation variant PD-L1 4NQ and PD-1 was decreased (FIG. 9A). In vitro binding experiments further demonstrated that glycosylation is required for the PD-L1 and PD-1 association (FIG. 9B). T cell-mediated tumor cell killing was measured in vitro by co-culturing BT549 PD-L1 WT and PD-L1 4NQ expressing stable cell lines with human primary T cells (time-lapse microscopy). Consistent with the loss of PD-1 binding, the PD-L1 4NQ stable cell line showed more T cell-mediated killing of cancer cells (FIG. 9C). In addition, the immunosuppressive function of PD-L1 was measured in vivo in a syngeneic 4T1 mouse model in which tumor growth was measured in BALB/c mice that had received either PD-L1 WT or PD-L1 4NQ expressing 4T1 cells. Compared with mice having cells that expressed PD-L1 WT, the mice having cells that expressed PD-L1 4NQ showed reduced tumor size and more activated cytotoxic T cells (FIGS. 9D and 9E). Together, these data demonstrate that the loss of PD-L1 glycosylation impairs its interaction with PD-1 and impairs the ability of the PD-1/PD-L1 interaction to allow tumor cells to evade immune surveillance by T-cells. Accordingly, tumor cells in which PD-L1 is non-glycosylated, or is aberrantly glycosylated, provide targets that are amenable to be killed by functional effector T-cells. This mechanism of preventing or blocking tumor cells from escaping T-cell immune surveillance by impaired glycosylation of their membrane-expressed PD-L1 further corroborates that the integrity of the PD-L1 glycophenotype is required for its immunosuppressive function.

In addition, the syngeneic 4T1 BALB/c mouse model as above was used to determine the effect of a representative dual function antibody, namely, STM073, on tumor growth (i.e., the immunosuppressive function) in the animals during a 16-day study period. Briefly, in the study, animals received 4T1 cells expressing wild type (glycosylated) PD-L1 ($1 \times 10^5$ 4 T1 cells) on Day 0. On Days 3, 5, 7, 9, 11 and 13 thereafter, the 4T1-animals were treated with STM073 MAb (100 µg) or IgG control antibody (100 µg) by injection. During the treatment period, mortality and tumor volume were assessed in the animals. FIG. 9F presents box graphs showing that tumor volume in the mice that were treated with the STM073 ("73") MAb was measurably lower compared with the tumor volume in control animals.

Example 6 Production of Glycosylated PD-L1-Binding Monoclonal Antibodies

Hybridomas producing monoclonal antibodies generated against glycosylated human PD-L1 were obtained by the fusion of SP2/0 murine myeloma cells with spleen cells isolated from human PD-L1-immunized BALB/c mice (n=6) (Antibody Solution, Inc.) according to standardized protocol. Before fusion, sera from the immunized mice were validated for binding to the PD-L1 immunogen using FACS analysis. Monoclonal antibody (MAb)-producing hybridomas were generated and the isotype of all of the MAbs was IgG1. The hybridomas that produced antibodies were again tested for specificity.

To identify anti-glycPD-L1 MAbs that were specific for and which preferentially bound glycosylated PD-L1 antigen (i.e., glycosylated PD-L1 specific MAbs) versus non-glycosylated PD-L1, different types of assays were performed. In a screening assay to detect preferential binding of MAbs to glycosylated PD-L1, antibody binding was determined based on the measurement of fluorescence intensity through FACS analysis (using cell membrane bound proteins). By way of example, the assay was performed using the BT549 human breast cancer cell line. Illustratively, BT549 cells overexpressing PD-L1 WT (fully glycosylated) were labeled with biotin according to conventional procedures and then mixed with BT549 cells overexpressing PD-L1 4NQ (fully unglycosylated PD-L1 variant). The mixed cells were incubated with anti-PD-L1 antibodies, e.g., anti-glycPD-L1 antibodies, and were further incubated with secondary antibodies conjugated with FITC as detection agent. After washing, fluorescence intensity (measured fluorescence intensity, MFI) was measured via FACS/flow cytometry analysis to assess the relative binding of the anti-PD-L1 antibodies to membrane bound PD-L1 WT (on cells) or to 4NQ PD-L1 (on cells). Antibodies that exhibited significantly higher MFI on WT PD-L1 versus 4NQ PD-L1 were selected for further evaluation. Results for the fluorescence binding analysis of the STM073 and STM108 dual function MAbs are presented in Table 6 below, which shows the MFI values for antibody binding to BT549 cells expressing wild type (glycosylated) PD-L1, (BT549PD-L1WT Cells) versus antibody binding to BT549 cells expressing variant (non-glycosylated 4NQ) PD-L1, (BT549PD-L1 4NQ Cells). The experimental results in Table 6 show an approximately 5-fold higher MFI value for STM073 MAb binding to BT549PD-L1WT cells (glycosylated PD-L1-expressing cells) compared with BT549PD-L1 4NQ cells (non-glycosylated PD-L1-expressing cells). Similarly, an approximately 4-fold higher MFI value was determined for STM108 binding to BT549PD-L1WT cells compared with BT549PD-L1 4NQ cells.

TABLE 6

| Measured Fluorescence Intensity Values for Anti-glycPD-L1 MAbs | | |
|---|---|---|
| MAb | MFI (BT549PD-L1WT Cells) | MFI (BT549PD-L1 4NQ Cells) |
| STM073 | 63.90 | 12.21 |
| STM108 | 117.42 | 27.57 |

Based on the binding analysis, forty-two candidate MAb-producing hybridomas were selected, grown in ADCF medium, and their supernatant containing monoclonal antibody was concentrated and purified.

In some cases, the purified MAbs were further tested for their ability to neutralize or inhibit the interaction between PD-L1 and PD-1 (PD-L1/PD-1 interaction) using a live-cell imaging assay, IncuCyte™, (Essen Bioscience). For this assay, BT-549 cells expressing PD-L1 were incubated with anti-human PD-L1 antibody and with fluorescent-labeled PD-1-Fc fusion proteins. Ligand and receptor binding was quantified by IncuCyte™ Zoom every hour, according to the manufacturer's instructions. Based on this assay, it was found that of the 42 MAbs tested, 15 MAbs completely blocked the binding of PD-L1 to PD-1. Some of the 15 MAbs that showed strong blocking efficacy also bound non-glycosylated PD-L1 to some extent.

In another assay, both glycosylated human PD-L1 protein and non-glycosylated PD-L1, i.e., PD-L1 protein treated with PNGase F, were coated onto a solid phase and tested for binding affinity of the MAbs to the PD-L1 antigens. It will be understood that "PD-L1 antigen" is synonymous with "PD-L1 protein." Twelve (12) of the MAbs showed a higher affinity interaction with glycosylated PD-L1 protein compared to non-glycosylated PD-L1 protein (PNGase F treated protein). For further specificity analysis, selected MAbs were analyzed by Western Blot and FACS flow cytometry analysis. From the various analyses, MAbs, such as STM073 and STM108, were found to specifically bind the glycosylated form of PD-L1 compared with the non-glycosylated form of PD-L1, which further validated the specificity of these MAbs for glycosylated PD-L1 antigen.

Figure 10A:
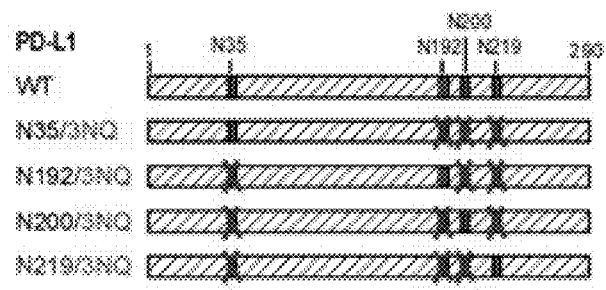
FIGS. 10A-10C. Schematic Diagram of Glycosylated and Non-glycosylated Forms of the PD-L1 Protein and Western Blot Analyses. A. Schematic depiction of wild type, glycosylated PD-L1 protein (PD-L1 WT) and four PD-L1 protein variants, each having one glycosylated amino acid residue and three non-glycosylated amino acid residues out of the four N-glycosylation sites of the PD-L1 protein (N35/3NQ; N192/3NQ; N200/3NQ; and N219/3NQ). The amino acids designated in black represent glycosylated residues; the amino acid sites shown in red are non-glycosylated in the variant PD-L1 proteins. B. Stable clones of BT 549 expressing N35/3NQ, N192/3NQ, N200/3NQ and N219/3NQ forms of the PD-L1 protein were generated. Some of the anti-glycPD-L1 antibodies showed a greater level of binding to certain of the PD-L1 glycosylation variants versus others as determined by Western blot analysis, demonstrating that those MAbs were site specific. As shown in B, for example, MAb STM073 recognized and bound the N35/3NQ, N192/3NQ and N200/3NQ PD-L1 variants, indicating that this monoclonal antibody bound to the N35, N192 and N200 regions of glycosylated PD-L1. C. shows the results of a Western blot of the STM073 MAb binding to lysates of liver cancer cell lines.
Figure 10B:
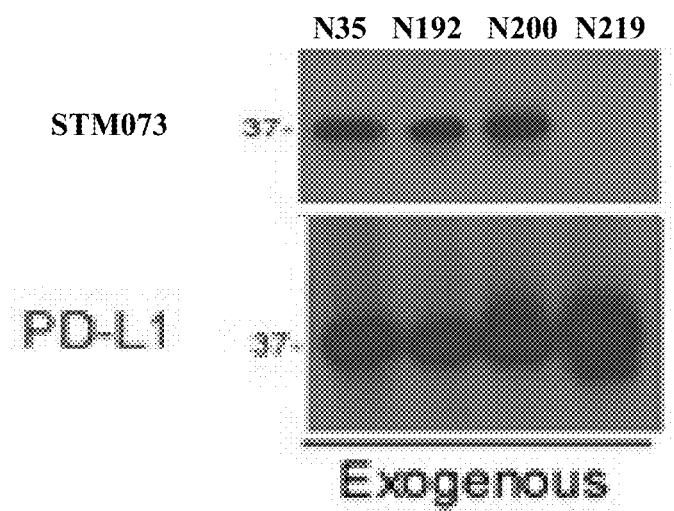
Figure 10C:
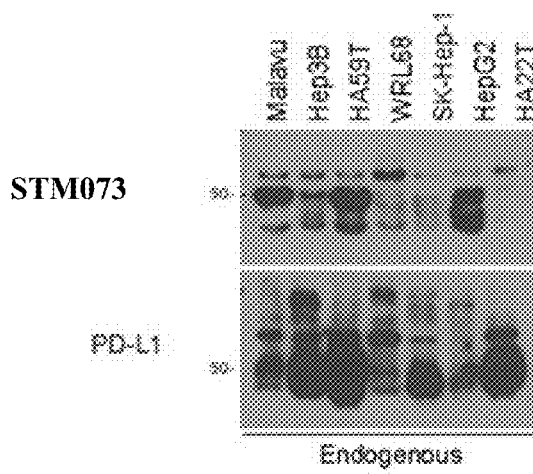

Example 7 Identification of Binding Regions of Specific Glycosylated PD-L1-Binding Monoclonal Antibodies To identify the regions of monoclonal anti-glycPD-L1 antibodies which bound to glycosylated PD-L1, wild type (glycosylated) PD-L1 (PD-L1 WT), and the glycosylation variant proteins N35/3NQ, N192/3NQ, N200/3NQ, and N219/3NQ (in which one of the glycosylation sites at position 35, 192, 200 or 219 is the wild type asparagine (N) at that position and the other three positions have been mutated to glutamine (Q) have been mutated so it is not glycosylated) (FIG. 10A) were overexpressed in PD-L1 knockdown BT549 cells. As determined by Western blot, some MAbs recognized particular PD-L1 mutants with higher levels of binding compared with other PD-L1 mutants, demonstrating that such MAbs were site-specific. For example, MAb STM073 bound the mutants N35/3NQ, N192/3NQ and N200/3NQ, but not mutant N219/3Q, demonstrating that this antibody bound to the N35, N192 and N200 regions of PD-L1, but not to N219 (FIG. 10B). Further, Western blot analysis using liver cancer cell lysate also revealed a differential pattern of PD-L1 glycosylation for a representative anti-glycPD-L1 antibody such as STM073 (FIG. 10C).

The histopathologic relevance of these MAbs was further demonstrated by immunohistochemical (IHC) staining. In a cytospin staining analysis, the anti-glycPD-L1 monoclonal antibodies consistently recognized and bound the glycosylated portion of the PD-L1 protein, but not unglycosylated PD-L1 protein. In a human triple negative breast cancer patient sample, the anti-glycPD-L1 monoclonal antibodies also showed membrane and cytoplasm staining in a 1:30 ratio. These data demonstrated that the anti-glycPD-L1 monoclonal antibodies can be used in biomarker analyses for detection of glycosylated PD-L1 as biomarker.

Example 8 Epitope Mapping of Glycosylated PD-L1-Binding Antibodies

Epitope mapping for the mouse monoclonal anti-glycPD-L1 antibody STM073 was performed by CovalX AG (Switzerland). To determine the nature of the epitope, e.g., either linear or conformational, recognized by the anti-glycPD PD-L1 antibodies generally, and the STM073 MAb in particular, studies were conducted to evaluate whether the interaction between the PD-L1 antigen proteins and the anti-PD-L1 antibodies could be inhibited by unstructured peptides generated by proteolysis of the antigen. If the peptides generated by complete proteolysis of the PD-L1 antigen are able to inhibit the binding of the antigen by the antibody, the interaction is not based on conformation, and the epitope is linear. A simple competition assay with a bank of overlapping peptides generated from the sequence of the antigen is sufficient to determine the sequence of the epitope. Alternatively, if the peptides generated by complete proteolysis of the PD-L1 antigen are unable to inhibit the binding of the antigen by the antibody, the conformation of the target is determined to be necessary for interaction, and the epitope is conformational, e.g., continuous (with a special conformation such as a loop) or discontinuous (due to tertiary structure). To further elucidate binding to a conformational epitope, covalent labeling, peptide mapping, and high resolution mass spectrometry were also employed.

Competition assays showed that peptides generated from the PD-L1 antigen did not inhibit the binding of MAb STM073 to the PD-L1 antigen, confirming that the STM073 MAb epitope is conformational and not linear. Using chemical cross-linking, High-Mass MALDI mass spectrometry and nLC-Orbitrap mass spectrometry, the interaction surfaces between the PD-L1 protein and the antibodies were characterized. Competition assays using pepsin proteolysis of PD-L1, mixture of the resulting pepsin-generated PD-L1 peptides with antibodies and intact PD-L1 protein, and analysis of the antigen/antibody interaction by known methods showed no detectable inhibition of binding of the STM073 monoclonal antibody to the PD-L1 antigen by the PD-L1 peptides. Accordingly, the epitope on PD-L1 recognized by the anti-PD-L1 MAb STM073 was determined to be conformational and not linear. The epitope of STM073 was determined to include amino acid residues H69, Y112, R113 and K124, which are underlined in the sequence starting with V68 and ending with V128 (with the region within positions 79 to 107 indicted as dashes) V<u>H</u>GEEDLKVQH------DAGV<u>YR</u>CMISYGGADY<u>K</u>RITV (SEQ ID NO: 85). STM108 was found to bind an epitope within the sequence LKVQHSSYRQR------EGYP-KAEVIWTSSDHQ, which are amino acids 74 to 84 and 158 to 173, respectively, of SEQ ID NO:1, and contacts residues S80, S81, K162 and S169 of SEQ ID NO. 1, within residues 74 to 173 of SEQ ID NO: 1.

Example 9 T Cell Killing Assay

T cell killing assays were utilized to determine the cytotoxic activity of anti-glycPD-L1 monoclonal antibodies as described herein on tumor cells. The protocol followed is as follows: On Day 0, serum-containing medium was removed from glycosylated wild type PD-L1- (PD-L1 WT) expressing BT549 RFP target cell cultures and gently rinsed twice with PBS. Cells were harvested and counted. The cell suspension was centrifuged (1000 RPM, 4 minutes) and the cell pellet was resuspended in culture medium at 50,000 cells/mL. Using a manual multichannel pipette, the cells were seeded (100 µL/well, i.e., 5000 cells/well) into every well of a flat-bottom microplate. The plate was allowed to stand at ambient temperature for 30 minutes and then was positioned into an IncuCyte ZOOM® live-cell imager where it was left to equilibrate for 20 minutes before scheduling the first scan. Twenty-four hour (24 hr) repeat scanning (10× objective) was scheduled for every 3 hours, with the first scan commencing immediately. Cell confluence was monitored for the next 18 hours (overnight) until the desired confluence (e.g., 20%) was achieved.

The next morning, the day of the assay (i.e., Day 1), a 10 µM solution of IncuCyte™ Caspase 3/7 apoptosis green fluorescence detection reagent (Essen BioScience 4440) was prepared in assay medium (4× final assay concentration of 2.5 µM) and warmed to 37° C. in an incubator. An anti-CD3 antibody (100 ng/mL)+IL-2 (10 ng/mL) T cell activator treatment was prepared at 4× final assay concentration in assay medium and warmed to 37° C. Test MAbs were also prepared. The target cell plate was removed from the incubator and the medium was aspirated, taking care not to damage the cell layer. Using a multichannel pipette, 25 µL of the warmed caspase 3/7 solution was transferred into each well. Thereafter, 25 µL of the warmed anti-CD3 antibody+ IL-2, and the antibodies, were placed into the appropriate wells of the cell plate. An additional 50 µL of medium containing the effector cells (PBMCs or Total T cells) was added to form a total assay volume of 100 μL. The de-bubbled cell plate was positioned in the IncuCyte ZOOM® instrument and allowed to equilibrate for 20 minutes prior to the first scan. 24-hr repeat scanning was scheduled for every 2-3 hours for up to 5 days. (Objective 10×; Vessel Type: Corning 3596; Scan Mode: Standard; Scan Pattern: 2 images per well; Channel: Phase+"Green" (+"Red" if NucLight™ Red target cells were used)).

Figure 11:
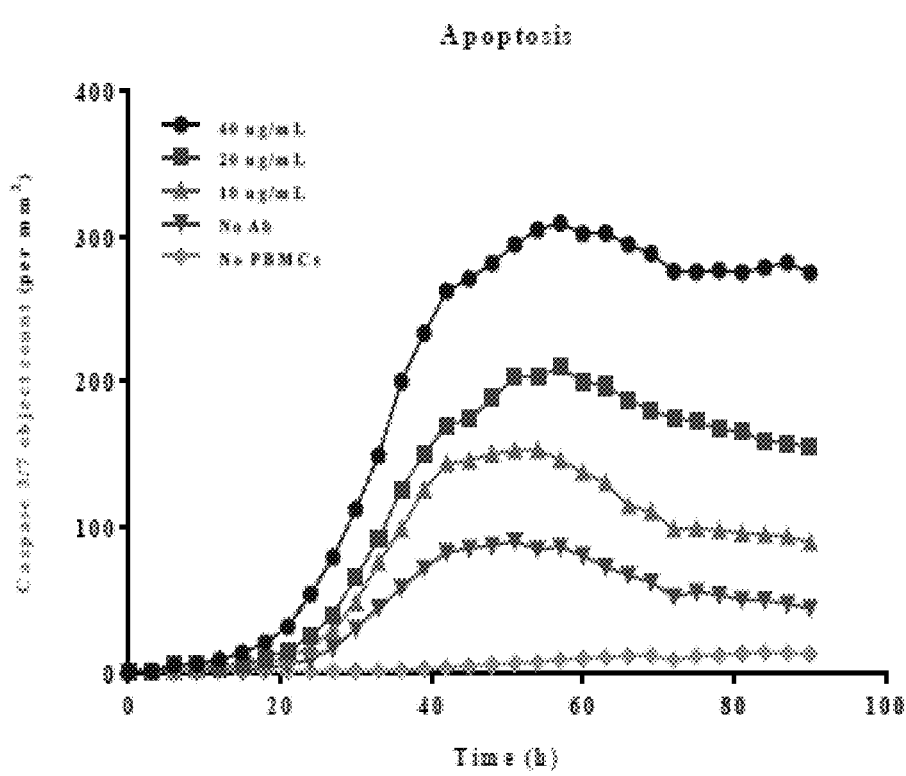
FIG. 11. Anti-glycPD-L1 Antibodies Enhance Tumor Cell Killing by T Cells. The STM073 MAb was used in different amounts in a cellular cytotoxicity assay as described in Example 10 to assess the cytotoxicity of PBMC-derived T-cells against tumor cells (BT549).

For analysis, target-cell apoptosis was quantified in the IncuCyte™ software by counting the total number of "large" green-fluorescent objects (nuclei) in the field of view over time. The proliferation of target cells was measured from the red object count, corresponding to the number of red cell nuclei. Data were expressed as the number of fluorescent objects per $mm^2$. Data showed that addition of antibodies as described herein, specifically STM073, enhanced tumor cell killing (FIG. 11).

Example 10 Binding Assay

To determine whether an anti-glycPD-L1 monoclonal antibody as described herein specifically inhibits the interaction of PD-1 and PD-L1, the following binding assay was performed. On Day 0 of the assay, serum-containing medium was removed from PD-L1-expressing BT549 target cell culture and gently rinsed twice with D-PBS. Cells were harvested and counted. The cell suspension was centrifuged (1000 RPM, 5 minutes) and the cell pellet was resuspended in culture medium at 50,000 cells/mL. A manual multichannel pipette was used to seed the cells (100 μL/well, i.e., 5000 cells/well) into every well of a flat-bottom microplate. The plate was allowed to stand at ambient temperature for 30 minutes. Thereafter, the plates containing the cells were incubated overnight in a 5% $CO_2$ incubator.

On Day 1 of the assay (i.e., the next morning), culture medium containing 1 μg/mL PD-1/Fc and a 1:400 dilution of Alex Fluor 488-goat anti-human IgG was prepared and warmed to 37° C. in an incubator. The cell plate was removed from the incubator and the medium was aspirated, taking care not to damage the cell layer. 50 μL of test antibody was added to each well in a dose-dependent manner. 50 μL of the culture medium containing PD-1/Fc and Alex Fluor 488-goat anti-human IgG was added to every well. The cell plate was positioned in the IncuCyte ZOOM® instrument and allowed to equilibrate for 20 minutes prior to the first scan. 24-hr automated repeat scanning (10×) was scheduled for every 1-2 hours for up to 24 hours. Objective: 10×; Vessel Type: Corning 3596; Scan Mode: Standard; Scan Pattern: 4 images per well; Channel: Phase+"Green".

Figures 12A, 12B, 12C:
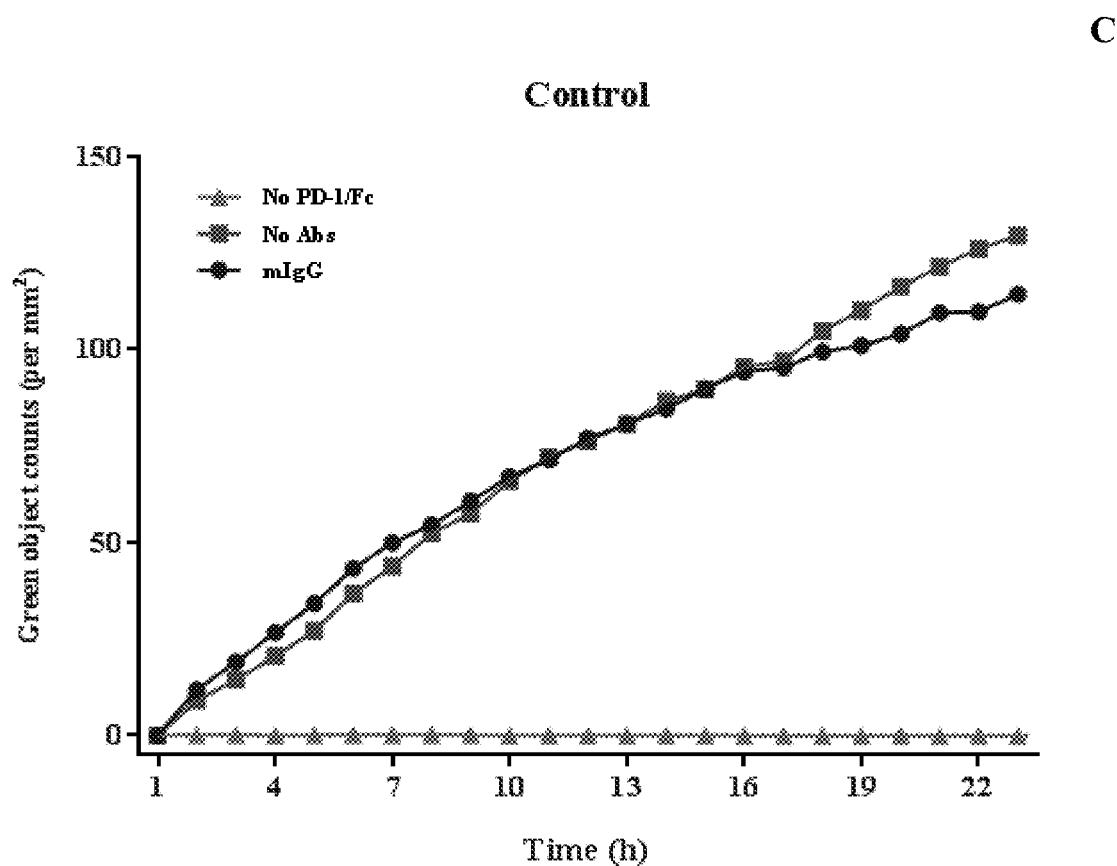
FIGS. 12A-12C. Binding Assays.

FIGS. 12A and 12B show that representative MAbs STM073 and STM108 inhibited binding of PD-1/Fc to cells expressing PD-L1 in a dose dependent manner. The control assay results are shown in FIG. 12C.

Example 11 PD-L1 Internalization Assay

Figure 13:
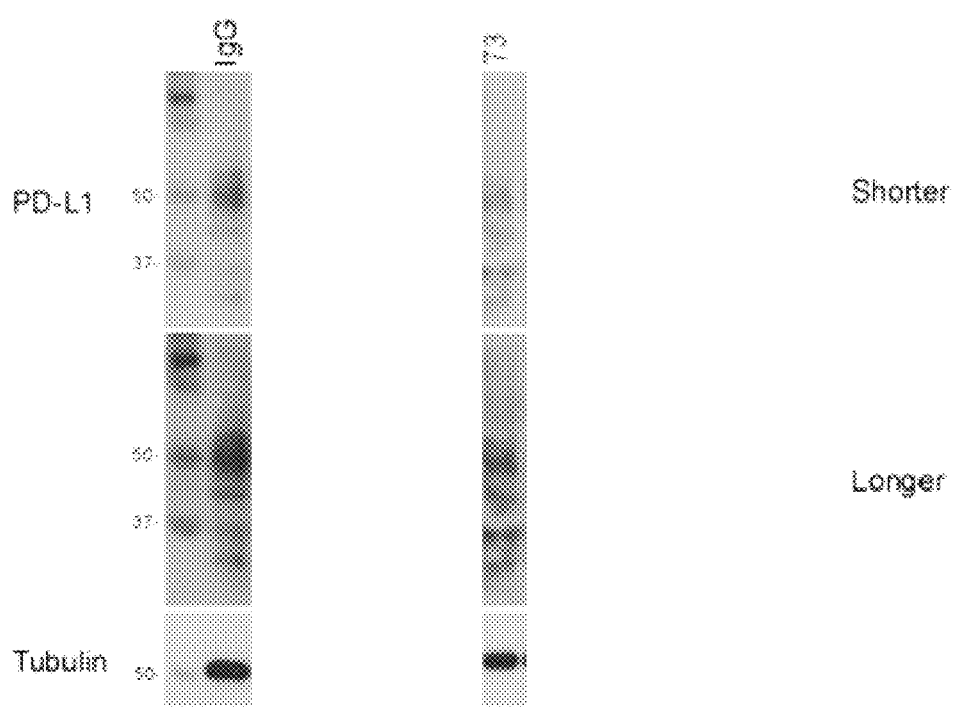
FIG. 13. Internalization of PD-L1 by Anti-glycPD-L1 Antibodies.

To determine whether an anti-glycPD-L1 monoclonal antibody promotes PD-L1 internalization and degradation, A431 cells were incubated in serum free medium overnight and then incubated with 10 μg of anti-glycPD-L1 antibody for two days. The cells were then harvested, and PD-L1 in the cells was assessed by Western blot. FIG. 13 shows that incubation with the STM073 shows a reduced level of PD-L1 in the cells compared to control (IgG).

Figures 14A, 14B, 14C, 14D, 14E:
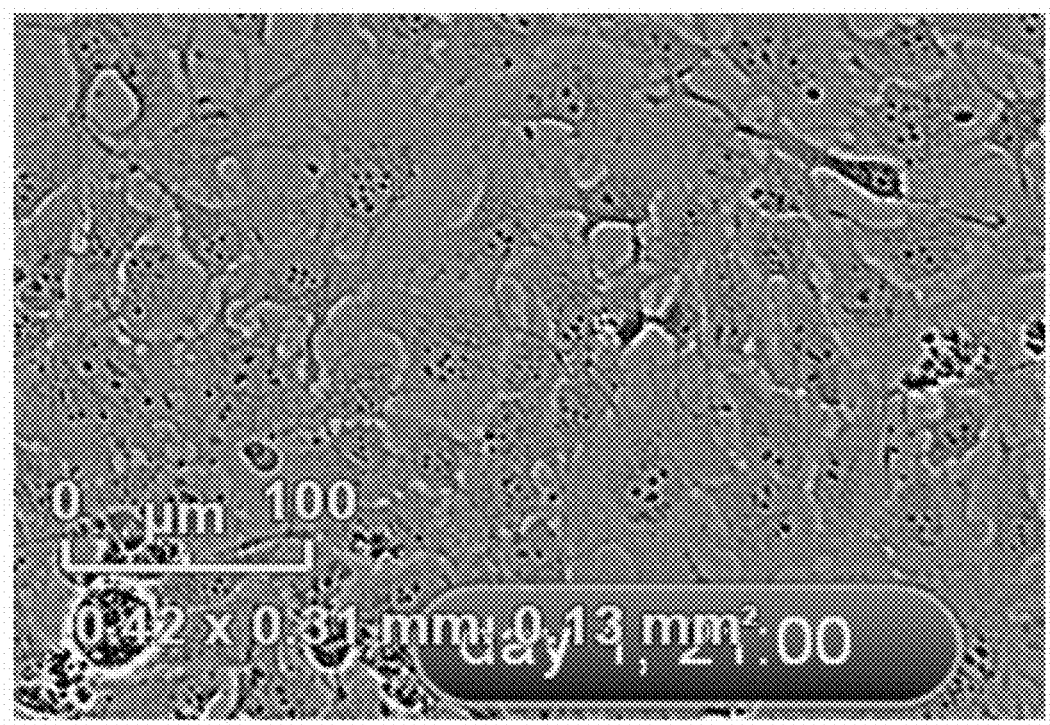
FIGS. 14A-14E. Visualization of Cellular Internalization of Anti-glycPD-L1 Antibodies. The STM073 and STM108 MAbs were labeled and incubated with different cancer cell types and internalization was visualized using an IncuCyte ZOOM® instrument as described in Example 11.

The cellular internalization of the STM073 and STM108 MAbs was visualized by labelling the antibodies with pHrodo™ Red dye using the pHrodo™ Red Microscale Labeling Kit (ThermoFischer Scientific, Rochester, N.Y.) according to the manufacturer's instructions. Briefly, for the analysis, cells were seeded at time 0; at 24 hours after seeding, cells were incubated with labeled STM073 or STM108 MAbs (5 μg/mL). After 1 hour, an image scan of the cells was begun using an IncuCyte ZOOM® instrument with scheduled 24-hour repeat scanning (10×) for every 1 hour. Objective: 10×; Vessel Type: Corning 356407; Scan Mode: Standard; Scan Pattern; 3 images per well; Channel: Phase+"Red." FIG. 14A: Wild type BT549 cells (human ductal carcinoma, breast cancer cell line) incubated with STM073; FIG. 14B: BT 549 cells overexpressing PD-L1 WT (glycosylated) incubated with STM073; FIG. 14C: NCI-H226 cells (human lung cancer cell line, squamous cell mesothelioma) incubated with STM073; FIG. 14D: MCF-7 cells (human breast cancer cell line, adenocarcinoma) incubated with STM073; and FIG. 14E: BT 549 cells expressing PD-L1 WT (glycosylated) incubated with STM108.

Figure 15A:
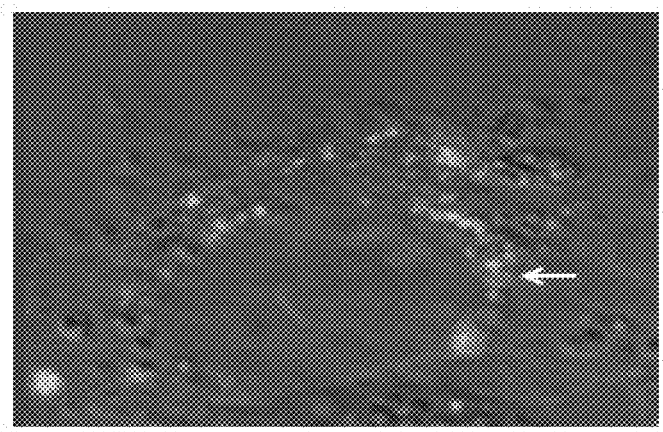
FIGS. 15A-15C. Internalization and Degradation of PD-L1 Following Binding By Anti-glycPD-L1 Antibodies.
Figure 15B:
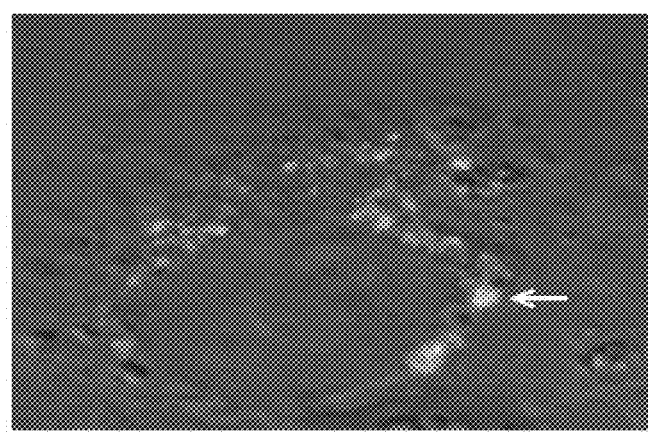
Figure 15C:
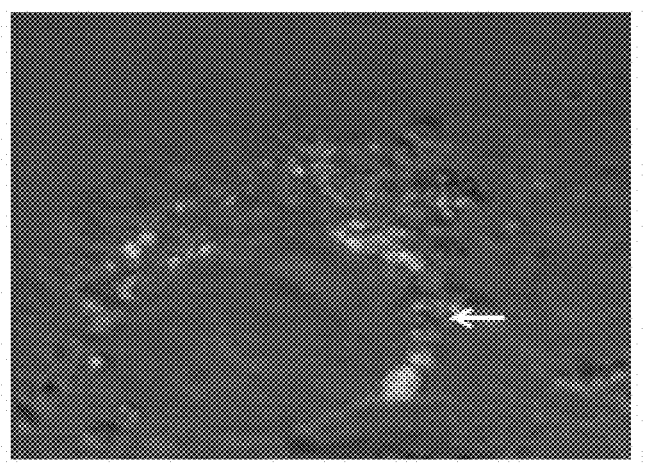

Example 12 Binding of PD-L1 by Anti-glycPD-L1 Antibodies Promotes PD-L1 Internalization and Degradation FIGS. 15A-15C provide an example of PD-L1 internalization and degradation via live cell imaging analysis following binding of anti-glycPD-L1 MAb STM108 to PD-L1 expressed on BT549-PD-L1 cells. In FIGS. 15A-15C, the anti-PD-L1 antibody is STM108 conjugated to a red fluorescent dye, pHrodo™ Red (succinimidyl ester (pHrodo™ Red, SE) using the pHrodo™ Red Microscale Labeling Kit, (ThermoFisher Scientific, Rochester, N.Y.), as described above in Example 11. Green staining reflects cells stained with LysoTracker® Green DND-26, which is a cell permeable green dye that stains acidic compartments (lysosomes) in live cells imaged via live cell imaging. FIG. 15A shows that at a first time point (Time 0), the STM108 antibody is internalized into cells as observed by the intense red intracellular staining of cells indicated by the arrow. FIG. 15B shows the weakened intracellular red staining in the same cells depicted in FIG. 15A, at a time 2 minutes after Time 0 in FIG. 15A. FIG. 15C shows the lack of red intracellular staining 4 minutes after Time 0 in FIG. 15A, which reflects the degradation of the STM108 antibody and/or the antibody-antigen complex inside the cells. These images reflect that an anti-glycPD-L1 antibody such as STM108 MAb effectuates internalization and degradation of PD-L1 after binding to PD-L1 expressed on the cell surface.

Example 13 Internalization of PD-L1 Bound by Anti-glycPD-L1 Antibodies in Tumor Cells Versus Total T Cells Anti-glycPD-L1 antibodies were tested for the ability to internalize into PD-L1 positive tumor cells after binding cell-surface expressed PD-L1, as compared to activated or non-activated T cells. The anti-glycPD-L1 antibodies STM004, STM073 and STM108, and mouse IgG as control were incubated with non-activated total T cells from peripheral blood, activated total T cells from peripheral blood and NCI-H226 cells, which express PD-L1. For T cell activation, total T cells were mixed with beads, e.g., inert, superparamagnetic beads, covalently coupled with anti-CD3 and anti-CD28 antibodies (e.g., ThermoFisher Scientific, Rochester, N.Y.) at a 1:1 ratio to stimulate T cells in a manner mimics stimulation by antigen-presenting cells (See, e.g., A. Trickett et al., 2003, *J. Immunol. Methods*, 275, Issues 1-2:251-255). All antibodies were labeled with pHrodo™ Red and internalization was visualized as described in Example 11. FIGS. 16A-16D and FIGS. 16E-16H show that none of the antibodies tested were internalized into non-activated total T cells or activated total T cells. FIGS. 16I-16L show that the dual function, internalizing STM073 and STM108 MAbs were internalized into NCI-H226 cells following incubation with these cells, as evidenced by red intracellular staining, compared with the labeled control antibody, mIgG (FIG. 16I) and with labeled non-internalizing STM004 MAb. (FIG. 16J), which showed no red intracellular staining. This example demonstrates that the dual function anti-glycPD-L1 antibodies are selectively internalized into PD-L1-expressing tumor cells but are not internalized into either activated or non-activated T cells.

Example 14 Efficacy of PD-L1 ADC in Tumor Cell Killing and Reduction of Tumor Volume Both in vitro and in vivo experiments were conducted to evaluate the efficacy of an ADC comprising an anti-human glycPD-L1 MAb, i.e., STM108 MAb, coupled to the cytotoxin MMAE in tumor killing and in reducing tumor volume. The STM108-ADC comprises the STM108 MAb chemically linked via cysteines to MC-vc-PAB-MMAE, as described hereinabove, for specific delivery of the MMAE cytotoxin payload to PD-L1-expressing tumor or cancer cells. Measured physical properties of the STM108-ADC (STM108-MC-vc-PAB-MMAE) are as follows:

| | |
|---|---|
| $A_{248nm}$ of ADC | 2.548 |
| $A_{280nm}$ of ADC | 3.635 |
| Ratio $A_{248nm}/A_{280nm}$ | 0.70 |
| Drug Antibody Ratio | 4.13 |

Figure 17A:
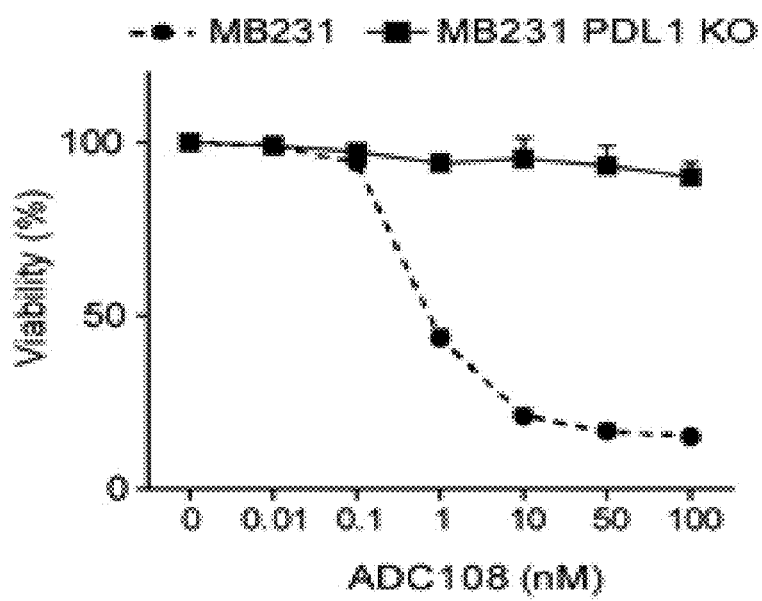
FIGS. 17A-17D. Anti-tumor Efficacy of an Anti-glycPD-L1 Antibody-ADC.
Figure 17B:
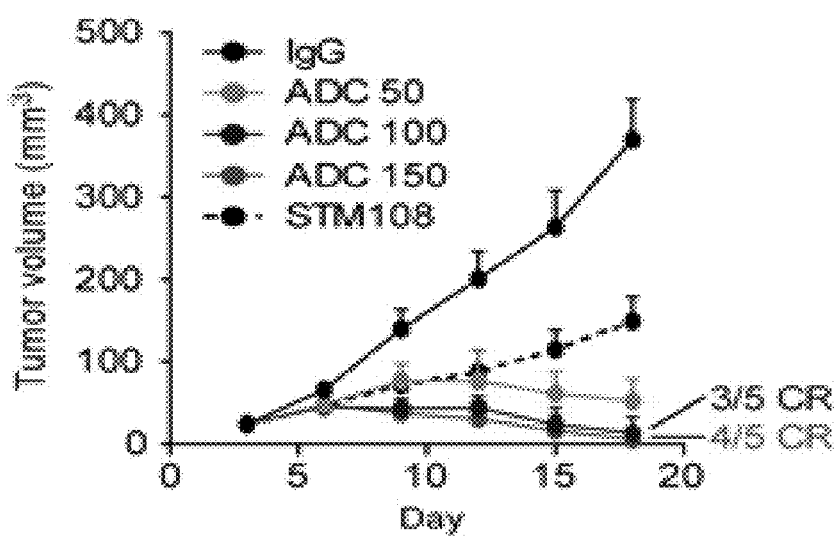

In connection with this Example, FIGS. 17A-17D present the results of experiments conducted to evaluate the efficacy of STM108-ADC in killing PD-L1-expressing and non-PD-L1-expressing tumor cells and in reducing the volume of tumors in tumor-grafted mice as compared to controls (IgG and STM108 MAb alone). FIG. 17A shows the % viability of PD-L1-expressing MDA-MB231 (human breast carcinoma cell line) tumor cells ("MB231") following exposure to different concentrations (nM) of STM108-ADC (filled black circles) compared with the % viability of MB231 cells molecularly engineered to knock out their expression of PD-L1 ("MB231 PDL1 KO") following exposure to different concentrations of STM108-ADC, i.e., "ADC108" (filled black squares). As observed, the viability of MB231 cells that did not express PD-L1 on their surface was not significantly affected by STM108-ADC at even the highest concentration, while the viability of PD-L1-expressing MB231 cells was significantly reduced, particularly at STM108-ADC concentrations of 1 nM up to 100 nM. In FIG. 17B, an MDA-MB231 mouse model of breast cancer was used in which animals grafted with tumors derived from MB231 cells were treated with either an IgG-MMAE control (100 µg); with STM108-ADC at 50 at 100 µg, or at 150 µg; or with STM108 MAb alone (100 m). The results demonstrated that tumor volume was effectively decreased in tumor-bearing animals treated with STM108-ADC at all dose levels, as well as, to some extent, with STM108 MAb (100 µg), compared with animals treated with the IgG-MMAE control. In addition, it was surprisingly found that complete remission ("CR") occurred in 3 out of 5 (3/5) animals treated with STM108-ADC (100 µg) and in 4 out of 5 (4/5) animals treated with STM108-ADC (150 µg) by about day 18.

Figure 17C:
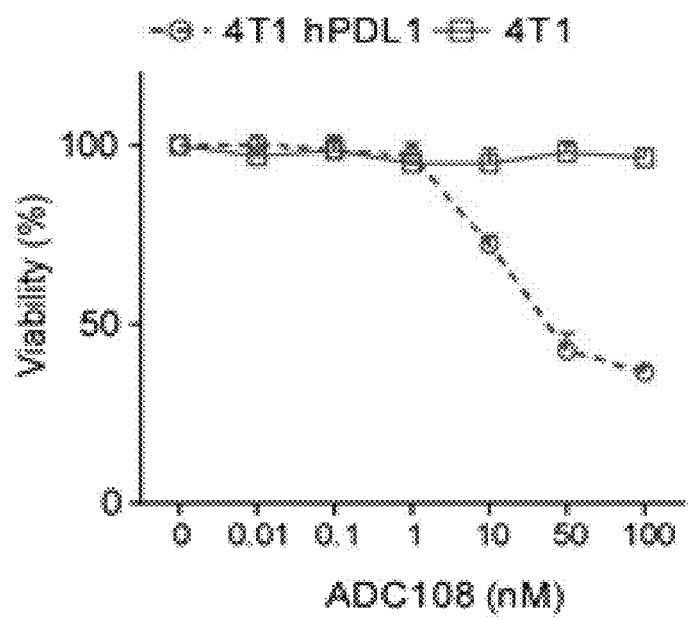

FIG. 17C shows the % viability of 4T1 mammary carcinoma cells molecularly engineered to express human PD-L1 on the cell surface ("4T1 hPDL1") following exposure to different concentrations (nM) of STM108-ADC (open red circles) compared with the % viability of 4T1 cells that naturally do not express PD-L1 ("4T1") following exposure to different concentrations of STM108-ADC, i.e., "ADC108" (open red squares). As observed, the viability of 4T1 cells that do not express PD-L1 on their surface was not significantly affected by STM108-ADC at even the highest concentration, while the viability of PD-L1-expressing 4T1 cells was reduced at STM108-ADC concentrations of greater than 10 nM to 100 nM.

4T1 syngeneic mouse models of breast cancer were used in which the animals (Balb/c mice) were grafted with tumors derived from 4T1 mammary carcinoma cells that had been molecularly engineered to express PD-L1 or the cell surface ("4T1 hPD-L1"), or in which the Balb/c mice were grafted with tumors derived from untransfected 4T1 mammary carcinoma cells that do not naturally express PD-L1 on the cell surface ("4T1"). All procedures with BALB/c mice (6- to 8-week-old females; Jackson Laboratories, Bar Harbor, Me., USA) were conducted under guidelines approved by the Institutional Animal Care and Use Committee at MD Anderson. Mice were divided according to the mean tumor volume in each group. 4T1 cells ($1\times10^5$ cells in 25 µL of medium mixed with 25 µL of Matrixgel Basement Membrane Matrix [BD Biosciences, San Jose, Calif., USA]) were injected into the mammary fat pad. IgG-MMAE control (100 µg), STM108 MAb (100 µg), or STM108-ADC (150 µg) were injected intraperitoneally on days 3, 5, 7, 9, 11, and 13 after tumor cell inoculation of mice. Tumors were measured every 3 days with a caliper, and tumor volume was calculated using the following formula: $\pi/6 \times length \times width$.

Figure 17D:
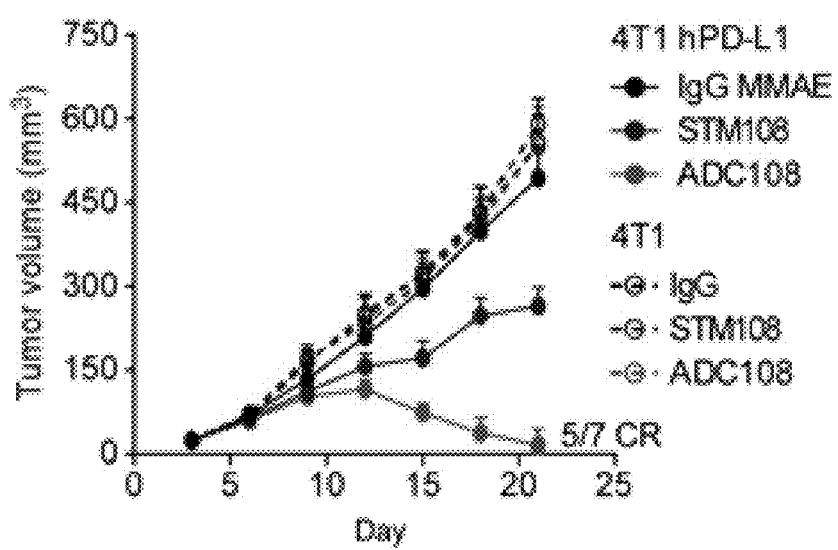

As observed in FIG. 17D, in animals harboring 4T1-derived tumors having little or no cell-surface PD-L1 expression (open circles/dotted lines), the results showed that tumor volume increased over time for all treatment types, i.e., IgG-MMAE control, STM108 MAb, or STM108-ADC. In animals harboring tumors derived from PD-L1-expressing 4T1 cells and treated with the IgG-MMAE control, tumor volume in treated animals also increased over time (solid black circles). By contrast, in animals harboring tumors derived from PD-L1-expressing 4T1 cells and treated with either the STM108 MAb (solid blue circles) or with STM108-ADC (solid red circles), tumor volume was effectively decreased. In addition, it was surprisingly found that complete remission ("CR") occurred in 5 out of 7 (5/7) animals treated with STM108-ADC by about day 21.

The beneficial and effective antineoplastic and therapeutic aspects related to the use of an ADC comprising an anti-glycPD-L1 MAb as described hereinabove, such as STM108, in treating cancers, e.g., two types of breast tumors, are underscored by the in vivo results showing significant reduction in tumor volume and complete remission of tumors in animals that had been treated with the anti-glycPD-L1 MAb ADC within 25 days after treatment, e.g., by about 15-23 days.

All of the methods disclosed and claimed herein can be made and executed without undue experimentation in light of the present disclosure. While the compositions and methods have been described in terms of embodiments and preferred embodiments, it will be apparent to those of skill in the art that variations may be applied to the methods and in the steps or in the sequence of steps of the methods described herein without departing from the concept, spirit and scope of that which is described. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the described embodiments as defined by the appended claims.

All patents, published patent applications, and other publications cited herein are hereby incorporated by reference in the present application.

What is claimed is:

1. An isolated antibody which binds to glycosylated PD-L1 comprising a $V_H$ domain comprising a CDR H1 with the amino acid sequence of SEQ ID NO: 4, a CDR H2 with the amino acid sequence of SEQ ID NO: 6, and a CDR H3 with the amino acid sequence of SEQ ID NO: 8 or a $V_H$ domain comprising a CDR H1 with the amino acid sequence of SEQ ID NO: 5, a CDR H2 with the amino acid sequence of SEQ ID NO: 7, and a CDR H3 with the amino acid sequence of SEQ ID NO: 9 and a $V_L$ domain comprising a CDR L1 with the amino acid sequence of SEQ ID NO: 12, a CDR L2 with the amino acid sequence of SEQ ID NO: 14, and a CDR L3 with the amino acid sequence of SEQ ID NO: 16.

2. The isolated antibody of claim 1, wherein the $V_H$ domain has the amino acid sequence of SEQ ID NO: 3 and the $V_L$ has the amino acid sequence of SEQ ID NO: 11.

3. An isolated antibody which binds to glycosylated PD-L1 comprising
   a $V_H$ domain comprising a CDR H1 with the amino acid sequence of SEQ ID NO: 20, a CDR H2 with the amino acid sequence of SEQ ID NO: 22, and a CDR H3 with the amino acid sequence of SEQ ID NO: 24, or a $V_H$ comprising a CDR H1 with the amino acid sequence of SEQ ID NO: 21 a CDR H2 with the amino acid sequence of SEQ ID NO: 23, and a CDR H3 with the amino acid sequence of SEQ ID NO: 25 and
   wherein said antibody has a $V_L$ domain comprising a CDR L1 with the amino acid sequence of SEQ ID NO: 28, a CDR L2 with the amino acid sequence of SEQ ID NO: 30, and a CDR L3 with the amino acid sequence of SEQ ID NO: 32.

4. An isolated antibody of claim 1 comprising a $V_H$ domain encoded by a nucleotide sequence that is at least 95% identical to the nucleotide sequence of SEQ ID NO: 2, and/or a $V_L$ domain encoded by a nucleotide sequence that is at least 95% identical to the nucleotide sequence of SEQ ID NO: 10.

5. The isolated antibody of claim 3, which has human antibody framework regions or a human constant domain.

6. The isolated antibody of claim 1, wherein the antibody is at least one selected from the group consisting of a Fab', a F(ab')2, a F(ab')3, a monovalent scFv, a bivalent scFv, a bispecific, and a biparatopic.

7. A composition comprising the antibody of claim 1 in a pharmaceutically acceptable carrier, diluent, excipient, or vehicle.

8. A method of treating a PD-L1 positive cancer in a subject in need, comprising administering to a subject having a PD-L1 positive cancer an effective amount of the isolated antibody of claim 1.

9. The method of claim 8, wherein the PD-L1 positive cancer is at least one cancer selected from the group consisting of a breast cancer, a lung cancer, a head & neck cancer, a prostate cancer, an esophageal cancer, a tracheal cancer, a skin cancer, a brain cancer, a liver cancer, a bladder cancer, a stomach cancer, a pancreatic cancer, an ovarian cancer, a uterine cancer, a cervical cancer, a testicular cancer, a colon cancer, a rectal cancer, and a skin cancer.

10. The isolated antibody of claim 1, wherein the antibody is conjugated to an antineoplastic agent to produce an antibody-drug conjugate (ADC).

11. The isolated antibody of claim 10, wherein the antibody is chemically conjugated to a maleimide and caproic acid (MC) attachment group, which is chemically conjugated to a cathepsin-cleavable linker, which is chemically conjugated to a paraminobenzoic acid (PAB) spacer, which is chemically conjugated to MMAE, thereby forming the ADC.

12. An ADC comprising a dual function anti-glycPD-L1 antibody chemically coupled to a cytotoxic drug, wherein the anti-glycPD-L1 antibody is that of claim 1.

13. The isolated antibody of claim 1, which has human antibody framework regions or a human constant domain.

14. The isolated antibody according to claim 3, wherein the antibody is at least one selected from the group consisting of a Fab', a F(ab')2, a F(ab')3, a monovalent scFv, a bivalent scFv, a bispecific, and a biparatopic.

15. An isolated antibody of claim 3 having a VH domain comprising the amino acid sequence of SEQ ID NO: 19 and VL domain comprising the amino acid sequence of SEQ ID NO: 27.

16. An isolated antibody of claim 3 comprising a $V_H$ domain encoded by a nucleotide sequence that is at least 95% identical to the nucleotide sequence of SEQ ID NO: 18, and a $V_L$ domain encoded by a nucleotide sequence that is at least 95% identical to the nucleotide sequence of SEQ ID NO: 26.

17. A composition comprising the antibody of claim 3 and a pharmaceutically acceptable carrier, diluent, excipient, or vehicle.

18. A method of treating a PD-L1 positive cancer in a subject in need of said treatment, said method comprising administering to the subject an effective amount of the antibody according to claim 3.

19. The method of claim 18, wherein the cancer is at least one cancer selected from the group consisting of a hematological cancer, a breast cancer, a lung cancer, a head & neck cancer, a prostate cancer, an esophageal cancer, a tracheal cancer, a skin cancer, a brain cancer, a liver cancer, a bladder cancer, a stomach cancer, a pancreatic cancer, an ovarian cancer, a uterine cancer, a cervical cancer, a testicular cancer, a colon cancer, a rectal cancer, and a skin cancer.

20. A method of assessing PD-L1 glycosylation in a biological sample, said method comprising contacting a biological sample with an antibody according to claim 3, wherein detection of binding of said antibody indicates that the sample comprises glycosylated PD-L1.

21. The method of claim 20, wherein the sample is a cell sample from a cancer or tumor of a subject.

22. A method of assessing PD-L1 glycosylation in a biological sample, said method comprising contacting a biological sample with an antibody according to claim 1, wherein detection of binding of said antibody indicates that the sample comprises glycosylated PD-L1.

23. The method of claim 22, wherein the sample is a cell sample from a cancer or tumor of a subject.

24. The isolated antibody of claim 1, wherein the antibody is an IgG antibody, an IgM antibody, or an IgA antibody.

25. The isolated antibody of claim 3, wherein the antibody is an IgG antibody, an IgM antibody, or an IgA antibody.

26. The isolated antibody of claim 3, wherein the antibody is conjugated to an antineoplastic agent to produce an antibody-drug conjugate (ADC).

27. The isolated antibody of claim 26, wherein the antibody is chemically conjugated to a maleimide and caproic acid (MC) attachment group, which is chemically conjugated to a cathepsin-cleavable linker, which is chemically conjugated to a paraminobenzoic acid (PAB) spacer, which is chemically conjugated to MMAE, thereby forming the ADC.

28. An ADC comprising a dual function anti-glycPD-L1 antibody chemically coupled to a cytotoxic drug, wherein the anti-glycPD-L1 antibody is that of claim 3.

* * * * *